United States Patent
Thompson et al.

(10) Patent No.: US 9,499,495 B2
(45) Date of Patent: Nov. 22, 2016

(54) QUINAZOLINES AND AZAQUINAZOLINES AS DUAL INHIBITORS OF RAS/RAF/MEK/ERK AND PI3K/AKT/PTEN/MTOR PATHWAYS

(71) Applicant: Asana Biosciences, LLC, Bridgewater, NJ (US)

(72) Inventors: Scott K. Thompson, Phoenixville, PA (US); Roger A. Smith, Chester Springs, PA (US); Sanjeeva Reddy, Chester Springs, PA (US); Tyler M. John, Phoenixville, PA (US); Vijay Kumar Nyavanandi, Hyderabad, IN (US); Hosahalli Subramanya, Bangalore (IN); Vijay Potluri, Hyderabad (IN); Sunil Kumar Panigrahi, Orissa (IN); Prabhakara Rao Nadipalli, Bachupally (IN); Saumitra Sengupta, Kolkata (IN)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

(21) Appl. No.: 14/783,903

(22) PCT Filed: Apr. 11, 2014

(86) PCT No.: PCT/US2014/033727
§ 371 (c)(1),
(2) Date: Oct. 12, 2015

(87) PCT Pub. No.: WO2014/169167
PCT Pub. Date: Oct. 16, 2014

(65) Prior Publication Data
US 2016/0068496 A1 Mar. 10, 2016

Related U.S. Application Data

(60) Provisional application No. 61/811,408, filed on Apr. 12, 2013.

(51) Int. Cl.
| | | |
|---|---|---|
| *C07D 239/94* | (2006.01) | |
| *C07D 403/04* | (2006.01) | |
| *C07D 401/04* | (2006.01) | |
| *C07D 471/04* | (2006.01) | |
| *A61K 45/06* | (2006.01) | |
| *C07D 401/14* | (2006.01) | |
| *C07D 519/00* | (2006.01) | |
| *C07D 413/14* | (2006.01) | |
| *G01N 33/50* | (2006.01) | |
| *G01N 33/574* | (2006.01) | |
| *A61K 31/5377* | (2006.01) | |
| *C07D 401/12* | (2006.01) | |
| *C07D 409/14* | (2006.01) | |

(52) U.S. Cl.
CPC ......... *C07D 239/94* (2013.01); *A61K 31/5377* (2013.01); *A61K 45/06* (2013.01); *C07D 401/04* (2013.01); *C07D 401/12* (2013.01); *C07D 401/14* (2013.01); *C07D 403/04* (2013.01); *C07D 409/14* (2013.01); *C07D 413/14* (2013.01); *C07D 471/04* (2013.01); *C07D 519/00* (2013.01); *G01N 33/5011* (2013.01); *G01N 33/57496* (2013.01)

(58) Field of Classification Search
CPC C07D 239/94; C07D 403/04; C07D 401/04; C07D 471/04; C07D 401/12; C07D 401/14; C07D 519/00; C07D 413/14; A61K 31/5377; A61K 45/06; G01N 33/5011; G01N 33/57496
USPC ....................................... 514/232.5; 544/106
See application file for complete search history.

(56) References Cited

FOREIGN PATENT DOCUMENTS

| WO | 2009039140 A1 | 3/2009 |
|---|---|---|
| WO | 2011101429 A1 | 8/2011 |
| WO | 2012118492 A1 | 9/2012 |

OTHER PUBLICATIONS

International Search Report from International Publication No. PCT/US2014/033727 mailed Jun. 24, 2014.

*Primary Examiner* — Kristin Vajda
(74) *Attorney, Agent, or Firm* — Lerner, David, Littenberg, Krumholz & Mentlik, LLP

(57) ABSTRACT

The present application provides novel quinazolines and azaquinazolines and pharmaceutically acceptable salts thereof. Also provided are methods for preparing these compounds. These compounds are useful in for co-regulating RAS/RAF/MEK/ERK and PI3K/AKT/PTEN/mTOR pathways by administering a therapeutically effective amount of one or more of the compounds of formula (I), wherein X, Y, T and $R^4$, and $R^6$ to $R^{8'}$ are defined herein, to a patient. By doing so, these compounds are effective in treating conditions associated with the dysregulation of the RAS/RAF/MEK/ERK and PI3K/AKT/PTEN/mTOR pathways. A variety of conditions can be treated using these compounds and include diseases which are characterized by abnormal cellular proliferation. In one embodiment the disease is cancer.

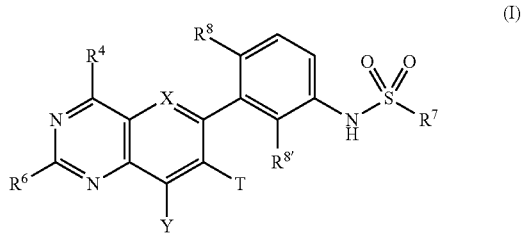

(I)

43 Claims, 1 Drawing Sheet

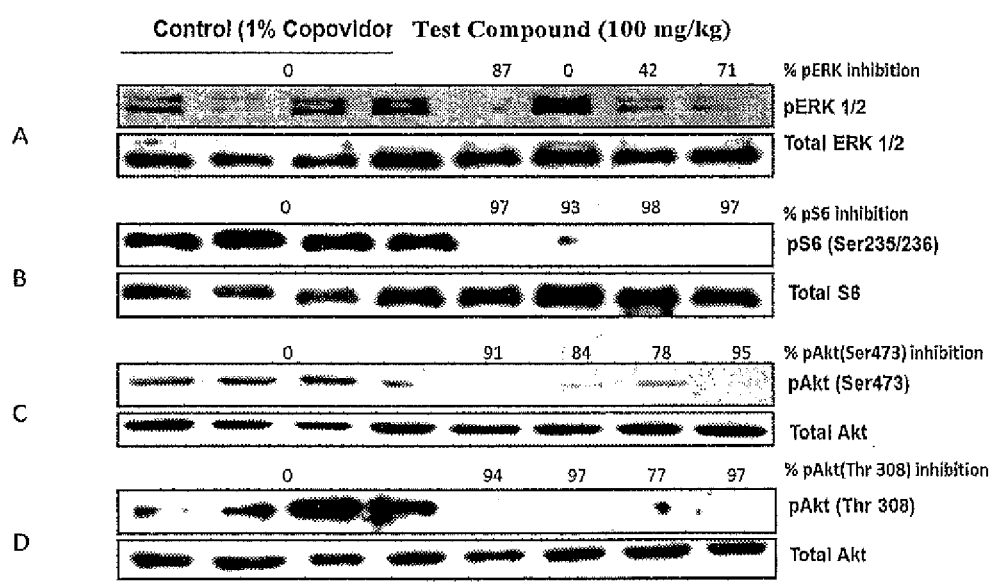

QUINAZOLINES AND AZAQUINAZOLINES AS DUAL INHIBITORS OF RAS/RAF/MEK/ERK AND PI3K/AKT/PTEN/MTOR PATHWAYS

CROSS-REFERENCE TO RELATED APPLICATIONS

The present application is a national phase entry under 35 U.S.C. §271 of International Application No. PCT/US2014/033727 filed Apr. 11, 2014, published in English, which claims priority from U.S. Provisional Application No. 61/811,408, filed Apr. 12, 2013, all of which are incorporated herein by reference.

BACKGROUND

Recent advances in understanding the molecular mechanisms of cancer have led to the discovery and development of anticancer therapeutic agents targeting important signaling pathways. These agents typically provide greater therapeutic benefit to the patients with lesser toxicity as compared to the conventional cytotoxic agents. However, patients often face the inevitable reality of recurrence of the cancer due to acquired resistance to the targeted therapeutic agents. There is a great unmet medical need to preempt or address such acquired resistance to cancer therapies.

Two pathways, RAS/RAF/MEK/ERK and PI3K/AKT/PTEN/mTOR, play an important role in the initiation and progression of tumors. Recently, there has been intense activity to discover and develop new agents targeting these two pathways. The RAS/RAF/MEK/ERK pathway is known to be dysregulated through genetic mutations in RAS, RAF or MEK genes, which leads to increased cell proliferation and angiogenesis. These mutations have been found in wide variety tumors. Inhibition of any of these targets was found to effectively inhibit the growth of tumors either in preclinical models or in humans. Recently, several compounds have been discovered which selectively inhibit one of these targets, RAF kinase. The inhibitors of RAF kinase include vemurafenib, dabrafenib, XL-281, LGX-818, CEP-32496 and ARQ-736. Vemurafenib is now an FDA-approved drug for treating the metastatic melanoma patients. Other compounds are in various stages of clinical development, including MEK-162, selumetinib, refametinib, E-6201, pimasertib, WX-554 and GDC-0973. Although several compounds targeting RAS protein have been identified, thus far none of them have been approved by the FDA.

Similar to the RAS pathway, PI3K/AKT/mTOR pathway also plays an important role in tumors, specifically in promoting the tumor cell survival and proliferation. This pathway is dysregulated through genetic changes in PI3K, AKT and PTEN genes. Several proteins in this pathway have been subjected for the drug discovery efforts, leading to the identification of many inhibitors against PI3K, AKT and mTOR proteins, and some of these inhibitors (such as temsirolimus and everolimus) have been approved by the FDA for various indications. Other inhibitors of the PI3K pathway are in various stages of clinical development, including the PI3K inhibitors GDC-0941, PX-866, XL-147, BKM-120, and BAY 80-6946, the mTOR inhibitors deforolimus, OSI-027 and AZD8055, the PI3K/mTOR dual inhibitors BEZ-235, XL-765, GDC-0980, GSK-2126458, PKI-587, and PF-04691502 and the AKT inhibitors MK-206, GDC-0068, GSK2636771, afuresertib, rigosertib and CLR-1401.

Despite some promising initial results in humans, several of the above-mentioned compounds are not able to provide a durable response due to the acquired resistance rendered by the activation of the alternative pathway(s) in the targeted cancer cells. For example, the inhibition of the PI3K pathway with agents such as temsirolimus leads to the subsequent activation of the RAS pathway, resulting in tumors which do not respond to this agent. Conversely, inhibition of RAS pathway leads to the activation of PI3K pathway. Preclinical data has demonstrated that the combinatorial inhibition of both pathways simultaneously gives a greater and more durable efficacy in tumor growth inhibition. These findings clearly indicate a need for combination therapies to overcome the acquired clinical resistance to single-pathway inhibitors. Several clinical trials with different combinations of two agents each inhibiting one of these two pathways have already been initiated. The most advanced combination clinical trial is in Phase II with AZD6244 (a MEK inhibitor) and MK2206 (an AKT inhibitor). However, combining two different agents in this manner can produce the significant disadvantages of added toxicity and higher cost.

Therefore, there is an unmet medical need to identify compounds with dual inhibitory activity against both pathways.

BRIEF DESCRIPTION OF THE FIGURES

The FIGURE is a Western blot showing inhibition of pERK, p S6RP, pAKT-5473 and pAKT-T308 in mouse xenograft RKO tumor cell lysates by a compound described herein.

SUMMARY OF THE INVENTION

The present invention provides a compound of formula (I), wherein X, Y, T, $R^4$, and $R^6$ to $R^{8'}$ are defined herein, a composition containing the compound of formula (I), and a kit containing the compound of formula (I).

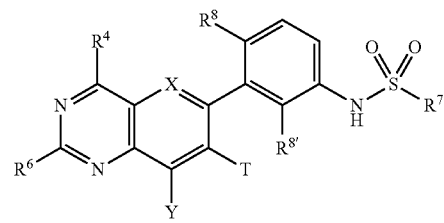

Also provided are methods for co-regulating RAS/RAF/MEK/ERK and PI3K/AKT/PTEN/mTOR which include administering a therapeutically effective amount of a compound to a patient. In one embodiment, co-regulation includes inhibiting the RAS/RAF/MEK/ERK pathway. In another embodiment, co-regulation includes inhibiting the PI3K/AKT/PTEN/mTOR pathway. In a further embodiment, co-regulation includes inhibiting RAS/RAF/MEK/ERK and PI3K/AKT/PTEN/mTOR pathways.

A method for treating a condition treatable by inhibiting the RAS/RAF/MEK/ERK and PI3K/AKT/PTEN/mTOR pathways is further provided. This method includes administering a therapeutically effective amount of a compound of formula (I) to a patient.

Further provided is a method for treating a disease characterized by an abnormal cellular proliferation resulting from dysregulated RAS/RAF/MEK/ERK and PI3K/AKT/

PTEN/mTOR pathways. The method includes administering a therapeutically effective amount of a compound of formula (I) to a patient. In one embodiment, the disease is cancer.

Other aspects and advantages of the invention will be readily apparent from the following detailed description of the invention.

DETAILED DESCRIPTION OF THE INVENTION

The present invention therefore provides compounds which inhibit both the RAS/RAF/MEK/ERK and PI3K/AKT/PTEN/mTOR pathways. In one embodiment, the compounds target B-RAF and mTOR. In another embodiment, the compounds target B-RAF and PI3K. In a further embodiment, the compounds target B-RAF, mTOR and PI3K. Such a compound useful herein is encompassed by formula (I):

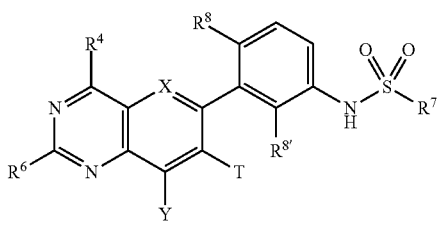

In this structure, X is CH or N, Y is H, optionally substituted $C_1$-$C_6$ alkyl, $OR^1$ or $NR^2R^3$, and T is H or $C_1$-$C_6$ alkoxy.

$R^1$ is optionally substituted $C_1$-$C_6$ alkyl, optionally substituted ($C_1$-$C_6$ alkyl)OH, optionally substituted ($C_1$-$C_6$ alkyl)OC$_1$-$C_6$ alkyl, optionally substituted $C_3$-$C_8$ cycloalkyl, optionally substituted ($C_1$-$C_6$ alkyl)NH$_2$, optionally substituted ($C_1$-$C_6$ alkyl)CO$_2$H, or optionally substituted ($C_1$-$C_6$ alkyl)CONH$_2$.

$R^2$ and $R^3$ are joined to form an optionally substituted heterocycle.

$R^4$ is optionally substituted morpholine. In one embodiment, $R^4$ is morpholine. In another embodiment, $R^4$ is substituted morpholine. In a further embodiment, $R^4$ is morpholine substituted by $C_1$-$C_6$ alkyl. In yet another embodiment, $R^4$ is:

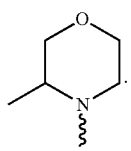

$R^7$ is optionally substituted aryl, optionally substituted $C_1$-$C_6$ alkyl, or optionally substituted heteroaryl; $R^8$ is H or halogen; and $R^{8'}$ is halogen. In one embodiment, $R^7$ is an optionally substituted aryl. In another embodiment, $R^7$ is phenyl substituted by one of more halogen. In a further embodiment, $R^7$ is

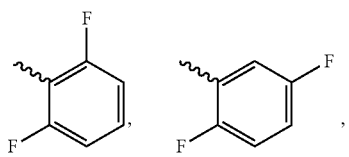

-continued

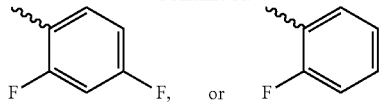

In still another embodiment, $R^7$ is optionally substituted $C_1$-$C_6$ alkyl. In yet a further embodiment, $R^7$ is $C_1$-$C_6$ alkyl optionally substituted by one or more F. In another embodiment, $R^7$ is i-propyl, i-butyl, n-propyl, ethyl, n-butyl, CH$_2$CH$_2$CH$_2$F, or CH$_2$CH$_2$CF$_3$. In still a further embodiment, $R^7$ is optionally substituted heteroaryl. In another embodiment, $R^7$ is thiophene.

$R^6$ is in formula (I) is an optionally substituted aryl or optionally substituted heteroaryl. In one embodiment, $R^6$ is

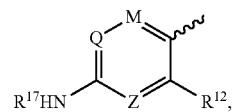

wherein M is N or $CR^{10}$; Q is N or $CR^{13}$; Z is N or $CR^{14}$; $R^{10}$ is H, $C_1$-$C_6$ alkyl, halogen, CN or $CF_3$; $R^{12}$ to $R^{14}$ are, independently, H, halogen, $C_1$-$C_6$ alkyl, or $CF_3$; $R'^7$ is NHC(O)NHNR$^9$, H, $C_1$-$C_6$ alkyl, ($C_1$-$C_6$ alkyl)-NH$_2$, ($C_1$-$C_6$ alkyl)-OH, ($C_1$-$C_6$ alkyl)-O—($C_1$-$C_6$ alkyl), CO($C_1$-$C_6$ alkyl) or SO$_2$($C_2$-$C_6$ alkyl); or $R^{13}$ and $R^{17}$ or $R^{14}$ and $R^{17}$ are joined to form an optionally unstaturated ring; and $R^9$ is $C_1$-$C_6$ alkyl, $C_1$-$C_6$ hydroxyalkyl, or heteroaryl. In another embodiment, $R^6$ is

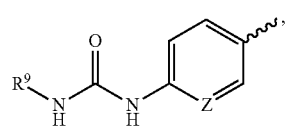

wherein Z is CH or N; and $R^9$ is $C_1$-$C_6$ alkyl, $C_1$-$C_6$ hydroxyalkyl, or heteroaryl. $R^9$ may be CH$_3$, CH$_2$CH$_2$OH, or pyridine-4-yl, among others. In a further embodiment, $R^6$ is an optionally substituted pyrimidine, optionally substituted pyridine, optionally substituted pyrrole[2,3-b]pyridine, optionally substituted indazole or optionally substituted benzimidazole. In still another embodiment, $R^6$ is

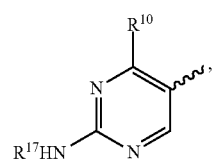

wherein $R^{10}$ is H, $C_1$-$C_6$ alkyl or trifluoromethyl; and $R^{17}$ is H, $C_1$-$C_6$ alkyl, ($C_1$-$C_6$ alkyl)-NH$_2$ or ($C_1$-$C_6$ alkyl)-OH. In yet a further embodiment, $R^6$ is

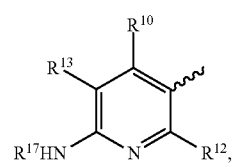

wherein $R^{10}$, $R^{12}$, and $R^{13}$ are, independently, H, halogen, $C_1$-$C_6$ alkyl, CN or $CF_3$; and $R^{17}$ is H, $C_1$-$C_6$ alkyl, ($C_1$-$C_6$ alkyl)-$NH_2$ or ($C_1$-$C_6$ alkyl)-OH; or $R^{13}$ and $R^{17}$ are joined to form an optionally unsaturated ring. In another embodiment, $R^6$ is

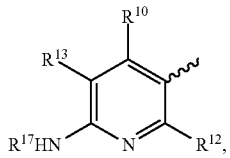

wherein $R^{10}$ is H, $C_1$-$C_6$ alkyl, halogen, CN or $CF_3$; $R^{12}$ is H or halogen; $R^{13}$ is H, halogen or $C_1$-$C_6$ alkyl; and $R^{17}$ is H, $C_1$-$C_6$ alkyl, ($C_1$-$C_6$ alkyl)-$NH_2$ or ($C_1$-$C_6$ alkyl)-OH; or $R^{13}$ and $R^{17}$ are joined to form an optionally unsaturated 5-membered ring. In still a further embodiment, $R^6$ is

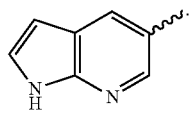

In yet a further embodiment, $R^6$ is

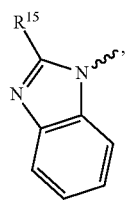

wherein $R^{15}$ is $C_1$-$C_6$ fluoroalkyl or $C_1$-$C_6$ hydroxyalkyl. In another embodiment, $R^6$ is

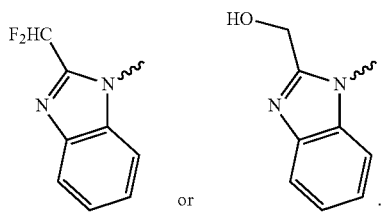

In still a further embodiment, $R^6$ is

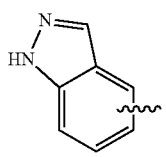

and is bound through any carbon atom. In yet another embodiment, $R^6$ is

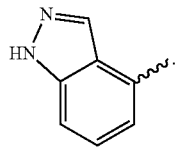

Representative "pharmaceutically acceptable salts" include but are not limited to water-soluble and water-insoluble salts. In one embodiment, the salt is of a base. The salt can be of a base selected from, e.g., alkali metal salt bases such as sodium, lithium, or potassium and organic bases, such as ammonium, mono-, di-, and trimethylammonium, mono-, di- and triethylammonium, mono-, di- and tripropylammonium, ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, among others.

In another embodiment, the salt is of an acid. The salt can be of an acid selected from, e.g., among acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic. Optionally, a composition of the invention may contain both a pharmaceutically acceptable salt and the free base form of a compound of the invention.

In a further embodiment, a compound of the invention may be a solvate. As used herein, a solvate does not significantly alter the physiological activity or toxicity of the compounds, and as such may function as pharmacological equivalents to non-solvate compounds of the invention. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$," where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched, or to a hydrocarbon group that consists of or contains a cyclic alkyl radical. In one embodiment, an alkyl contains 1 to 6 (inclusive) carbon atoms or integers or ranges there between (2, 3, 4, or 5). In another embodiment, an alkyl contains 1 to 5 (inclusive) carbon atoms or ranges there between. In a further embodiment, an alkyl contains 1 to 4 (inclusive) carbon atoms. In yet another embodiment, an alkyl contains 1 to 3 (inclusive) carbon atoms. In still a further embodiment, an alkyl contains 1 or 2 carbon atoms. Examples of alkyl groups that are hydrocarbon chains include, but are not limited to, methyl, ethyl, propyl, butyl, pentyl, and hexyl, where all isomers of these examples are contemplated. Examples of alkyl groups that consist of or contain a cyclic alkyl radical include, but are not limited to, cyclopropyl, cyclobutyl, cyclopentyl, 3,3-dimethylcyclobutyl, (cyclopropyl)methyl, and (cyclopentyl)methyl. An alkyl can be unsubstituted or substituted with one or more groups including, without limitation, halogen, OH, $NH_2$, $N(C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), optionally substituted heterocycle, and $NO_2$. In one embodiment, the substituted alkyl is $CH_2OH$.

"Alkoxy" refers to (alkyl)O, where the alkyl is optionally substituted and is defined above. In one embodiment, an alkoxy contains 1 to 6 (inclusive) carbon atoms or integers or ranges there between (2, 3, 4, or 5). In another embodiment, an alkoxy contains 1 to 5 (inclusive) carbon atoms or ranges there between. In a further embodiment, an alkoxy contains 1 to 4 (inclusive) carbon atoms. In yet another embodiment, an alkoxy contains 1 to 3 (inclusive) carbon atoms. In still a further embodiment, an alkoxy contains 1 or 2 carbon atoms. Examples of alkoxy include, but are not limited to, methoxy, ethoxy, propoxy, and butoxy. The alkyl radical of an alkoxy group can be unsubstituted or substituted as defined above for "alkyl".

"Hydroxyalkyl" refers to (alkyl)OH, where the alkyl is optionally substituted and is defined above. The OH moiety of the hydroxyalkyl may be bound to any carbon atom, for example, any one of the internal carbon atoms or the terminal carbon atom of a hydrocarbon alkyl chain. In one embodiment, a hydroxyalkyl contains 1 to 6 (inclusive) carbon atoms or integers or ranges there between (2, 3, 4, or 5). In another embodiment, a hydroxyalkyl contains 1 to 5 (inclusive) carbon atoms or ranges there between. In a further embodiment, a hydroxyalkyl contains 1 to 4 (inclusive) carbon atoms. In yet another embodiment, a hydroxyalkyl contains 1 to 3 (inclusive) carbon atoms. In still a further embodiment, a hydroxyalkyl contains 1 or 2 carbon atoms. Examples of a hydroxyalkyl include, but are not limited to, $CH_2OH$, $CH_2CH_2OH$, $CH(OH)CH_3$, $CH_2CH_2CH_2OH$, $CH_2CH(OH)CH_3$, $CH(OH)CH_2CH_3$, $C(OH)(CH_3)_2$, (2-hydroxy)-cyclopentyl, (3-hydroxy)-cyclobutyl, and the like.

"Aryl" refers to an aromatic hydrocarbon group containing carbon atoms. In one embodiment, the aryl contains 6-10 carbon atoms, and is phenyl or is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, OH, $NH_2$, $N(C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), $C_1$ to $C_6$ alkyl, CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$. In one embodiment, an aryl is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2(C_1$ to $C_6$ alkyl), or $NHSO_2(C_1$ to $C_6$ alkyl). In another embodiment, an aryl is substituted with one halogen, OH, CN, $NH_2$, $C_1$ to $C_6$ alkylamino, $C_1$ to $C_6$ alkyl substituted with OH, $C_1$ to $C_6$ alkoxy, $CF_3$, $OCF_3$, $SO_2CH_3$, $NHCOCH_3$, or $NHSO_2CH_3$. In a further embodiment, an aryl is substituted with one halogen, OH, CN, $N(CH_3)_2$, $CH_2OH$, $OCH_3$, $OCF_3$, $CF_3$, $SO_2CH_3$, $NHCOCH_3$, or $NHSO_2CH_3$.

"Halogen" refers to F, Cl, Br and I.

The term "heteroatom" refers to a sulfur, nitrogen, or oxygen atom.

"Heteroaryl" refers to a monocyclic aromatic 5- or 6-membered ring containing at least one ring heteroatom. In one embodiment, the heteroaryl contains 1 to 5 carbon atoms (inclusive) or integers or ranges there between (2, 3, or 4). In a further embodiment, the heteroaryl contains 2 to 5 carbon atoms (inclusive). In another embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In yet a further embodiment, the bicyclic heteroaryl is a pyridine fused to a 5- or 6-membered monocyclic heteroaryl. In another embodiment, the bicyclic heteroaryl is a pyrimidine fused to a 5- or 6-membered monocyclic heteroaryl. In yet a further embodiment, the bicyclic heteroaryl is a pyridazine fused to a 5- or 6-membered monocyclic heteroaryl. In still another embodiment, the heteroaryl ring has 1 or 2 nitrogen atoms in the ring. In a further embodiment, the heteroaryl ring has 1 nitrogen atom and 1 oxygen atom. In yet another embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, pyrazole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, $C_1$ to $C_6$ alkyl, OH, $C_1$ to $C_6$ hydroxyalkyl, $C_1$ to $C_6$ haloalkyl, $NH_2$, $N(C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), NH($C_1$ to $C_6$ hydroxyalkyl), N($C_1$ to $C_6$ hydroxyalkyl)$_2$, C(O)NH[—($C_1$ to $C_6$ alkyl)-N($C_1$ to $C_6$ alkyl)$_2$], C(O)NH[—($C_1$ to $C_6$ alkyl)-NH($C_1$ to $C_6$ alkyl)], C(O)N($C_1$ to $C_6$ alkyl)[—($C_1$ to $C_6$ alkyl)-N($C_1$ to $C_6$ alkyl)$_2$] and NO$_2$. In one embodiment, a heteroaryl is substituted with one or more halogen, OH, CN, NH$_2$, $C_1$ to $C_6$ alkylamino, $C_1$ to $C_6$ alkyl substituted with OH, $C_1$ to $C_6$ alkoxy, $C_1$ to $C_6$ haloalkyl, OCF$_3$, SO($C_1$ to $C_6$ alkyl), NHCOCH$_3$, or NHSO$_2$($C_1$ to $C_6$ alkyl). In another embodiment, a heteroaryl is substituted with one halogen, OH, CN, N(CH$_3$)$_2$, CH$_2$OH, OCH$_3$, OCF$_3$, CF$_3$, SO$_2$CH$_3$, NHCOCH$_3$, or NHSO$_2$CH$_3$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges there between (4, 5, or 6). In a further embodiment, the heterocycle contains 4 to 7 carbon atoms (inclusive). In another embodiment, the heterocycle contains 4 to 6 carbon atoms (inclusive). In still a further embodiment, the heterocycle contains 5 or 6 carbon atoms (inclusive). Examples of heterocycles include, but are not limited, to aziridine, oxirane, thiirane, morpholine, thiomorpholine, pyrroline, pyrrolidine, azepane, dihydrofuran, THF, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In yet another embodiment, the heterocycle contains 1 or 2 nitrogen atoms, 3 to 6 carbon atoms, and 1 oxygen atom. In still a further embodiment, the heterocycle is morpholine. In one embodiment, the heterocycle is morpholine and is substituted with one or more $C_1$ to $C_3$ alkyl. In another embodiment, the heterocycle is morpholine and 2 carbons of the heterocycle are joined to form a 4- or 5-membered ring. A heterocycle may be unsubstituted or substituted with one or more groups including, without limitation, halogen, $C_1$ to $C_6$ alkyl, OH, NH$_2$, N($C_1$ to $C_3$ alkyl)C(O)($C_1$ to $C_6$ alkyl), NHC(O)($C_1$ to $C_6$ alkyl), NHC(O)H, C(O)NH$_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), NH($C_1$ to $C_6$ hydroxyalkyl), W$_1$ to $C_6$ hydroxyalkyl)$_2$, C(O)NH[—($C_1$ to $C_6$ alkyl)-N($C_1$ to $C_6$ alkyl)$_2$], C(O)NH[—($C_1$ to $C_6$ alkyl)-NH($C_1$ to $C_6$ alkyl)], C(O)N($C_1$ to $C_6$ alkyl)[—($C_1$ to $C_6$ alkyl)-N($C_1$ to $C_6$ alkyl)$_2$] and NO$_2$. In one embodiment, a heterocycle is substituted with one or more halogen, OH, CN, NH$_2$, $C_1$ to $C_6$ alkylamino, $C_1$ to $C_6$ alkyl substituted with OH, $C_1$ to $C_6$ alkoxy, $C_1$ to $C_6$ haloalkyl, OCF$_3$, SO$_2$($C_1$ to $C_6$ alkyl), NHCOCH$_3$, or NHSO$_2$($C_1$ to $C_6$ alkyl). In another embodiment, a heterocycle is substituted with one F, OH, CN, NH$_2$, N(CH$_3$)$_2$, CH$_2$OH, OCH$_3$, OCF$_3$, CF$_3$, SO$_2$CH$_3$, NHCOCH$_3$, or NHSO$_2$CH$_3$.

"Optionally-substituted —CH$_2$CH$_2$CH$_2$—, —CH$_2$CH$_2$CH$_2$CH$_2$—, or —CH$_2$CH$_2$CH$_2$CH$_2$CH$_2$—" refers to —CH$_2$CH$_2$CH$_2$—, —CH$_2$CH$_2$CH$_2$CH$_2$—, or —CH$_2$CH$_2$CH$_2$CH$_2$CH$_2$— wherein 1 or 2 of the hydrogen atoms are replaced with OH, NH$_2$, NHCH$_3$, N(CH$_3$)$_2$, halogen, alkoxy, CF$_3$, OCF$_3$, or CN.

"$C_1$ to $C_6$ haloalkyl" refers to a $C_1$ to $C_6$ alkyl group, as defined above, wherein one or more of the $C_1$ to $C_6$ alkyl group's hydrogen atoms has been replaced with F, Cl, Br, or I. Each substitution can be independently selected from F, Cl, Br, or I. Representative examples of a $C_1$ to $C_6$ haloalkyl group include, but are not limited to, CH$_2$F, CF$_3$, CH$_2$CF$_3$, and the like.

"Alkylsulfonyl" refers to an (alkyl)SO$_2$-⌒ group, which is bound through the SO$_2$ moiety. The alkyl group is defined and optionally substituted as described above. Examples of alkylsulfonyl include, but are not limited to, CH$_3$SO$_2$, CH$_3$CH$_2$CH$_2$SO$_2$, CH$_3$CH(CH$_3$)SO$_2$, CH$_3$CH$_2$CH$_2$CH$_2$SO$_2$, CH$_3$CH(CH$_3$)CH$_2$SO$_2$, (CH$_3$)$_3$CSO$_2$, and the like.

"Alkylamino" refers to an NH or N group, the nitrogen atom of said group being attached to 1 or 2 alkyl substituents, respectively, where alkyl is as defined above. The alkylamino is bound through the nitrogen atom of the group. In one embodiment, alkylamino refers to a (alkyl)NH-⌒ group. In another embodiment, alkylamino refers to a (alkyl)(alkyl)N-⌒ group, i.e., a "dialkylamino". When the nitrogen atom is bound to 2 alkyls, each alkyl group may be independently selected. In another embodiment, two alkyl groups on the nitrogen atom may be taken together with the nitrogen to which they are attached to form a 3- to 7-membered nitrogen-containing heterocycle wherein up to two of the carbon atoms of the heterocycle can be replaced with N(H), N($C_1$ to $C_6$ alkyl), N(aryl), N(heteroaryl), O, S, S(O), or S(O)$_2$. Examples of alkylamino include, but are not limited to CH$_3$NH, CH$_3$CH$_2$NH, CH$_3$CH$_2$CH$_2$NH, CH$_3$CH$_2$CH$_2$CH$_2$NH, (CH$_3$)$_2$CHNH, (CH$_3$)$_2$CHCH$_2$NH, CH$_3$CH$_2$CH(CH$_3$)NH, (CH$_3$)$_3$CNH, N(CH$_3$)$_2$, N(CH$_2$CH$_3$)(CH$_3$), N(CH$_2$CH$_3$)$_2$, N(CH$_2$CH$_2$CH$_3$)$_2$, N(CH$_2$CH$_2$CH$_2$CH$_3$)$_2$, N(CH(CH$_3$)$_2$)(CH$_3$), and the like.

"Aminoalkyl" refers to an alkyl group having an NH$_2$ substituent. The aminoalkyl is bound through one carbon atom of the group. That is, alkylamino refers to a NH$_2$(alkyl)-⌒ group. Examples of aminoalkyl include, but are not limited to CH$_2$NH$_2$, CH$_2$CH$_2$NH$_2$, CH$_2$CH$_2$CH$_2$NH$_2$, CH$_2$CH$_2$CH$_2$CH$_2$NH$_2$, C(CH$_3$)$_2$NH$_2$, C(CH$_3$)$_2$CH$_2$NH$_2$, and the like.

"Alkylcarbonylamino" refers to an (alkyl)C(O)NH-⌒ group, which is bound through the nitrogen atom. The alkyl group is defined and optionally substituted as described above. Examples of alkylcarbonylamino include, but are not limited to, CH$_3$CONH, CH$_3$CH$_2$CONH, CH$_3$CH$_2$CH$_2$CONH, CH$_3$CH(CH$_3$)CONH, and the like.

"Alkylsulfonylamino" refers to an (alkyl)SO$_2$NH-⌒ group which is bound through the nitrogen atom. The alkyl group is defined and optionally substituted as described above. Examples of alkylsulfonylamino include, but are not limited to CH$_3$SO$_2$NH, CH$_3$CH$_2$SO$_2$NH, CH$_3$CH$_2$CH$_2$SO$_2$NH, CH$_3$CH(CH$_3$)SO$_2$NH, and the like.

"Alkylaminocarbonyl" refers to an (alkyl)NHC(O)— group, which is bound through the carbonyl moiety. The alkyl group is defined and optionally substituted as described above. Examples of alkylaminocarbonyl include, but are not limited to, CH₃NHCO, CH₃CH₂NHCO, CH₃CH₂CH₂NHCO, CH₃CH(CH₃)NHCO, and the like.

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term "treating" or "treatment" is meant to encompass administering to a subject a compound of the present invention for the purposes of amelioration of one or more symptoms of a disease or disorder, including palliative care. A "therapeutically effective amount" refers to the minimum amount of the active compound which effects treatment.

The following abbreviations are used herein and have the indicated definitions: ACN is acetonitrile; conc. is concentrated; DMSO is dimethylsulfoxide; DCM is dichloromethane; DIPEA is diisopropylethylamine; DMF is N,N-dimethylformamide; dppf is 1,1'-bis(diphenylphosphino)ferrocene; EDTA is ethylenediamine tetraacetic acid; EGTA is ethylene glycol tetraacetic acid; ELISA is enzyme-linked immunosorbent assay; ESI is electrospray ionization; EI is electron impact ionization; HEPES is (4-(2-hydroxyethyl)-1-piperazineethanesulfonic acid; HPLC is high performance liquid chromatography; Hz is hertz; KOAc is potassium acetate; LC is liquid chromatography; MS is mass spectroscopy; MeOH is methanol; MHz is megahertz; mM is millimolar; mL is milliliter; min is minutes; mol is moles; M⁺ is molecular ion; [M+H]⁺ is protonated molecular ion; N is normality; NMR is nuclear magnetic resonance; PIP2 is 5-bisphosphate; PBS is phosphate buffered saline; PH is pleckstrin homology; PPh₃ is triphenylphosphine; psi is pound per square inch; PPM is parts per million; rt is room temperature; TLC is thin layer chromatography; TEA is triethylamine; THF is tetrahydrofuran; and XTT is sodium 2,3,-bis(2-methoxy-4-nitro-5-sulfophenyl)-5-[(phenylamino)-carbonyl]-2H-tetrazolium inner salt.

The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

Methods useful for making the compounds of formula (I) are set forth in the Examples below and generalized in Schemes 1-16. One of skill in the art will recognize that Schemes 1-16 can be adapted to produce the other compounds of formula (I) and pharmaceutically acceptable salts of compounds of formula (I) according to the present invention.

The following methods outline the synthesis of the compounds of formula (I). The following examples are presented to illustrate certain embodiments of the present invention, but should not be construed as limiting the scope of this invention.

Scheme 1

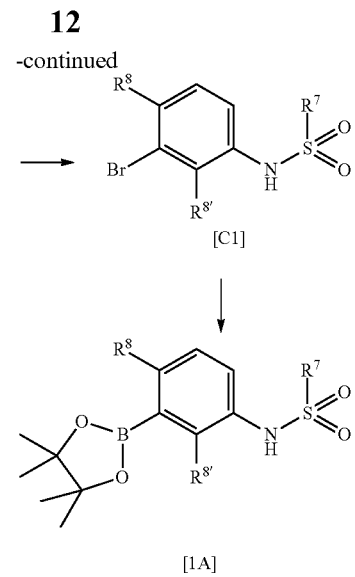

Scheme 1 depicts the synthesis of boronic acid pinacol ester intermediate [1A]. In one embodiment, a bromo substituted benzoic acid [A1] is converted to the corresponding aniline [B1]. In one embodiment, the benzoic acid is reacted with diphenylphosphoryl azide (DPPA). The aniline may then be converted to corresponding sulfonamide [C1]. In one embodiment, the aniline is reacted with a sulfonyl chloride. In another embodiment, the reaction is performed in the presence of a base such as pyridine. The intermediate boronic acid pinacol ester [1A] may then be formed by reacting the sulfonamide with a diboron reagent. In one embodiment, the sulfonamide is reacted with bis(pinacolato)diboron.

Scheme 1A

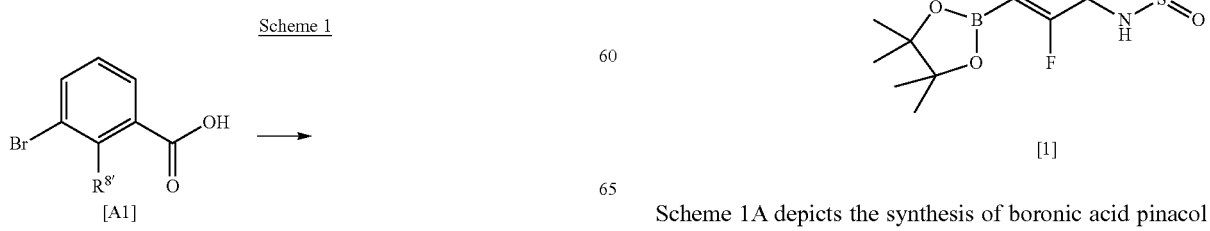

Scheme 1A depicts the synthesis of boronic acid pinacol ester intermediate [1]. 3-Bromo-2-fluoro benzoic acid is converted into the corresponding aniline [B] using DPPA. The aniline is then converted to corresponding sulfonamide using a sulfonyl chloride and pyridine in dichloromethane. The intermediate boronic acid pinacol ester [1] was formed by reacting the sulfonamide with bis(pinacolato)diboron.

mation to the sulfonamide [C] was achieved using aniline [B] (described in Scheme 1). In one embodiment, the reaction was performed in the presence of a base such as pyridine and DMAP. The intermediate boronic acid pinacol ester [1] as formed as described in Scheme 1A.

Scheme 2

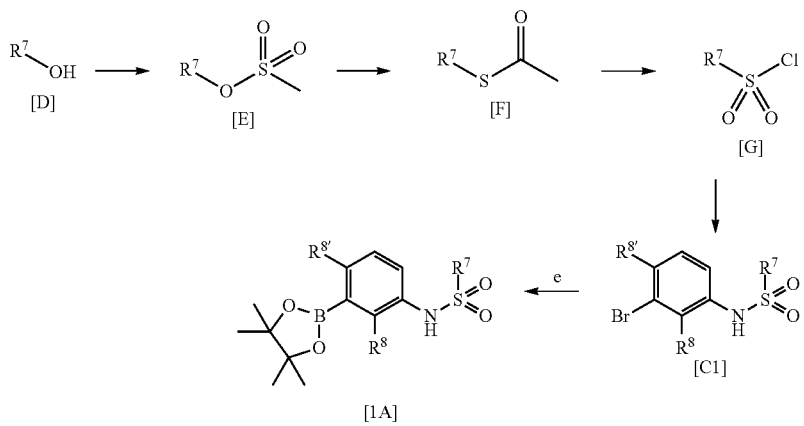

Scheme 2 provides the second route for the preparation of intermediate [1A]. In this route, alcohol $R^7OH$ [D] was reacted a sulfonyl chloride provide sulfonate ester [E]. The sulfonate ester [E] was then converted to the corresponding ethanethioate [F]. In one embodiment, the reaction was performed using potassium thioacetate. This ethanethioate [F] was then oxidized to $R^7SO_2Cl$ [G]. In one embodiment, the oxidation was performed using chlorine gas. The transformation to sulfonamide [C1] was achieved using aniline [B] (described in Scheme 1). The intermediate boronic acid pinacol ester [1A] was formed as described in Scheme 1.

Scheme 3

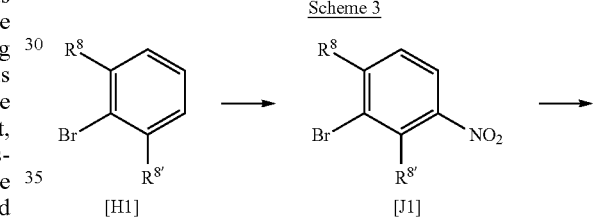

Scheme 2A

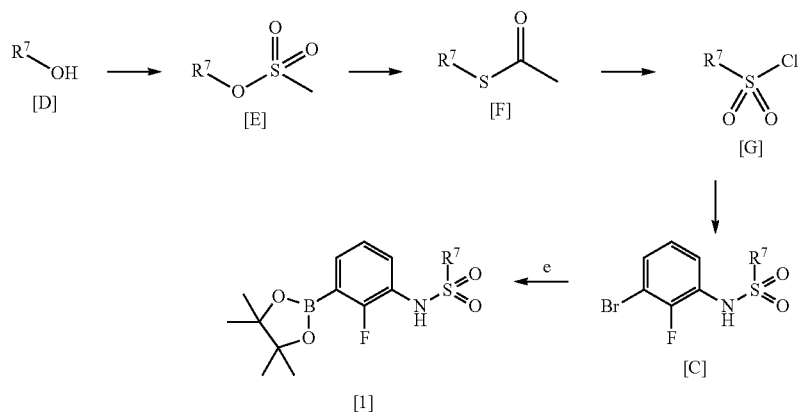

Scheme 2A provides the second route for the preparation of intermediate [1]. In this route, alcohol $R^7OH$ [D] was reacted a sulfonyl chloride provide a sulfonate ester. The sulfonate ester [E] was then converted to the corresponding ethanethioate [F]. In one embodiment, this reaction was performed using potassium thioacetate. This ethanethioate [F] was then oxidized to $R^3SO_2Cl$. In one embodiment, the oxidation was performed using chlorine gas. The transfor- -continued

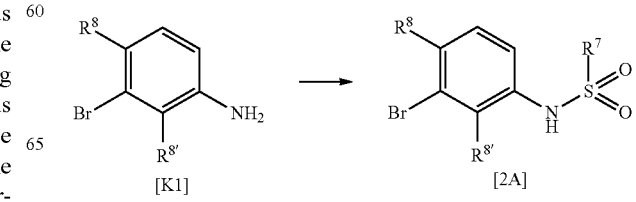

Scheme 3 depicts the synthesis of boronic acid pinacol ester intermediate [2A]. Substituted bromobenzene [H1] is converted to the corresponding nitro compound [J1]. In one embodiment, the nitro compound is preparing using a nitric acid in sulfuric acid. The nitro compound is then reduced to the corresponding aniline [K1]. In one embodiment, the reduction is performed using $SnCl_2 \cdot 2H_2O$. Aniline [K1] is then converted to the corresponding sulfonamide intermediate [2A] using $R^7SO_2Cl$ as described in Scheme 1. In one embodiment, the reaction is performed in a base such as DMAP and pyridine.

Scheme 3A

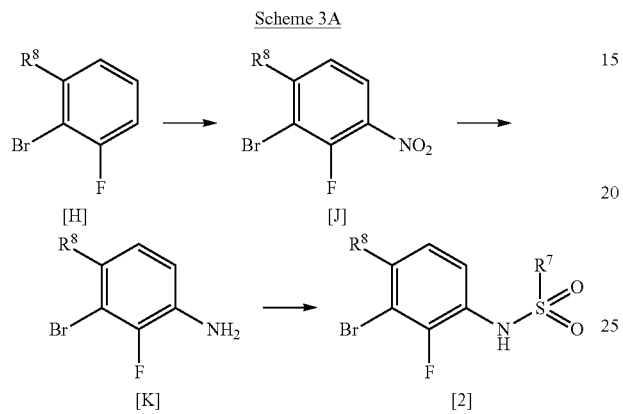

Scheme 3A depicts the synthesis of boronic acid pinacol ester intermediate [2]. Substituted bromofluoro benzene [H] is converted to the corresponding nitro compound [J] using a nitration mixture in sulfuric acid. Nitro compound [J] is then reduced to the corresponding aniline [K] using $SnCl_2 \cdot 2H_2O$. The aniline is then converted into corresponding sulfonamide intermediate [2] using $R^7SO_2Cl$, DMAP and pyridine.

Scheme 4

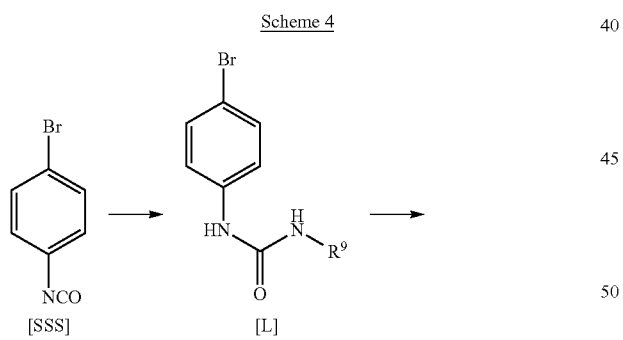

Scheme 4 provides a method for the synthesis of boronic acid pinacol ester intermediate [3]. In this route, 4-bromophenylisocyanate [SSS] was reacted with $R^9NH_2$ to form the corresponding urea [L]. Intermediate boronic acid pinacole ester [3] was then formed by reacting urea [L] with bis(pinacolato)diboron.

Scheme 5

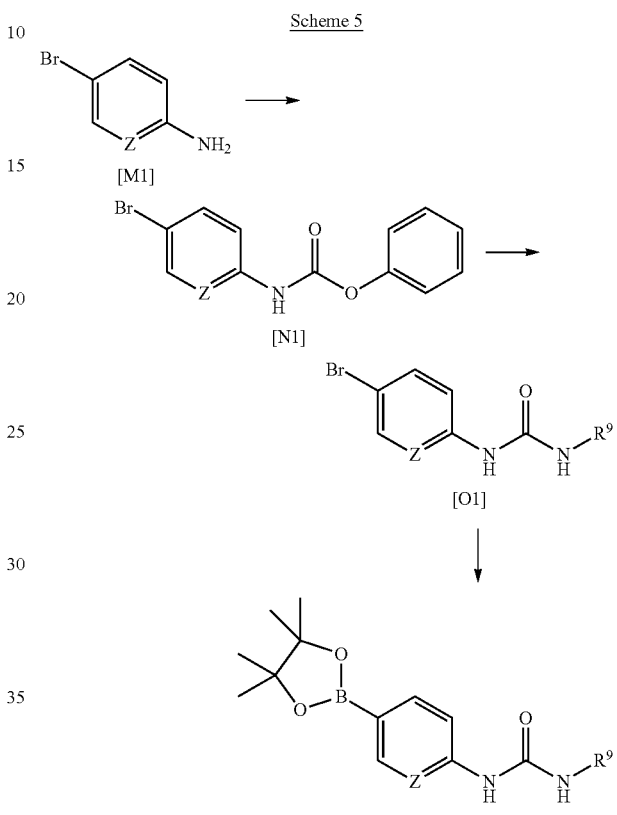

Scheme 5A provides the preparation of intermediate [4A]. Specifically, compound [M1] was reacted with phenylchloroformate in the presence of diisopropylethylamine. The resultant compound [N1] was heated to elevated temperatures in a sealed tube. Urea compound [O1] was then reacted with bis(pinacolato)diboron to provide intermediate compound [4A].

Scheme 5A

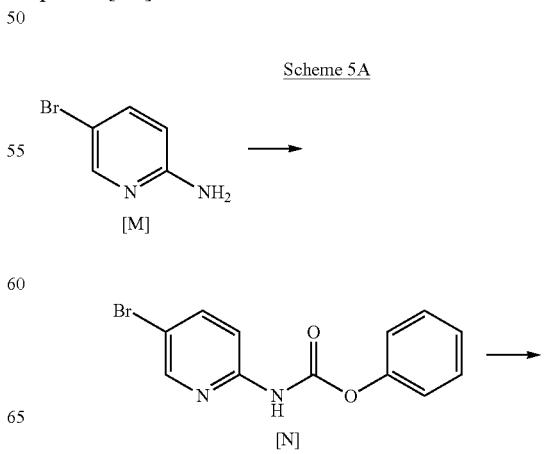

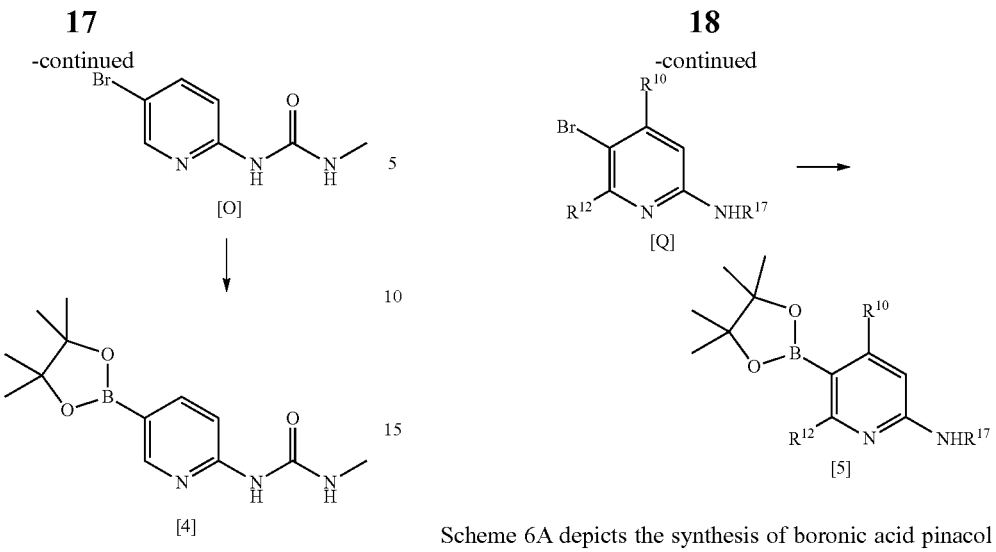

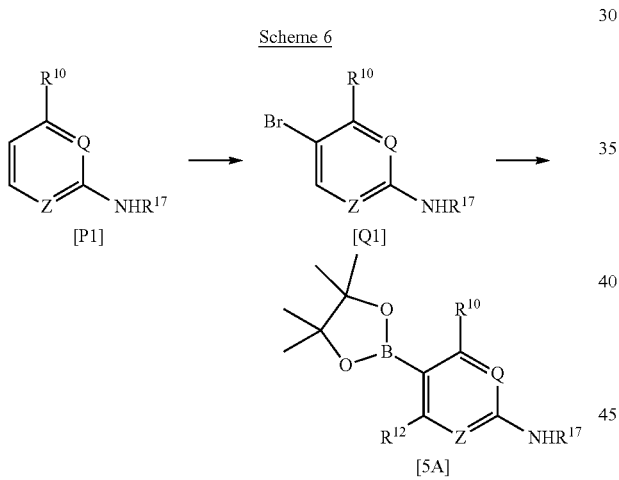

Scheme 5A provides the preparation of intermediate [4]. Specifically, 5-bromopyridin-2-amine was reacted with phenylchloroformate in the presence of diisopropylethylamine. The resultant phenyl(5-bromopyridin-2-yl)carbamate, methylamine was heated to elevated temperatures in a sealed tube. 1-(5-Bromopyridin-2-yl)-3-methylurea was then reacted with bis(pinacolato)diboron to provide intermediate compound [4].

Scheme 6 depicts the synthesis of boronic acid pinacol ester intermediate [5A]. In one embodiment, compound [P1] was brominated to the 5-bromo compound [Q1]. In one embodiment, the bromination was performed using N-bromosuccinimide. The 5-bromo compound [Q1] was then converted into the corresponding boronic acid pinacol ester intermediate [5A]. In one embodiment, the reaction was performed using bis(pinacolato)diboron.

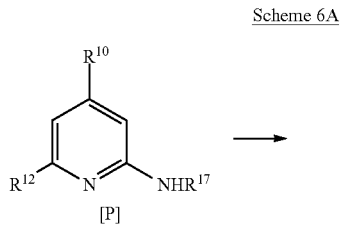

Scheme 6A depicts the synthesis of boronic acid pinacol ester intermediate [5]. In one embodiment, compound [P] was brominated to the 5-bromo compound [Q]. In one embodiment, the bromination was performed using N-bromosuccinimide. The 5-bromo compound [Q] was then converted into the corresponding boronic acid pinacol ester intermediate [5]. In one embodiment, the reaction was performed using bis(pinacolato)diboron.

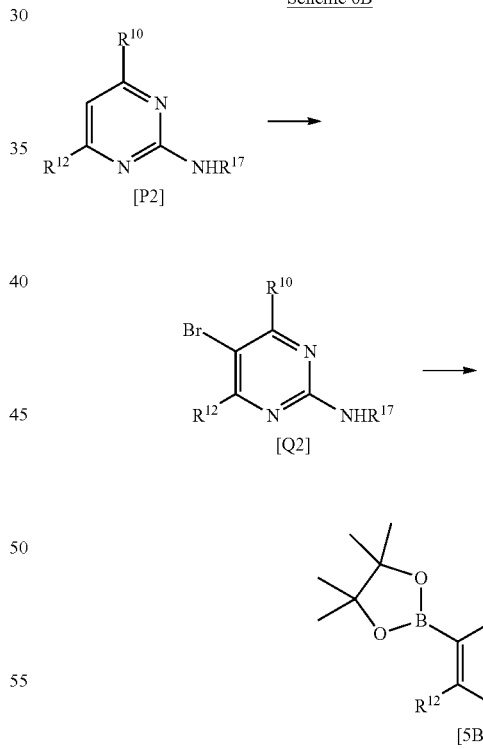

Scheme 6B depicts the synthesis of boronic acid pinacol ester intermediate [5B]. In one embodiment, compound [P2] was brominated to the 5-bromo compound [Q2]. In one embodiment, the bromination was performed using N-bromosuccinimide. The 5-bromo compound [Q2] was then converted into the corresponding boronic acid pinacol ester intermediate [5B]. In one embodiment, the reaction was performed using bis(pinacolato)diboron.

Scheme 7

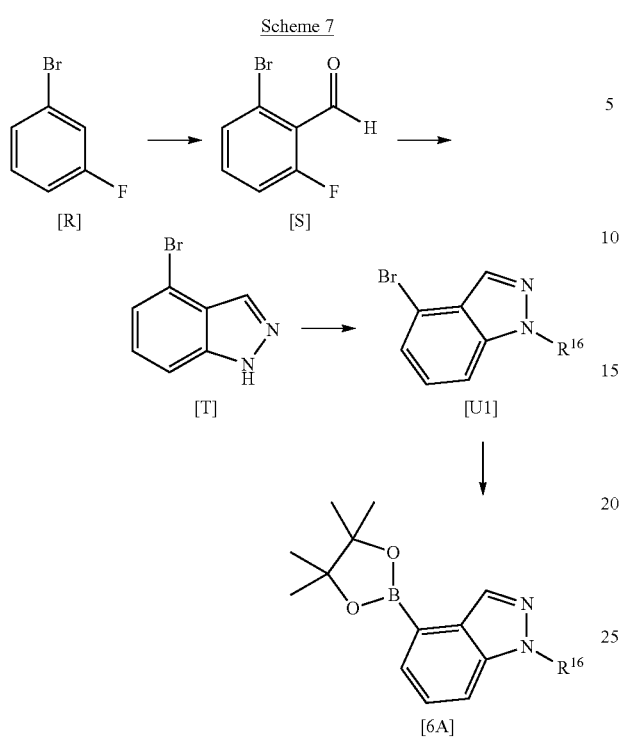

Scheme 7 provides the route for the preparation of intermediate [6A]. In this route, 3-fluoro bromobenzene was converted into the corresponding formyl compound [S]. In one embodiment, the conversion was performed using diisopropylamine and n-butyllithium. Formyl compound [S] was then reacted with hydrazinehydrate to form bromoindazole [T]. Compound [T] is then $R^{16}$-protected. In one embodiment, the protection was performed using 3,4-dihydro-2H-pyran. The intermediate boronic acid pinacol ester [6A] was then formed by reacting compound [U1] with bis(pinacolato)diboron.

Scheme 7A

Scheme 7A provides the route for the preparation of intermediate [6]. In this route, 3-fluoro bromobenzene was converted into the corresponding formyl compound [S]. In one embodiment, the conversion was performed using diisopropylamine and n-butyllithium. Formyl compound [S] was then reacted with hydrazine hydrate to form bromoindazole [T]. Compound [T] was protected with tetrahydropyran using 3,4-dihydro-2H-pyran. The intermediate boronic acid pinacol ester [6] was then formed by reacting compound [U] with bis(pinacolato)diboron.

Scheme 8

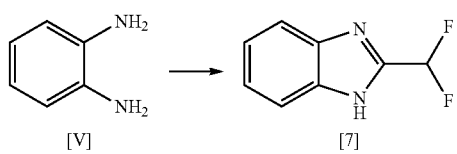

Scheme 8 details the preparation of difluromethylbenzimidazole intermediate [7]. In this route, o-phenylenediamine [V] was converted to difluoromethylbenzimidazole intermediate [7] using difluoroacetic acid.

Scheme 9

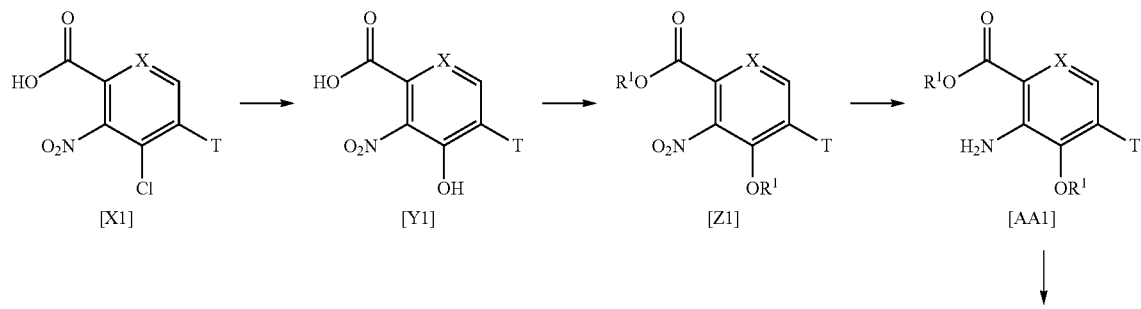

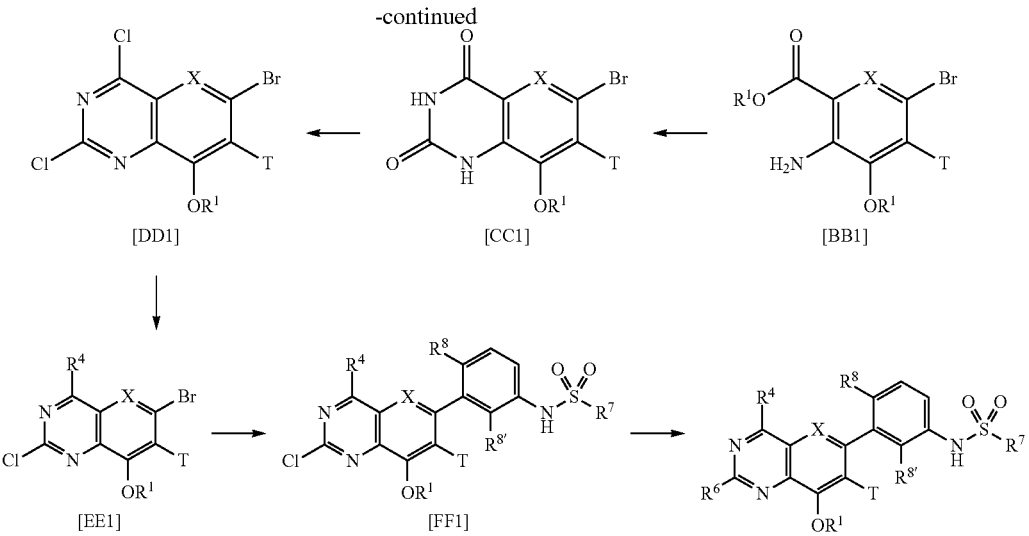

Scheme 9 provides the synthesis of compounds which are encompassed by formula (I). Specifically, compound [X1] was converted to compound [Y1] using a strong base. In one embodiment, the strong base is potassium hydroxide. Compound [Y1] was then R'-substituted. In one embodiment, the R'-substitution was performed using an alkylating agent. Resultant compound [Z1] was then reduced to the corresponding aniline [AA1]. Compound [AA1] was then brominated to form the corresponding bromo compound [BB1]. In one embodiment, the bromination was performed using bromine Bromo compound [BB1] was then converted to the corresponding quinazolinedione [CC1] using urea. The quinazolinedione was then chlorinated at $2^{nd}$ and $4^{th}$ positions to provide compound [DD1]. In one embodiment, the chlorination was performed using a chlorinating agent such as $POCl_3$. The $4^{th}$ position of quinazoline [DD1] was then substituted by reaction with morpholine. The $6^{th}$ position of quinazoline compound [EE1] was then coupled with intermediate [1A]. Finally, the title compound was $R^6$-substituted. In one embodiment, the reaction was performed using any one of intermediates [3], [4A], [5A], [5B] or [6A].

Scheme 9A

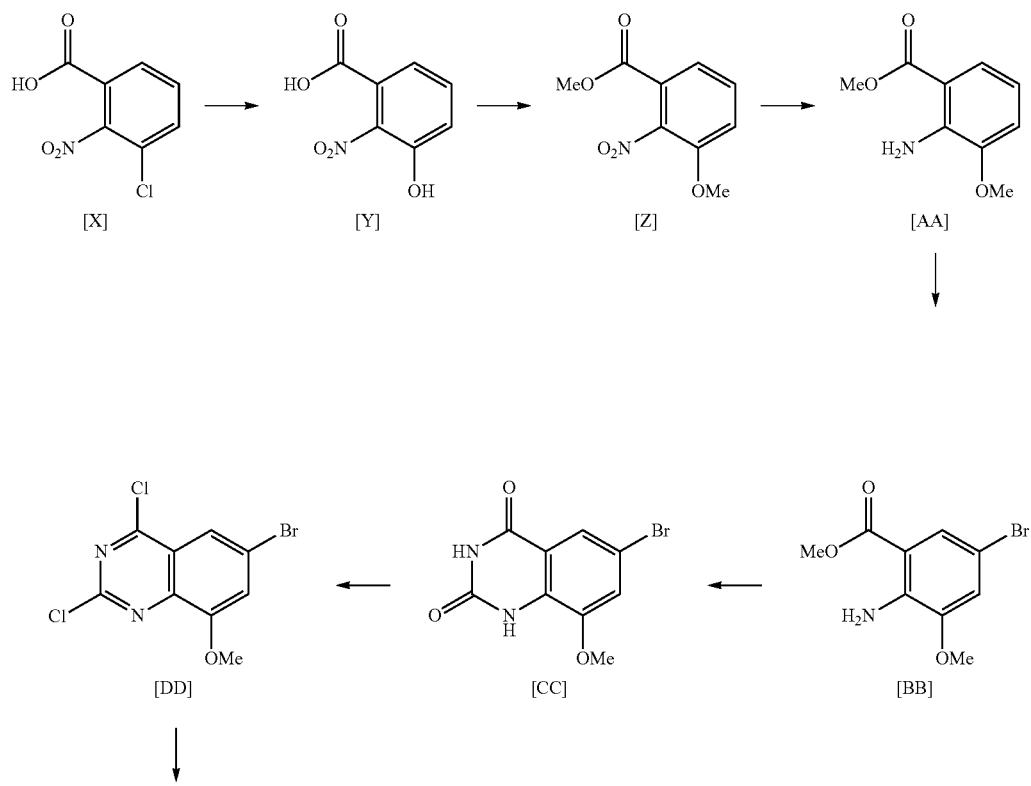

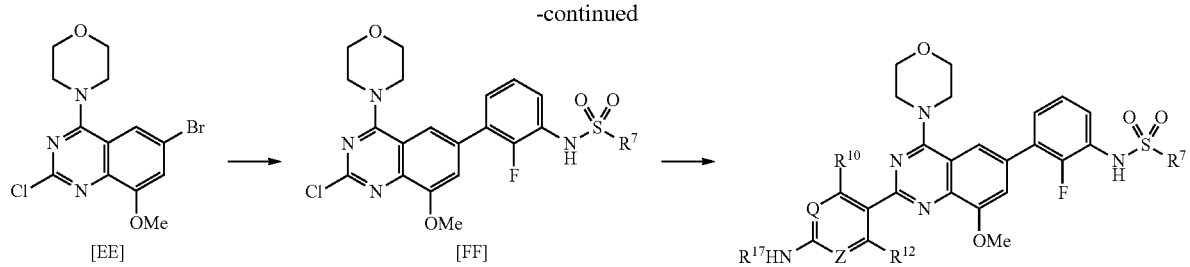

Scheme 9A provides the synthesis of compounds which are encompassed by the structural formula (I). Specifically, 3-chloro-2-nitrobenzoic acid [X] was converted to the corresponding 3-hydroxy-2-nitrobenzoic acid [Y] using a strong base such potassium hydroxide. The resultant acid was then alkylated with an alkylating agent such as methyl iodide. The resulting dimethyl compound [Z] was then reduced to the corresponding aniline [AA]. In one embodiment, the reduction was performed using Pd/C and hydrogen gas. The aniline was then brominated to form the corresponding bromo compound [BB]. In one embodiment, the bromination was performed using bromine. The bromo compound [BB] was then converted to the corresponding quinazolinedione [CC] using urea. The quinazolinedione was then chlorinated at $2^{nd}$ and $4^{th}$ positions. In one embodiment, the chlorination was performed using a chlorinating agent such as POCl$_3$. The $4^{th}$ position of quinazoline [DD] was then substituted by reaction with morpholine. The $6^{th}$ position of quinazoline [EE] was then coupled with intermediate [1]. Finally, the title compound was formed by reacting the compound [FF] with intermediate [3], [4], [5], or [6].

Scheme 10

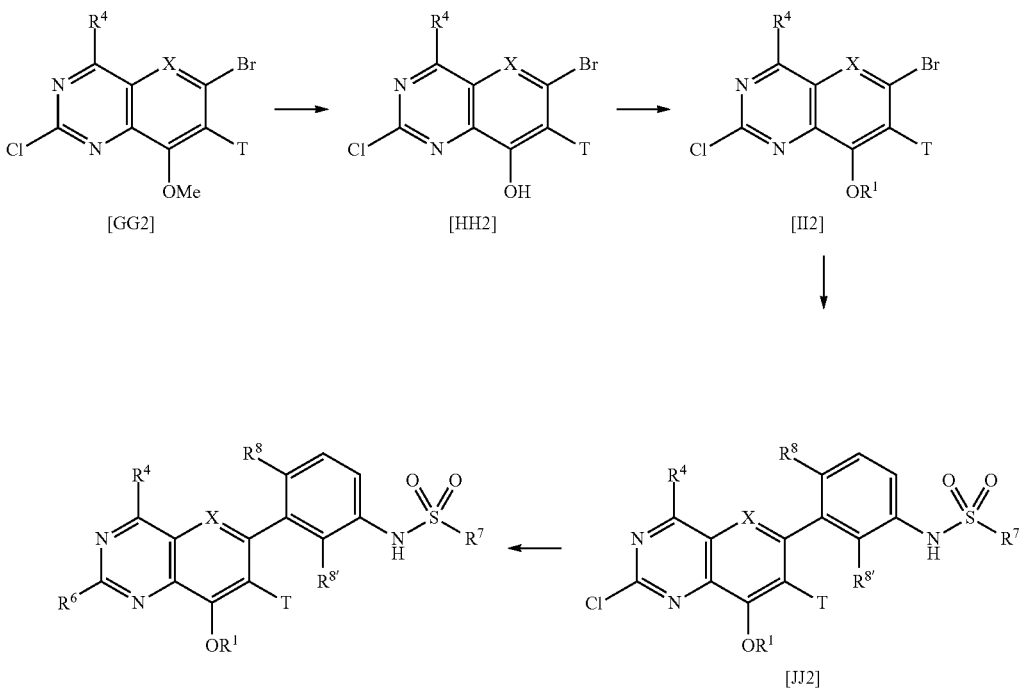

Scheme 10 provides the synthesis of compounds which are encompassed by formula (I). In this scheme, compound [GG2] was converted to phenol compound [HH2]. In one embodiment, the reaction was performed using boron tribromide. Phenol compound [HH2] was then R$^1$-substituted at the OH group. In one embodiment, the substitution was performed using an R$^1$-alkyl halide. The $6^{th}$ position of compound [II2] was then substituted to form compound [JJ2]. Finally, the title compound was formed by R$^6$-substituting compound [JJ2].

Scheme 10A

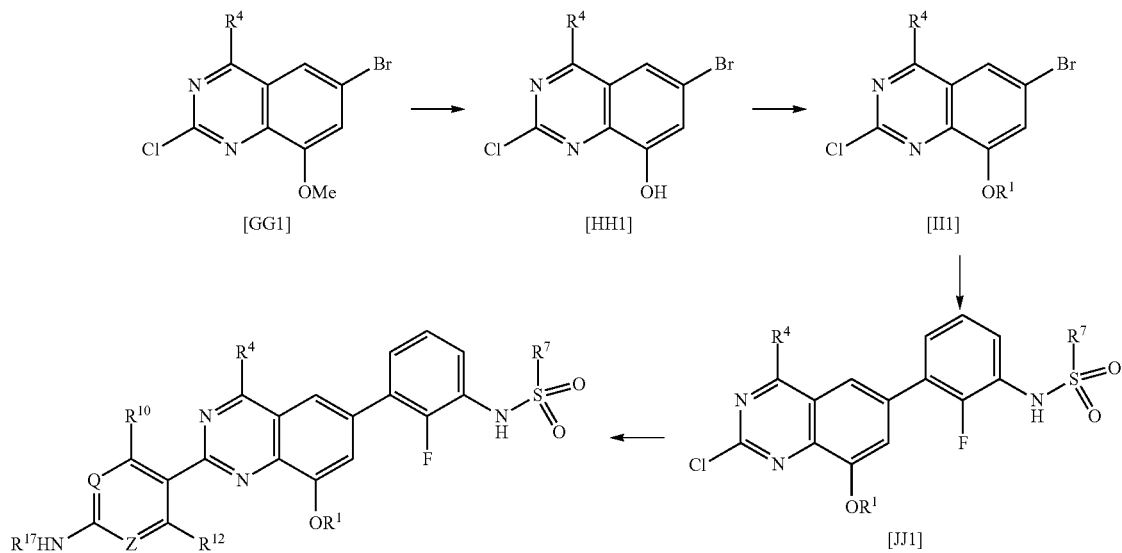

Scheme 10A provides the synthesis of compounds which are encompassed by formula (I). In this scheme, compound [GG1] was converted to phenol compound [HH1]. In one embodiment, the reaction is performed using boron tribromide. Phenol compound [HH1] was then $R^1$-substituted at the OH group. In one embodiment, the alkylation was performed using an $R^1$-alkyl halide. The $6^{th}$ position of compound [II1] was then coupled with intermediate [1] (described in Scheme 1A) to form compound [JJ1]. Finally, the title compound was formed by reacting compound [JJ1] with intermediate [5A].

Scheme 10B

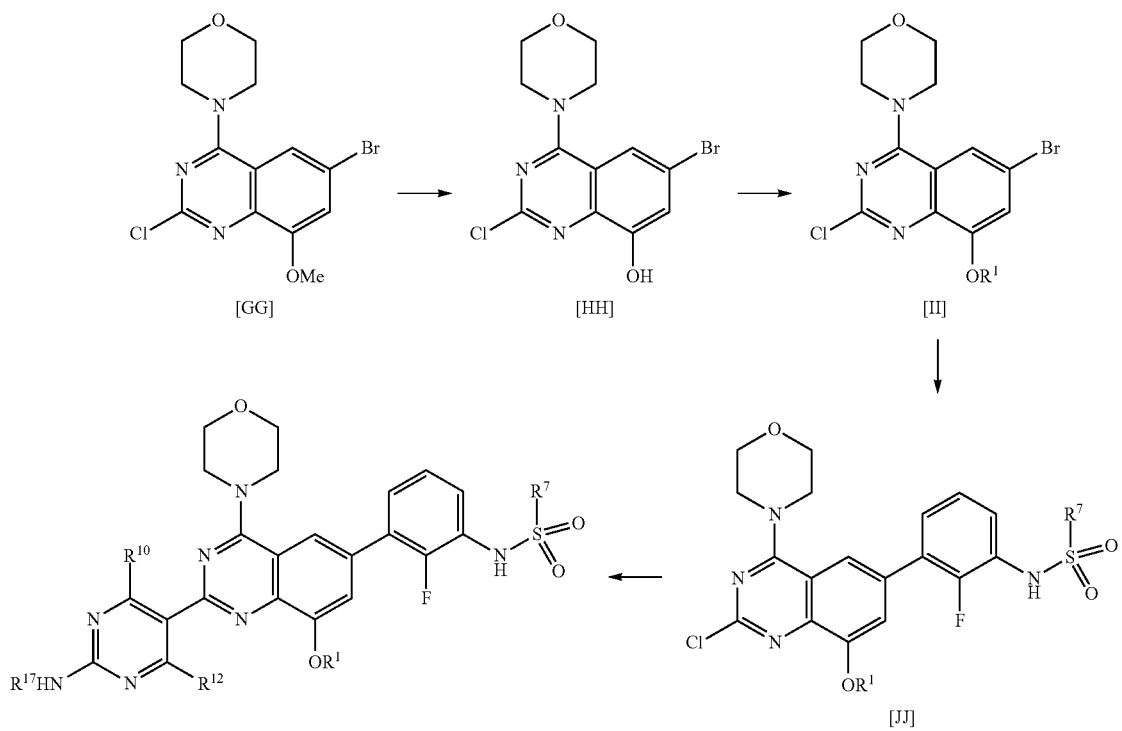

$R^1$ = Alkyl or substituted alkyl

Scheme 10B provides the synthesis of compounds which are encompassed by formula (I). In this scheme, compound

[GG] was converted to phenol compound [HH]. In one embodiment, the reaction is performed using boron tribromide. Phenol compound [HH] was then converted to compound [II] using an $R^1$-alkyl halide. The $6^{th}$ position of compound [II] was then coupled with intermediate [1] to form compound [JJ]. Finally, the title compound was formed by reacting compound [JJ] with intermediate [5B].

iodide. Methyl ester [LL2] was then reduced to aniline [MM2]. In one embodiment, the reduction was performed using Pd/C and hydrogen gas. The aniline compound [MM2] was then brominated to form bromo compound [NN2]. In one embodiment, the bromination was performed using bromine. Bromo compound [NN2] was then converted to quinazolinedione [OO2] using urea. Quinazolinedione [OO2]

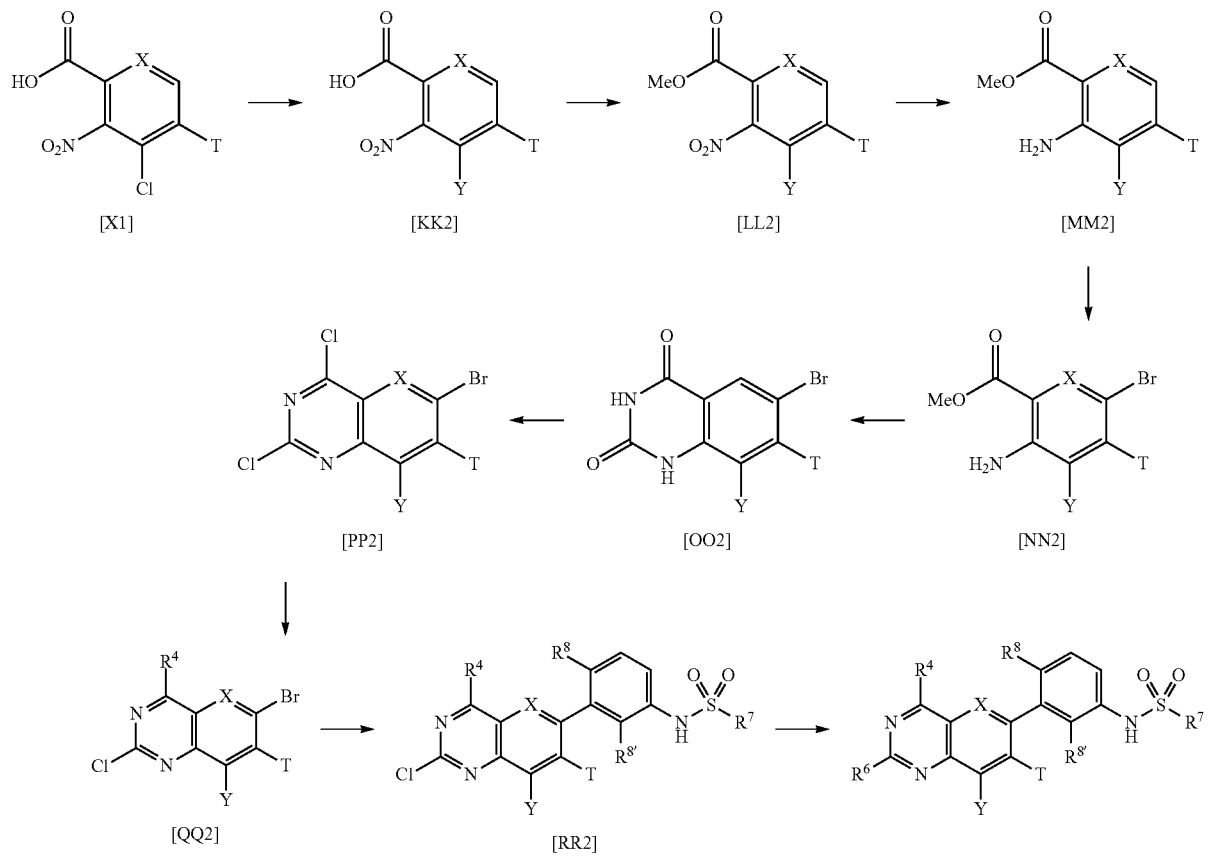

Scheme 11

Scheme 11 provides the synthesis of compounds which are encompassed by formula (I). Specifically, the chloro group in compound [X1] was replaced with a $NR^2R^3$ group. In one embodiment, the reaction was performed using $NHR^2R^3$. In another embodiment, the reaction was performed using morpholine. The acid group of compound [KK2] was then alkylated to form the alkyl ester. In one embodiment, the alkylation was performed using methyl was then chlorinated at the $2^{nd}$ and $4^{th}$ positions to form compound [PP2]. In one embodiment, the chlorination was performed using $POCl_3$. The $4^{th}$ position of quinazoline [PP2] was then substituted by reaction with an optionally substituted morpholine ($R^4$) to afford compound [QQ2]. The $6^{th}$ position of compound [QQ2] was then substituted to form compound [RR2]. Finally, the title compound was formed by $R^6$-substituting compound [RR2].

Scheme 11A

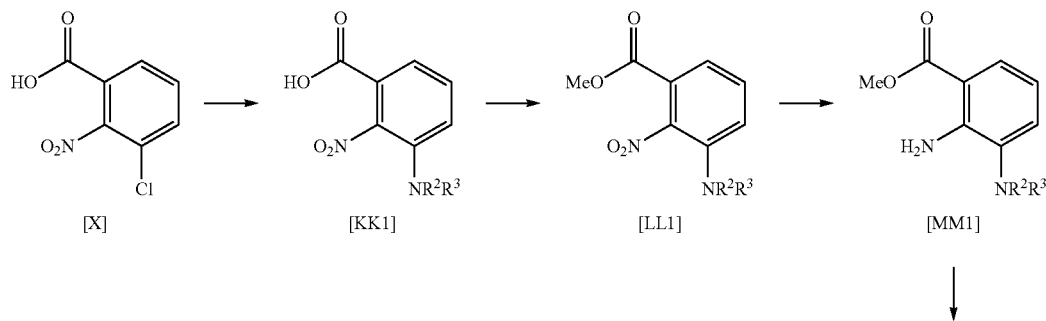

-continued

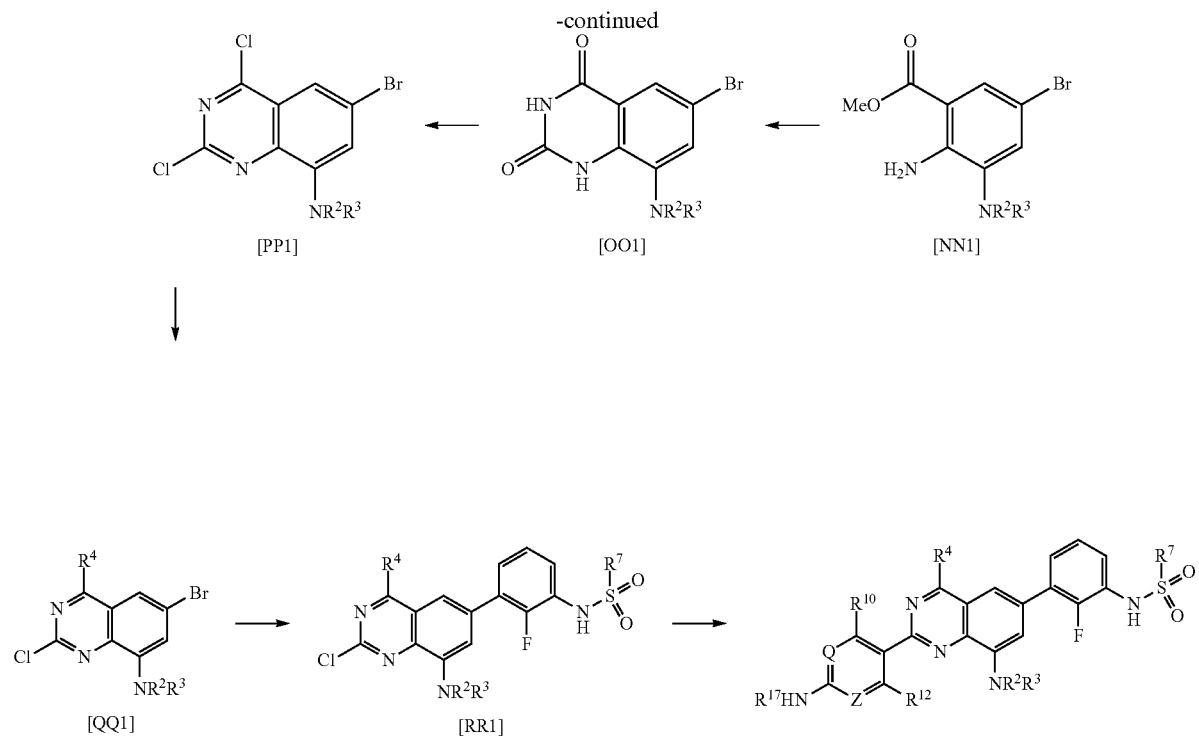

Scheme 11A provides the synthesis of compounds which are encompassed by formula (I). Specifically, the chloro group in compound [X] was replaced with a NR²R³ group. In one embodiment, the reaction was performed using NHR²R³. In another embodiment, the reaction was performed using morpholine. The acid group of compound [KK1] was then alkylated to form alkyl ester [LL1]. In one embodiment, the alkylation was performed using methyl iodide. The methyl ester was then reduced to aniline [MM1]. In one embodiment, the reduction was performed using Pd/C and hydrogen gas. The aniline compound [MM1] was then brominated to form bromo compound [NN1]. In one embodiment, the bromination was performed using bromine. Bromo compound [NN1] was then converted to quinazolinedione [OO1] using urea. Quinazolinedione [OO1] was then chlorinated at the $2^{nd}$ and $4^{th}$ positions to form compound [PP1]. In one embodiment, the chlorination was performed using $POCl_3$. The $4^{th}$ position of quinazoline [PP]] was then substituted by reaction with an optionally substituted morpholine ($R^4$) to afford compound [QQ1]. The $6^{th}$ position of compound [QQ1] was then coupled with intermediate [1] to form compound [RR1]. Finally, the title compound was formed by reacting compound [RR1] with intermediate [5A].

Scheme 11B

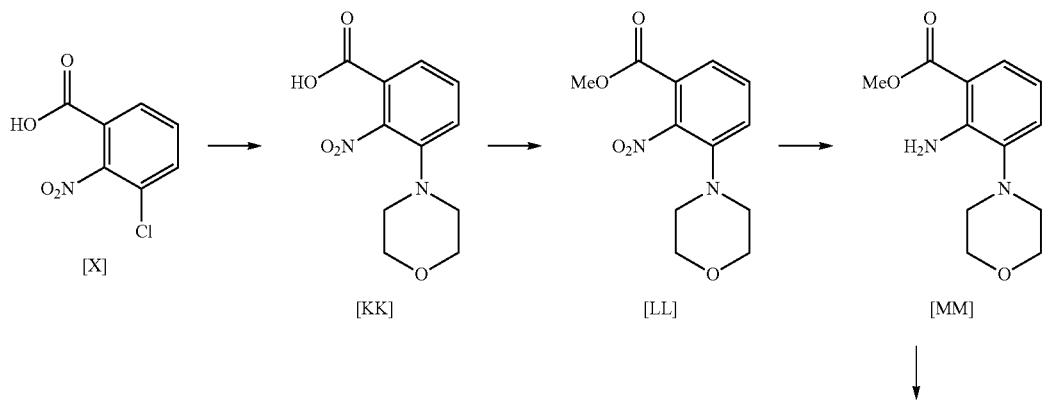

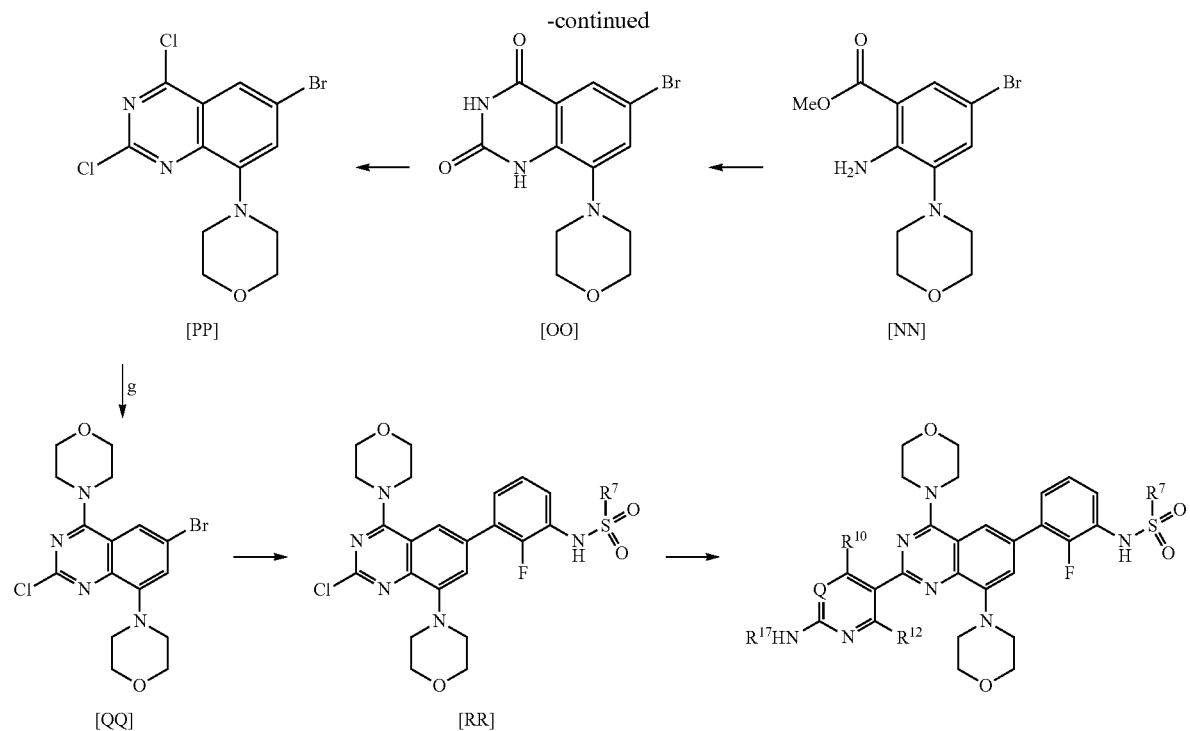

Scheme 11B provides the synthesis of compounds which are encompassed by formula (I). Specifically, 3-chloro-2-nitrobenzoic acid [X] was converted to the corresponding 3-morpholino compound [KK] using morpholine. The morpholine compound [KK] was then alkylated with methyl iodide to form methyl ester [LL]. The methyl ester was then reduced to aniline [MM]. In one embodiment, the reduction was performed using Pd/C and hydrogen gas. The aniline compound [MM] was then brominated to form bromo compound [NN]. In one embodiment, the bromination was performed using bromine Bromo compound [NN] was then converted to quinazolinedione [OO] using urea. Quinazolinedione [OO] was then chlorinated at the $2^{nd}$ and $4^{th}$ positions to form compound [PP]. In one embodiment, the chlorination was performed using $POCl_3$. The $4^{th}$ position of quinazoline [PP] was then substituted by reaction with morpholine to afford compound [QQ]. The 6th position of compound [QQ] was then coupled with intermediate [1] to form compound [RR]. Finally, the title compound was formed by reacting compound [RR] with intermediate [5A].

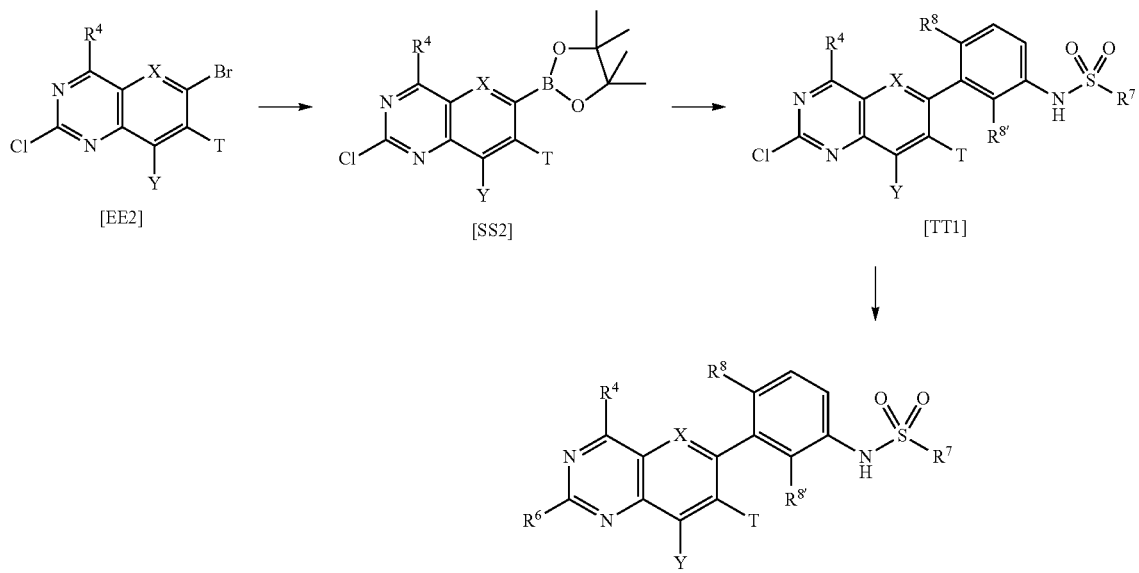

Scheme 12 provides the synthesis of compounds which encompassed by formula (I). Specifically, compound [EE2] was converted to the corresponding boronic acid pinacol ester [SS2] using bis(pinacolato)diboron. Boronic acid pinacol ester [SS2] was then substituted to afford compound [TT1]. Finally, $R^6$-substituttion of compound [TT1] provided the title product.

Scheme 12A

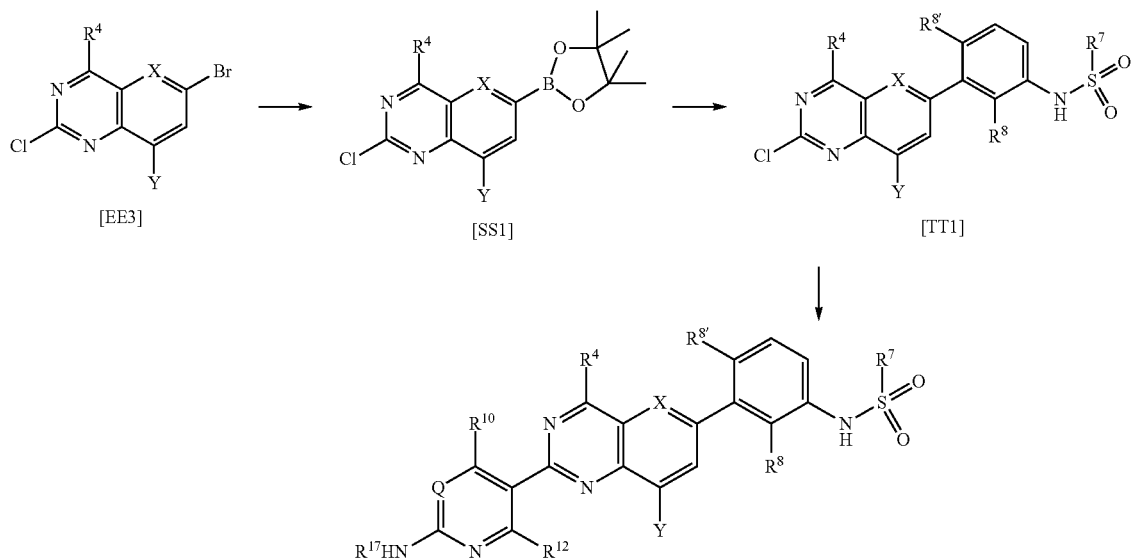

Scheme 12A provides the synthesis of compounds which encompassed by formula (I). Specifically, compound [EE3] was converted to the corresponding boronic acid pinacol ester [SS1] using bis(pinacolato)diboron. Boronic acid pinacol ester [SS1] was then coupled with intermediate [2] to afford compound [TT1]. Finally, reaction of compound [TT1] with intermediate [5A] provided the title product.

Scheme 12B

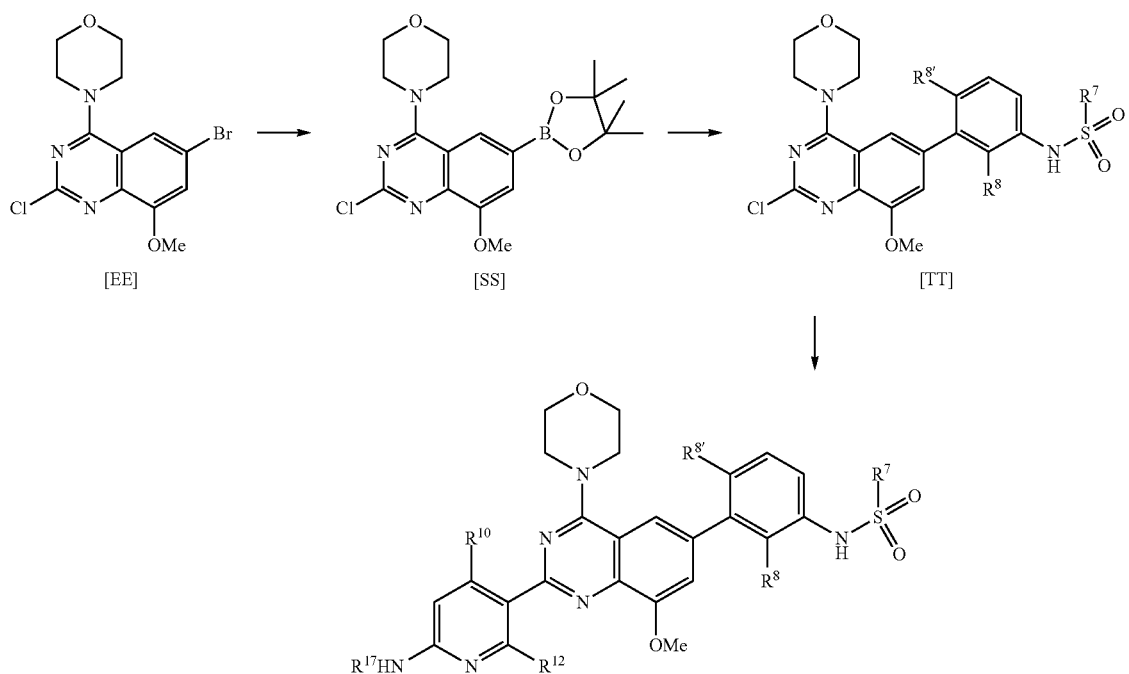

Scheme 12B provides the synthesis of compounds which encompassed by formula (I). In this scheme, morpholine compound [EE] was converted to the corresponding boronic acid pinacol ester [SS] using bis(pinacolato)diboron. Boronic acid pinacol ester [SS] was then coupled with intermediate [2] to afford compound [TT]. Finally, reaction of compound [TT] with intermediate [5] provided the title product.

nous chloride dehydrate. Compound [WW2] was cyclized to compound [XX2]. In one embodiment, the cyclization was performed using triphosgene. Compound [XX2] was then chlorinated at $2^{nd}$ and $4^{th}$ positions to form the corresponding trichloro compound [YY2]. In one embodiment, the chlorination was performed using a chlorinating agent such as $POCl_3$. The 4th position of compound [YY2] was then

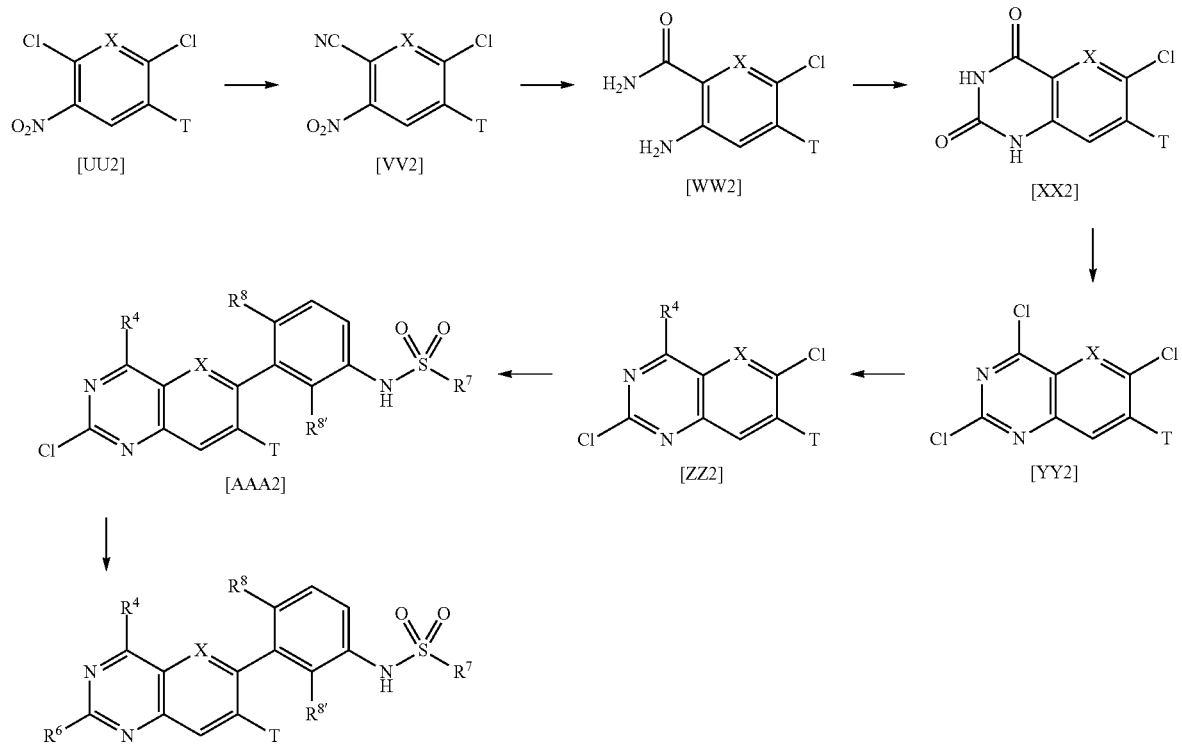

Scheme 13

Scheme 13 provides the synthesis of compounds encompassed by formula (I). Specifically, compound [UU2] was converted to compound [VV2] using CuCN. The cyano compound was then reduced to afford compound [WW2]. In one embodiment, the reduction was performed using stan- $R^4$-substituted. In one embodiment, the $R^4$-substitution was performed using morpholine. The $6^{th}$ position of compound [ZZ2] was then substituted to form compound [AAA2]. Finally, the title compound was formed by $R^6$-substituting compound [AAA2].

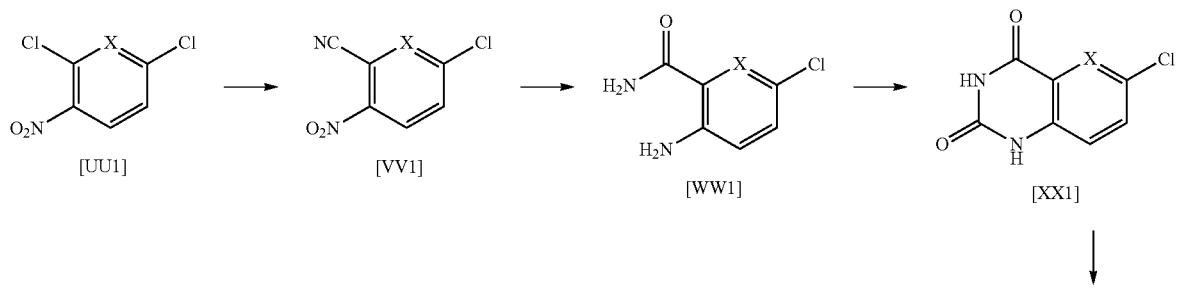

Scheme 13A

-continued

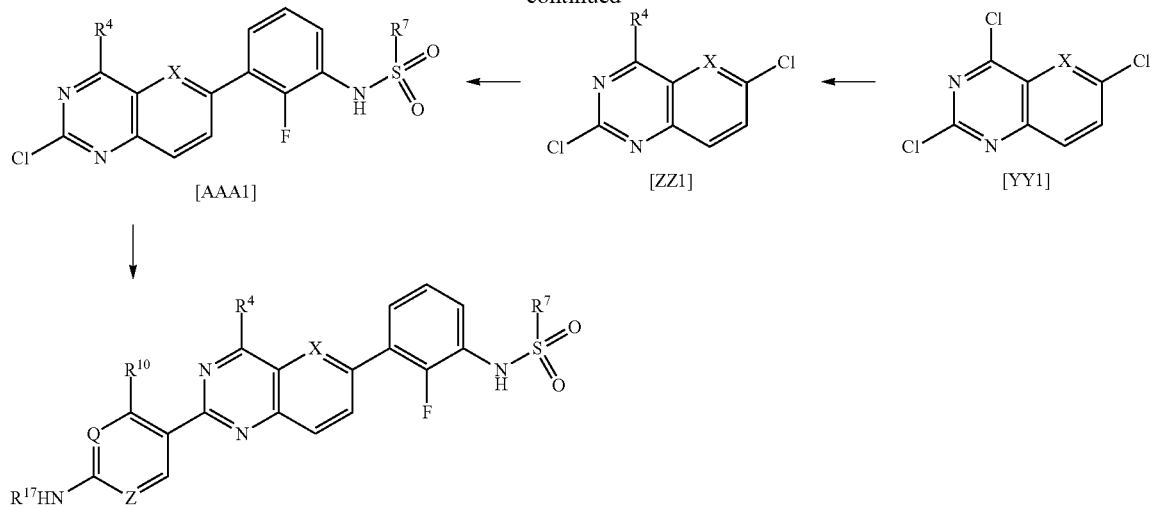

Scheme 13A provides the synthesis of compounds encompassed by formula (I). Specifically, compound [UU1] was converted to compound [VV1] using CuCN. Cyano compound [VV1] was then reduced to afford compound [WW1]. In one embodiment, the reduction was performed using stannous chloride dehydrate. The picolinamide compound [WW1] was cyclized to 5-azaquinazolinedione [XX1]. In one embodiment, the cyclization was performed using triphosgene. Compound [XX1] was then chlorinated at $2^{nd}$ and $4^{th}$ positions to form the corresponding trichloro compound [YY1] using a chlorinating agent such as $POCl_3$. The $4^{th}$ position of the azaquinazoline [YY1] was then $R^4$-substituted. The $6^{th}$ position of the resultant compound [ZZ1] was then coupled with intermediate [1] to form compound [AAA1]. Finally, the title compound was formed by reacting compound [AAA1] with intermediate [5A] or [6].

Scheme 13B

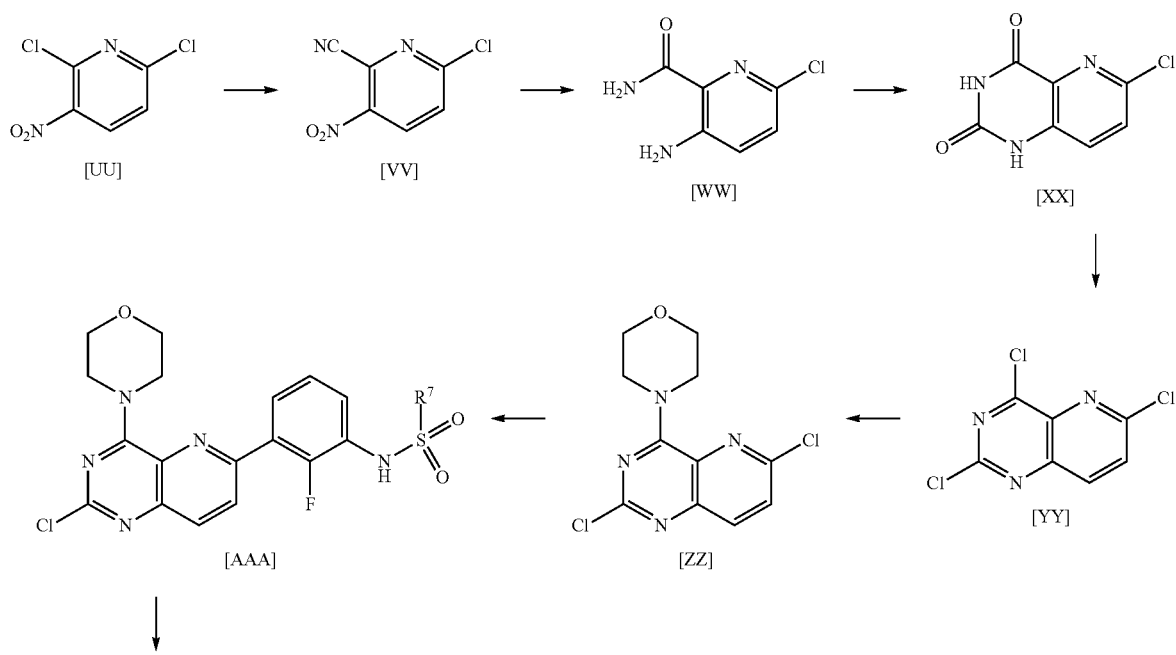

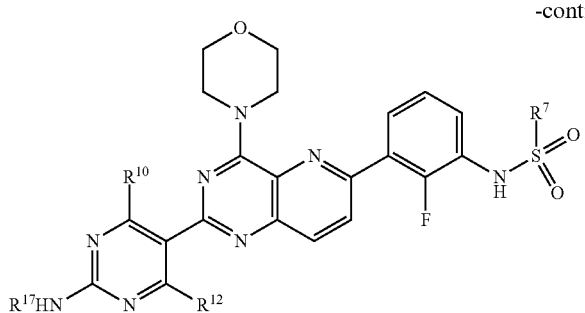

Scheme 13B provides the synthesis of compounds encompassed by formula (I). Specifically, 2,6-dichloro 3-nitropyridine [UU] was converted into 6-chloro-3-nitropicolinonitrile [VV] using CuCN. Cyano compound [VV] was then reduced to afford 3-amino-6-chloropicolinamide [WW]. In one embodiment, the reduction was performed using stannous chloride dehydrate. The picolinamide compound [WW] was cyclized to 5-azaquinazolinedione [XX]. In one embodiment, the cyclization was performed using triphosgene. 5-Azaquinazolinedione [XX] was then chlorinated at $2^{nd}$ and $4^{th}$ positions to form the corresponding trichloro compound [YY] using a chlorinating agent such as POCl$_3$. The $4^{th}$ position of the azaquinazoline [YY] was then substituted with morpholine using morpholine. The $6^{th}$ position of the resultant compound [ZZ] was then coupled with intermediate [1] to form compound [AAA]. Finally, the title compound was formed by reacting compound [AAA] with intermediate [5B] or [6].

Scheme 14

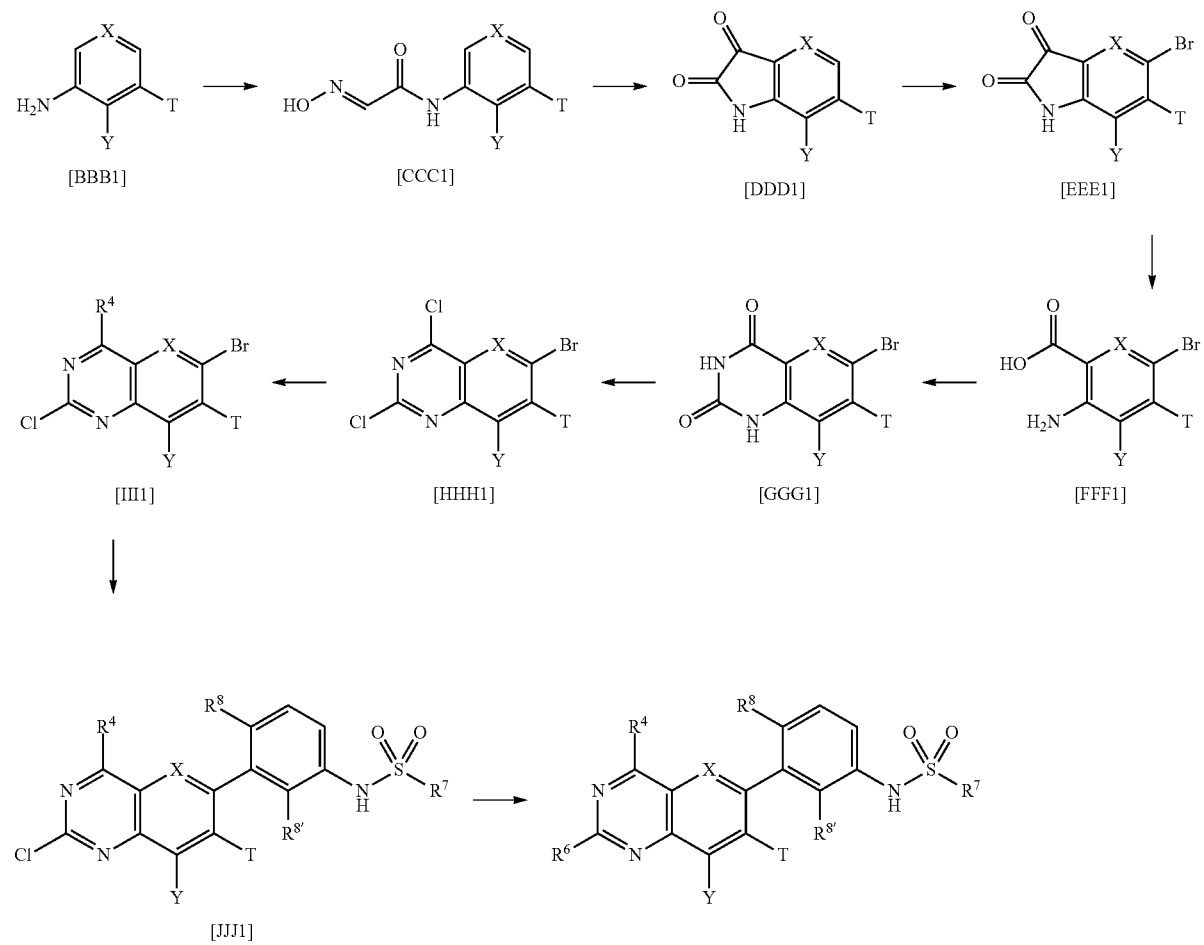

Scheme 14 provides the synthesis of compounds encompassed by formula (I). Specifically, compound [BBB1] was converted into the corresponding hydroxyimino [CCC1]. In one embodiment, this reaction was performed using chloral hydrate and NH₂OH.HCl. Reaction of hydroxyimino compound [CCC1] with a strong acid resulted in the preparation of cyclic isatin [DDD1]. In one embodiment, the strong acid was H₂SO₄. Isatin compound [DDD1] was brominated to afford compound [EEE1]. In one embodiment, the bromination was performed using bromine. The isatin ring of bromo compound [EEE1] was then cleaved. In one embodiment, this reaction was performed using aqueous H₂O₂ and NaOH. The resultant amino benzoic acid [FFF1] was converted to quinazoline dione [GGG1] using urea. Quinazolinedione [GGG1] was then chlorinated at $2^{nd}$ and $4^{th}$ positions to form compound [HHH1]. In one embodiment, the chlorination was performed using POCl₃. The $4^{th}$ position of quinazoline [HHH1] was then R⁴-substituted to afford compound [III1]. The $6^{th}$ position of compound [III1] was substituted to form compound [JJJ1]. Finally, the title compound was formed by R⁶-substituting compound [JJJ1].

Scheme 14A provides the synthesis of compounds encompassed by formula (I). Specifically, compound [BBB] was converted into the corresponding hydroxyimino [CCC] using chloral hydrate and NH₂OH.HCl. Reaction of hydroxyimino compound [CCC] with a strong acid resulted in the preparation of cyclic isatin [DDD]. In one embodiment, the strong acid was H₂SO₄. Isatin compound [DDD] was brominated to afford compound [EEE]. In one embodiment, the bromination was performed using bromine. The isatin ring of bromo compound [EEE] was then cleaved using aqueous H₂O₂ and NaOH. The resultant amino benzoic acid [FFF] was converted into quinazoline dione [GGG] using urea. Quinazolinedione [GGG] was then chlorinated at $2^{nd}$ and $4^{th}$ positions to form compound [HHH] using a chlorinating agent such as POCl₃. The $4^{th}$ position of quinazoline [III] was then R⁴-substituted to afford compound [III]. The $6^{th}$ position of [III] was then

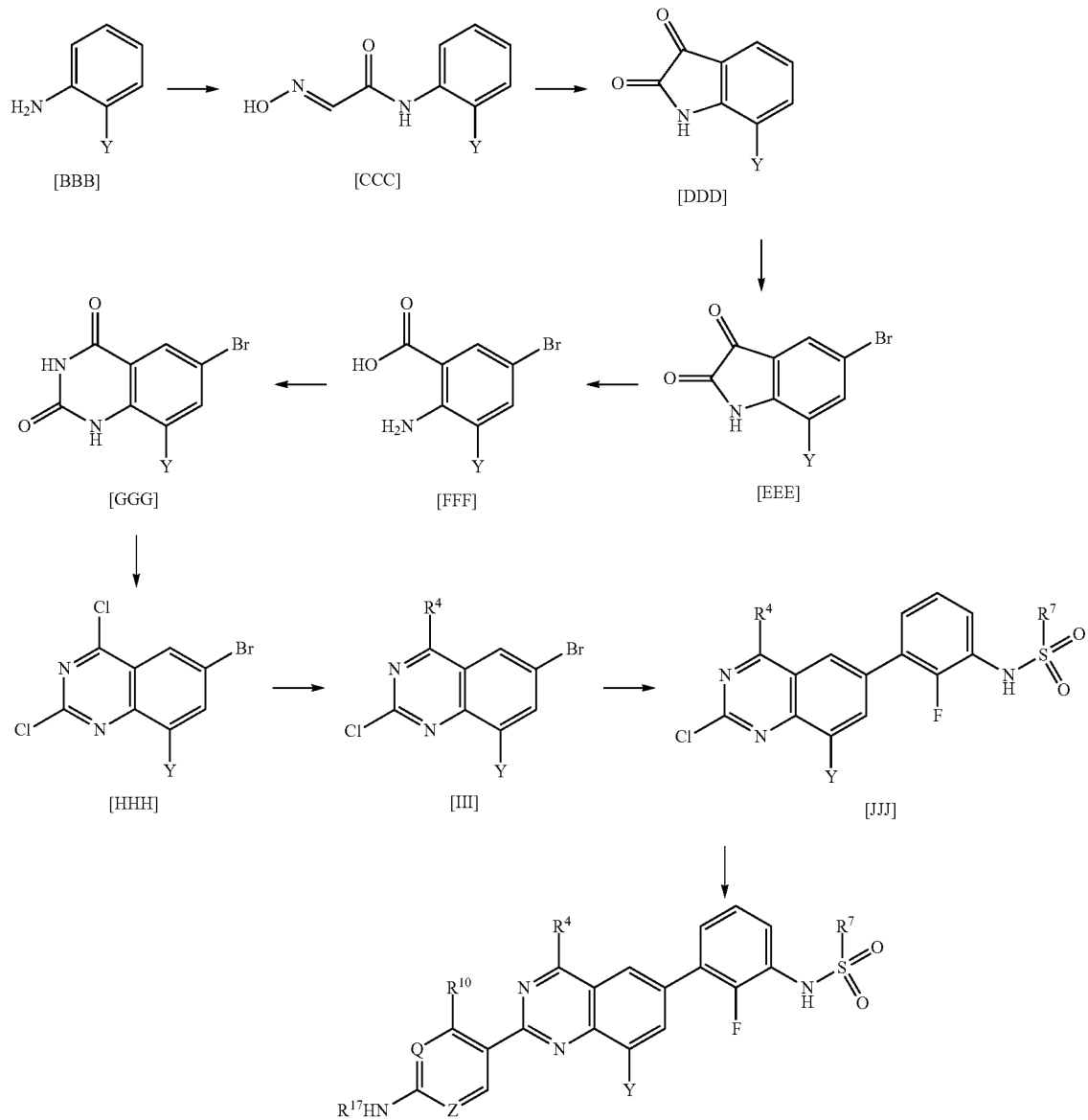

coupled with intermediate [1] to form compound [JJJ] using. Finally, the title compound was formed by reacting compound [JJJ] with intermediate [5A] or [6].

Scheme 15

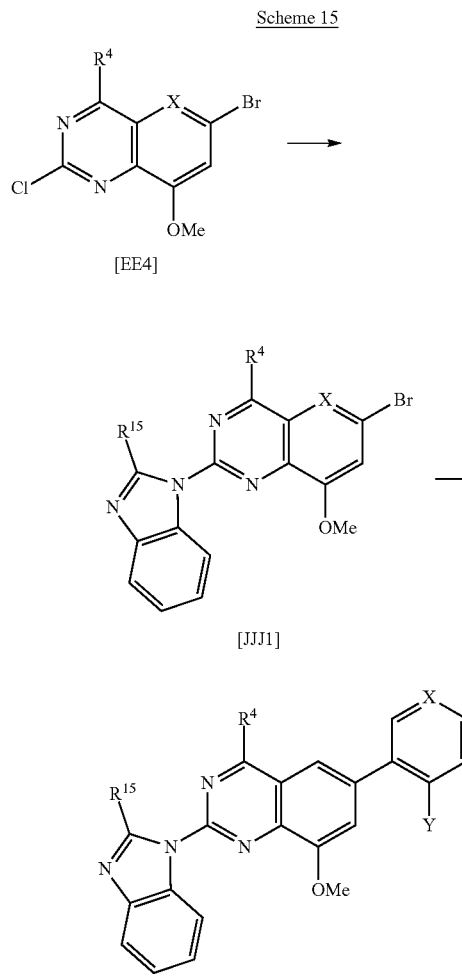

[EE4]

[JJJ1]

Scheme 15A

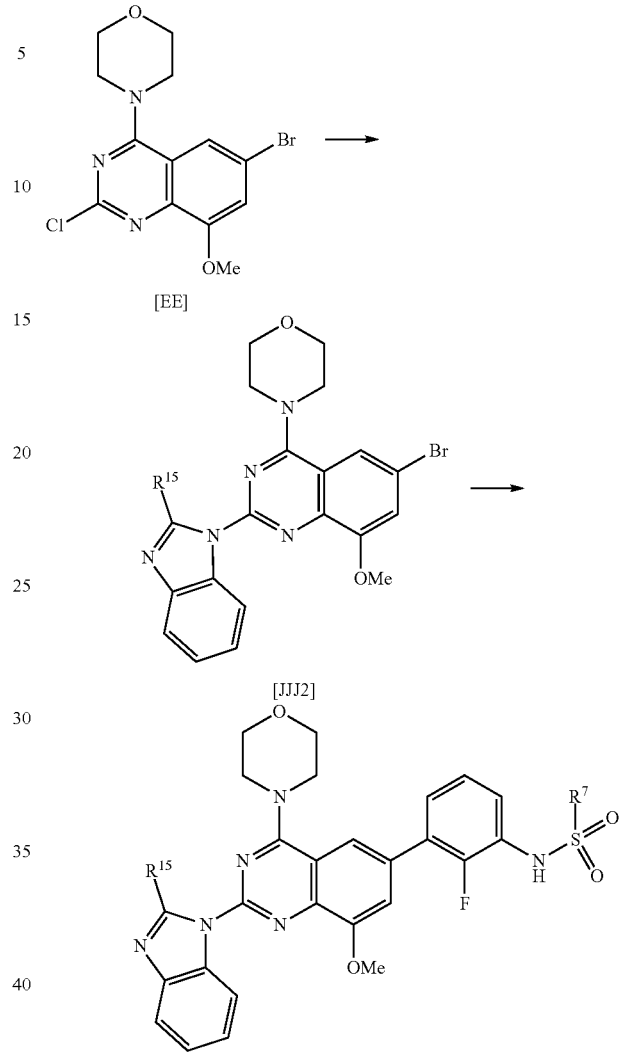

[EE]

[JJJ2]

Scheme 15 provides the synthesis of compounds encompassed by formula (I). Specifically, compound [EE4] was coupled with intermediate [7] or [8] to form compound [JJJ1]. Finally, the title compound was formed by reacting compound [JJJ1] with intermediate [1].

Scheme 15A provides the synthesis of compounds encompassed by formula (I). Specifically, compound [EE] was coupled with intermediate [7] or [8] to form compound [JJJ2]. Finally, the title compound was formed by reacting compound [JJJ2] with intermediate [1].

Scheme 16

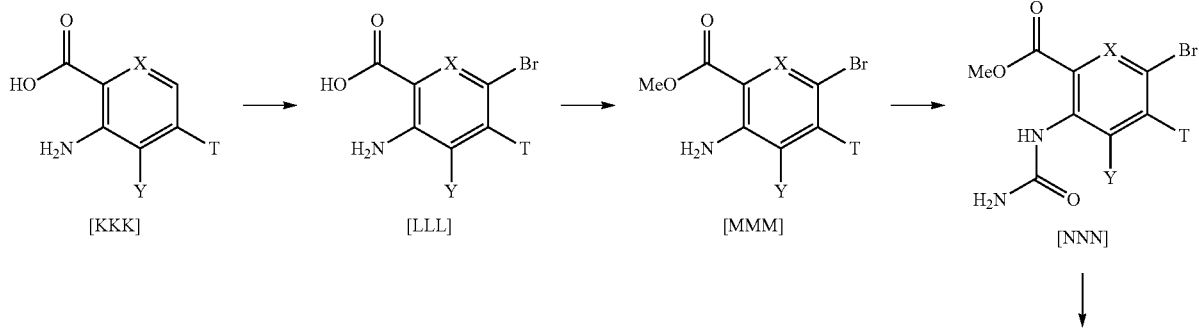

[KKK]  [LLL]  [MMM]  [NNN]

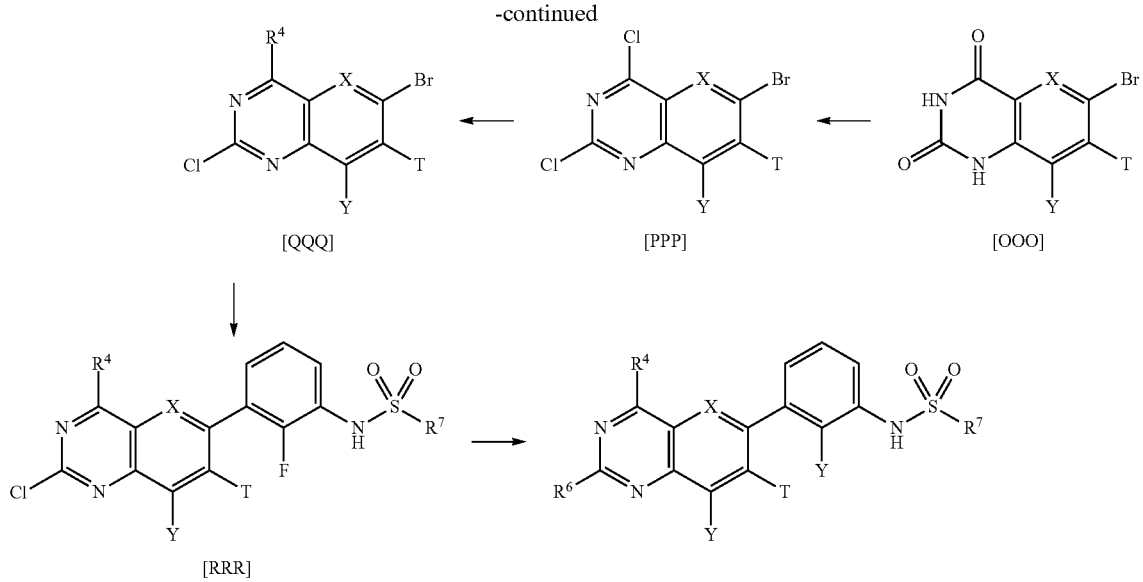

Scheme 16 provides the synthesis of compounds which are encompassed by formula (I). Specifically, compound [KKK] was brominated to form bromo compound [LLL]. In one embodiment, the bromination was performed using bromine. Bromo compound [LLL] was then methylated to form methyl ester [MMM]. In one embodiment, the methylation was performed using methyl iodide. Methyl ester [MMM] was then converted to urea compound [NNN] by reaction with potassium cyanate. Urea compound [NNN] was then converted to quinazolinedione [OOO] by treatment with a strong base. In one embodiment, the strong base is sodium hydroxide. Quinazolinedione [OOO] was then chlorinated at the $2^{nd}$ and $4^{th}$ positions to form compound [PPP]. In one embodiment, the chlorination was performed using $POCl_3$. The $4^{th}$ position of quinazoline [PPP] was then substituted by reaction with an optionally substituted morpholine ($R^4$) to afford compound [QQQ]. The $6^{th}$ position of compound [QQQ] was then substituted to form compound [RRR]. Finally, the title compounds were formed by $R^6$-substituting compound [RRR].

Pharmaceutical compositions useful herein contain a compound of formula (I) in a pharmaceutically acceptable carrier optionally with other pharmaceutically inert or inactive ingredients. In another embodiment, a compound of formula (I) is present in a single composition. In a further embodiment, a compound of formula (I) is combined with one or more excipients and/or other therapeutic agents as described below.

The pharmaceutical compositions of the invention comprise an amount of a compound of formula (I) or a pharmaceutically acceptable salt thereof that is effective for regulating one or both of the RAS/RAF/MEK/ERK and PI3K/AKT/PTEN/mTOR pathways in a subject. Specifically, the dosage of the compound of formula (I) to achieve a therapeutic effect will depend on the formulation, age, weight and sex of the patient and route of delivery. It is also contemplated that the treatment and dosage of the compound of formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the therapeutically effective amount of the compound of formula (I) can be determined by the attending physician and depends on the condition treated, the compound administered, the route of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The therapeutically effective amounts described herein refer to total amounts administered for a given time period; that is, if more than one compound of formula (I) or a pharmaceutically acceptable salt thereof is administered, the therapeutically effective amounts correspond to the total amount administered.

The pharmaceutical compositions containing a compound of formula (I) may be formulated neat or with one or more pharmaceutical carriers for administration. The amount of the pharmaceutical carrier(s) is determined by the solubility and chemical nature of the compound of formula (I), chosen route of administration and standard pharmacological practice. The pharmaceutical carrier(s) may be solid or liquid and may incorporate both solid and liquid carriers. A variety of suitable liquid carriers is known and may be readily selected by one of skill in the art. Such carriers may include, e.g., DMSO, saline, buffered saline, hydroxypropylcyclodextrin, and mixtures thereof. Similarly, a variety of solid carriers and excipients are known to those of skill in the art. The compounds of formula (I) may be administered by any route, taking into consideration the specific condition for which it has been selected. The compounds of formula (I) may, be delivered orally, by injection, inhalation (including orally, intranasally and intratracheally), ocularly, transdermally, intravascularly, subcutaneously, intramuscularly, sublingually, intracranially, epidurally, rectally, and vaginally, among others.

Although the compound of formula (I) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formula (I). For example, the unit dosage can be packaged compositions, e.g., packeted powders, vials, ampoules, prefilled syringes or sachets containing liquids.

Examples of excipients which may be combined with one or more compound of formula (I) include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formula (I) which is delayed or otherwise controlled. Those of skill in the art know suitable sustained delivery devices. For use in such sustained delivery devices, the compound of formula (I) is formulated as described herein.

In addition to the components described above for use in the composition and the compound of formula (I), the compositions and kits described herein may contain one or more medications or therapeutic agents which are used to treat cancers, including, e.g., cancers characterized by tumors, including solid tumors, and "liquid" or non-solid tumor cancers (e.g., lymphoma). In one embodiment, the medication is a chemotherapeutic. Examples of chemotherapeutics include those recited in the "Physician's Desk Reference", 64$^{th}$ Edition, Thomson Reuters, 2010, which is hereby incorporated by reference. Therapeutically effective amounts of the additional medication(s) or therapeutic agents are well known to those skilled in the art. However, it is well within the attending physician to determine the amount of other medication to be delivered.

The compounds of formula (I) and/or other medication(s) or therapeutic agent(s) may be administered in a single composition. However, the present invention is not so limited. In other embodiments, the compounds of formula (I) may be administered in one or more separate formulations from other compounds of formula (I), chemotherapeutic agents, or other agents as is desired.

Also provided herein are kits or packages of pharmaceutical formulations containing the compounds of formula (I) or compositions described herein. The kits may be organized to indicate a single formulation or combination of formulations to be taken at each desired time.

Suitably, the kit contains packaging or a container with the compound of formula (I) formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formula (I) or compositions described herein can be a single dose or for continuous or periodic discontinuous administration. For continuous administration, a package or kit can include the compound of formula (I) in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forceps, measuring spoon, eye dropper or any such medically approved delivery means.

In one embodiment, a kit is provided and contains a compound of formula (I). The compound of formula (I) may be in the presence or absence of one or more of the carriers or excipients described above. The kit may optionally contain instructions for administering the medication and the compound of formula (I) to a subject having a disease characterized by the dysregulation of one of both of the RAS/RAF/MEK/ERK and PI3K/AKT/PTEN/mTOR pathways.

In a further embodiment, a kit is provided and contains a compound of formula (I) in a second dosage unit, and one or more of the carriers or excipients described above in a third dosage unit. The kit may optionally contain instructions for administering the medication and the compound of formula (I) to a subject having a disease characterized by the dysregulation of one or both of the RAS/RAF/MEK/ERK and PI3K/AKT/PTEN/mTOR pathway.

The compounds described herein are useful in regulating conditions which are associated with the one or more of the RAS/RAF/MEK/ERK and PI3K/AKT/PTEN/mTOR pathways. In one embodiment, such a disease is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, including, without limitation, cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma. In one embodiment, the disease characterized by abnormal cellular proliferation is cancer of the prostate. In another embodiment, the abnormal cellular proliferation is associated with at least one solid tumor.

In a further embodiment, the compounds of formula (I) regulate PI3K activity. Compounds of formula (I) have the ability to inhibit at least one of the four isoforms of PI3K ($\alpha$, $\beta$, $\delta$, $\gamma$) or combinations thereof.

As used herein, the term "selectivity" as used in reference to activity to one or more isoform of PI3K refers to compounds which exhibit different activity to the isoforms of PI3K. A compound which shows PI3K isoform selectivity exhibits higher inhibition of one, two, or three of the $\alpha$, $\beta$, $\delta$, $\gamma$ isoforms. In one embodiment, a compound which selectively regulates one, two or three of these isoforms exhibits no or substantially no activity against the other isoforms. For example, certain compounds may show selectivity for the $\alpha$ and $\delta$ PI3K isoforms. Other compounds described herein may have selectivity for PI3K$\alpha$, PI3K$\beta$, and PI3K $\delta$. Still other compounds described herein may have selectivity for PI3K$\alpha$ and PI3K$\beta$. Yet other compounds may have selectivity for only single isoform, e.g., $\alpha$ or $\delta$.

Compounds associated with activity for the a isoform may be particularly well suited for treatment of conditions associated with this PI3K isoform, including, e.g., breast and gastric cancers, colorectal tumors, glioblastomas, and prostate cancer, and lung cancers.

In another embodiment, some of the compounds of formula (I) regulate the pathway of the PI3K-$\beta$ isoform. In still a further embodiment, the compounds of formula (I) regulate the pathway of the PI3K-$\delta$ isoform. In yet another embodiment, the compounds of formula (I) regulate the pathway of the PI3K-$\gamma$ isoform.

The ability of compounds to inhibit the PI3K-$\delta$ and PI3K-$\gamma$ isoforms has been described with the ability to treat acute and chronic inflammatory disorders. See, e.g., RC Camps et al, Nat Rev Immunol., 2007, Mar. 7(3): 191-201. Other inflammatory disorders have been associated more specifically with the PI3K delta isoform, including neutrophil-associated inflammation. Models for testing the ability of compounds to reduce inflammation in inflammatory arthritis are known, e.g., as described by Camps et al, Nature Med., 2005, 11, 936-943. Camps et al (2005) also describes models useful in assessing the ability of compounds to reduce inflammation in peritonitis. Models for testing the ability of compounds to reduce inflammation and/or improve healing after myocardial infarction are described by Siragusa et al, Circ. Res. (2010), 106, 757-768. A model for testing the ability of compounds to prevent bleomycin-induced pulmonary fibrosis is described by Wei et al, Biochem Biophys Res Comm 2010, 397: 311-317 and Brent et al, Toxicology, 2000, 147: 1-13.

The term "regulation" or variations thereof as used herein refers to the ability of a compound of formula (I) to inhibit one or more components of a biological pathway. In one embodiment, "regulation" refers to inhibition of mTOR activity. In another embodiment, "regulation" refers to inhibition of one or more isoforms of PI3K activity. Regulation may be selective, as defined above. In a further embodiment, "regulation" refers to inhibition of RAS activity. In yet another embodiment, "regulation" refers to inhibition of RAF activity. In still a further embodiment, "regulation" refers to inhibition of MEK activity. In another embodiment, "regulation" refers to inhibition of ERK activity. In a further embodiment, "regulation" refers to inhibition of AKT activity. In a further embodiment, "regulation" refers to inhibition of S6RP or S6K activity. In a further embodiment, regulation refers to inhibition of two or more of the immediately preceding pathways. In yet another embodiment, regulation includes inhibition of the RAS/RAF/MEK/ERK pathway. In a further embodiment, regulation includes inhibition of the PI3K/AKT/PTEN/mTOR pathway. In still another embodiment, regulation includes inhibition of the RAS/RAF/MEK/ERK and PI3K/AKT/PTEN/mTOR pathways.

The utility of the compounds of formula (I) can be illustrated, for example, by their activity in the in vitro tumor cell proliferation assay described below. The compounds of formula (I) exhibit an RAS/RAF/MEK/ERK and/or PI3K/AKT/PTEN/mTOR inhibitory activity, and therefore can be utilized in order to inhibit abnormal cell growth in which any one of these separate pathways plays a role. Thus, the compounds of formula (I) are effective in the treatment of disorders with which abnormal cell growth actions of RAS/RAF/MEK/ERK and/or PI3K/AKT/PTEN/mTOR dysregulation are associated, such as cancer. One of skill in the art would recognize that is an established link between activity in tumor cell proliferation assays in vitro and anti-tumor activity in the clinical setting. For example, the therapeutic utility of a variety of pharmaceutical agents, e.g, taxol (Silvestrini, Stem Cells, 1993, 11(6):528-535), taxotere (Bissery, Anti Cancer Drugs, 1995, 6(3):330) and topoisomerase inhibitors (Edelman, Cancer Chemother. Pharmacol., 1996, 37(5):385-39), have been demonstrated by using in vitro tumor proliferation assays.

In one embodiment, methods for regulating the RAS/RAF/MEK/ERK and/or PI3K/AKT/PTEN/mTOR pathway are provided and include administering a therapeutically effective amount of a compound of formula (I) to a patient in need thereof.

In a further embodiment, methods for co-regulating the RAS/RAF/MEK/ERK and PI3K/AKT/PTEN/mTOR pathways are provided and include administering a therapeutically effective amount of a compound of formula (I) to a patient in need thereof.

In another desirable embodiment, methods for treating a disease characterized by an abnormal cellular growth resulting from a dysregulated RAS/RAF/MEK/ERK and/or PI3K/AKT/PTEN/mTOR pathway are provided and include administering of a therapeutically effective amount of a compound of formula (I) to a patient in need thereof.

In a further desirable embodiment, methods for treating a condition treatable by inhibiting the RAS/RAF/MEK/ERK and/or PI3K/AKT/PTEN/mTOR pathway are provided and include administering a therapeutically effective amount of a compound of formula (I) to a patient in need thereof.

As described herein, a therapeutically effective amount of a compound when used for the treatment of cancer is an amount which may reduce the number of cancer cells in fluids (e.g., blood, peripheral cells or lymphatic fluids), reduce tumor size, inhibit metastasis, inhibit tumor growth and/or ameliorate one or more of the symptoms of the cancer. For cancer therapy, efficacy can be measured for example, by assessing the time to disease progression and/or determining the response rate.

As described herein, a therapeutically effective amount of a compound when used for the treatment of an inflammatory disorder is an amount which may delay the onset of or reduce the severity or duration of an inflammatory response, or which mitigates one or more symptoms of an inflammatory response. For treatment of an inflammatory disorder, efficacy can be measured, for example, by a reduction in physiologic signs of inflammation (e.g., redness, swelling, heat, loss of function) or by measuring changes in the levels of cells (e.g., monocytes, macrophages and other mononuclear cells) or molecules (e.g., pro-inflammatory cytokines) associated with inflammation.

RAS/RAF/MEK/ERK and/or PI3K/AKT/PTEN/mTOR pathways are known to be deregulated in various cancers due to specific mutations in different members of each pathway. For example, in RAS/RAF/MEK/ERK pathway, RAS protein is mutated frequently at residues 12, 13 and 61 (see, e.g., Prio et al, Cancer Research (2012) 72(10): 2457-2467) while B-RAF is mutated only at amino acid position 600. The RAS gene mutations are easily detected in tumor samples using the methods known in the art such as described by Sarkar et al (Diagn Mol Pathol. (1995) 4(4): 266-73), while B-RAF mutations can be detected with an FDA approved kit available from Roche (Cobas® 4800 BRAF V600 Mutation Test). In the PI3K/AKT/PTEN/mTOR pathway, PI3K-alpha isozyme, PTEN and less frequently AKT are mutated in a wide variety of solid tumors. The PI3K-alpha subunit is commonly mutated at residues 542, 545 and 1047 (see, e.g., Karakas et al, British J. Cancer (2006), 94:455-459). Similarly, mutations have been identified in PTEN tumor suppressor gene in a broad range of solid tumors. Most of the PTEN mutations render loss of PTEN activity through either frame-shift or non-sense mutations. About 3% of breast cancer tumors exhibit mutations in AKT protein at position 17 (Yi et al, Oncotarget (2013) 4(1), 29-34).

Identifying a mammalian subject, e.g., a human patient, who will respond positively to treatment with compounds of the invention prior to initiation of treatment (also termed herein "predetermining or selecting") can be accomplished by assaying a sample from a cancer patient to detect one or more of the RAS, B-RAF, PI3K-α isozyme (or another selected PI3K isozyme or combinations thereof as described herein), PTEN or AKT mutations discussed above.

A suitable sample may be obtained from the body of a subject and may include, e.g., tissue samples, cells, extracellular matter, circulating cancer cells in blood or lymphatic fluid. These samples may be from humans or non-human mammalian animals. Tissue samples may be from any organ, including disease states of such organs, the blood circulatory system, and any circulating tumor cells. Tissue samples such as tumor biopsies may be obtained using known procedures. Tissue specimens may also include xenograft tumor samples, e.g., those from animals in drug dose or toxicology studies.

For example, a patient can be tested for the presence of a B-RAF mutation and an mTOR mutation, for a B-RAF mutation and a PI3K mutation, or for a B-RAF mutation, an mTOR and a PI3K pathway mutation. As discussed above, these mutations can be detected using any suitable technique known in the art, including fluorescence in situ hybridization, PCR-based sequencing of relevant portions of a given gene, restriction fragment length polymorphism analysis, or by monitoring expression levels of a given gene product (e.g., protein or RNA). B-RAF, mTOR and PI3K mutations can also be detected by measuring activity of biomarkers in the RAS/RAF/MEK/ERK and/or PI3K/AKT/PTEN/mTOR pathways. Thus, there is provided a method for treating a condition treatable by inhibiting the RAS/RAF/MEK/ERK and PI3K/AKT/PTEN/mTOR pathways, comprising selecting a patient who has a B-RAF, PI3K and/or PTEN mutation; and administering a therapeutically effective amount of at least one compound of formula (I).

The compounds of the invention show different profiles of inhibition for various target proteins in the RAS/RAF/MEK/

ERK and PI3K/AKT/PTEN/mTOR pathways. In one profile, compounds of the invention can inhibit B-RAF and mTOR. In another profile, compounds of the invention can inhibit B-RAF and one or more PI3K isoform. In another profile, compounds of the invention can inhibit B-RAF, mTOR and one or more PI3K isoform. The activity of certain protein biomarkers can therefore be used to monitor the efficacy of compounds of formula (I) once administered to a patient. For example, compounds of formula (I) which have dual activity as B-RAF and mTOR inhibitors will cause a reduced activity of pERK and pS6RP or pS6K. Combinations of biomarkers suitable for showing efficacy of the compounds of the inventions are shown in Table 1.

TABLE 1

| Activity Profile of compounds of formula (I) | Combination of biomarkers |
| --- | --- |
| B-RAF + mTOR inhibitor | pERK and (pS6RP or pS6K) |
| B-RAF + PI3K inhibitor | pERK and pAKT |
| B-RAF + mTOR + PI3K inhibitor | pERK, (pS6RP or pS6K) and pAKT |

Showing a reduced activity of one or a combination of these biomarkers (e.g., as shown in Table 1) can, for example, be used as a surrogate for the efficacy of tumor growth inhibition in patients. Thus, there is provided a method of monitoring the efficacy of compound of formula (I), or a method for treating a condition treatable by inhibiting the RAS/RAF/MEK/ERK and PI3K/AKT/PTEN/mTOR pathways, comprising administering at least one compound of formula (I) to a patient, evaluating the activity of pERK, (pS6RP or pS6K) or pAKT (for example, pAKT-5473 and/or pAKT-T308) or a combination thereof, and adjusting the amount of the compound administered until the activity of the pERK, (pS6RP or pS6K) or pAKT or a combination thereof is reduced to a predetermined activity level as compared to the activity level in an untreated patient. For example, the activity of pERK can be reduced by by at least about 50%, at least about 55%, at least about 60%, at least about 65%, at least about 70%, at least about 75%, at least about 80%, at least about 85%, at least about 90%, or at least about 99%. In another example, the activity of pERK can be reduced by about 80% to about 100%. The activity of (pS6RP or pS6K) or pAKT can be reduced for example by at least about 50%, at least about 55%, at least about 60%, at least about 65%, at least about 70%, at least about 75%, at least about 80%, at least about 85%, at least about 90%, at least about 95%, at least about 99%. In another example, the activity of (pS6RP or pS6K) or pAKT can be reduced by about 50% to about 100%. Compounds having any one of these pERK, (pS6RP or pS6K), or pAKT activity reduction profiles and characterized by no, minimal, or lower reduction of the other biomarkers may be still be utilized. However, compounds which have activity reduction profiles in two of these biomarkers, or all three of these biomarkers are particularly well suited for the uses described herein.

As used herein "pAKT activity profile" refers to the level of activation or phosphorylation of AKT ("pAKT") compared to the level of non-activated or non-phosphorylated AKT in a given sample. In one example, the sample is a solid tumor cell or tissue. In another example, the sample is a non-solid tumor cancer cell or tissue. The pAKT activity profile can be expressed in terms of a ratio (e.g., amount of pAKT in a cancer cell treated with a compound of formula (I) divided by amount of phosphorylated AKT in a cancer cell of the same type that was not treated with a compound of formula (I)). In a typical measurement of pAKT activity profiles, each treatment or patient sample and the untreated control samples are normalized against total AKT (i.e., phosphorylated AKT plus non-phosphorylated AKT) in the same sample. The normalized amount of pAKT in each treatment or patient sample is then divided by the amount of pAKT in the untreated control sample, and this number is multiplied by 100 to obtain the percent remaning in pAKT activity for a given sample. The percent remaining can then be subtracted from 100 to give the percent reduction in pAKT activity. The pAKT activity profile may also be expressed in terms of the level of activation of the pathway by measuring amounts of phosphorylated downstream targets of AKT. A "reduced pAKT activity profile" refers to activation or phosphorylation levels of overall AKT in a sample that are lower than a baseline value. Such a baseline value may be determined based on the basal levels of a single cell type. Alternatively, a baseline value may be based on the average or mean level of pAKT in a given population of sample cells. In one example, for a pAKT activity profile as used herein refers to an average value based on the pAKT activity profile of tumor cells from patients which are untreated with a compound of the invention.

As used herein "pERK activity profile" refers to the level of activation or phosphorylation of ERK ("pERK") compared to the level of non-activated or non-phosphorylated ERK in a given sample. In one example, the sample is a solid tumor cell or tissue, or a non-solid tumor cancer cell or tissue. The pERK activity profile can be expressed in terms of a ratio (e.g., amount of pERK in a cancer cell treated with a compound of formula (I) divided by amount of non-phosphorylated ERK in a cancerous cell of the same type that was not treated with a compound of formula (I)). In a typical measurement of pERK activity profiles, each treatment or patient sample and the untreated control samples are normalized against total ERK (i.e., phosphorylated ERK plus non-phosphorylated ERK). The normalized amount of pERK in each treatment or patient sample is then divided by the amount of pERK in the untreated control sample, and this number is multiplied by 100 to obtain the percent remaining in pERK activity for a given sample. The percent remaining can then be subtracted from 100 to give the percent reduction in pERK activity. The pERK activity profile may also be expressed in terms of the level of activation of the pathway by measuring amounts of phosphorylated downstream targets of ERK. A "reduced pERK activity profile" refers to activation or phosphorylation levels of overall ERK in a sample that are lower than a baseline value. Such a baseline value may be determined based on the basal levels of a single cell type. Alternatively, a baseline value may be based on the average or mean level of pERK in a given population of sample cells. In one example, for a pERK activity profile as used herein refers to an average value based on the pERK activity profile of tumor cells from patients which are untreated with a compound of the invention.

One of the proteins measured to determine efficacy of compounds of formula (I) is phospho-S6 ribosomal protein (pS6RP). Alternatively, in order to determine pS6K activity, a serine/threonine protein kinase pS6K (which encodes alternative isoforms $P70^{S6K}$ or $P85^{S6K}$) is measured. As used herein "pS6RP or pS6K activity profile" refers to the level of activation or phosphorylation of S6RP or S6K ("pS6RP or pS6K") compared to the level of non-activated or non-phosphorylated S6RP or S6K in a given sample. In one example, the sample is a solid tumor cell or tissue or a non-solid tumor cancer cell or tissue. The pS6RP or pS6K activity profile can be expressed in terms of a ratio (e.g., amount of pS6RP or pS6K in a cancer cell treated with a compound of formula (I) divided by amount of non-phosphorylated S6RP or S6K in a cancerous cell of the same type that was not treated with a compound of formula (I)). In a typical measurement of pS6RP or pS6K activity profiles, each treatment or patient sample and the untreated control samples are normalized against total S6RP or S6K (i.e., phosphorylated S6RP or S6K plus non-phosphorylated S6RP or S6K). The normalized amount of pS6RP or pS6K in each treatment or patient sample is then divided by the amount of pS6RP or pS6K in the untreated control sample, and this number is multiplied by 100 to obtain the percent remaining in pS6RP or pS6K activity for the given treatment or patient sample. The percent remaining can then be subtracted from 100 to give the percent reduction in pS6RP or pS6K activity. The pS6RP or pS6K activity profile may also be expressed in terms of the level of activation of the pathway by measuring amounts of phosphorylated downstream targets of S6RP or S6K. For example, S6RP is downstream of S6K, and phosphorylation levels of S6RP can be used a measure of pS6K activity. A "reduced pS6RP or pS6K activity profile" refers to activation or phosphorylation levels of overall pS6RP or pS6K in a sample that are lower than a baseline value. Such a baseline value may be determined based on the basal levels of a single cell type. Alternatively, a baseline value may be based on the average or mean level of pS6RP or pS6K in a given population of sample cells. In one example, for a pS6RP or pS6K activity profile as used herein refers to an average value based on the pS6RP or pS6K activity profile of cancer cells from patients which are untreated with a compound of the invention.

Any suitable technique for showing reduced activity of these biomarkers can be used in the methods of invention; for example, by detecting the proteins by traditional Western blot assay (see, e.g., the AKT Western Blot Assay Kits (Cell Signaling Technology, Danverse, Mass.) or with an In-Cell Western (ICW) assay, as shown in Example 90 below. See also the techniques described in Falchook et al, Lancet (2012), 379:1893-1901. Additionally, methods for measuring levels of AKT activation and amounts of pAKT in a sample are known. For example, immunoprecipitation assays such as, e.g., the AKT Activity Assay Kits (Abcam®, San Francisco, Calif.), a chemoluminescence-linked immunosorbent assay (Cicenas et al, Breast Can Res., 7(4): R394 (2005), or the AlphaScreen SureFire Aktl (p-Thr308) Assay Kit (Perkin-Elmer, Waltham, Mass.) may be used. Other commercially available assay kits include the pS6RP kit from iHistochem (San Diego, Calif.] and the pERK assay kits (MesoScale, Calif.). Still other techniques or kits will be readily apparent to one of skill in the art.

A method for treating a condition treatable by inhibiting the RAS/RAF/MEK/ERK and PI3K/AKT/PTEN/mTOR pathways, comprising administering a first dosage amount of a one or more compounds of formula (I) to a patient; assaying a sample from the patient following administration of the compound to determine if the activity level of pERK, pS6RP or pS6K or pAKT or a combination thereof has been reduced by a predetermined activity level as compared to the activity in an untreated patient; and administering a second dosage amount of the one or more compounds of formula (I) to the patient. The first and second dosage amounts may be the same and in the range of about 0.01 mg/kg to 500 mg/kg body weight. Alternatively, within this range, the first and second dosages may be ascending or descending doses. For example, if a second dosage amount may be higher than a first dosage amount (i.e., ascending). Alternatively, a second dosage amount may be lower than a first dosage amount (i.e., a descending dose), is at the lower about 0.01 mg/kg to about 0.1 mg, a second dosage amount may be a higher dose about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg.

As used herein, an "untreated patient" refers to a patient who has not been administered a therapeutically effective amount of one or more of the compounds of formula (I).

Also described herein is a method for monitoring the efficacy of a compound of formula (I) which involves administering a first dosage amount of at least one compound of formula (I) to a patient, assaying a sample from the patient following administration of the compound to determine if the activity level of pERK, pS6RP or pS6K or pAKT or a combination thereof has been reduced by a predetermined activity level as compared to the activity in an untreated patient; and administering a second dosage amount of the compound.

When monitoring the efficacy of therapy, the sample obtained from the patient may include a variety of samples including, e.g., whole blood or blood derivatives (e.g., plasma, peripheral blood), lymphatic fluids, or tissue samples, may be selected.

The method described herein allow therapy to be customized to the needs of an individual subject, where desired, by allowing adjustment of doses upward, downward, or to be retained at a flat (unchanged) dose depending upon the needs of the individual. Thus, a first dosage and a second dosage following assaying a sample from the patient may be ascending doses, flat doses, or descending doses as needed.

The following examples are illustrative only and are not intended to limit the present invention.

EXAMPLES

Preparation 1: N-(2-Fluoro-3-(4,4,5,5-tetramethyl-1,3,2-dioxaborolan-2-yl)phenyl)propane-1-sulfonamide

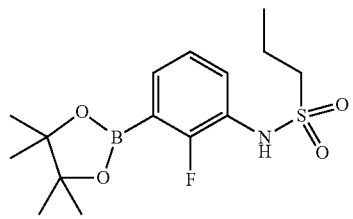 [SMILES: CCCS(=O)(=O)Nc1cccc(B2OC(C)(C)C(C)(C)O2)c1F]

Step 1: 3-bromo-2-fluoroaniline

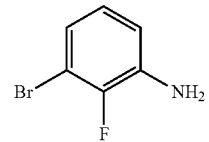

To a stirred solution of 3-bromo-2-fluoro benzoic acid (10 g, 0.04566 mol) in N,N-dimethyl formamide (80 mL), were added dropwise triethylamine (19 mL, 0.13669 mol) and diphenylphosphoryl azide (14.8 mL, 0.05378 mol) at 0° C. sequentially. The reaction mixture was stirred for 2 h at 0° C. Water (27 mL) was added and the reaction mixture was heated at 80° C. for 2 h. The reaction mixture was cooled to room temperature, diluted with water (200 mL) and extracted with diethyl ether (3×150 mL). The combined organic layers were washed with cold water (2×200 mL), dried over anhydrous sodium sulfate and evaporated under reduced pressure. The residue obtained was treated with hexane (100 mL), filtered, and the filter cake was washed with hexane (2×100 mL). The filtrate was evaporated under reduced pressure to afford the title compound (4.3 g, 50%) as a brown liquid. $^1$H NMR (400 MHz, DMSO-$d_6$): δ 6.82-6.70 (m, 3H), 5.43 (brs, 2H); ESI-MS: Calculated mass: 188.96; Observed mass: 188.10 [M−H]$^-$.

Step 2:
N-(3-bromo-2-fluorophenyl)propane-1-sulfonamide

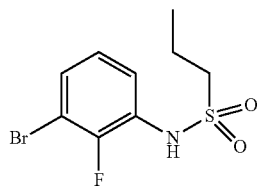

To a stirred solution of 3-bromo-2-fluoroaniline (1.8 g, 0.00952 mol) in DCM (18 mL) were added dropwise pyridine (1.35 mL, 0.017 mol) and propane sulfonyl chloride (1.57 mL, 0.017 mol) at room temperature. The reaction mixture was stirred overnight at the same temperature. The reaction mixture was diluted with water (50 mL) and extracted with dichloromethane (2×50 mL). The combined organic layers were washed with 1N HCl (25 mL), brine solution and dried over anhydrous sodium sulfate, then filtered. The filtrate was evaporated under reduced pressure. The crude product was purified using column chromatography (100-200 mesh silica gel; 2% EtOAc in hexane) to afford the title compound (700 mg, 25%). $^1$H NMR (400 MHz, DMSO-$d_6$): δ 9.85 (s, 1H), 7.52 (t, J=8.4 Hz, 1H), 7.42 (t, J=8.4 Hz, 1H), 7.14 (t, J=8.40 Hz, 1H), 3.32-3.10 (m, 2H), 1.76-1.70 (m, 2H), 0.97 (t, J=7.2 Hz, 3H); ESI-MS: Calculated mass: 294.96; Observed mass: 296.0 [M+H]$^+$.

Step 3: N-(2-fluoro-3-(4,4,5,5-tetramethyl-1,3,2-dioxaborolan-2-yl)phenyl)propane-1-sulfonamide

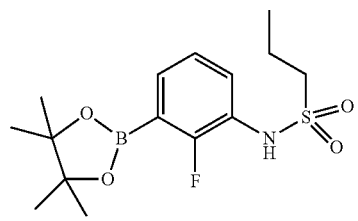 [SMILES: CCCS(=O)(=O)Nc1cccc(B2OC(C)(C)C(C)(C)O2)c1F]

A 100 mL round bottom flask was charged with N-(3-bromo-2-fluorophenyl)propane-1-sulfonamide (0.65 g, 0.0022 mol), toluene (20 mL), potassium acetate (0.64 g, 0.0066 mol) and bis(pinacolato)diboron (0.83 g, 0.0033 mol). The reaction mixture was degassed with nitrogen for 15 min. To this mixture was added Pd(dppf)Cl$_2$.DCM (89 mg, 0.00011 mol) and the mixture was degassed again with nitrogen for 5 min. The reaction mixture was stirred overnight at 100° C. The reaction mixture was filtered through the Celite® reagent, the filter cake was washed with ethyl acetate (50 mL), and the filtrate was evaporated under reduced pressure. The residue obtained was washed with n-hexane (50 mL) and dried under vacuum to provide the title compound as a solid. The crude product was used in the next step without further purification. $^1$H NMR (400 MHz, DMSO-$d_6$): δ 9.59 (brs, 1H), 7.53 (t, J=8.0 Hz, 1H), 7.44 (t, J=7.2 Hz, 1H), 7.18 (t, J=8.0 Hz, 1H), 3.06 (t, J=7.6 Hz, 2H), 1.78-1.68 (m, 2H), 1.30 (s, 12H), 0.96 (t, J=8.0 Hz, 3H); ESI-MS: Calculated mass: 343.14; Observed mass: 342.20 [M−H$^-$].

Preparation 2: 3-Fluoro-N-(2-fluoro-3-(4,4,5,5-tetramethyl-1,3,2-dioxaborolan-2-yl)phenyl)propane-1-sulfonamide

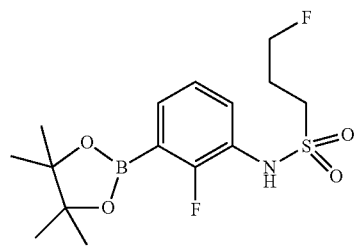 [SMILES: CC1(C)OB(c2cccc(NS(=O)(=O)CCCF)c2F)OC1(C)C]

Step 1: 3-fluoropropyl methanesulfonate

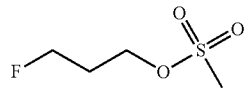

To a stirred solution of 3-fluoro propanol (15 g, 0.19208 mol) in dichloromethane (210 mL) were added drop wise triethylamine (32 mL, 0.2302 mol) followed by methananesulfonyl chloride (16.3 mL, 0.21068 mol) at 0° C. and the reaction mixture was stirred for 3 h at 0° C. The reaction mixture was diluted with water (150 mL) and extracted with DCM (2×150 mL). The combined organic layers were washed with saturated sodium bicarbonate solution, followed by brine solution and dried over anhydrous sodium sulfate, then filtered. The filtrate was evaporated and the crude product was purified using column chromatography (100-200 mesh silica gel, 30% EtOAc in hexane) to afford the title compound (20 g, 66%). $^1$H NMR (400 MHz, DMSO-$d_6$): δ 4.60 (t, J=6.0 Hz, 1H), 4.48 (t, J=6.0 Hz, 1H), 4.29 (t, J=6.4 Hz, 2H), 3.18 (s, 3H), 2.12-2.0 (m, 2H).

Step 2: (3-Fluoropropyl)ethanethioate

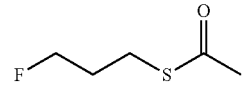

To a stirred solution of 3-fluoropropyl methanesulfonate (20 g, 0.12807 mol) in dimethyl sulfoxide (200 mL) was added potassium thioacetate (17.5 g, 0.15323 mol) at room temperature and the reaction mixture was stirred for 12 h at room temperature. Water (300 mL) was added and the reaction mixture was extracted with diethyl ether (3×150 mL). The combined organic layers were washed with brine solution and dried over anhydrous sodium sulfate, then filtered. The filtrate was evaporated under reduced pressure to afford the title compound (15 g, 86%). $^1$H NMR (400 MHz, DMSO-$d_6$): δ 4.52 (t, J=5.6 Hz, 1H), 4.40 (t, J=6.0 Hz, 1H), 2.91 (t, J=7.6 Hz, 2H), 2.33 (s, 3H), 1.94-1.84 (m, 2H).

Step 3: 3-fluoropropane-1-sulfonyl chloride

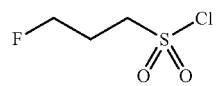

Chlorine gas was passed through a stirred solution of (3-fluoropropyl)ethanethioate (15 g) in a 1:1 mixture of DCM and water (150 mL) at −20° C. for 3 h (until the aqueous color changed to green). The flow of chlorine gas was stopped and reaction mixture was maintained at −20° C. for 2 more h. After confirming the completion of reaction by TLC, reaction mixture was extracted with DCM (2×300 mL). The combined organic layers were washed with 10% sodium bisulfite solution (2×200 mL) followed by brine solution and dried over anhydrous sodium sulfate, then filtered. The filtrate was evaporated under reduced pressure to afford the title compound (13 g, 73%). $^1$H NMR (400 MHz, DMSO-$d_6$): δ 4.58 (t, J=6.0 Hz, 1H), 4.46 (t, J=5.6 Hz, 1H), 2.70 (t, J=7.2 Hz, 2H), 2.05-1.92 (m, 2H).

Step 4: N-(3-bromo-2-fluorophenyl)-3-fluoropropane-1-sulfonamide

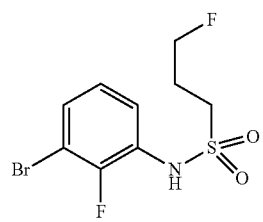 [SMILES: O=S(=O)(CCCF)Nc1cccc(Br)c1F]

To a stirred solution of 3-bromo-2-fluoroaniline (3 g, 0.0158 mol) in dichloromethane (300 mL) were added dropwise pyridine (12.53 mL, 0.158 mol) and 3-fluoropropane-1-sulfonyl chloride (7.64 mL, 0.047 mol) at 0° C. To the resulting mixture was added DMAP (0.387 g, 0.00317 mol) at 0° C. The reaction mixture was stirred overnight at room temperature. Water (500 mL) was added and the reaction mixture was extracted with DCM (2×100 mL). The combined organic layers were washed with 1N HCl (50 mL) followed by brine and dried over anhydrous sodium sulfate, then filtered. The filtrate was evaporated under reduced pressure and the crude product was purified using column chromatography (100-200 mesh silica gel, 10% EtOAc in hexane) to afford the title compound (3.4 g, 69%). $^1$H NMR (400 MHz, DMSO-$d_6$): δ 9.99 (s, 1H), 7.54 (t, J=7.6 Hz, 1H), 7.42 (t, J=8.4 Hz, 1H), 7.16 (t, J=8.4 Hz, 1H), 4.61 (t, J=3.2 Hz, 1H), 4.49 (t, J=4.0 Hz, 1H), 3.25 (t, J=5.6 Hz, 2H), 2.16-2.03 (m, 2H); ESI-MS: Calculated mass: 312.96; Observed mass: 314.0 [M+H]$^+$.

Step 5: 3-fluoro-N-(2-fluoro-3-(4,4,5,5-tetramethyl-1,3,2-dioxaborolan-2-yl)phenyl)propane-1-sulfonamide

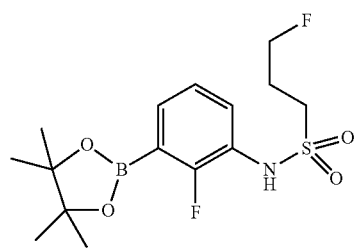 [SMILES: CC1(C)OB(c2cccc(NS(=O)(=O)CCCF)c2F)OC1(C)C]

A 250 mL round bottom flask was charged with N-(3-bromo-2-fluorophenyl)-3-fluoropropane-1-sulfonamide (3.4 g, 0.0108 mol), bis(pinacolato)diboron (4.13 g, 0.0162 mol) potassium acetate (3.19 g, 0.032 mol) and toluene (90 mL). The reaction mixture was degassed with nitrogen for 15 min. To the mixture was added Pd(dppf)Cl$_2$.DCM (883 mg, 0.00108 mol) and the mixture was degassed with nitrogen again for 10 min and stirred overnight at 100° C. The reaction mixture was cooled to room temperature, filtered through the Celite® reagent and the filter cake was washed with ethyl acetate (500 mL). The filtrate was evaporated under reduced pressure and the crude residue was washed with n-hexane (2×50 mL). The residue was dried under vacuum to afford the title compound (4 g, crude). The crude product was used in the next step without any further purification. ESI-MS: Calculated mass: 361.13; Observed mass: 360.2 [M−H$^-$].

Preparation 3: N-(3-Bromo-2,4-difluorophenyl)propane-1-sulfonamide

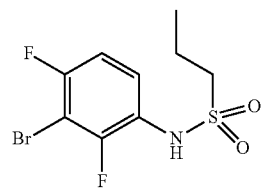

Step 1: 2-Bromo-1,3-difluoro-4-nitrobenzene

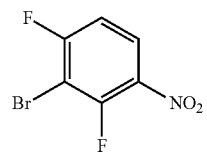 [SMILES: O=[N+]([O-])c1ccc(F)c(Br)c1F]

A mixture of concentrated HNO$_3$ (6 mL, 0.143 mol) and concentrated H$_2$SO$_4$ (6 mL, 0.111 mol) was added dropwise to a stirred solution of 2-bromo-1,3-difluorobenzene (10 g, 0.057 mol) in concentrated H$_2$SO$_4$ (30 mL, 0.56 mol) at 0° C. After the addition was complete, the reaction mixture was stirred at room temperature for 2 h. The reaction mixture was then neutralized to pH 7 with saturated sodium hydroxide solution and extracted with ethyl acetate (2×250 mL). The combined organic layers were dried, filtered and evaporated to provide the title compound (8.75 g, 71%). $^1$H NMR (400 MHz, CDCl$_3$): δ 8.15-8.10 (m, 1H), 7.15-7.11 (m, 1H); ESI-MS: Calculated mass: 236.92; Observed mass: 235.90 [M–H]$^-$.

Step 2: 3-Bromo-2,4-difluoroaniline

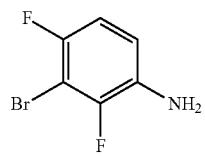

A mixture of 2-bromo-1,3-difluoro-4-nitrobenzene (8.5 g, 0.035 mol), concentrated HCl (24 mL, 0.789 mol), SnCl$_2$.2H$_2$O (24.3 g, 0.107 mol) and a small amount of diethyl ether (10 mL) was heated in an oil bath at 60° C. for 40 min. The reaction mixture was then cooled, neutralized with saturated sodium hydroxide solution and extracted with ethyl acetate (2×250 mL). The combined organic layers were dried, filtered and evaporated to provide the title compound as a solid (9.51 g, crude). $^1$H NMR (400 MHz, DMSO-d$_6$): δ 6.95 (t, J=8.8 Hz, 1H), 6.80-6.74 (m, 1H), 5.27 (brs, 2H); ESI-MS: Calculated mass: 206.95; Observed mass: 206.0 [M–H$^-$].

Step 3: N-(3-Bromo-2,4-difluorophenyl)propane-1-sulfonamide

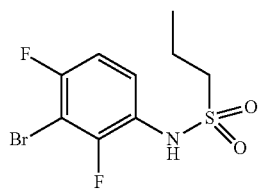 [SMILES: CCCS(=O)(=O)Nc1ccc(F)c(Br)c1F]

To a stirred solution of 3-bromo-2,4-difluoroaniline (1.93 g, 0.0093 mol) in dichloromethane (20 mL) were added dropwise pyridine (1.5 mL, 0.0186 mol), propane-1-sulfonyl chloride (1.98 g, 0.0139 mol) and DMAP (113 mg, 0.0009 mol) at 0° C. The reaction mixture was stirred overnight at room temperature. Water (20 mL) was added and the reaction mixture was extracted with dichloromethane (2×50 mL). The combined organic layers were washed with 1N HCl (20 mL) then brine solution, dried over anhydrous sodium sulfate and filtered. The filtrate was evaporated under reduced pressure and the crude product was purified using column chromatography (100-200 mesh silica gel, 10% EtOAc in hexane) to afford the title compound (2.5 g, 86%). $^1$H NMR (400 MHz, DMSO-d$_6$): δ 9.81 (s, 1H), 7.49-7.43 (m, 1H), 7.28-7.23 (m, 1H), 3.11-3.07 (m, 2H), 1.78-1.69 (m, 2H), 0.97 (t, J=7.2 Hz, 3H).

Preparation 4: 1-Methyl-3-(4-(4,4,5,5-tetramethyl-1,3,2-dioxaborolan-2-yl)phenyl)urea

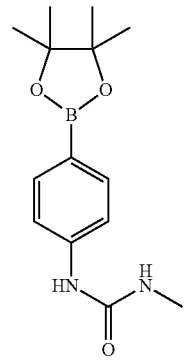

Step 1: 1-(4-Bromophenyl)-3-methylurea

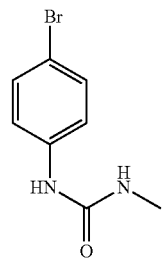

To a stirred solution of 4-bromophenylisocyanate (3 g, 0.01515 mol) in acetonitrile (40 mL) was added dropwise saturated aqueous methylamine (60 mL) at room temperature and stirring continued for 10 min at room temperature. A white solid was separated which was filtered, washed with hexane (30 mL) and dried under vacuum to afford the title compound (4.1 g). $^1$H NMR (400 MHz, DMSO-d$_6$): δ 8.62 (s, 1H), 7.36 (s, 4H), 6.03-6.02 (m, 1H), 2.62 (d, J=4.8 Hz, 3H); ESI-MS: Calculated mass: 227.99; Observed mass: 229.0 [M+H]$^+$.

Step 2: 1-Methyl-3-(4-(4,4,5,5-tetramethyl-1,3,2-dioxaborolan-2-yl)phenyl)urea

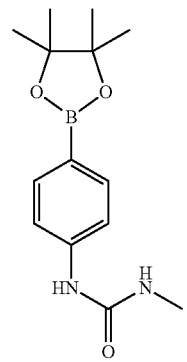

A 250 mL round bottom flask was charged with 1-(4-bromophenyl)-3-methylurea (4 g, 0.01789 mol), bis(pinacolato)diboron (5.9 g, 0.02323 mol), KOAc (5.2 g, 0.05306 mol) and toluene (70 mL). The reaction mixture was degassed with nitrogen for 15 min and to the mixture was added Pd(dppf)Cl$_2$DCM (430 mg, 0.00052 mol), and the resulting mixture was degassed with nitrogen again for 5 min and stirred overnight at 100° C. The reaction mixture was cooled to room temperature, filtered through the Celite® reagent and the filter cake was washed with ethyl acetate (2×50 mL). The filtrate was evaporated under reduced pressure and the crude residue was purified using column chromatography (100-200 mesh silica gel, 2% MeOH in DCM) to afford the title compound (2 g, 40%). $^1$H NMR (400 MHz, DMSO-d$_6$): δ 8.63 (s, 1H), 7.51 (d, J=8.8 Hz, 2H), 7.39 (d, J=8.4 Hz, 2H), 6.05 (d, J=4.4 Hz, 1H), 2.63 (d, J=4.4 Hz, 3H), 1.26 (s, 12H); ESI-MS: Calculated mass: 276.16; Observed mass: 277.20 [M+H]$^+$.

Preparation 5: 1-Methyl-3-(5-(4,4,5,5-tetramethyl-1,3,2-dioxaborolan-2-yl)pyridin-2-yl)urea

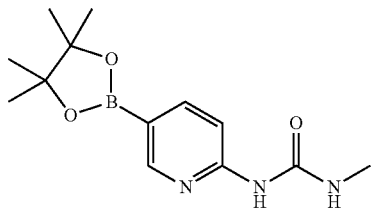

Step 1: Phenyl (5-bromopyridin-2-yl)carbamate

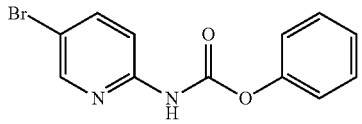 [SMILES: O=C(Nc1ccc(Br)cn1)Oc1ccccc1]

To a stirred solution of 5-bromopyridin-2-amine (1 g, 0.00578 mol) in dichloromethane (40 mL) were added dropwise diisopropylethylamine (2 mL, 0.01156 mol) and phenylchloroformate (0.87 mL, 0.00693 mol) sequentially at 0° C. and stirring was continued for 2 h at room temperature. Water (10 mL) was added to the reaction mixture, the obtained solid was filtered and dried to afford the title compound (1 g, 59%). $^1$H NMR (400 MHz, DMSO-d$_6$): δ 10.93 (brs, 1H), 8.45 (brs, 1H), 8.02 (d, J=8.80 Hz, 1H), 7.80 (d, J=8.80, 1H), 7.46-7.42 (m, 2H), 7.30-7.22 (m, 3H).

Step 2: 1-(5-Bromopyridin-2-yl)-3-methylurea

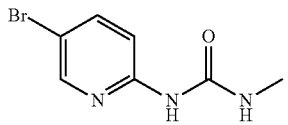

A sealed tube was charged with phenyl (5-bromopyridin-2-yl)carbamate (1 g, 0.00341 mol) and 2M methylamine in THF (17 mL, 0.0341 mol). The reaction mixture was stirred for 5 h at 100° C. The reaction mixture was concentrated under vacuum, and the residue was dissolved in dichloromethane (50 mL) then washed with 1N sodium hydroxide solution (10 mL). The organic layer was dried over anhydrous sodium sulfate, filtered and evaporated under reduced pressure to afford the title compound (650 mg, 82%). $^1$H NMR (400 MHz, DMSO-d$_6$): δ 9.32 (brs, 1H), 8.27 (d, J=2.4 Hz, 1H), 7.87 (dd, J'=8.80 Hz, J''=2.4 Hz, 1H), 7.47-7.45 (m, 2H), 2.70 (d, J=4.4 Hz, 3H); LC-MS: Calculated mass: 228.99; Observed mass: 230.10 [M+H]$^+$.

Step 3: 1-Methyl-3-(5-(4,4,5,5-tetramethyl-1,3,2-dioxaborolan-2-yl)pyridin-2-yl)urea

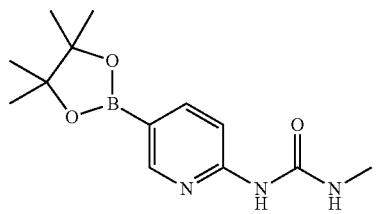

A 100 mL round bottom flask was charged with 1-(5-bromopyridin-2-yl)-3-methylurea (650 mg, 0.0028 mol), KOAc (830 mg, 0.00846 mol), bis(pinacolato)diboron (930 mg, 0.0036 mol) and toluene (15 mL). The reaction mixture was degassed with nitrogen for 10 min. To this was added Pd(dppf)Cl$_2$DCM (231 mg, 0.00028 mol) again degassed with nitrogen for 10 min and stirred for 16 h at 100° C. The reaction mixture was filtered through the Celite® reagent and washed with EtOAc (100 mL). The filtrate was evaporated under reduced pressure and the residue was washed with n-hexane (30 mL) to afford the title compound (300 mg, 38%). $^1$H NMR (400 MHz, DMSO-d$_6$): δ 9.43 (brs, 1H), 8.38 (s, 1H), 7.83 (dd, J'=8.40 Hz, J''=2.0 Hz, 1H), 7.55-7.49 (m, 1H), 7.32 (d, J=8.40 Hz, 1H), 2.72 (d, J=4.40 Hz, 3H), 1.35 (s, 12H).

Preparation 6: 5-(4,4,5,5-Tetramethyl-1,3,2-dioxaborolan-2-yl)-4-(trifluoromethyl)pyridin-2-amine

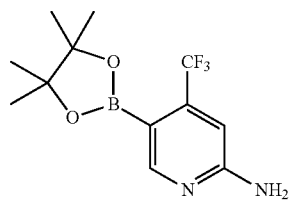 [SMILES: CC1(C)OB(c2cnc(N)cc2C(F)(F)F)OC1(C)C]

Step 1: 5-Bromo-4-(trifluoromethyl)pyridin-2-amine

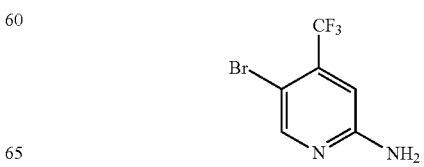

To a stirred solution of 4-(trifuloromethyl)pyridine-2amine (2.5 g, 0.01542 mol) in dichloromethane (250 mL) was added N-bromosuccinimide (2.74 g, 0.01542 mol) in portions under dark conditions at room temperature and stirring was continued at room temperature for 6 h. The reaction mixture was diluted with 1N NaOH solution (20 mL) and extracted with DCM (2×100 mL). The combined organic layers were dried over sodium sulfate, filtered and evaporated under reduced pressure to afford the title compound (3.2 g, 86%). $^1$H NMR (400 MHz, CDCl$_3$): δ 8.28 (s, 1H), 6.77 (s, 1H), 4.73 (brs, 2H); ESI-MS: Calculated mass: 239.95; Observed mass: 239.10 [M−H]$^−$.

Step 2: 5-(4,4,5,5-Tetramethyl-1,3,2-dioxaborolan-2-yl)-4-(trifluoromethyl)pyridin-2-amine

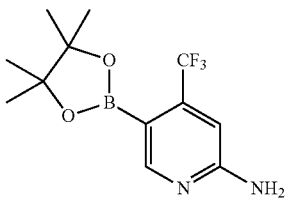 [SMILES: CC1(C)OB(c2cnc(N)cc2C(F)(F)F)OC1(C)C]

A 250 mL round bottom flask was charged with 5-bromo-4-(trifluoromethyl)pyridin-2-amine (3.2 g, 0.013 mol), bis(pinacolato)diboron (4.74 g, 0.0186 mol), KOAc (5.22 g, 0.053 mol) and 1,4-dioxane (100 mL). The reaction mixture was degassed with nitrogen for 15 min and to the mixture was added Pd(dppf)Cl$_2$.DCM (544 mg, 0.00066 mol). The resulting mixture was degassed with nitrogen again for 10 min and stirring continued overnight at 100° C. The reaction mixture was cooled to room temperature, filtered through the Celite® reagent and the filter cake was washed with EtOAc (300 mL). The filtrate was evaporated under reduced pressure to afford the title compound (5 g, crude). The crude product was used in the next step without further purification. ESI-MS: Calculated mass: 288.13; Observed mass: 289.0 [M+H]$^+$.

Preparation 7: 1-(Tetrahydro-2H-pyran-2-yl)-4-(4,4,5,5-tetramethyl-1,3,2-dioxaborolan-2-yl)-1H-indazole

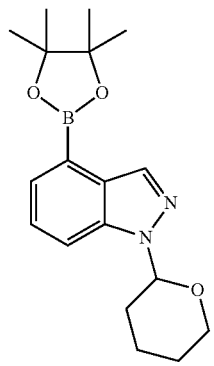 [SMILES: CC1(C)OB(c2cccc3c2cnn3C2CCCCO2)OC1(C)C]

Step 1: 2-Bromo-6-fluorobenzaldehyde

To a stirred solution of diisopropylamine (1.4 mL, 0.00571 mol) in dry tetrahydrofuran (7.2 mL) was added dropwise n-butyllithium (1.6M in hexane) (3.56 mL, 0.00571 mol) at 0° C. and stirring was continued for 15 min at 0° C. The reaction mixture was cooled to −78° C. and 1-bromo-3-fluorobenzene (1 g, 0.00571 mol) was added over 10 min After stirring for 1 h at −78° C., anhydrous N,N-dimethylformamide (7.2 mL) was added dropwise over 5 min and the resulting mixture was stirred for another 20 min at −78° C. The reaction was quenched with addition of acetic acid (0.6 mL) followed by water (15 mL) and the mixture was warmed to room temperature. The mixture was extracted with ethyl acetate (2×20 mL) and the combined organic layers were washed with water (2×10 mL) followed by brine solution and dried over anhydrous sodium sulfate. The solvent was evaporated under vacuum to afford the title compound as a pale yellow solid (850 mg, 73%). $^1$H NMR (400 MHz, DMSO-d$_6$): δ 10.21 (s, 1H), 7.66-7.61 (m, 2H), 7.45-7.42 (m, 1H). ESI-MS: Calculated mass: 201.94; Observed mass: 202.0 [M]$^+$.

Step 2: 4-Bromo-1H-indazole

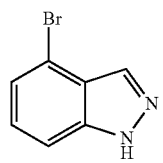

To a stirred solution of 2-bromo-6-fluorobenzaldehyde (850 mg, 0.004 mol) in DMSO (1 mL) was added hydrazinehydrate (4.5 mL) at room temperature and the resulting mixture was stirred overnight at 80° C. The reaction mixture was cooled to room temperature, water (10 mL) was added and the mixture was extracted with ethyl acetate (2×100 mL). The combined organic layers were washed with brine solution, dried over anhydrous sodium sulfate and filtered. The filtrate was evaporated under reduced pressure to afford the title compound as a yellow solid (700 mg, 84%). %). $^1$H NMR (400 MHz, DMSO-d$_6$): δ 13.44 (brs, 1H), 8.03 (s, 1H), 7.57 (d, J=8.0 Hz, 1H), 7.34 (d, J=7.20 Hz, 1H), 7.28 (t, J=7.60 Hz, 1H); ESI-MS: Calculated mass: 195.96; Observed mass: 197.0 [M+H]$^+$.

Step 3: 4-Bromo-1-(tetrahydro-2H-pyran-2-yl)-1H-indazole

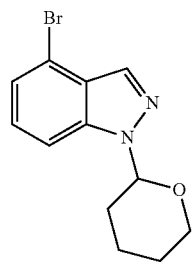 [SMILES: Brc1cccc2c1cnn2C1CCCCO1]

To a stirred solution of 4-bromo-1H-indazole (700 mg, 0.003645 mol) in N,N-dimethylformamide (10 mL) were added 3,4-dihydro-2H-pyran (0.4 mL, 0.004375 mol) and para toluene sulfonic acid (1.04 g, 0.005467 mol). The reaction mixture was stirred overnight at 70° C., cooled to room temperature, diluted with water (50 mL) and extracted with ethyl acetate (2×50 mL). The combined organic layers were washed with brine solution, dried over anhydrous sodium sulfate and filtered. The filtrate was evaporated under reduced pressure and the crude product was purified using column chromatography (100-200 mesh silica gel, 15% EtOAc in hexane) to afford the title compound (550 mg, 53%). $^1$H NMR (400 MHz, DMSO-d$_6$): δ 8.08 (s, 1H), 7.78 (d, J=8.40 Hz, 1H), 7.42 (d, J=7.20 Hz, 1H), 7.35 (t, J=8.40 Hz, 1H), 5.80 (dd, J'=9.6 Hz, J"=2.80 Hz, 1H), 3.89-3.86 (m, 1H), 3.77-3.71 (m, 1H), 2.49-2.32 (m, 1H), 2.06-1.95 (m, 2H), 1.77-1.60 (m, 1H), 1.59-1.56 (m, 2H).

Step 4: 1-(Tetrahydro-2H-pyran-2-yl)-4-(4,4,5,5-tetramethyl-1,3,2-dioxaborolan-2-yl)-1H-indazole

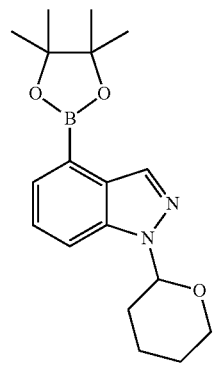 [SMILES: CC1(C)OB(c2cccc3c2cnn3C2CCCCO2)OC1(C)C]

A 50 mL round bottom flask was charged with 4-bromo-1-(tetrahydro-2H-pyran-2-yl)-1H-indazole (550 mg, 0.001956 mol), KOAc (575 mg, 0.00586 mol), bis(pinacolato)diboron (645 mg, 0.002543 mol) and 1,4-dioxane (10 mL). The reaction mixture was degassed with nitrogen for 20 min and to the reaction mixture was added Pd(dppf)Cl$_2$.DCM (159 mg, 0.00019 mol). The resulting mixture was degassed with nitrogen again for 10 min and was stirred overnight at 100° C. The reaction mixture was filtered through Celite® reagent and washed with ethyl acetate (30 mL). The filtrate was evaporated and the crude product was purified using column chromatography (100-200 mesh silica gel, 20% EtOAc in hexane) to afford the title compound as a liquid (590 mg, 91%). $^1$H NMR (400 MHz, DMSO-d$_6$): δ 8.20 (s, 1H), 7.87 (d, J=8.0 Hz, 1H), 7.54 (d, J=5.6 Hz, 1H), 7.43 (t, J=6.8 Hz, 1H), 5.86 (dd, J'=9.20 Hz, J"=2.4 Hz, 1H), 3.89-3.86 (m, 1H), 3.77-3.70 (m, 1H), 2.54-2.40 (m, 1H), 2.05-1.92 (m, 2H), 1.77-1.60 (m, 1H), 1.59-1.57 (m, 2H), 1.35 (s, 12H); ESI-MS: Calculated mass: 328.20; Observed mass: 329.0 [M+H]$^+$.

Preparation 8: 2-(Difluoromethyl)-1H-benzo[d]imidazole

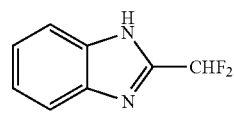 [SMILES: FC(F)c1nc2ccccc2[nH]1]

To a stirred solution of 0-phenylenediamine (1 g, 0.00925 mol) in 4N HCl (10 mL) was added difluoroacetic acid (0.977 g, 0.01018 mol) and the resulting mixture was heated at reflux for 2 h. The reaction mixture was cooled to room temperature, neutralized with sodium carbonate and the solid obtained was collected by filtration and washed with water (30 mL), then dried under vacuum to afford the title compound (1 g, 64%). $^1$H NMR (400 MHz, CDCl$_3$): δ 10.64 (brs, 1H), 7.82-7.57 (m, 2H), 7.37 (dd, J'=6.0 Hz, J"=3.20 Hz, 2H), 6.92 (t, J=53.6 Hz, 1H); ESI-MS: Calculated mass: 168.05; Observed mass: 169.0 [M+H]$^+$.

Preparation 9: 2-(((Tert-butyldimethylsilyl)oxy)methyl)-1H-benzo[d]imidazole

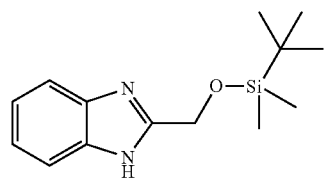 [SMILES: CC(C)(C)[Si](C)(C)OCc1nc2ccccc2[nH]1]

Step 1: (1H-Benzo[d]imidazol-2-yl)methanol

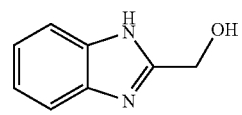 [SMILES: OCc1nc2ccccc2[nH]1]

To a stirred solution of 0-phenylenediamine (5 g, 0.046 mol) in 4N HCl (50 mL) was added 2-hydroxyacetic acid (4.2 g, 0.0555 mol) and stirring was continued for 3 h at 100° C. The reaction mixture was cooled to room temperature, neutralized with saturated sodium bicarbonate solution and the solid obtained was collected by filtration and dried to afford the title compound (3.5 g, 73%). $^1$H NMR (400 MHz, DMSO-d$_6$): δ 12.28 (brs, 1H), 7.52-7.44 (m, 2H), 7.12 (d, J=4.80 Hz, 2H), 5.66 (t, J=6.0 Hz, 1H), 4.68 (d, J=5.2 Hz, 2H).

Step 2: 2-(((Tert-butyldimethylsilyl)oxy)methyl)-1H-benzo[d]imidazole

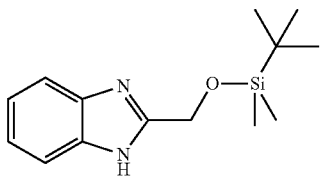 [SMILES: CC(C)(C)[Si](C)(C)OCc1nc2ccccc2[nH]1]

To a stirred solution of (1H-benzo[d]imidazol-2-yl)methanol (2 g, 0.0135 mol) in pyridine (30 mL) was added tert-butyl dimethylsilyl chloride (3.46 g, 0.02296 mol) at room temperature and stirring was continued for 4 h at room temperature. The pyridine was evaporated under vacuum, and the residue was taken up in dichloromethane (50 mL). The organic layer was washed with saturated sodium bicarbonate and brine solution, dried over anhydrous sodium sulfate and filtered. The filtrate was evaporated under reduced pressure and the crude product was purified using column chromatography (100-200 mesh silica gel, 20% EtOAc in hexane) to afford the title compound (3.1 g, 87%). $^1$H NMR (400 MHz, DMSO-d$_6$): δ 12.23 (brs, 1H), 7.51 (brs, 2H), 7.15 (dd, J'=6.0 Hz, J'=2.80 Hz, 2H), 4.85 (s, 2H), 0.90 (s, 9H), 0.10 (s, 6H); ESI-MS: Calculated mass: 262.15; Observed mass: 263.20 [M+H]$^+$.

Example 1

2,6-Difluoro-N-(2-fluoro-3-(8-methoxy-2-(4-(3-methylureido)phenyl)-4-morpholinoquinazolin-6-yl)phenyl)benzenesulfonamide

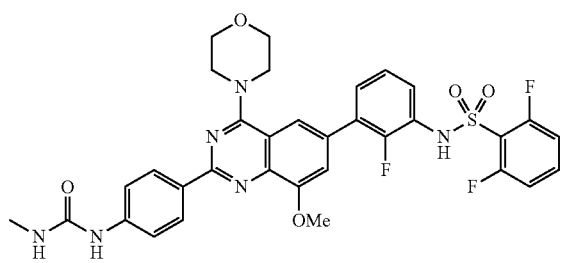 [SMILES: CNC(=O)Nc1ccc(-c2nc(N3CCOCC3)c3cc(-c4cccc(NS(=O)(=O)c5c(F)cccc5F)c4F)cc(OC)c3n2)cc1]

Step 1: 3-Hydroxy-2-nitrobenzoic acid

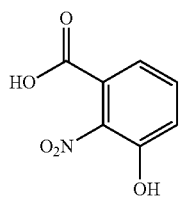 [SMILES: O=C(O)c1cccc(O)c1[N+](=O)[O-]]

3-chloro-2-nitrobenzoic acid (30 g, 0.148 mol) was dissolved in aqueous potassium hydroxide solution (240 g, 4.277 mol, in 300 mL H$_2$O) at room temperature and then heated at 110° C. for 12 h. The reaction mixture was cooled to room temperature, diluted with water, acidified with conc. HCl at 0° C. to pH 2, and extracted with ethyl acetate (2×500 mL). The combined organic layers were washed with brine solution, dried over anhydrous sodium sulfate, filtered and the filtrate was evaporated under reduced pressure to afford the title compound (27 g, 99%). $^1$H NMR (400 MHz, DMSO-d6): δ 13.8 (brs, 1H), 11.21 (s, 1H), 7.47 (t, J=8.0 Hz, 1H), 7.39 (dd, J'=8.0 Hz, J''=1.6 Hz, 1H), 7.30 (dd, J'=7.6 Hz, J''=0.8 Hz, 1H); ESI-MS: Calculated mass: 183.02; Observed mass: 182.10 [M–H$^-$].

Step 2: Methyl 3-methoxy-2-nitrobenzoate

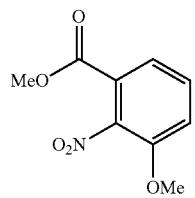 [SMILES: COC(=O)c1cccc(OC)c1[N+](=O)[O-]]

To a stirred suspension of 3-hydroxy-2-nitrobenzoic acid (27 g, 0.147 mol) and potassium carbonate (81.3 g, 0.589 mol) in N,N-dimethyl formamide (270 mL) was added methyl iodide (36.87 mL, 0.589 mol) dropwise at 0° C. After the addition was complete, the reaction mixture was stirred at room temperature overnight. The solid separated out after the addition of ice-cold water to the reaction mixture was collected by filtration and dried to afford the title compound (27 g, 86%). $^1$H NMR (400 MHz, DMSO-d$_6$): δ 7.72-7.64 (m, 2H), 7.58 (dd, J'=7.2 Hz, J''=1.2 Hz, 1H), 3.92 (s, 3H), 3.83 (s, 3H); ESI-MS: Calculated mass: 211.05; Observed mass: 212.10 [M+H]$^+$.

Step 3: Methyl 2-amino-3-methoxybenzoate

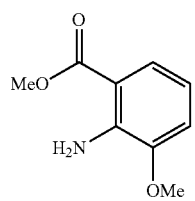 [SMILES: COC(=O)c1cccc(OC)c1N]

A mixture of methyl 3-methoxy-2-nitrobenzoate (27 g, 0.127 mol) and 10% Pd—C (13 g) in 500 mL, of methanol was stirred at room temperature for 2 h at 60 PSI in a Parr hydrogenation apparatus. After confirming the completion of reaction by TLC, the reaction mixture was filtered through Celite® reagent and the Celite® reagent was washed with 20% MeOH in ethyl acetate (2 L). The filtrate was concentrated under reduced pressure and the solid obtained was dried under high vacuum to afford the title compound (22 g, 95%). $^1$H NMR (400 MHz, DMSO-d$_6$): δ 7.33 (dd, J'=8.4 Hz, J''=1.2 Hz, 1H), 6.97 (dd, J'=7.6 Hz, J''=0.8 Hz, 1H), 6.52 (t, J=8.4 Hz, 1H), 6.32 (brs, 2H), 3.81 (s, 3H), 3.72 (s, 3H); ESI-MS: Calculated mass: 181.07; Observed mass: 182.0 [M+H]$^+$.

Step 4: Methyl 2-amino-5-bromo-3-methoxybenzoate

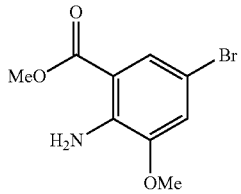

To a stirred solution of methyl 2-amino-3-methoxybenzoate (22 g, 0.121 mol) in acetic acid (220 mL) was added bromine (7.5 mL, 0.145 mol) dropwise at 0° C. The reaction mixture was stirred at room temperature for 1 h. After the completion, the reaction mixture was poured into 1 L of cold water and stirred for 30 min at room temperature and extracted with ethyl acetate (2×500 mL). The combined organic layers were washed with saturated sodium bicarbonate solution (2×1 L) followed by brine solution, then dried over anhydrous sodium sulfate and filtered. The filtrate was concentrated under reduced pressure and the crude product was purified using column chromatography (100-200 mesh silica gel, 10% EtOAc in hexane) to afford the title compound as a white solid (20 g, 63% yield). $^1$H NMR (400 MHz, DMSO-d$_6$): δ 7.42 (d, J=2.0 Hz, 1H), 7.09 (d, J=2.0 Hz, 1H), 6.47 (brs, 2H), 3.85 (s, 3H), 3.81 (s, 3H); ESI-MS: Calculated mass: 258.98; Observed mass: 260.10 [M+H]$^+$.

Step 5: 6-Bromo-8-methoxyquinazoline-2,4(1H,3H)-dione

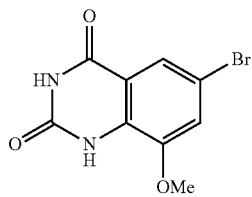 [SMILES: COc1cc(Br)cc2c(=O)[nH]c(=O)[nH]c12]

A mixture of urea (46 g, 0.768 mol) and methyl 2-amino-6-bromo-3-methoxybenzoate (20 g, 0.076 mol) was heated at 180° C. for 6 h. After confirming the completion of reaction by TLC, the reaction mixture was allowed to cool to 60° C. and 250 mL of water was added. The aqueous reaction mixture was stirred at 60° C. for 30 min and the solid was collected by filtration and dried under vacuum. The solid compound obtained (20 g, 86%) was taken into the next step without any further purification. $^1$H NMR (400 MHz, DMSO-d$_6$): δ 11.43 (brs, 1H), 10.70 (brs, 1H), 7.53 (d, J=2.0 Hz, 1H), 7.43 (d, J=1.6 Hz, 1H), 3.89 (s, 3H); ESI-MS: Calculated mass: 269.96; Observed mass: 269.0 [M−H]$^-$.

Step 6: 6-Bromo-2,4-dichloro-8-methoxyquinazoline

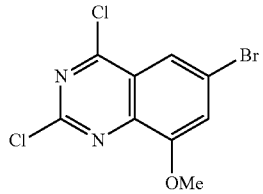 [SMILES: COc1cc(Br)cc2c(Cl)nc(Cl)nc12]

To a stirred suspension of 6-bromo-8-methoxyquinazoline-2,4(1H,3H)-dione (20 g, 0.074 mol) in 200 mL of phosphorousoxychloride (POCl$_3$) were added dropwise diisopropyl ethylamine (10.7 mL, 0.059 mol) and N,N-dimethylformamide (3 mL) sequentially. The reaction mixture was maintained at 130° C. overnight. POCl$_3$ was removed by distillation and the crude residue was azeotroped twice with toluene. The resulting crude product was poured into ice-cold water (1 L) and stirred for 1 h at room temperature. The precipitated yellow solid was collected by filtration and dried under vacuum to afford the title compound (18 g, 78%). $^1$H NMR (400 MHz, DMSO-d$_6$): δ 7.92 (d, J=2.0 Hz, 1H), 7.73 (d, J=2.0 Hz, 1H), 4.04 (s, 3H); ESI-MS: Calculated mass: 305.90; Observed mass: 307.00 [M+H]$^+$.

Step 7: 4-(6-Bromo-2-chloro-8-methoxyquinazolin-4-yl)morpholine

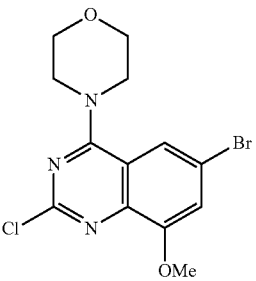 [SMILES: COc1cc(Br)cc2c(N3CCOCC3)nc(Cl)nc12]

To a stirred solution of 6-bromo-2,4-dichloro-8-methoxyquinazoline (18 g, 0.058 mol) and diisoproylethylamine (30 mL, 0.174 mol) in dichloromethane (180 mL) was added morpholine (5.1 mL, 0.058 mol) dropwise slowly at 0° C. After the addition was complete, the reaction mixture was stirred until TLC analysis indicated complete consumption of starting material (0° C. for 10 min) The reaction mixture was diluted with water (250 mL) and extracted with dichloromethane (2×500 mL). The combined organic layers were washed with brine, dried over anhydrous sodium sulfate, filtered and concentrated under reduced pressure. The crude product was purified using column chromatography (100-200 mesh silica gel, 30% EtOAc in hexane) to afford the title compound as a yellow solid (12 g, 57%). $^1$H NMR (400 MHz, DMSO-d$_6$): δ 7.63 (d, J=1.2 Hz, 1H), 7.44 (d, J=2.0 Hz, 1H), 3.94 (s, 3H), 3.80-3.74 (m, 8H); ESI-MS: Calculated mass: 356.99; Observed mass: 358.0 [M+H]$^+$.

Step 8: N-(3-(2-Chloro-8-methoxy-4-morpholino-quinazolin-6-yl)-2-fluorophenyl)-2,6-difluorobenzenesulfonamide

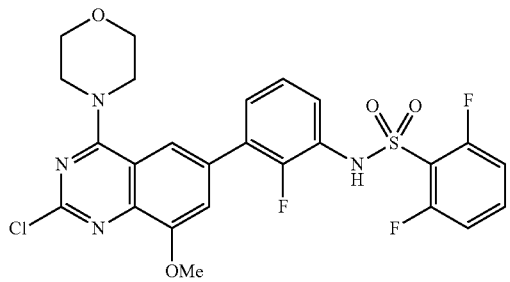 [SMILES: COc1cc(-c2cccc(NS(=O)(=O)c3c(F)cccc3F)c2F)cc2c(N3CCOCC3)nc(Cl)nc12]

To a 100 mL round bottom flask were added 4-(6-bromo-2-chloro-8-methoxyquinazolin-4-yl)morpholine (250 mg, 0.7 mmol), N,N-dimethylformamide (8 mL), water (2 mL), 2,6-difluoro-N-(2-fluoro-3-(4,4,5,5-tetramethyl-1,3,2-dioxaborolan-2-yl) phenyl) benzene sulfonamide (375 mg, 0.9 mmol) and sodium carbonate (150 mg, 1.4 mmol) The reaction mixture was degassed with nitrogen for 10 min. To this mixture was added Pd(PPh$_3$)$_2$Cl$_2$ (48 mg, 0.07 mmol) was added and the resulting mixture was degassed again for 5 min. The reaction mixture was stirred at 80° C. for 3 h. Water (50 mL) was added to the reaction mixture followed by extraction with ethyl acetate (2×100 mL). The combined organic layers were washed with brine, dried over anhydrous sodium sulfate, filtered and concentrated under reduced pressure. The crude product was purified using column chromatography (100-200 mesh silica gel, 2% MeOH in DCM) to afford the title compound (175 mg, 44%). $^1$H NMR (400 MHz, DMSO-d$_6$): δ 10.9 (s, 1H), 7.77-7.70 (m, 1H), 7.55 (t, J=7.68 Hz, 1H), 7.49 (s, 1H), 7.37-7.25 (m, 5H), 3.94 (s, 3H), 3.81-3.73 (m, 8H); ESI-MS: Calculated mass: 564.08; Observed mass: 565.20 [M+H]$^+$.

Step 9: 2,6-Difluoro-N-(2-fluoro-3-(8-methoxy-2-(4-(3-methylureido)phenyl)-4-morpholinoquinazolin-6-yl)phenyl)benzenesulfonamide

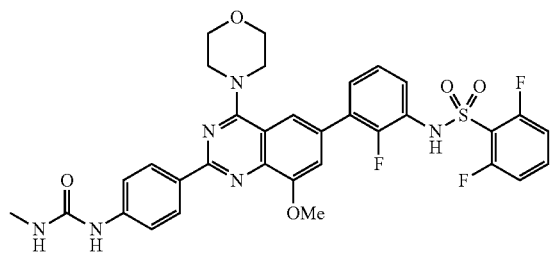 [SMILES: CNC(=O)Nc1ccc(-c2nc(N3CCOCC3)c3cc(-c4cccc(NS(=O)(=O)c5c(F)cccc5F)c4F)cc(OC)c3n2)cc1]

To a 100 mL round bottom flask, were added N-(3-(2-chloro-8-methoxy-4-morpholinoquinazolin-6-yl)-2-fluorophenyl)-2,6-difluorobenzenesulfonamide (175 mg, 0.31 mmol), N,N-dimethylformamide (8 mL), water (2 mL), 1-methyl-3-(4-(4,4,5,5-tetramethyl-1,3,2-dioxaborolan-2-yl)phenyl)urea (130 mg, 0.46 mmol) and sodium carbonate (131 mg, 1.24 mmol) The reaction mixture was degassed with nitrogen for 10 min. To this mixture was added Pd(PPh$_3$)$_2$Cl$_2$ (21 mg, 0.03 mmol) and the resulting mixture was degassed with nitrogen again for 5 min. The reaction mixture was stirred overnight at 80° C. Water (50 mL) was added to the reaction mixture followed by extraction with ethyl acetate (2×100 mL). The organic layer was washed with brine, dried over anhydrous sodium sulfate, filtered and concentrated under reduced pressure. The crude product was purified using column chromatography (100-200 mesh silica gel, 3% MeOH in DCM) to afford the title compound (80 mg, 38%). $^1$H NMR (400 MHz, DMSO-d$_6$): δ 10.89 (s, 1H), 8.79 (s, 1H), 8.35 (d, J=8.8 Hz, 2H), 7.74-7.70 (m, 1H), 7.57-7.53 (m, 3H), 7.49 (s, 1H), 7.35-7.28 (m, 4H), 7.21 (s, 1H), 7.09-7.08 (m, 1H), 4.0 (s, 3H), 3.80-3.75 (m, 8H), 2.66 (d, J=4.4 Hz, 3H); ESI-MS: Calculated mass: 678.19; Observed mass: 679.3 [M+H]$^+$.

Example 2

N-(3-(2-(1H-indazol-4-yl)-8-methoxy-4-morpholino quinazolin-6-yl)-2-fluorophenyl) propane-1-sulfonamide

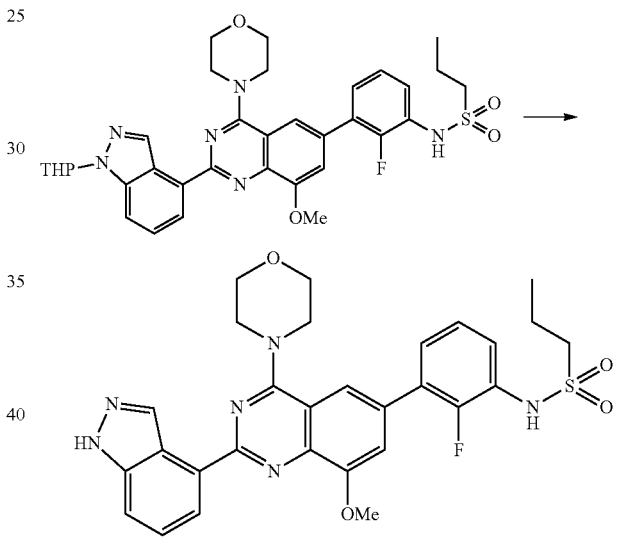

To a stirred solution of N-(2-fluoro-3-(8-methoxy-4-morpholino-2-(1-(tetrahydro-2H-pyran-2-yl)-1H-indazol-4-yl) quinazolin-6-yl)phenyl)propane-1-sulfonamide (200 mg, 0.312 mmol) in dichloromethane (3 mL) was added trifluoroacetic acid (3 mL) dropwise at room temperature and the reaction mixture was stirred for 1 h at room temperature. The reaction mixture was evaporated under reduced pressure, the residue was neutralized with saturated sodium bicarbonate solution and then extracted with ethyl acetate (3×50 mL). The combined organic layers were washed with brine solution, dried over anhydrous sodium sulfate, filtered and evaporated under reduced pressure. The crude product was purified using preparative HPLC to afford the title compound (26 mg, 14%). $^1$H NMR (400 MHz, DMSO-d$_6$): δ 13.21 (s, 1H), 9.75 (s, 1H), 9.17 (s, 1H), 8.37 (d, J=6.8 Hz, 1H), 7.72 (s, 1H), 7.69 (s, 1H), 7.58 (t, J=7.2 Hz, 1H), 7.56-7.50 (m, 1H), 7.47 (s, 2H), 7.34 (t, J=8.0 Hz, 1H), 4.12 (s, 3H), 3.86-3.84 (m, 8H), 3.19-3.15 (m, 2H), 1.82-1.76 (m, 2H), 1.02-0.99 (m, 3H); ESI-MS: Calculated mass: 576.20; Observed mass: 577.40 [M+H]$^+$.

Example 3

N-(3-(2-(6-((2-aminoethyl)amino)pyridin-3-yl)-4-morpholinopyrido[3,2-d]pyrimidin-6-yl)-2-fluorophenyl)propane-1-sulfonamide

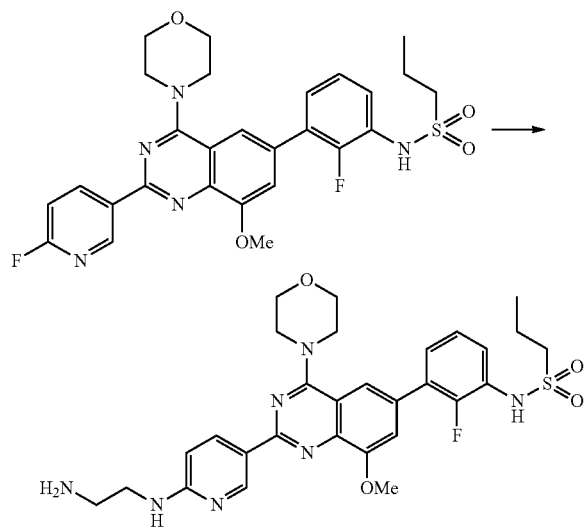

A mixture of N-(2-fluoro-3-(2-(6-fluoropyridin-3-yl)-8-methoxy-4-morpholinoquinazolin-6-yl)phenyl)propane-1-sulfonamide (190 mg) and ethylenediamine (1.9 mL) was heated at 70° C. for 1 h in a sealed tube. After confirming completion of the reaction by TLC, the reaction mixture was directly evaporated under reduced pressure. The crude product was purified using preparative HPLC to afford the title compound (70 mg, 34%). $^1$H NMR (400 MHz, DMSO-d$_6$): δ 9.10 (s, 1H), 8.38 (d, J=8.8 Hz, 1H), 7.58 (brs, 1H), 7.39 (t, J=7.2 Hz, 1H), 7.34 (s, 1H), 7.14-7.07 (m, 3H), 7.59 (d, J=8.8 Hz, 1H), 4.01 (s, 3H), 3.80-3.77 (m, 8H), 2.96 (t, J=7.2 Hz, 2H), 2.84 (t, J=5.6 Hz, 2H), 2.79 (t, J=6.4 Hz, 2H), 2.78-2.61 (m, 2H), 1.75-1.69 (m, 2H), 0.94-0.85 (m, 3H); ESI-MS: Calculated mass: 595.24; Observed mass: 596.2 [M+H]$^+$.

Example 4

N-(3-(2-(6-aminopyridin-3-yl)-8-(2-hydroxyethoxy)-4-morpholino quinazolin-6-yl)-2-fluorophenyl)propane-1-sulfonamide

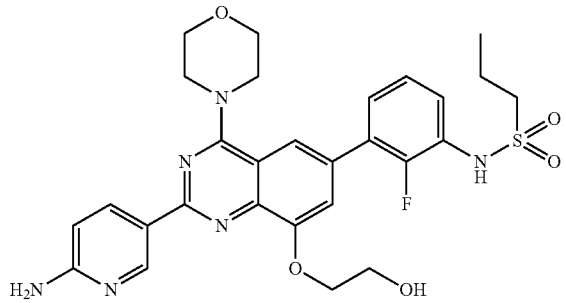 [SMILES: CCCS(=O)(=O)Nc1cccc(-c2cc(OCCO)c3nc(-c4ccc(N)nc4)nc(N4CCOCC4)c3c2)c1F]

Step 1:
6-Bromo-2-chloro-4-morpholinoquinazolin-8-ol

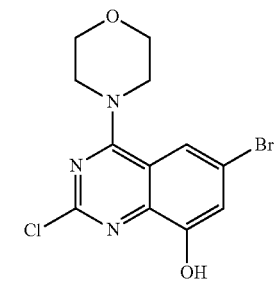 [SMILES: Oc1cc(Br)cc2c(N3CCOCC3)nc(Cl)nc12]

To a stirred solution of 4-(6-bromo-2-chloro-8-methoxyquinazolin-4-yl)morpholine (2 g, 0.0056 mol) in dichloromethane (40 mL) was added borontribromide (8.42 g, 0.033 mol) dropwise at 0° C. The reaction mixture was stirred at room temperature for 16 h and poured into ice-cold water. The resulting mixture was neutralized with saturated sodium bicarbonate solution to pH 7 and extracted with dichloromethane (2×100 mL). The combined organic layers were dried over anhydrous sodium sulfate, filtered and evaporated under reduced pressure to afford the title compound (800 mg, crude). This product was used in the next step without further purification. ESI-MS: Calculated mass: 342.97; Observed mass: 342.10[M−H]$^-$.

Step 2: 2-((6-Bromo-2-chloro-4-morpholinoquinazolin-8-yl)oxy)ethanol

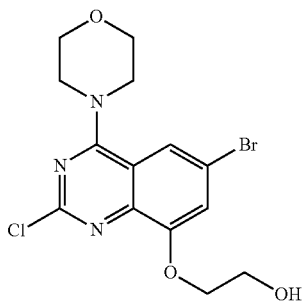 [SMILES: OCCOc1cc(Br)cc2c(N3CCOCC3)nc(Cl)nc12]

To a stirred suspension of 6-bromo-2-chloro-4-morpholinoquinazolin-8-ol (0.8 g, 0.0023 mol) and potassium carbonate (1.12 g, 0.0081 mol) in N,N-dimethylformamide (15 mL) was added 2-bromoethanol (0.43 g, 0.0034 mol) at room temperature. The reaction temperature was increased to 80° C. and stirring was continued for another 18 h. Water (50 mL) was added to the reaction mixture followed by extraction with ethyl acetate (3×50 mL). The organic layers were combined, dried over anhydrous sodium sulfate, filtered and evaporated. The crude product was purified using column chromatography (100-200 mesh silica gel; 2% MeOH in DCM) to afford the title compound (200 mg, 22%). $^1$H NMR (400 MHz, DMSO-d$_6$): δ 7.64 (d, J=1.2 Hz, 1H), 7.49 (d, J=1.68 Hz, 1H), 4.98 (t, J=5.2 Hz, 1H), 4.18 (t, J=4.4 Hz, 2H), 3.82-3.74 (m, 10H); ESI-MS: Calculated mass: 387.0; Observed mass: 388.20 [M+H]$^+$.

Step 3: N-(3-(2-Chloro-8-(2-hydroxyethoxy)-4-morpholinoquinazolin-6-yl)-2-fluorophenyl)propane-1-sulfonamide

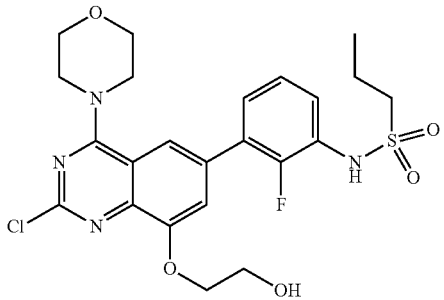 [SMILES: CCCS(=O)(=O)Nc1cccc(-c2cc(OCCO)c3nc(Cl)nc(N4CCOCC4)c3c2)c1F]

A stirred mixture of 2-((6-bromo-2-chloro-4-morpholinoquinazolin-8-yl)oxy)ethanol (0.2 g, 0.000516 mol), N-(2-fluoro-3-(4,4,5,5-tetramethyl-1,3,2-dioxaborolan-2-yl)phenyl)propane-1-sulfonamide (0.21 g, 0.00062 mol) and sodium carbonate (0.1 g, 0.001 mol) in 25 mL of DMF and H$_2$O (4:1 mixture) was degassed with nitrogen for 15 min. To this mixture was added Pd(PPh$_3$)$_2$Cl$_2$ (36 mg, 0.000051 mol) and the resulting mixture was degassed with nitrogen again for 10 min. The reaction mixture was stirred at 80° C. for 1 h. The reaction mixture was cooled to room temperature, water (50 mL) was added and the resulting mixture was extracted with ethyl acetate (3×50 mL). The organic layers were combined, washed with water followed by brine solution and concentrated under reduced pressure. The crude product was purified using column chromatography (100-200 mesh silica gel; 2% MeOH in DCM) to afford the title compound (180 mg, 66%). $^1$H NMR (400 MHz, DMSO-d6): δ 9.73 (d, J=7.6 Hz, 1H), 7.69 (s, 1H), 7.64-7.47 (m, 3H), 7.34-7.29 (m, 1H), 4.93 (t, J=5.2 Hz, 1H), 4.31 (t, J=4.8 Hz, 2H), 3.92-3.76 (m, 10H), 3.17-3.10 (m, 2H), 1.8-1.74 (m, 2H), 1.01-0.96 (m, 3H); ESI-MS: Calculated mass: 524.13; Observed mass: 525.2 [M+H]$^+$.

Step 4: N-(3-(2-(6-Aminopyridin-3-yl)-8-(2-hydroxyethoxy)-4-morpholino quinazolin-6-yl)-2-fluorophenyl)propane-1-sulfonamide

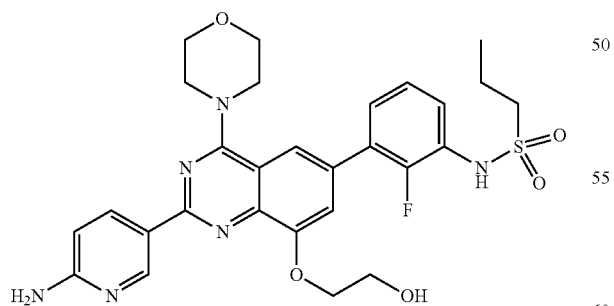

A stirred mixture of N-(3-(2-chloro-8-(2-hydroxyethoxy)-4-morpholinoquinazolin-6-yl)-2-fluorophenyl)propane-1-sulfonamide (0.18 g, 0.00034 mol), 5-(4,4,5,5-tetramethyl-1,3,2-dioxaborolan-2-yl)pyridin-2-amine (98 mg, 0.00044 mol) and sodium carbonate (0.14 g, 0.0013 mol) in 25 mL of DMF and H$_2$O (4:1 mixture) was degassed with nitrogen for 15 min. To this mixture was added Pd(PPh$_3$)$_2$Cl$_2$ (24 mg, 0.000034 mol) and the resulting mixture was degassed with nitrogen again for 10 min. The reaction mixture was stirred at 80° C. for 1 h. The reaction mixture was cooled to room temperature, water (50 mL) was added and the resulting mixture was extracted with ethyl acetate (3×50 mL). The organic layers were combined, washed with water followed by brine solution and concentrated under reduced pressure. The crude product was purified using preparative HPLC to afford the title compound (8 mg, 4%). $^1$H NMR (400 MHz, DMSO-d6): δ 9.72 (s, 1H), 9.05 (d, J=2.4 Hz, 1H), 8.4 (dd, J'=8.8 Hz, J"=2.0 Hz, 1H), 7.63 (s, 1H), 7.52 (t, J=7.2 Hz, 1H), 7.46-7.43 (m, 2H), 7.31 (t, J=8.0 Hz, 1H), 6.56 (d, J=8.4 Hz, 1H), 6.51 (brs, 2H), 4.98 (t, J=4.4 Hz, 1H), 4.29 (t, J=4.8 Hz, 2H), 3.88-3.77 (m, 10H), 3.16 (t, J=8.0 Hz, 2H), 1.81-1.73 (m, 2H), 1.05 (t, J=6.8 Hz, 3H); ESI-MS: Calculated mass: 582.21; Observed mass: 583.1 [M+H]$^+$.

Example 5

N-(3-(2-(6-aminopyridin-3-yl)-4,8-dimorpholinoquinazolin-6-yl)-2-fluorophenyl)-3-fluoropropane-1-sulfonamide

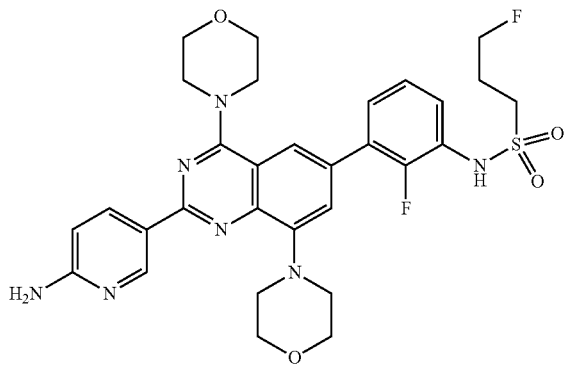 [SMILES: Nc1ccc(-c2nc(N3CCOCC3)c3cc(-c4cccc(NS(=O)(=O)CCCF)c4F)cc(N4CCOCC4)c3n2)cn1]

Step 1: 3-Morpholino-2-nitrobenzoic acid

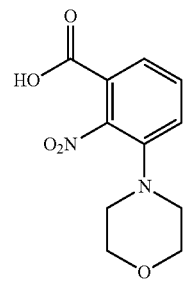 [SMILES: O=C(O)c1cccc(N2CCOCC2)c1[N+](=O)[O-]]

A stirred mixture of 3-chloro2-nitrobenzoic acid (5 g, 0.024 mol) and morpholine (40 mL) was heated at 130° C. for 48 h. The reaction mixture was cooled to room temperature, water (150 mL) was added and the resulting mixture was acidified with 1N hydrochloric acid to pH 2. The solid separated after 1 h was collected by filtration and dried under vacuum to afford the title compound (6.2 g, 98%). $^1$H NMR (400 MHz, DMSO-d$_6$): δ 13.9 (brs, 1H), 7.83-7.77 (m, 2H), 7.35 (t, J=7.6 Hz, 1H), 3.65-3.62 (m, 4H), 2.90-2.88 (m, 4H); ESI-MS: Calculated mass: 252.07; Observed mass: 251.0 [M−H]⁻.

Step 2: Methyl 3-morpholino-2-nitrobenzoate

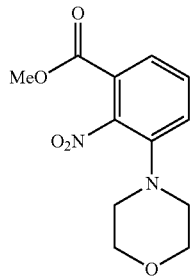

To a stirred suspension of 3-morpholino-2-nitrobenzoic acid (6.2 g, 0.024 mol) and potassium carbonate (6.78 g, 0.049 mol) in N,N-dimethylformamide (62 mL), was added methyl iodide (6.98 g, 0.049 mol) at 0° C. The reaction mixture was stirred for 3 h at room temperature. Ice-cold water (300 mL) was added and the resulting mixture was stirred for 30 min at room temperature. The solid separated out was collected by filtration and dried under vacuum to afford the title compound (5.6 g, 85%). $^1$H NMR (400 MHz, DMSO-d6): δ 7.86 (dd, J'=7.6 Hz, J"=1.6 Hz, 1H), 7.79 (dd, J'=7.6 Hz, J"=1.6 Hz, 1H), 7.71 (t, J=8.4 Hz, 1H), 3.83 (s, 3H), 3.65-3.63 (m, 4H), 2.91-2.89 (m, 4H).

Step 3: Methyl 2-amino-3-morpholinobenzoate

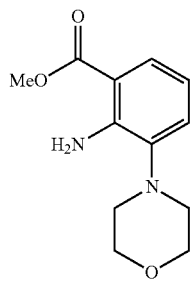

A mixture of methyl 3-morpholino-2-nitrobenzoate (5.6 g) and 10% Pd—C(1.5 g) in 56 mL of methanol was stirred for 2 h at 60 PSI hydrogen pressure in a Parr hydrogenation apparatus. After confirming completion of reaction by TLC, the reaction mixture was filtered through Celite® reagent and the Celite® reagent was washed with methanol (200 mL). The filtrate was concentrated under reduced pressure and the solid obtained was dried under high vacuum to afford the title compound (4.5 g, 97%). $^1$H NMR (400 MHz, DMSO-d$_6$): δ 7.52 (d, J=6.8 Hz, 1H), 7.17 (d, J=6.8 Hz, 1H), 6.56 (t, J=7.68 Hz, 1H), 6.4 (brs, 2H), 3.79-3.75 (m, 7H), 2.78-2.76 (m, 4H); ESI-MS: Calculated mass: 236.12; Observed mass: 237.10 [M+H]⁺.

Step 4: Methyl 2-amino-5-bromo-3-morpholinobenzoate

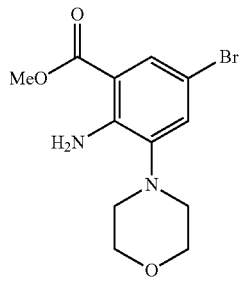

To a stirred solution of methyl 2-amino-3-morpholinobenzoate (4.5 g, 0.02044 mol) in acetic acid (45 mL) was added bromine (3.92 g, 0.024 mol) dropwise at 0° C. The reaction mixture was stirred at room temperature for 1 h. After the completion of the reaction, the reaction mixture was poured into 1 L of cold water and the resulting mixture was stirred for 30 min at room temperature, then extracted with ethyl acetate (2×500 mL). The combined organic layers were washed with saturated sodium bicarbonate solution followed by brine solution, dried over anhydrous sodium sulfate and filtered. The filtrate was concentrated under reduced pressure and the crude product was purified using column chromatography (100-200 mesh silica gel, 20% EtOAc in hexane) to afford the title compound (4.4 g, 68%). $^1$H NMR (400 MHz, DMSO-d$_6$): δ 7.61 (d, J=2.0 Hz, 1H), 7.23 (d, J=2.2 Hz, 1H), 6.50 (brs, 2H), 3.80-3.75 (m, 7H), 2.80-2.78 (m, 4H); ESI-MS: Calculated mass: 314.03; Observed mass: 313.20 [M−H]⁻.

Step 5: 6-Bromo-8-morpholinoquinazoline-2,4(1H,3H)-dione

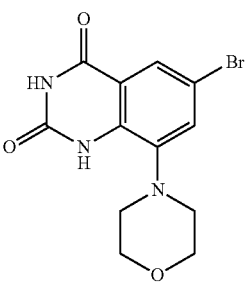 [SMILES: O=c1[nH]c(=O)c2cc(Br)cc(N3CCOCC3)c2[nH]1]

A mixture of urea (8.4 g, 0.14 mol) and methyl 2-amino-5-bromo-3-morpholinobenzoate (4.4 g, 0.014 mol) was heated at 200° C. for 3 h. After confirming the completion of reaction by TLC, the reaction mixture was allowed to cool to 60° C. and 100 mL of water was added. The aqueous reaction mixture was stirred at 100° C. for 15 min and the solid was collected by filtration and dried under vacuum. The solid compound obtained (4 g, 86%) was taken into the next step without further purification. $^1$H NMR (400 MHz, DMSO-d$_6$): δ 7.73 (d, J=2.4 Hz, 1H), 6.60 (d, J=2.4 Hz, 1H), 3.84-3.82 (m, 4H), 2.84-2.82 (m, 4H); ESI-MS: Calculated mass: 325.01; Observed mass: 324.0 [M−H]⁻.

Step 6: 4-(6-Bromo-2,4-dichloroquinazolin-8-yl)morpholine

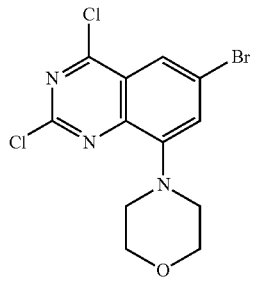 [SMILES: Clc1nc(Cl)c2cc(Br)cc(N3CCOCC3)c2n1]

To a stirred suspension of 6-bromo-8-morpholinoquinazoline-2,4(1H,3H)-dione in 100 mL of phosphorousoxychloride (POCl$_3$) were added dropwise diisopropylethylamine (1.41 g, 0.0109 mol) and N,N-dimethylformamide (2.5 ml) sequentially. The reaction mixture was maintained at 130° C. overnight. The excess POCl$_3$ was removed by distillation and the crude residue was azeotroped with toluene (2×100 mL). The resulting crude product was poured into ice-cold water and the precipitated solid was collected by filtration and dried under vacuum to afford the title compound (4.4 g), which was used in the next step without further purification. $^1$H NMR (400 MHz, DMSO-d$_6$): δ 7.93 (d, J=1.6 Hz, 1H), 7.51 (d, J=2.0 Hz, 1H), 3.83-3.81 (m, 4H), 3.40-3.38 (m, 4H).

Step 7: 4,4'-(6-Bromo-2-chloroquinazoline-4,8-diyl)dimorpholine

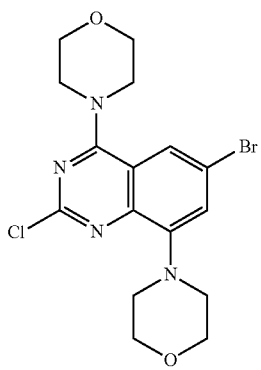 [SMILES: Clc1nc(N2CCOCC2)c2cc(Br)cc(N3CCOCC3)c2n1]

To a stirred solution of 4-(6-bromo-2,4-dichloroquinazolin-8-yl)morpholine (4.4 g, 0.012 mol) and diisoproylethylamine (4.71 g, 0.036 mol) in dichloromethane (130 mL) was added morpholine (1.062 g, 0.012 mol) dropwise slowly at 0° C. After the addition was complete, the reaction mixture was stirred at 0° C. for 30 min. The reaction mixture was diluted with water (200 mL) and extracted with dichloromethane (2×500 mL). The combined organic layers were washed with brine, dried over anhydrous sodium sulfate, filtered and concentrated under reduced pressure. The crude product was purified using column chromatography (100-200 mesh silica gel, 20% EtOAc in hexane) to afford the title compound (3.2 g, 64%). $^1$H NMR (400 MHz, DMSO-d$_6$): δ 7.6 (d, J=2.0 Hz, 1H), 7.23 (d, J=2.0 Hz, 1H), 3.80-3.73 (m, 12H), 3.31-3.28 (m, 4H); ESI-MS: Calculated mass: 412.03; Observed mass: 413.20 [M+H]$^+$.

Step 8: 4,4'-(6-bromo-2-chloroquinazoline-4,8-diyl)dimorpholine

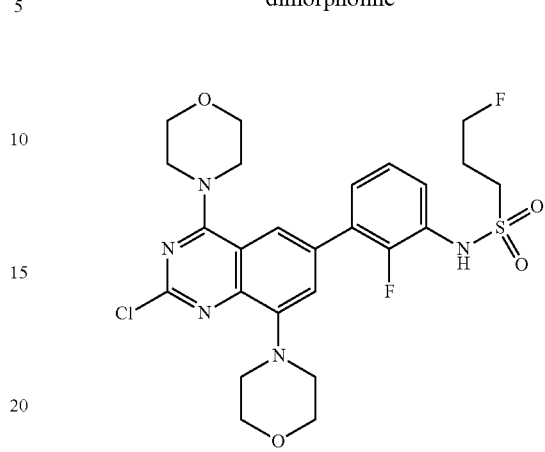

A stirred mixture of 4,4'-(6-bromo-2-chloroquinazoline-4,8-diyl)dimorpholine (0.6 g, 0.0014 mol), 3-fluoro-N-(2-fluoro-3-(4,4,5,5-tetramethyl-1,3,2-dioxaborolan-2-yl)phenyl)propane-1-sulfonamide (0.788 g, 0.00218 mol) and sodium carbonate (0.308 g, 0.0029 mol) in 30 mL of DMF and H$_2$O (4:1 mixture) was degassed with nitrogen for 15 min. To this mixture was added Pd(PPh$_3$)$_2$Cl$_2$ (103 mg, 0.00014 mol) and the resulting mixture was degassed with nitrogen again for 10 min. The reaction mixture was stirred at 80° C. for 1 h. The reaction mixture was cooled to room temperature, water (100 mL) was added and the resulting mixture was extracted with ethyl acetate (2×200 mL). The organic layers were combined, washed with water followed by brine solution and concentrated under reduced pressure. The crude product was purified using column chromatography (100-200 mesh silica gel; 50% EtOAc in hexane) to afford the title compound (150 mg, 18%). NMR (400 MHz, DMSO-d$_6$): δ 9.86 (brs, 1H), 7.62 (s, 1H), 7.54 (t, J=6.4 Hz, 1H), 7.45 (t, J=6.8 Hz, 1H), 7.31 (t, J=8.0 Hz, 2H), 6.62 (t, J=6.0 Hz, 1H), 4.5 (t, J=6.0 Hz, 1H), 3.80-3.76 (m, 12H), 3.31-3.27 (m, 4H), 3.31-3.325 (m, 2H), 2.17-2.10 (m, 2H); ESI-MS: Calculated mass: 567.15; Observed mass: 566.30 [M−H]$^-$.

Step 9: 4,4'-(6-Bromo-2-chloroquinazoline-4,8-diyl)dimorpholine

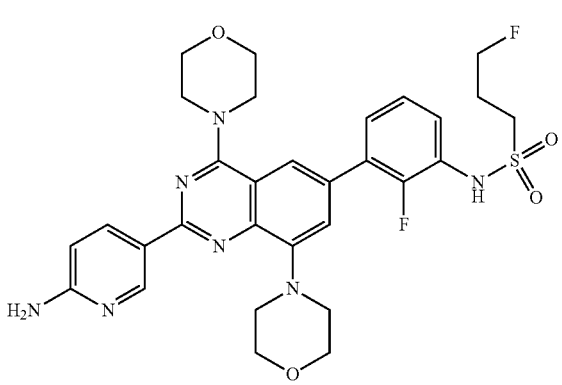 [SMILES: Nc1ccc(-c2nc(N3CCOCC3)c3cc(-c4cccc(NS(=O)(=O)CCCF)c4F)cc(N4CCOCC4)c3n2)cn1]

A stirred mixture of N-(3-(2-chloro-4,8-dimorpholinoquinazolin-6-yl)-2-fluorophenyl)-3-fluoropropane-1-sulfonamide (0.15 g, 0.00026 mol), 5-(4,4,5,5-tetramethyl-1,3,2-dioxaborolan-2-yl)pyridin-2-amine (75 mg, 0.00034 mol) and sodium carbonate (0.112 g, 0.0010 mol) in 25 mL of DMF and H$_2$O (4:1 mixture) was degassed with nitrogen for 15 min. To this mixture was added Pd(PPh$_3$)$_2$Cl$_2$ (18 mg, 0.000026 mol) and the resulting mixture was degassed with nitrogen again for 10 min. The reaction mixture was stirred at 80° C. for 1 h. The reaction mixture was cooled to room temperature, water (50 mL) was added and the resulting mixture was extracted with ethyl acetate (3×50 mL). The organic layers were combined, washed with water followed by brine solution and concentrated under reduced pressure. The crude product was purified using preparative HPLC to afford the title compound (30 mg, 18%). $^1$H NMR (400 MHz, DMSO-d6): δ 9.85 (brs, 1H), 9.02 (d, J=6.8 Hz, 1H), 8.33 (dd, J'=8.8 Hz, J"=2.4 Hz, 1H), 7.6 (s, 1H), 7.52 (t, J=7.2 Hz, 1H), 7.43 (t, J=6.0 Hz, 1H), 7.3 (t, J=8.4 Hz, 1H), 7.2 (s, 1H), 6.54 (d, J=8.4 Hz, 1H), 6.44 (brs, 2H), 4.62 (t, J=6.0 Hz, 1H), 4.50 (t, J=5.6 Hz, 1H), 3.9 (brs, 4H), 3.81-3.77 (m, 8H), 3.50-3.40 (m, 4H), 3.33-3.20 (m, 2H), 2.21-2.09 (m, 2H); ESI-MS: Calculated mass: 625.23; Observed mass: 626.4 [M+H]$^+$.

Example 6

N-(3-(2-(2-aminopyrimidin-5-yl)-8-methoxy-4-morpholinoquinazolin-6-yl)-2,4-difluorophenyl)propane-1-sulfonamide

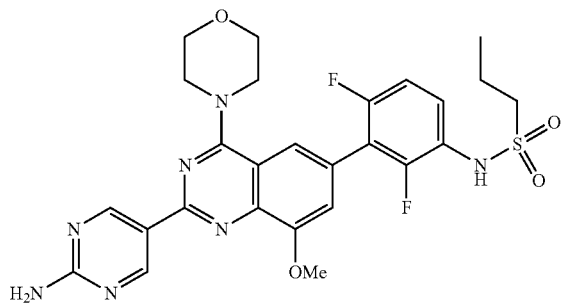 [SMILES: CCCS(=O)(=O)Nc1ccc(F)c(-c2cc(OC)c3nc(-c4cnc(N)nc4)nc(N4CCOCC4)c3c2)c1F]

Step 1: 4-(2-chloro-8-methoxy-6-(4,4,5,5-tetramethyl-1,3,2-dioxaborolan-2-yl)quinazolin-4-yl)morpholine

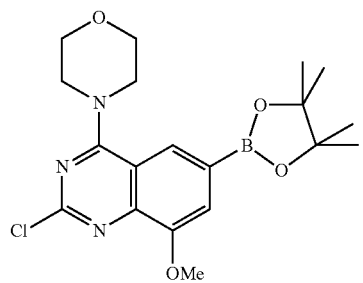 [SMILES: COc1cc(B2OC(C)(C)C(C)(C)O2)cc2c(N3CCOCC3)nc(Cl)nc12]

A 250 mL round bottom flask was charged with 4-(6-bromo-2-chloro-8-methoxyquinazolin-4-yl)morpholine (2 g; 0.0056 mol), toluene (150 mL), Bis(pinacolato)diboron (1.7 g, 0.0067 mol) and KOAc (1.09 g, 0.011 mol). The reaction mixture was degassed with nitrogen for 15 min. To this mixture was added Pd(dppf)Cl$_2$DCM (228 mg, 0.00028 mol) and the resulting mixture was degassed again with nitrogen for 10 min. The reaction mixture was stirred for 3 h at 80° C. The reaction mixture was filtered through Celite® reagent and the Celite® reagent was washed with toluene (200 mL). The filtrate was evaporated under reduced pressure and the residue was washed with hexane (200 mL) to provide the title compound as solid (2 g, 88%). The crude product was used in the next step without further purification. NMR (400 MHz, DMSO-d$_6$): δ 7.8 (s, 1H), 7.36 (s, 1H), 3.93 (s, 3H), 3.87-3.73 (m, 8H), 1.32 (s, 12H); ESI-MS: Calculated mass: 405.16; Observed mass: 406.20 [M+H]$^+$.

Step 2: N-(3-(2-chloro-8-methoxy-4-morpholinoquinazolin-6-yl)-2,4-difluorophenyl) propane-1-sulfonamide

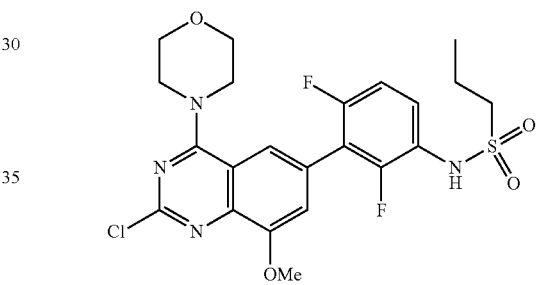

A 100 mL round bottom flask was charged with N-(3-bromo-2,4-difluorophenyl)propane-1-sulfonamide (0.65 g, 0.002 mol), 4-(2-chloro-8-methoxy-6-(4,4,5,5-tetramethyl-1,3,2-dioxaborolan-2-yl)quinazolin-4-yl)morpholine (0.83 g, 0.002 mol), DME (20 mL) and 2M aqueous sodium carbonate (0.438 g in 2 mL water). The reaction mixture was degassed with nitrogen for 15 min. To this mixture was added Pd(dppf)Cl$_2$DCM (169 mg, 0.0002 mol) was added and the resulting mixture was degassed with nitrogen again for 10 min. The reaction mixture was stirred for 2 h at 90° C. The reaction mixture was diluted with water (75 mL) and the resulting mixture was extracted with ethyl acetate (2×250 mL). The combined organic layers were washed with brine, dried over anhydrous sodium sulfate, filtered and evaporated under reduced pressure. The crude product was purified using column chromatography (230-400 mesh silica gel; 1% MeOH in DCM) to afford the title compound (200 mg, 18%). $^1$H NMR (400 MHz, DMSO-d$_6$): δ 9.70 (brs, 1H), 7.62 (s, 1H), 7.50-7.47 (m, 1H), 7.39 (s, 1H), 7.27 (t, J=8.4 Hz, 1H), 3.93 (s, 3H), 3.80-3.74 (m, 8H), 3.15-3.12 (m, 2H), 1.79-1.74 (m, 2H), 0.98 (t, J=7.2 Hz, 3H); ESI-MS: Calculated mass: 512.10; Observed mass: 513.20 [M+H]$^+$.

Step 3: N-(3-(2-(2-aminopyrimidin-5-yl)-8-methoxy-4-morpholinoquinazolin-6-yl)-2,4-difluorophenyl)propane-1-sulfonamide

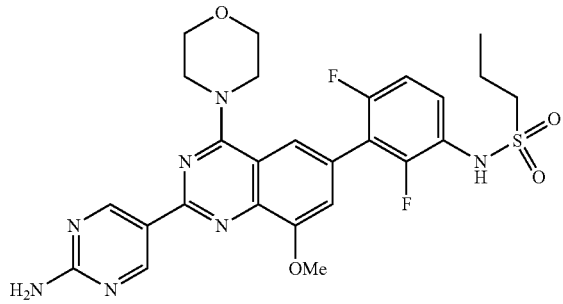 [SMILES: CCCS(=O)(=O)Nc1ccc(F)c(-c2cc(OC)c3nc(-c4cnc(N)nc4)nc(N4CCOCC4)c3c2)c1F]

A 50 mL round bottom flask was charged with N-(3-(2-chloro-8-methoxy-4-morpholinoquinazolin-6-yl)-2,4-difluorophenyl)propane-1-sulfonamide (0.1 g, 0.00019 mol), 5-(4,4,5,5-tetramethyl-1,3,2-dioxaborolan-2-yl)pyrimidin-2-amine (0.063 g, 0.00028 mol), sodium carbonate (0.060 g, 0.00056 mol), N,N-dimethylformamide (4 mL) and water (1 mL). The reaction mixture was degassed with nitrogen for 10 min. To this mixture Pd(PPh$_3$)$_2$Cl$_2$ (0.013 g, 0.000019 mol) was added and the resulting mixture was degassed with nitrogen again for 5 min. The reaction mixture was stirred for 16 h at 80° C. The reaction mixture was passed through Celite® reagent, the Celite® reagent was washed with ethyl acetate (50 mL) and the filtrate was evaporated under reduced pressure. The crude product was purified using column chromatography (100-200 mesh silica gel; 3% MeOH in DCM) to afford the title compound (35 mg, 31%). $^1$H NMR (400 MHz, DMSO-d$_6$): δ 9.69 (brs, 1H), 9.19 (s, 2H), 7.59 (s, 1H), 7.51-7.45 (m, 1H), 7.33 (s, 1H), 7.25 (t, J=8.0 Hz, 1H), 7.19 (brs, 2H), 3.98 (s, 3H), 3.79-3.78 (m, 8H), 3.16-3.12 (m, 2H), 1.80-1.74 (m, 2H), 0.99 (t, J=7.2 Hz, 3H); ESI-MS: Calculated mass: 571.18; Observed mass: 570.2 [M−H]$^+$.

Example 7

N-(3-(2-(2-aminopyrimidin-5-yl)-4-morpholinopyrido[3,2-d]pyrimidin-6-yl)-2-fluorophenyl)propane-1-sulfonamide

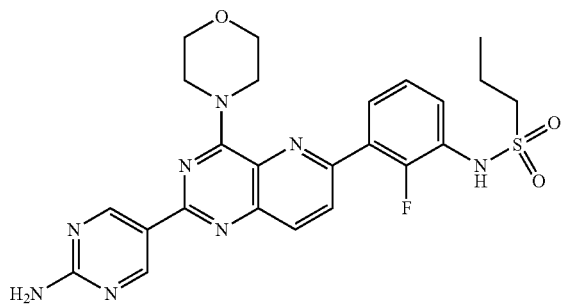 [SMILES: CCCS(=O)(=O)Nc1cccc(-c2ccc3nc(-c4cnc(N)nc4)nc(N4CCOCC4)c3n2)c1F]

Step 1: 6-chloro-3-nitropicolinonitrile

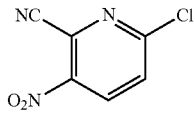

To a stirred mixture of 2,6-dichloro 3-nitropyridine (10 g, 0.0518 mol) in NMP (100 mL) was added CuCN (9.7 g, 0.1083 mol) and the reaction mixture was heated at 180° C. for 1 h. The reaction mixture was cooled to room temperature and the deep brown mixture was poured into ice-cold water (300 mL) and filtered through Celite® reagent. The solid was extracted with 10% methanol in DCM (4×250 mL) and the aqueous layer was extracted with EtOAc (3×500 mL). The pooled organic layers were washed with brine, dried over anhydrous sodium sulfate, filtered and concentrated under reduced pressure. The crude product was purified using column chromatography (100-200 mesh silica gel; 10% EtOAc in hexane) to afford the title compound (3.5 g, 36%). $^1$H NMR (400 MHz, DMSO-d$_6$): δ 8.82 (d, J=8.8 Hz, 1H), 8.17 (d, J=9.6 1H).

Step 2: 3-amino-6-chloropicolinamide

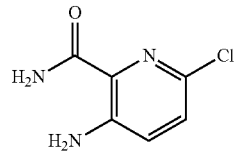

To a stirred mixture of 6-chloro-3-nitropicolinonitrile (3 g, 0.01639 mol) in ethanol (40 mL) was added stannous chloride dehydrate (14.7 g, 0.06515 mol) at room temperature then the resulting mixture was heated at 90° C. for 2 h. The reaction mixture was cooled to room temperature and the ethanol was evaporated under reduced pressure. The residue was diluted with ethyl acetate, neutralized with saturated sodium bicarbonate solution and pH was adjusted to 8-9 with 2M sodium hydroxide solution. The resulting mixture was passed through Celite® reagent and the aqueous layer was extracted with ethyl acetate (2×250 mL). The combined organic layers were washed with brine, dried over anhydrous sodium sulfate, filtered and evaporated under reduced pressure to afford the title compound (2.2 g, 78%). $^1$H NMR (400 MHz, DMSO-d$_6$): δ 7.70 (brs, 1H), 7.41 (brs, 1H), 7.30 (d, J=8.8 Hz, 1H), 7.22 (d, J=8.8 Hz, 1H), 7.0 (brs, 2H); ESI-MS: Calculated mass: 171.02; Observed mass: 170.2. [M−H]$^-$.

Step 3: 6-chloropyrido[3,2-d]pyrimidine-2,4(1H,3H)-dione

To a stirred mixture of 3-amino-6-chloropicolinamide (2.8 g, 0.0163 mol) in 1,4-dioxane (90 ml) was added triphosgene (4.85 g, 0.0163 mol) at room temperature. The reaction mixture was heated at 100° C. for 1.5 h. The reaction mixture was cooled to room temperature, water (1 L) was added and the solid was collected by filtration. The solid was washed with ethyl acetate to afford the title compound (2.3 g, 72%). $^1$H NMR (400 MHz, DMSO-$d_6$): δ 11.61 (brs, 1H), 11.36 (brs, 1H), 7.72 (d, J=8.4 Hz, 1H), 7.62 (d, J=8.4 Hz, 1H); ESI-MS: Calculated mass: 197.0; Observed mass: 196.10 [M−H]$^-$.

Step 4: 2,4,6-trichloropyrido[3,2-d]pyrimidine

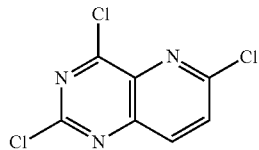 [SMILES: Clc1ccc2nc(Cl)nc(Cl)c2n1]

To a stirred suspension of 6-chloropyrido[3,2-d]pyrimidine-2,4(1H,3H)-dione (2.3 g, 0.0116 mol) in phosphorousoxychloride (30 mL) were added diisopropylethylamine (2.53 g, 0.0195 mol) and N,N-dimethylformamide (1 mL) at room temperature. After the addition was complete, the reaction mixture was stirred at 130° C. for 20 h. The excess phosphorousoxychloride was removed by distillation and the residue was azeotroped with toluene. The dark gummy solid obtained was used in the next step without further purification (2.71 g crude).

Step 5: 4-(2,6-dichloropyrido[3,2-d]pyrimidin-4-yl)morpholine

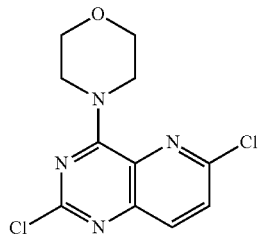 [SMILES: Clc1ccc2nc(Cl)nc(N3CCOCC3)c2n1]

To a stirred solution of 2,4,6-trichloropyrido[3,2-d]pyrimidine (2.71 g, 0.0116 mol) and diisopropylethylamine (4.49 g, 0.0348 mol) in dichloromethane (50 mL) morpholine (1.01 g, 0.0116 mol) was added drowpise at 0° C. The reaction mixture was stirred for 30 min at 0° C. Water (100 mL) was added and the reaction mixture was extracted with dichloromethane (2×250 mL). The combined organic layers were washed with brine, dried over anhydrous sodium sulfate, filtered and evaporated under reduced pressure. The crude product was purified using column chromatography (100-200 mesh silica gel; 10% EtOAc in hexane) to afford the title compound (2.2 g, 66%). $^1$H NMR (400 MHz, DMSO-$d_6$): δ 8.12 (d, J=8.8 Hz, 1H), 7.90 (d, J=8.8 Hz, 1H), 4.94-4.90 (brs, 4H), 3.78-3.77 (m, 4H); ESI-MS: Calculated mass: 284.02; Observed mass: 285.10 [M+H]$^+$.

Step 6: N-(3-(2-chloro-4-morpholinopyrido[3,2-d]pyrimidin-6-yl)-2-fluorophenyl)propane-1-sulfonamide

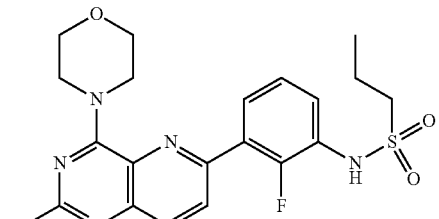

To a stirred solution of 4-(2,6-dichloropyrido[3,2-d]pyrimidin-4-yl)morpholine (0.5 g, 0.00176 mol) and N-(2-fluoro-3-(4,4,5,5-tetramethyl-1,3,2-dioxaborolan-2-yl)phenyl)propane-1-sulfonamide (0.6 g, 0.00175 mol) in acetonitrile (20 mL) was added an aqueous solution of potassium carbonate (486 mg in 2.5 mL water, 0.0035 mol). The reaction mixture was degassed with nitrogen for 15 min. To this mixture was added Pd(PPh$_3$)$_4$ (60 mg, 0.000051 mol) and the resulting mixture was degassed with nitrogen again for 10 min. The reaction mixture was stirred at room temperature for 30 min. The solvent was evaporated under reduced pressure and the residue purified using column chromatography (100-200 mesh silica gel; 1.5% MeOH in DCM) to afford the title compound (350 mg, 42%). $^1$H NMR (400 MHz, DMSO-$d_6$): δ 9.80 (brs, 1H), 8.20-8.14 (m, 2H), 7.68 (t, J=6.8 Hz, 1H), 7.56-7.52 (m, 1H), 7.35 (t, J=8.0 Hz, 1H), 5.35-4.60 (brm, 2H), 4.40-3.90 (brm, 2H), 3.81-3.79 (m, 4H), 3.16-3.13 (m, 2H), 1.80-1.72 (m, 2H), 0.98 (t, J=8.0 Hz, 3H); ESI-MS: Calculated mass: 465.10; Observed mass: 466.20 [M+H]$^+$.

Step 7: N-(3-(2-(2-aminopyrimidin-5-yl)-4-morpholinopyrido[3,2-d]pyrimidin-6-yl)-2-fluorophenyl)propane-1-sulfonamide

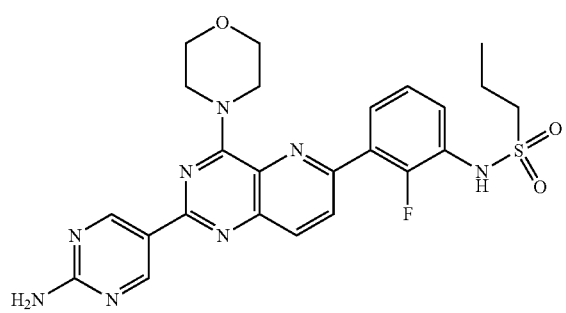 [SMILES: CCCS(=O)(=O)Nc1cccc(-c2ccc3nc(-c4cnc(N)nc4)nc(N4CCOCC4)c3n2)c1F]

To a stirred solution of N-(3-(2-chloro-4-morpholinopyrido[3,2-d]pyrimidin-6-yl)-2-fluorophenyl)propane-1-sulfonamide (0.175 g, 0.000376 mol) and 5-(4,4,5,5-tetramethyl-1,3,2-dioxaborolan-2-yl)pyrimidin-2-amine (0.20 g, 0.000936 mol) in DMF (8 mL) was added an aqueous solution of sodium carbonate (0.159 g in 2 mL water, 0.0015 mol) at room temperature. The reaction mixture was degassed with nitrogen for 15 min. To this mixture was added Pd(PPh$_3$)$_2$Cl$_2$ (26 mg, 0.000037 mol) and the resulting mixture was degassed with nitrogen for 10 min. The reaction mixture was heated at 80° C. for 1.5 h. The reaction mixture was passed through Celite® reagent and the Celite® reagent was washed with ethyl acetate (100 mL). The organic layer was washed with water (2×50 mL), followed by brine solution, dried over anhydrous sodium sulfate and filtered. The solvent was evaporated under reduced pressure and the crude product was purified using column chromatography (neutral alumina; 7% MeOH in DCM) to afford the title compound (6 mg, 3%). NMR (400 MHz, DMSO-$d_6$): δ 9.80 (brs, 1H), 9.18 (brs, 2H), 8.22 (d, J=8.8 Hz, 1H), 8.11 (d, J=8.4 Hz, 1H), 7.69 (t, J=6.0 Hz, 1H), 7.52 (t, J=7.2 Hz, 1H), 7.35 (t, J=7.6 Hz, 1H), 7.19 (brs, 2H), 4.65-4.40 (brm, 4H), 3.83 (brs, 4H), 3.20-3.14 (m, 2H), 1.78-1.76 (m, 2H), 0.99 (t, J=6.4 Hz, 3H); ESI-MS: Calculated mass: 524.18; Observed mass: 523.4 [M–H]⁻.

Example 8

N-(3-(2-(6-aminopyridin-3-yl)-8-methyl-4-morpholinoquinazolin-6-yl)-2-fluorophenyl)propane-1-sulfonamide

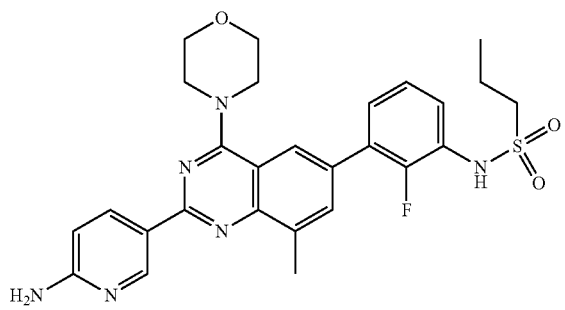 [SMILES: CCCS(=O)(=O)Nc1cccc(-c2cc(C)c3nc(-c4ccc(N)nc4)nc(N4CCOCC4)c3c2)c1F]

Step 1: (E)-2-(hydroxyimino)-N-(o-tolyl)acetamide

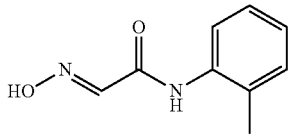

A three neck 2 L round bottom flask was charged with chloral hydrate (39.9 g, 0.241 mol), anhydrous sodium sulfate (312.2 g, 1.75 mol) and water (880 mL). The solution was stirred and heated at 40° C. until the mixture became clear. To this mixture was added o-toluidine (23.4 g, 0.219 mol dissolved in 135 mL of water and 19 mL of hydrochloric acid) and hydroxylamine hydrochloride (50.2 g, 0.723 mol). The resulting solution was heated at 100° C. for 1.5 h and then cooled to room temperature. The product precipitated out of solution after standing for 16 h at room temperature. The solid was collected by filtration and dried to afford the title compound (27 g, 69%). ¹H NMR (400 MHz, DMSO-$d_6$): δ 12.17 (s, 1H), 9.48 (brs, 1H), 7.67 (s, 1H), 7.47 (d, J=7.60 Hz, 1H), 7.21 (d, J=7.2 Hz, 1H), 7.20-7.09 (m, 2H), 2.20 (s, 3H); ESI-MS: Calculated mass: 178.07; Observed mass: 177.30 [M–H]⁻.

Step 2: 7-methylindoline-2,3-dione

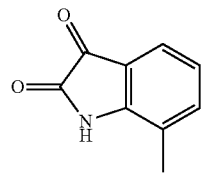

To a preheated (50° C.) solution of concentrated sulfuric acid (93.39 mL) under rapid stirring was added slowly 2-(hydroxyimino)-N-(o-tolyl)acetamide (27 g, 0.151 mol), keeping the temperature of the reaction between 60° C. and 70° C. Once the addition was complete, the reaction mixture was heated to 80° C. and stirred for 20 min. The reaction mixture was then allowed to cool to room temperature and poured over crushed ice (800 g). A crude rust colored precipitate was formed which was extracted with ethyl acetate (2×300 mL) followed by 10% methanol in dichloromethane. The combined organic layers were dried over sodium sulfate, filtered and the filtrate was evaporated under reduced pressure to afford the title compound (7 g, 28%) as an orange solid. ¹H NMR (400 MHz, DMSO-$d_6$): δ 11.08 (s, 1H), 7.42 (d, J=7.2 Hz, 1H), 7.33 (d, J=7.2 Hz, 1H), 6.98 (t, J=7.6 Hz, 1H), 2.19 (s, 3H); ESI-MS: Calculated mass: 161.05; Observed mass: 160.10 [M–H]⁻.

Step 3: 5-bromo-7-methylindoline-2,3-dione

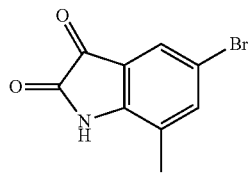

To a stirred mixture of 7-methylindoline-2,3-dione (7 g, 0.043 mol) in chloroform (700 mL) was added a solution of bromine (2.8 mL, 0.053 mol) in chloroform (100 mL) dropwise over 15 min at room temperature. The reaction mixture was heated at 80° C. for 24 h and then cooled to 0° C., which resulted in precipitation of the product as a red solid. The solid was collected by suction filtration and dried under vacuum to afford the title compound (8 g, 77%). ¹H NMR (400 MHz, DMSO-$d_6$): δ 11.20 (s, 1H), 7.64 (d, J=1.2 Hz, 1H), 7.42 (d, J=7.2 Hz, 1H), 2.18 (s, 3H); ESI-MS: Calculated mass: 238.96; Observed mass: 238.30 [M–H]⁻.

Step 4: 2-amino-5-bromo-3-methylbenzoic acid

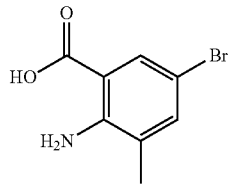

A mixture of 5-bromo-7-methylindoline-2,3-dione (8 g, 0.033 mol), sodium chloride (4.5 g, 0.09 mol) and sodium hydroxide (3.6 g, 0.09 mol) was dissolved in water (96 mL) with stirring to give a yellow solution. The reaction mixture was cooled to 0° C. and to this mixture was added slowly a solution of 30% hydrogen peroxide (7 mL) and sodium hydroxide (6.27 g) in 83 mL of water. The reaction mixture was stirred for another 1.5 h at 0° C. and then quenched with glacial acetic acid to give a tan precipitate. The solid was filtered, washed thoroughly with cold water and dried under vacuum to afford the title compound (5.8 g, 75%). $^1$H NMR (400 MHz, DMSO-$d_6$): δ 7.69 (d, J=2.4 Hz, 1H), 7.26 (s, 1H), 2.0 (s, 3H); ESI-MS: Calculated mass: 228.97; Observed mass: 228.10 [M−H]$^−$.

Step 5:
6-bromo-8-methylquinazoline-2,4(1H,3H)-dione

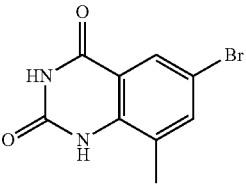

A mixture of urea (15.28 g, 0.254 mol) and 2-amino-5-bromo-3-methylbenzoic acid (7.6 g, 0.031 mol) was heated at 180° C. for 4 h. After confirming the completion of reaction by TLC, the reaction mixture was allowed to cool to 80° C. and water (200 mL) was added. The aqueous reaction mixture was stirred at 80° C. for 30 min and the precipitate was collected by filtration. The solid compound (8.4 g, little impure) obtained was taken into the next step without further purification. $^1$H NMR (400 MHz, DMSO-$d_6$): δ 7.82 (d, J=2.0 Hz, 1H), 7.68 (d, J=1.6 Hz, 1H), 2.33 (s, 3H); ESI-MS: Calculated mass: 253.97; Observed mass: 255.20 [M+H]$^+$.

Step 6: 6-bromo-2,4-dichloro-8-methylquinazoline

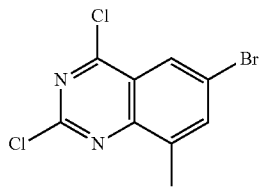

To a stirred suspension of 6-bromo-8-methylquinazoline-2,4(1H,3H)-dione (9.4 g, 0.037 mol) in phosphorus oxychloride (84 mL) were added dropwise diisoproylethylamine (5.14 mL, 0.037 mol) and N,N-dimethylformamide (1.3 mL) at room temperature. The reaction mixture was heated at 130° C. for 24 h. Excess phosphorusoxychloride was removed by distillation and the residue was azeotroped with toluene. The reaction mixture was cooled to room temperature, poured into water (150 mL) and stirred for 30 min. The solid that separated was collected by filtration and dried under vacuum to afford the title compound (8.8 g, 92%). $^1$H NMR (400 MHz, DMSO-$d_6$): δ 8.28 (s, 1H), 8.22 (s, 1H), 2.64 (s, 3H).

Step 7: 4-(6-bromo-2-chloro-8-methylquinazolin-4-yl)morpholine

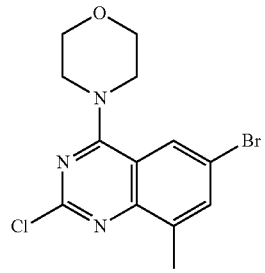 [SMILES: Cc1cc(Br)cc2c(N3CCOCC3)nc(Cl)nc12]

To a stirred solution of 6-bromo-2,4-dichloro-8-methylquinazoline (8.8 g, 0.030 mol) in dichloromethane (300 mL) were added diisopropylethylamine (10 mL, 0.06 mol) and morpholine (2.7 mL, 0.03 mol) at 0° C. then the reaction mixture was stirred for 30 min at 0° C. Water (100 mL) was added and the reaction mixture was filtered through Celite® reagent, and the Celite® reagent was washed with dichloromethane (200 mL). The organic layer was separated and the aqueous layer was extracted with dichloromethane (2×200 mL). The combined organic layers were washed with brine, dried over anhydrous sodium sulfate, filtered and concentrated under reduced pressure. The crude product was purified using column chromatography (60-120 mesh silica gel; 20% EtOAc in hexane) to afford the title compound as a yellow solid (9 g, 87%). $^1$H NMR (400 MHz, DMSO-$d_6$): δ 7.97 (d, J=2.0 Hz, 1H), 7.88 (d, J=0.8 Hz, 1H), 3.83-3.73 (m, 8H), 2.53 (s, 3H).

Step 8: N-(3-(2-chloro-8-methyl-4-morpholinoquinazolin-6-yl)-2-fluorophenyl)propane-1-sulfonamide

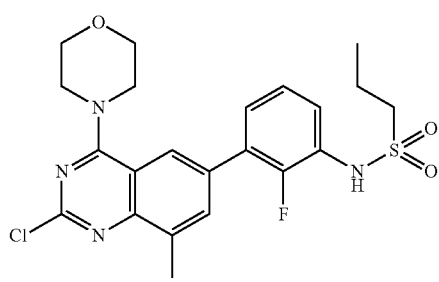 [SMILES: CCCS(=O)(=O)Nc1cccc(-c2cc(C)c3nc(Cl)nc(N4CCOCC4)c3c2)c1F]

A 50 mL round bottom flask was charged with 4-(6-bromo-2-chloro-8-methylquinazolin-4-yl)morpholine (0.3 g, 0.000879 mol), N-(2-fluoro-3-(4,4,5,5-tetramethyl-1,3,2-dioxaborolan-2-yl)phenyl)propane-1-sulfonamide (0.36 g, 0.00105 mol), sodium carbonate (0.184 g in 2 mL water, 0.00174 mol) and DMF (8 mL). The reaction mixture was degassed with nitrogen for 15 min. To this mixture was added Pd(PPh$_3$)$_2$Cl$_2$ (60 mg, 0.0000879 mol) and the resulting mixture was degassed with nitrogen again for 10 min. The reaction mixture was stirred for 12 h at 80° C. The reaction mixture was diluted with ethyl acetate (40 mL), filtered through Celite® reagent, and the Celite® reagent was washed with ethyl acetate (100 mL). The organic layer was washed with cold water (50 mL), dried over anhydrous sodium sulfate, filtered and evaporated under reduced pressure. The crude product was purified using column chromatography (230-400 mesh silica gel; 1% MeOH in DCM) to afford the title compound (200 mg, 47%). $^1$H NMR (400 MHz, DMSO-d$_6$): δ 9.73 (brs, 1H), 8.14 (s, 1H), 8.11 (s, 1H), 7.49-7.42 (m, 2H), 7.30 (t, J=8.0 Hz, 1H), 3.85-3.76 (m, 8H), 3.17-3.11 (m, 2H), 2.63 (s, 3H), 1.82-1.72 (m, 2H), 0.85 (t, J=6.4 Hz, 3H); ESI-MS: Calculated mass: 478.12; Observed mass: 479.3 [M+H]$^+$.

Step 9: N-(3-(2-(6-aminopyridin-3-yl)-8-methyl-4-morpholinoquinazolin-6-yl)-2-fluorophenyl)propane-1-sulfonamide

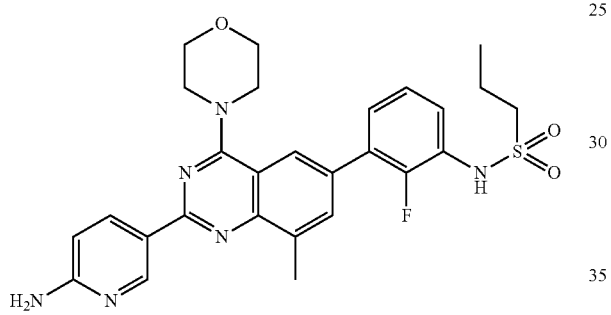

A 50 mL round bottom flask was charged with N-(3-(2-chloro-8-methyl-4-morpholinoquinazolin-6-yl)-2-fluorophenyl)propane-1-sulfonamide (0.2 g, 0.00040 mol), 5-(4,4,5,5-tetramethyl-1,3,2-dioxaborolan-2-yl)pyridin-2-amine (0.18 g, 0.0008 mol), aqueous sodium carbonate (0.169 g in 2 mL water, 0.0016 mol) and DMF (8 mL). The reaction mixture was degassed with nitrogen for 15 min. To this mixture was added Pd(PPh$_3$)$_2$Cl$_2$ (28 mg, 0.00004 mol) and the resulting mixture was degassed with nitrogen for 10 min. The reaction mixture was stirred at 80° C. for 12 h. The reaction mixture was filtered through Celite® reagent and the Celite® reagent was washed with ethyl acetate (100 mL). The organic layer was washed with cold water (2×50 mL), dried over anhydrous sodium sulfate, filtered and concentrated under reduced pressure. The crude product was purified using preparative HPLC to afford the title compound (13 mg, 6%). $^1$H NMR (400 MHz, DMSO-d$_6$): δ 9.70 (brs, 1H), 9.08 (d, J=2.0 Hz, 1H), 8.42 (dd, J'=8.8 Hz, J''=1.6 Hz, 1H), 7.90 (s, 1H), 7.81 (s, 1H), 7.44 (t, J=8.4 Hz, 2H), 7.29 (t, J=7.6 Hz, 1H), 6.55 (d, J=8.8 Hz, 1H), 6.45 (brs, 2H), 3.81-3.79 (m, 8H), 3.14 (t, J=7.2 Hz, 2H), 2.69 (s, 3H), 1.80-1.74 (m, 2H), 1.02 (t, J=6.4 Hz, 3H); ESI-MS: Calculated mass: 536.2; Observed mass: 537.1 [M+H]$^+$.

Example 9

N-(3-(2-(2-(difluoromethyl)-1H-benzo[d]imidazol-1-yl)-8-methoxy-4-morpholinoquinazolin-6-yl)-2-fluorophenyl)propane-1-sulfonamide

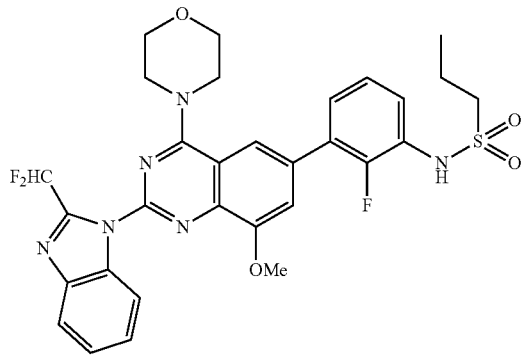 [SMILES: CCCS(=O)(=O)Nc1cccc(-c2cc(OC)c3nc(-n4c(C(F)F)nc5ccccc54)nc(N4CCOCC4)c3c2)c1F]

Step 1: 4-(6-bromo-2-(2-(difluoromethyl)-1H-benzo[d]imidazol-1-yl)-8-methoxyquinazolin-4-yl)morpholine

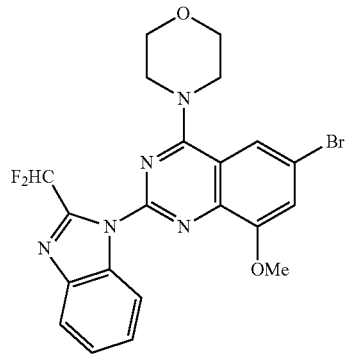 [SMILES: COc1cc(Br)cc2c(N3CCOCC3)nc(-n3c(C(F)F)nc4ccccc43)nc12]

To a stirred mixture of 4-(6-bromo-2-chloro-8-methoxyquinazolin-4-yl)morpholine (300 mg, 0.00084 mol) and potassium carbonate (348 mg, 0.00251 mol) in N,N-dimethylformamide (10 ml) was added 2-(difluoromethyl)-1H-benzo[d]imidazole (169 mg, 0.001 mol) at room temperature. The reaction mixture was heated at 80° C. for 16 h. The reaction mixture was added to ice-cold water (100 mL). The solid separated was collected by filtration, washed with 5% EtOAc in hexane and dried under vacuum to afford the title compound as white solid (230 mg, 56%). $^1$H NMR (400 MHz, DMSO-d$_6$): δ 8.67 (d, J=8.40 Hz, 1H), 7.96 (t, J=53.2 Hz, 1H), 7.87 (d, J=8.0 Hz, 1H), 7.73 (d, J=2.0 Hz, 1H), 7.54 (d, J=2.0 Hz, 1H), 7.53-7.43 (m, 2H), 4.05 (s, 3H), 3.94-3.83 (m, 8H); ESI-MS: Calculated mass: 489.06; Observed mass: 490.20 [M+H]$^+$.

Step 2: N-(3-(2-(2-(difluoromethyl)-1H-benzo[d]imidazol-1-yl)-8-methoxy-4-morpholinoquinazolin-6-yl)-2-fluorophenyl)propane-1-sulfonamide

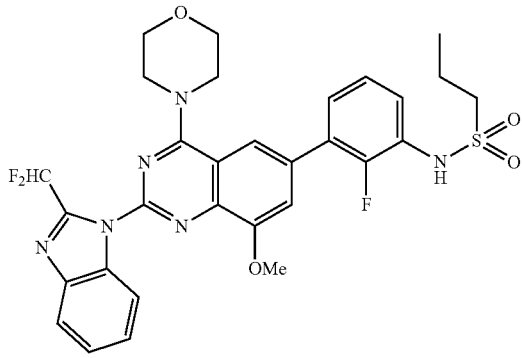 [SMILES: CCCS(=O)(=O)Nc1cccc(-c2cc(OC)c3nc(-n4c(C(F)F)nc5ccccc54)nc(N4CCOCC4)c3c2)c1F]

A 50 mL round bottom flask, was charged with 4-(6-bromo-2-(2-(difluoromethyl)-1H-benzo[d]imidazol-1-yl)-8-methoxyquinazolin-4-yl)morpholine (0.12 g, 0.000245 mol), N-(2-fluoro-3-(4,4,5,5-tetramethyl-1,3,2-dioxaborolan-2-yl)phenyl)propane-1-sulfonamide (0.126 g, 0.000367 mol), sodium carbonate (0.077 g, 0.000726 mol) and 10 mL of DMF and water mixture (4:1). The reaction mixture was degassed with nitrogen for 15 min. To this mixture was added Pd(PPh$_3$)$_2$Cl$_2$ (17 mg, 0.00002 mol) and the resulting mixture was degassed with nitrogen again for 10 min. The reaction mixture was heated at 80° C. for 2 hours. Water (50 mL) was added and the resulting mixture was extracted with ethyl acetate (2×50 mL). The combined organic layers were washed with brine, dried over anhydrous sodium sulfate, filtered and evaporated under reduced pressure. The crude product was purified using column chromatography (230-400 mesh silica gel; 2% MeOH in DCM) to afford the title compound (46 mg, 30%). $^1$H NMR (400 MHz, DMSO-d$_6$): δ 9.75 (brs, 1H), 8.72 (d, J=8.4 Hz, 1H), 8.02 (s, 1H), 7.88 (d, J=8.0 Hz, 1H), 7.59 (s, 1H), 7.57-7.44 (m, 5H), 7.34 (t, J=7.6 Hz, 1H), 4.09 (s, 3H), 3.93-3.85 (m, 8H), 3.17 (t, J=7.6 Hz, 2H), 1.82-1.76 (m, 2H), 1.09 (t, J=7.6 Hz, 3H); ESI-MS: Calculated mass: 626.19; Observed mass: 625.4 [M–H]$^−$.

Example 10

(TBDMS Deprotection): N-(2-fluoro-3-(2-(2-(hydroxymethyl)-1H-benzo[d]imidazol-1-yl)-8-methoxy-4-morpholinoquinazolin-6-yl)phenyl)propane-1-sulfonamide

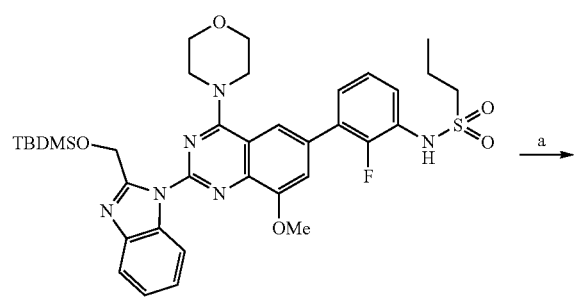

-continued

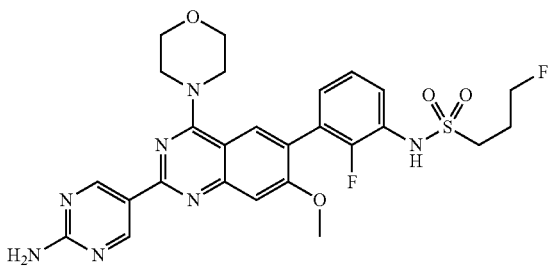 [SMILES: COc1cc2nc(-c3cnc(N)nc3)nc(N3CCOCC3)c2cc1-c1cccc(NS(=O)(=O)CCCF)c1F]

To a stirred solution of N-(3-(2-(2-(tert-butyldimethylsilyl)oxy)methyl)-1H-benzo [d]imidazol-1-yl)-8-methoxy-4-morpholinoquinazolin-6-yl)-2-fluorophenyl)propane-1-sulfonamide (0.2 g, 0.000277 mol) in dichloromethane (10 mL) was added tetra-n-butylammonium fluoride (1M in solution in THF, 0.18 g, 0.000689 mol) at room temperature and the stirring was continued for 16 h. The reaction mixture was diluted with water (50 mL), neutralized with saturated sodium bicarbonate solution and extracted with dichloromethane (2×100 mL). The combined organic layers were dried over anhydrous sodium sulfate and concentrated under reduced pressure. The crude product was purified using preparative HPLC to afford the title compound (17 mg, 10%). $^1$H NMR (400 MHz, DMSO-d$_6$): δ 9.75 (s, 1H), 8.45 (d, J=8.4 Hz, 1H), 7.73 (d, J=2.0 Hz, 1H), 7.70 (s, 1H), 7.55-7.51 (m, 2H), 7.47 (t, J=7.6 Hz, 1H), 7.40 (t, J=7.6 Hz, 1H), 7.35-7.30 (m, 2H), 6.01 (t, J=6.4 Hz, 1H), 4.96 (d, J=7.2 Hz, 2H), 4.06 (s, 3H), 3.96-3.95 (m, 4H), 3.88-3.87 (m, 4H), 3.15 (t, J=7.2 Hz, 2H), 1.79-1.77 (m, 2H), 1.0 (t, J=7.6 Hz, 3H); ESI-MS: Calculated mass: 606.2; Observed mass: 605.30 [M–H]$^−$.

Example 11

N-(3-(2-(2-aminopyrimidin-5-yl)-7-methoxy-4-morpholinoquinazolin-6-yl)-2-fluorophenyl)-3-fluoropropane-1-sulfonamide Step 1: 2-Amino-5-bromo-4-methoxybenzoic acid

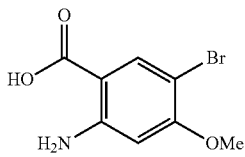

To a stirred suspension of 2-amino-4-methoxybenzoic acid (5 g, 0.029 mol) in acetic acid (100 mL) was added bromine (1.23 mL, 0.023 mol) dropwise at 0° C. The reaction mixture was stirred at room temperature for 8 h. The separated solid was filtered, washed with water (30 mL) and dried under vacuum to afford the product as white solid (6.3 g, 86%). As per the LC-MS data this solid contains 14% of starting material, 22% of dibromo byproduct and 61% of desired compound. $^1$H NMR (400 MHz, DMSO-$d_6$): δ 7.76 (s, 1H), 6.42 (s, 1H), 3.72 (s, 3H); ESI-MS: Calculated mass: 244.97; Observed mass LC-MS: 246.0 [M+H]$^+$ RT: 2.07 min.

Step 2: Methyl 2-amino-5-bromo-4-methoxybenzoate

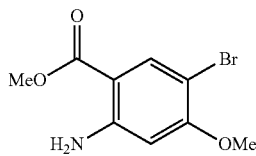

To a stirred suspension of 2-amino-5-bromo-4-methoxybenzoic acid (6.3 g, 0.025 mol) and potassium carbonate (7.06 g, 0.051 mol) in N,N-dimethyl formamide (63 mL) was added methyl iodide (5.45 g, 0.038 mol) dropwise at 0° C. After the addition was complete, the reaction mixture was stirred at room temperature for 1 h. The mixture was poured into ice cold water (500 mL) and extracted with ethyl acetate (2×200 mL). The combined organic layers were washed with water (100 mL) followed by brine solution, dried over anhydrous sodium sulfate and filtered. The filtrate was evaporated under reduced pressure and the crude product was purified using column chromatography (100-200 mesh silica gel, 20% EtOAc in hexane) to afford the title compound as white solid (5.5 g, 83% yield). $^1$H NMR (400 MHz, DMSO-$d_6$): δ 7.78 (s, 1H), 6.85 (brs, 2H), 6.44 (s, 1H), 3.80 (s, 3H), 3.75 (s, 3H). ESI-MS: Calculated mass: 258.98; Observed mass: 258.3 [M−H]$^−$.

Step 3: 6-Bromo-7-methoxyquinazoline-2,4(1H,3H)-dione

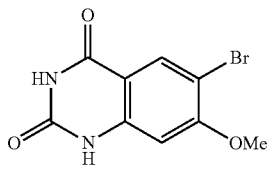 [SMILES: COc1cc2[nH]c(=O)[nH]c(=O)c2cc1Br]

To a stirred suspension of methyl 2-amino-5-bromo-4-methoxybenzoate (5.5 g, 0.021 mol) in acetic acid (25 mL) was added 0.1 M aqueous solution of potassium cyanate (7.49 g, 0.10 mol) dropwise at room temperature. The reaction mixture was stirred at 50° C. for 24 h. The solid separated was filtered, washed with water (20 mL) followed by 10% EtOAc in hexane (50 mL) and dried under vacuum to afford the corresponding urea.

To the stirred suspension of the above urea in methanol (20 mL) was added 2N sodium hydroxide (10 mL). The reaction mixture was stirred at 90° C. for 1 h. The mixture was cooled to room temperature, acidified with 3M hydrochloric acid to pH 3. The solid obtained was filtered and dried under vacuum to afford the title compound as white solid (3.5 g, 61% yield). $^1$H NMR (400 MHz, DMSO-$d_6$): δ 11.29 (s, 1H), 11.18 (s, 1H), 7.94 (s, 1H), 6.74 (s, 1H), 3.90 (s, 3H).

Step 4: 6-Bromo-2,4-dichloro-7-methoxyquinazoline

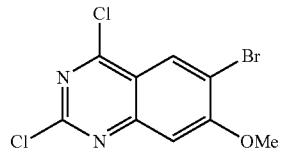 [SMILES: COc1cc2nc(Cl)nc(Cl)c2cc1Br]

To a stirred suspension of 6-bromo-7-methoxyquinazoline-2,4(1H,3H)-dione (1.7 g, 0.006 mol) in phosphorousoxychloride (25.5 mL; POCl$_3$) were added diisopropyl ethylamine (1.7 mL) and N,N-dimethylformamide (0.85 mL) sequentially. The reaction mixture was maintained at 130° C. for 8 h. POCl$_3$ was removed by distillation and the crude residue was azeotroped twice with toluene to afford the title compound (1.7 g, crude). This compound was used in the next step without any further purification.

Step 5: 4-(6-Bromo-2-chloro-7-methoxy-4,4a-dihydroquinazolin-4-yl)morpholine

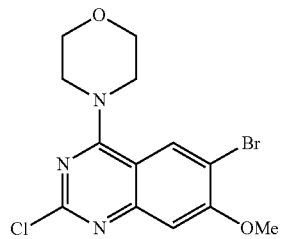 [SMILES: COc1cc2nc(Cl)nc(N3CCOCC3)c2cc1Br]

To a stirred solution of 6-bromo-2,4-dichloro-7-methoxyquinazoline (1.7 g, 0.005 mol) and diisopropylethylamine (3.62 mL, 0.022 mol) in dichloromethane (100 mL) was added morpholine (0.48 mL, 0.005 mol) slowly at 0° C. After the addition was complete, the reaction mixture was stirred at 0° C. for 30 min. The reaction mixture was diluted with water (50 mL) and extracted with dichloromethane (2×200 mL). The organic layer was washed with brine, dried over anhydrous sodium sulfate, filtered and concentrated under reduced pressure. The crude product was purified using column chromatography (100-200 mesh silica gel, 30% EtOAc in hexane) to afford the title compound as off white solid (850 mg, 43% yield). $^1$H NMR (400 MHz, DMSO-d$_6$): δ 8.19 (s, 1H), 7.29 (s, 1H), 3.99 (s, 3H), 3.83-3.74 (m, 8H); ESI-MS: Calculated mass: 356.99; Observed mass: 358.20 [M+H]$^+$.

Step 6: N-(3-(2-Chloro-7-methoxy-4-morpholinoquinazolin-6-yl)-2-fluorophenyl)-3-fluoropropane-1-sulfonamide

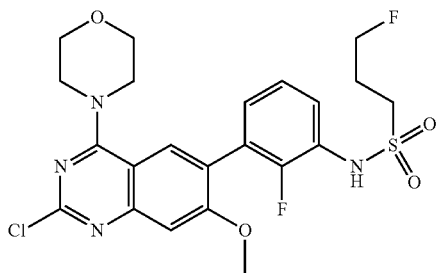 [SMILES: COc1cc2nc(Cl)nc(N3CCOCC3)c2cc1-c1cccc(NS(=O)(=O)CCCF)c1F]

To a 100 mL round bottom flask were added 4-(6-bromo-2-chloro-7-methoxy-4,4a-dihydroquinazolin-4-yl)morpholine (1 g, 0.0027 mol), N,N-dimethylformamide (20 mL), water (5 mL), 3-fluoro-N-(2-fluoro-3-(4,4,5,5-tetramethyl-1,3,2-dioxaborolan-2-yl)phenyl)propane-1-sulfonamide (2.01 g, 0.0055 mol) and sodium carbonate (589 mg, 0.005 mol). The reaction mixture was degassed with nitrogen for 10 min. To this mixture was added Pd(PPh$_3$)$_2$Cl$_2$ (195 mg, 0.0002 mol) and the resulting mixture was degassed again for 5 min. The reaction mixture was stirred at 80° C. for 1 h. Water (50 mL) was added and the reaction mixture was extracted with ethyl acetate (2×100 mL). The organic layer was washed with brine, dried over anhydrous sodium sulfate, filtered and concentrated under reduced pressure. The crude product was purified using column chromatography (100-200 mesh silica gel, 30% EtOAc in hexane) to afford the title compound (800 mg, 57% yield). $^1$H NMR (400 MHz, DMSO-d$_6$): δ 9.83 (brs, 1H), 7.93 (s, 1H), 7.45 (t, J=8.0 Hz, 1H), 7.34 (t, J=6.4 Hz, 1H), 7.30 (s, 1H), 7.28-7.24 (m, 1H), 4.61 (t, J=6.0 Hz, 1H), 4.49 (t, J=6.0 Hz, 1H), 3.93 (s, 3H), 3.88-3.72 (m, 8H), 3.24-3.19 (m, 2H), 2.18-2.01 (m, 2H); ESI-MS: Calculated mass: 512.1; Observed mass: 511.3 [M−H]$^-$.

Step 7: N-(3-(2-(2-Aminopyrimidin-5-yl)-7-methoxy-4-morpholinoquinazolin-6-yl)-2-fluorophenyl)-3-fluoropropane-1-sulfonamide

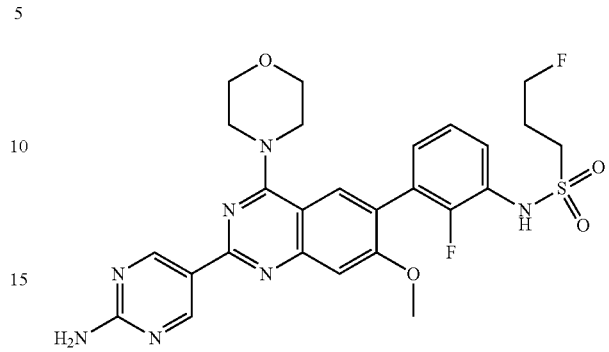

To a 100 mL round bottom flask, were added N-(3-(2-chloro-7-methoxy-4-morpholinoquinazolin-6-yl)-2-fluorophenyl)-3-fluoropropane-1-sulfonamide (200 mg, 0.0003 mol), N,N-dimethylformamide (10 mL), water (2 mL), 5-(4,4,5,5-tetramethyl-1,3,2-dioxaborolan-2-yl)pyrimidin-2-amine (172 mg, 0.0007 mol) and sodium carbonate (164 mg, 0.0015 mol). The reaction mixture was degassed with nitrogen for 10 min. To this mixture was added Pd(PPh$_3$)$_2$Cl$_2$ (27 mg, 0.00003 mol) and the resulting mixture was degassed again for 5 min. The reaction mixture was stirred at 80° C. for 1 h. Water (50 mL) was added and the reaction mixture was extracted with 10% MeOH in EtOAc (2×50 mL). The organic layer was washed with brine, dried over anhydrous sodium sulfate, filtered and concentrated under reduced pressure. The crude product was purified using column chromatography (100-200 mesh silica gel, 4% MeOH in DCM) to get the desired product in 85% purity. This product was again purified using preparative HPLC to afford the title compound as an off white solid (62 mg, 28% yield). $^1$H NMR (400 MHz, DMSO-d$_6$): δ 9.84 (s, 1H), 9.20 (s, 2H), 7.81 (s, 1H), 7.44 (t, J=7.6 Hz, 1H), 7.37-7.34 (m, 2H), 7.27 (t, J=8.0 Hz, 1H), 7.19 (brs, 2H), 4.61 (t, J=6.0 Hz, 1H), 4.49 (t, J=6.0 Hz, 1H), 3.91 (s, 3H), 3.78-3.68 (m, 8H), 3.23-3.22 (m, 2H), 2.17-2.10 (m, 2H); Calculated mass: 571.18; Observed mass: 572.3[M+H]$^+$.

ESI-MS characterization data for Examples 1-120 are provided in Table 2.

TABLE 2

| Ex | Structure | Structure Name | Mass (ESI-MS) | Scheme |
|---|---|---|---|---|
| 1 | 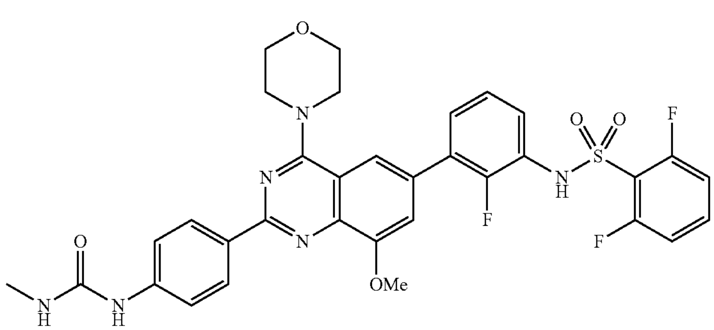 [SMILES: CNC(=O)Nc1ccc(-c2nc(N3CCOCC3)c3cc(-c4cccc(NS(=O)(=O)c5c(F)cccc5F)c4F)cc(OC)c3n2)cc1] | 2,6-difluoro-N-(2-fluoro-3-(8-methoxy-2-(4-(3-methylureido)phenyl)-4-morpholinoquinazolin-6-yl)phenyl)benzenesulfonamide | 679.30 [M + H]$^+$ | 9 |

TABLE 2-continued

| Ex | Structure | Structure Name | Mass (ESI-MS) | Scheme |
|---|---|---|---|---|
| 2 | 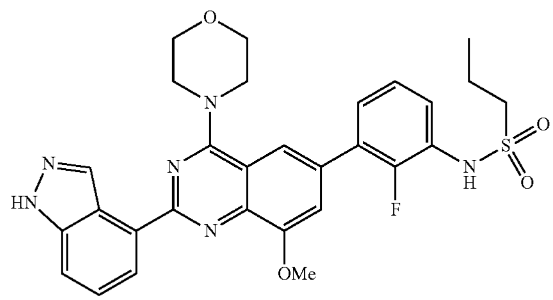 [SMILES: CCCS(=O)(=O)Nc1cccc(-c2cc(OC)c3nc(-c4cccc5[nH]ncc45)nc(N4CCOCC4)c3c2)c1F] | N-(3-(2-(1H-indazol-4-yl)-8-methoxy-4-morpholinoquinazolin-6-yl)-2-fluorophenyl)propane-1-sulfonamide | 577.40 [M + H]+ | 9 |
| 3 | 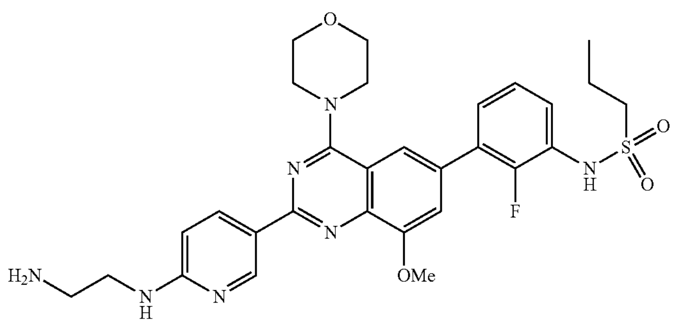 [SMILES: CCCS(=O)(=O)Nc1cccc(-c2cc(OC)c3nc(-c4ccc(NCCN)nc4)nc(N4CCOCC4)c3c2)c1F] | N-(3-(2-(6-((2-aminoethyl)amino)pyridin-3-yl)-8-methoxy-4-morpholinoquinazolin-6-yl)-2-fluorophenyl)propane-1-sulfonamide | 596.20 [M + H]+ | 9 |
| 4 | 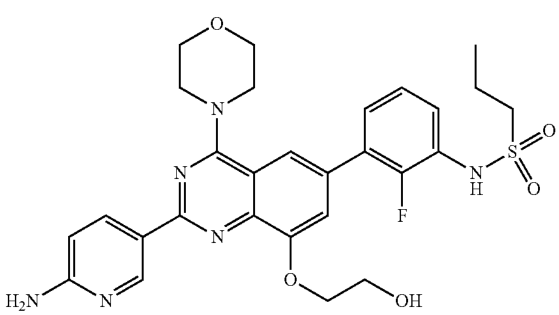 [SMILES: CCCS(=O)(=O)Nc1cccc(-c2cc(OCCO)c3nc(-c4ccc(N)nc4)nc(N4CCOCC4)c3c2)c1F] | N-(3-(2-(6-aminopyridin-3-yl)-8-(2-hydroxyethoxy)-4-morpholinoquinazolin-6-yl)-2-fluorophenyl)propane-1-sulfonamide | 583.10 [M + H]+ | 10 |
| 5 | 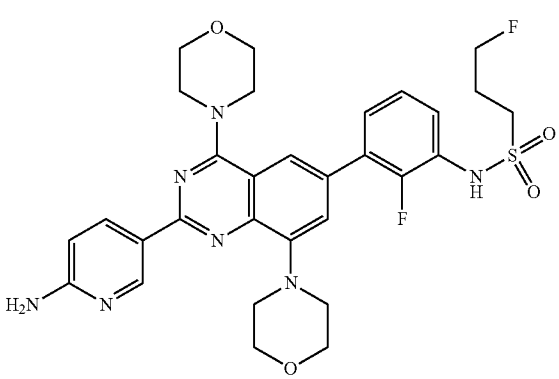 [SMILES: Nc1ccc(-c2nc(N3CCOCC3)c3cc(-c4cccc(NS(=O)(=O)CCCF)c4F)cc(N4CCOCC4)c3n2)cn1] | N-(3-(2-(6-aminopyridin-3-yl)-4,8-dimorpholinoquinazolin-6-yl)-2-fluorophenyl)-3-fluoropropane-1-sulfonamide | 626.40 [M + H]+ | 11 |

TABLE 2-continued

| Ex | Structure | Structure Name | Mass (ESI-MS) | Scheme |
|---|---|---|---|---|
| 6 | 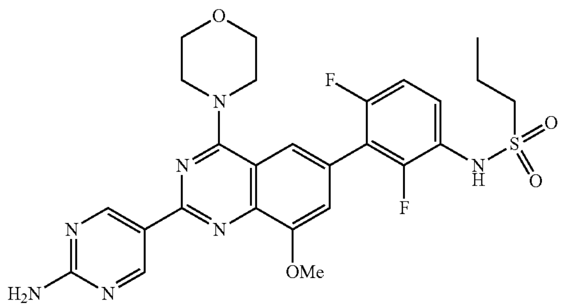 | N-(3-(2-(2-aminopyrimidin-5-yl)-8-methoxy-4-morpholinoquinazolin-6-yl)-2,4-difluorophenyl)propane-1-sulfonamide | 570.20 [M − H]− | 12 |
| 7 | 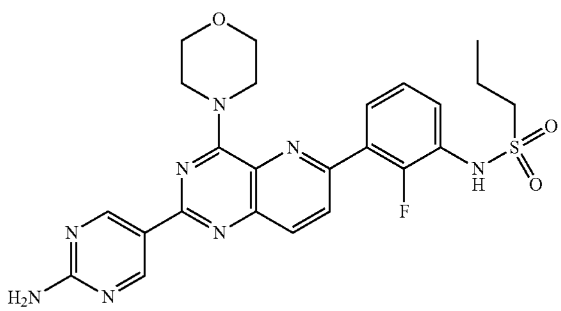 [SMILES: CCCS(=O)(=O)Nc1cccc(-c2ccc3nc(-c4cnc(N)nc4)nc(N4CCOCC4)c3n2)c1F] | N-(3-(2-(2-aminopyrimidin-5-yl)-4-morpholinopyrido[3,2-d]pyrimidin-6-yl)-2-fluorophenyl)propane-1-sulfonamide | 523.40 [M − H]− | 13 |
| 8 | 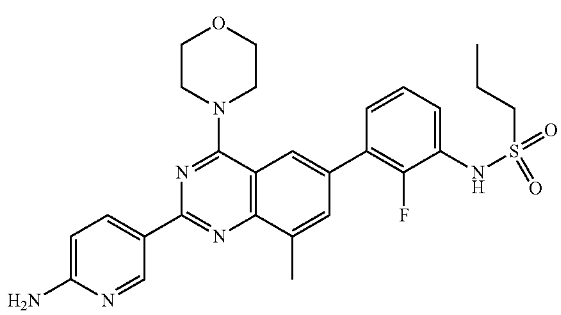 [SMILES: CCCS(=O)(=O)Nc1cccc(-c2cc(C)c3nc(-c4ccc(N)nc4)nc(N4CCOCC4)c3c2)c1F] | N-(3-(2-(6-aminopyridin-3-yl)-8-methyl-4-morpholinoquinazolin-6-yl)-2-fluorophenyl)propane-1-sulfonamide | 537.10 [M + H]+ | 14 |
| 9 | 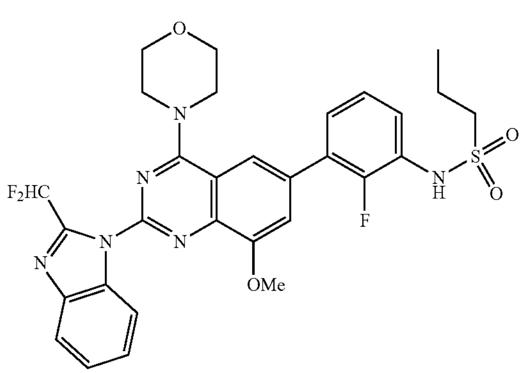 [SMILES: CCCS(=O)(=O)Nc1cccc(-c2cc(OC)c3nc(-n4c(C(F)F)nc5ccccc54)nc(N4CCOCC4)c3c2)c1F] | N-(3-(2-(2-(difluoromethyl)-1H-benzo[d]imidazol-1-yl)-8-methoxy-4-morpholinoquinazolin-6-yl)-2-fluorophenyl)propane-1-sulfonamide | 625.40 [M − H]− | 15 |

TABLE 2-continued

| Ex | Structure | Structure Name | Mass (ESI-MS) | Scheme |
|---|---|---|---|---|
| 10 | 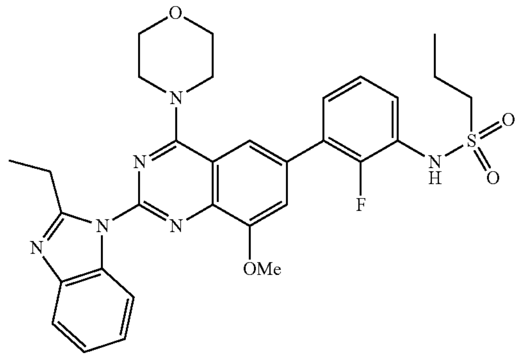 [SMILES: CCCS(=O)(=O)Nc1cccc(-c2cc(OC)c3nc(-n4c(CC)nc5ccccc54)nc(N4CCOCC4)c3c2)c1F] | N-(2-fluoro-3-(2-(2-(hydroxymethyl)-1H-benzo[d]imidazol-1-yl)-8-methoxy-4-morpholinoquinazolin-6-yl)phenyl)propane-1-sulfonamide | 605.30 [M − H]⁻ | 15 |
| 11 | 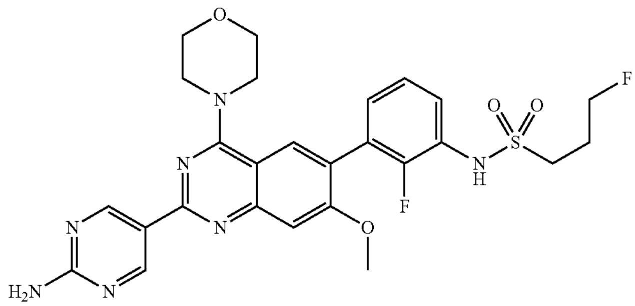 [SMILES: COc1cc2nc(-c3cnc(N)nc3)nc(N3CCOCC3)c2cc1-c1cccc(NS(=O)(=O)CCCF)c1F] | N-(3-(2-(2-aminopyrimidin-5-yl)-7-methoxy-4-morpholinoquinazolin-6-yl)-2-fluorophenyl)-3-fluoropropane-1-sulfonamide | 572.30 [M + H]⁺ | 16 |
| 12 | 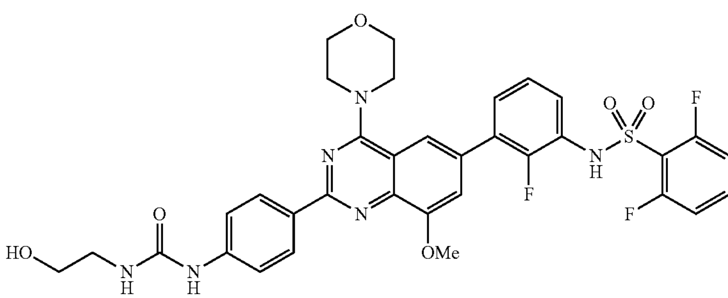 [SMILES: COc1cc(-c2cccc(NS(=O)(=O)c3c(F)cccc3F)c2F)cc2c(N3CCOCC3)nc(-c3ccc(NC(=O)NCCO)cc3)nc12] | 2,6-difluoro-N-(2-fluoro-3-(2-(4-(3-(2-hydroxyethyl)ureido)phenyl)-8-methoxy-4-morpholinoquinazolin-6-yl)phenyl)benzenesulfonamide | 707.50 [M − H]⁻ | 9 |
| 13 | 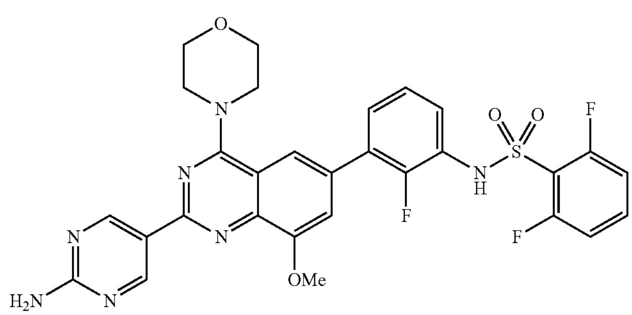 [SMILES: COc1cc(-c2cccc(NS(=O)(=O)c3c(F)cccc3F)c2F)cc2c(N3CCOCC3)nc(-c3cnc(N)nc3)nc12] | N-(3-(2-(2-aminopyrimidin-5-yl)-8-methoxy-4-morpholinoquinazolin-6-yl)-2-fluorophenyl)-2,6-difluorobenzenesulfonamide | 622.20 [M − H]⁻ | 9 |
| 14 | 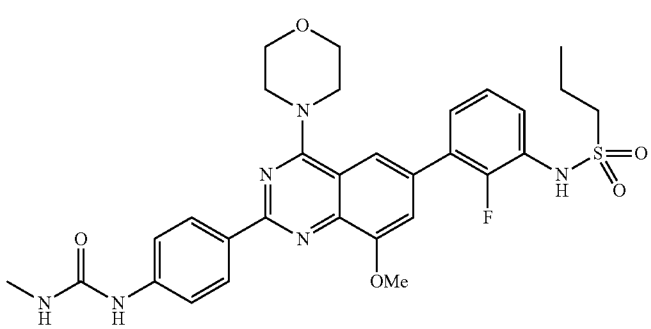 [SMILES: CCCS(=O)(=O)Nc1cccc(-c2cc(OC)c3nc(-c4ccc(NC(=O)NC)cc4)nc(N4CCOCC4)c3c2)c1F] | N-(2-fluoro-3-(8-methoxy-2-(4-(3-methylureido)phenyl)-4-morpholinoquinazolin-6-yl)phenyl)propane-1-sulfonamide | 609.50 [M + H]⁺ | 9 |

TABLE 2-continued

| Ex | Structure | Structure Name | Mass (ESI-MS) | Scheme |
|---|---|---|---|---|
| 15 | 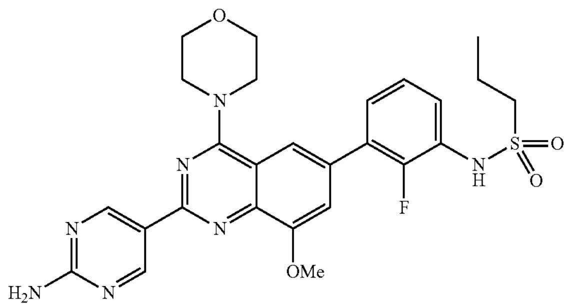 [SMILES: CCCS(=O)(=O)Nc1cccc(-c2cc(OC)c3nc(-c4cnc(N)nc4)nc(N4CCOCC4)c3c2)c1F] | N-(3-(2-(2-aminopyrimidin-5-yl)-8-methoxy-4-morpholinoquinazolin-6-yl)-2-fluorophenyl)propane-1-sulfonamide | 554.20 [M + H]+ | 9 |
| 16 | 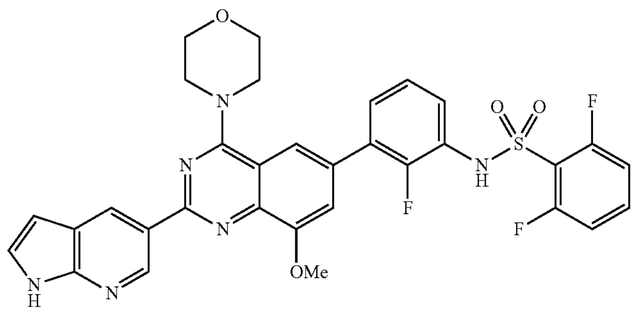 [SMILES: COc1cc(-c2cccc(NS(=O)(=O)c3c(F)cccc3F)c2F)cc2c(N3CCOCC3)nc(-c3cnc4[nH]ccc4c3)nc12] | 2,6-difluoro-N-(2-fluoro-3-(8-methoxy-4-morpholino-2-(1H-pyrrolo[2,3-b]pyridin-5-yl)quinazolin-6-yl)phenyl)benzenesulfonamide | 647.30 [M + H]+ | 9 |
| 17 | 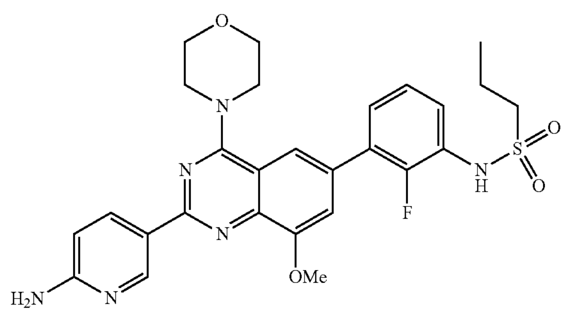 [SMILES: CCCS(=O)(=O)Nc1cccc(-c2cc(OC)c3nc(-c4ccc(N)nc4)nc(N4CCOCC4)c3c2)c1F] | N-(3-(2-(6-aminopyridin-3-yl)-8-methoxy-4-morpholinoquinazolin-6-yl)-2-fluorophenyl)propane-1-sulfonamide | 551.30 [M − H]− | 9 |
| 18 | 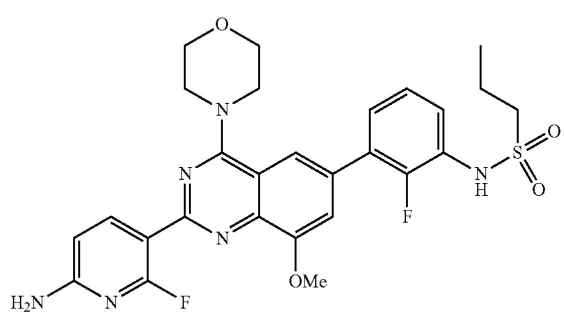 [SMILES: CCCS(=O)(=O)Nc1cccc(-c2cc(OC)c3nc(-c4ccc(N)nc4F)nc(N4CCOCC4)c3c2)c1F] | N-(3-(2-(6-amino-2-fluoropyridin-3-yl)-8-methoxy-4-morpholinoquinazolin-6-yl)-2-fluorophenyl)propane-1-sulfonamide | 571.40 [M + H]+ | 9 |
| 19 | 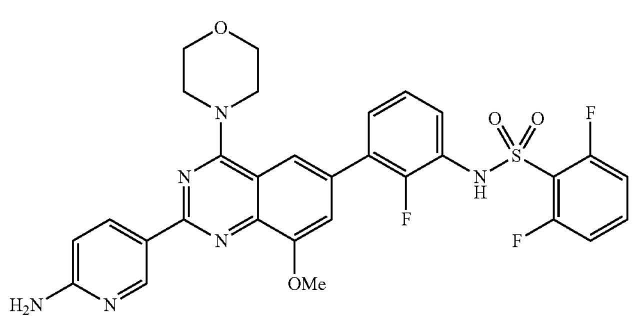 [SMILES: COc1cc(-c2cccc(NS(=O)(=O)c3c(F)cccc3F)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2-fluorophenyl)-2,6-difluorobenzenesulfonamide | 623.20 [M + H]+ | 9 |

TABLE 2-continued

| Ex | Structure | Structure Name | Mass (ESI-MS) | Scheme |
|---|---|---|---|---|
| 20 | 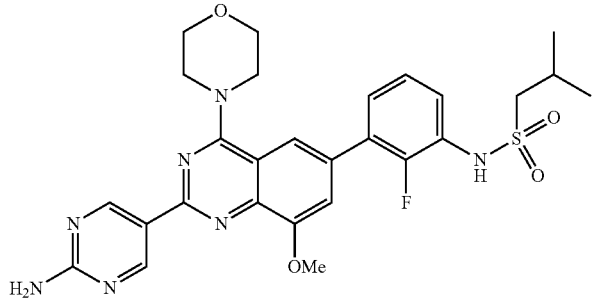 [SMILES: COc1cc(-c2cccc(NS(=O)(=O)CC(C)C)c2F)cc2c(N3CCOCC3)nc(-c3cnc(N)nc3)nc12] | N-(3-(2-(2-aminopyrimidin-5-yl)-8-methoxy-4-morpholinoquinazolin-6-yl)-2-fluorophenyl)-2-methylpropane-1-sulfonamide | 568.30 [M + H]$^+$ | 9 |
| 21 | 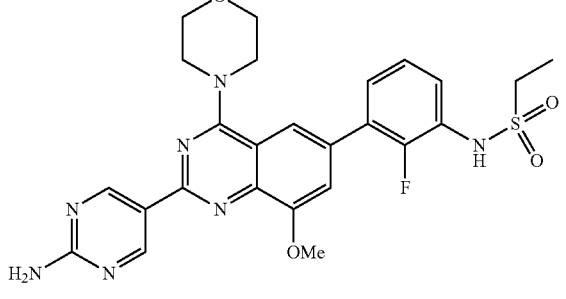 | N-(3-(2-(2-aminopyrimidin-5-yl)-8-methoxy-4-morpholinoquinazolin-6-yl)-2-fluorophenyl)\ethanesulfonamide | 538.30 [M − H]$^-$ | 9 |
| 22 | 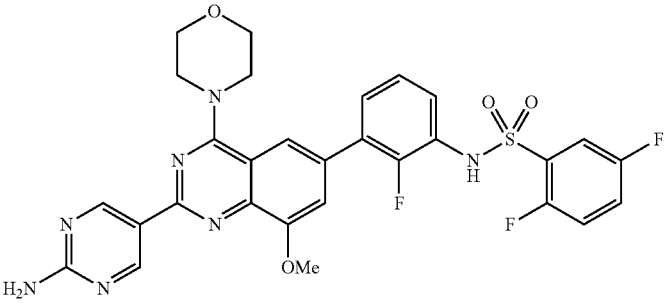 [SMILES: COc1cc(-c2cccc(NS(=O)(=O)c3cc(F)ccc3F)c2F)cc2c(N3CCOCC3)nc(-c3cnc(N)nc3)nc12] | N-(3-(2-(2-aminopyrimidin-5-yl)-8-methoxy-4-morpholinoquinazolin-6-yl)-2-fluorophenyl)-2,5-difluorobenzenesulfonamide | 622.30 [M − H]$^-$ | 9 |
| 23 | 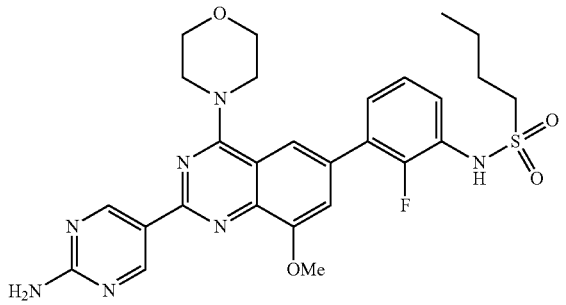 [SMILES: CCCCS(=O)(=O)Nc1cccc(-c2cc(OC)c3nc(-c4cnc(N)nc4)nc(N4CCOCC4)c3c2)c1F] | N-(3-(2-(2-aminopyrimidin-5-yl)-8-methoxy-4-morpholinoquinazolin-6-yl)-2-fluorophenyl)butane-1-sulfonamide | 566.30 [M − H]$^-$ | 9 |
| 24 | 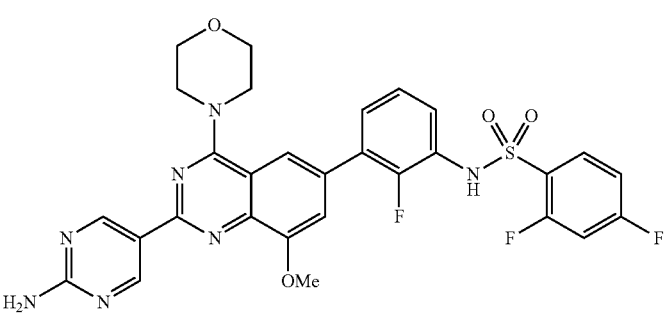 [SMILES: COc1cc(-c2cccc(NS(=O)(=O)c3ccc(F)cc3F)c2F)cc2c(N3CCOCC3)nc(-c3cnc(N)nc3)nc12] | N-(3-(2-(2-aminopyrimidin-5-yl)-8-methoxy-4-morpholinoquinazolin-6-yl)-2-fluorophenyl)-2,4-difluorobenzenesulfonamide | 622.30 [M − H]$^-$ | 9 |

TABLE 2-continued

| Ex | Structure Name | Mass (ESI-MS) | Scheme |
|---|---|---|---|
| 25 | N-(3-(2-(6-amino-4-(trifluoromethyl)pyridin-3-yl)-8-methoxy-4-morpholinoquinazolin-6-yl)-2-fluorophenyl)propane-1-sulfonamide | 621.30 [M + H]⁺ | 9 |
| 26 | N-(3-(2-(6-amino-5-methylpyridin-3-yl)-8-methoxy-4-morpholinoquinazolin-6-yl)-2-fluorophenyl)propane-1-sulfonamide | 567.30 [M + H]⁺ | 9 |
| 27 | N-(3-(2-(2-aminopyrimidin-5-yl)-8-methoxy-4-morpholinoquinazolin-6-yl)-2-fluorophenyl)-3-fluoropropane-1-sulfonamide | 570.40 [M − H]⁻ | 9 |
| 28 | N-(3-(2-(6-aminopyridin-3-yl)-8-methoxy-4-morpholinoquinazolin-6-yl)-2-fluorophenyl)-2,5-difluorobenzenesulfonamide | 623.40 [M + H]⁺ | 9 |
| 29 | N-(3-(2-(6-aminopyridin-3-yl)-8-methoxy-4-morpholinoquinazolin-6-yl)-2-fluorophenyl)-2-fluorobenzenesulfonamide | 603.30 [M − H]⁻ | 9 |

TABLE 2-continued

| Ex | Structure | Structure Name | Mass (ESI-MS) | Scheme |
|---|---|---|---|---|
| 30 | 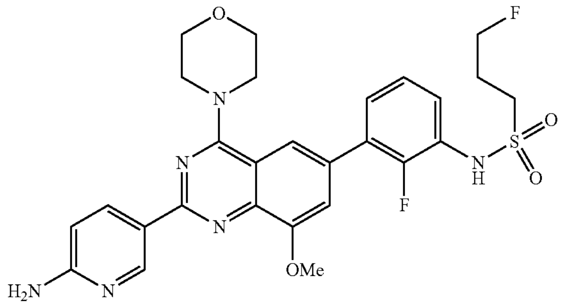 [SMILES: COc1cc(-c2cccc(NS(=O)(=O)CCCF)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2-fluorophenyl)-3-fluoropropane-1-sulfonamide | 571.30 [M + H]+ | 9 |
| 31 | 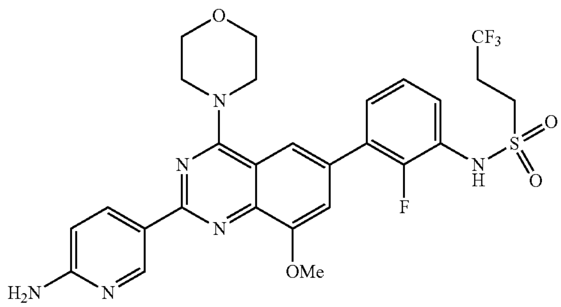 [SMILES: COc1cc(-c2cccc(NS(=O)(=O)CCC(F)(F)F)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2-fluorophenyl)-3,3,3-trifluoropropane-1-sulfonamide | 605.20 [M − H]− | 9 |
| 32 | 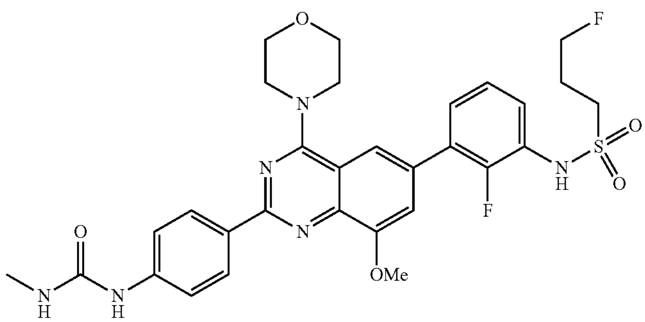 [SMILES: CNC(=O)Nc1ccc(-c2nc(N3CCOCC3)c3cc(-c4cccc(NS(=O)(=O)CCCF)c4F)cc(OC)c3n2)cc1] | 3-fluoro-N-(2-fluoro-3-(8-methoxy-2-(4-(3-methylureido)phenyl)-4-morpholinoquinazolin-6-yl)phenyl)propane-1-sulfonamide | 627.40 [M + H]+ | 9 |
| 33 | 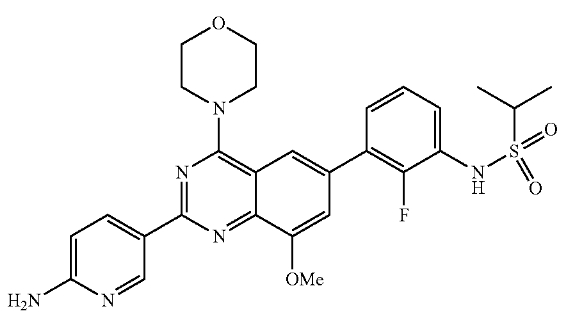 [SMILES: COc1cc(-c2cccc(NS(=O)(=O)C(C)C)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2-fluorophenyl)propane-2-sulfonamide | 551.20 [M − H]− | 9 |
| 34 | 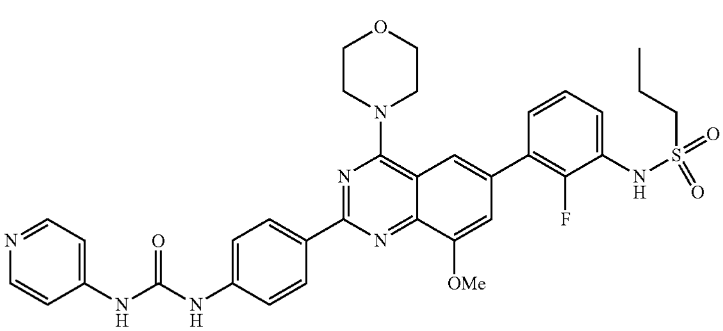 [SMILES: CCCS(=O)(=O)Nc1cccc(-c2cc(OC)c3nc(-c4ccc(NC(=O)Nc5ccncc5)cc4)nc(N4CCOCC4)c3c2)c1F] | N-(2-fluoro-3-(8-methoxy-4-morpholino-2-(4-(3-(pyridin-4-yl)ureido)phenyl)quinazolin-6-yl)phenyl)propane-1-sulfonamide | 672.20 [M + H]+ | 9 |

TABLE 2-continued

| Ex | Structure | Structure Name | Mass (ESI-MS) | Scheme |
|---|---|---|---|---|
| 35 | 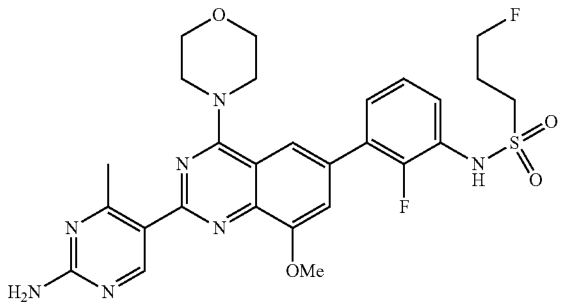 [SMILES: COc1cc(-c2cccc(NS(=O)(=O)CCCF)c2F)cc2c(N3CCOCC3)nc(-c3cnc(N)nc3C)nc12] | N-(3-(2-(2-amino-4-methylpyrimidin-5-yl)-8-methoxy-4-morpholinoquinazolin-6-yl)-2-fluorophenyl)-3-fluoropropane-1-sulfonamide | 586.30 [M + H]+ | 9 |
| 36 | 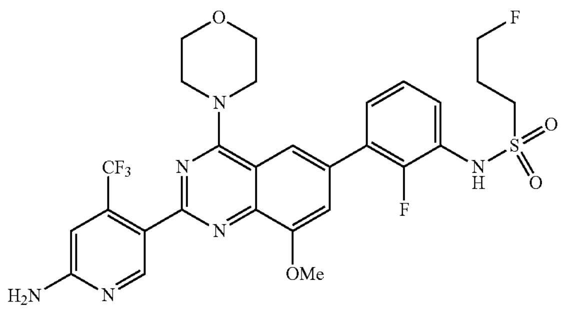 [SMILES: COc1cc(-c2cccc(NS(=O)(=O)CCCF)c2F)cc2c(N3CCOCC3)nc(-c3cnc(N)cc3C(F)(F)F)nc12] | N-(3-(2-(6-amino-4-(trifluoromethyl)pyridin-3-yl)-8-methoxy-4-morpholinoquinazolin-6-yl)-2-fluorophenyl)-3-fluoropropane-1-sulfonamide | 639.0 [M + H]+ | 9 |
| 37 | 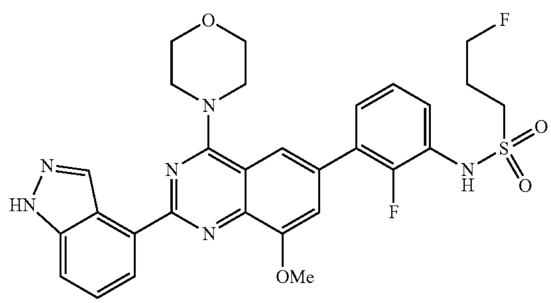 [SMILES: COc1cc(-c2cccc(NS(=O)(=O)CCCF)c2F)cc2c(N3CCOCC3)nc(-c3cccc4[nH]ncc34)nc12] | N-(3-(2-(1H-indazol-4-yl)-8-methoxy-4-morpholinoquinazolin-6-yl)-2-fluorophenyl)-3-fluoropropane-1-sulfonamide | 595.30 [M + H]+ | 9 |
| 38 | 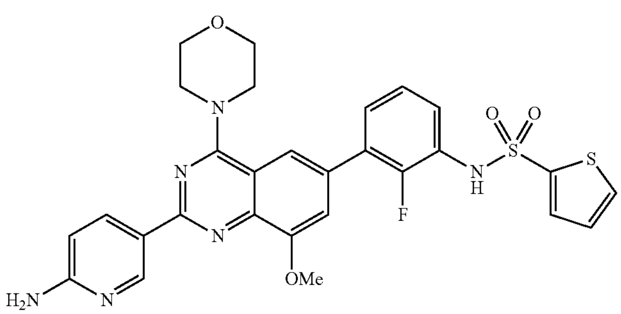 [SMILES: COc1cc(-c2cccc(NS(=O)(=O)c3cccs3)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2-fluorophenyl)thiophene-2-sulfonamide | 593.20 [M + H]+ | 9 |
| 39 | 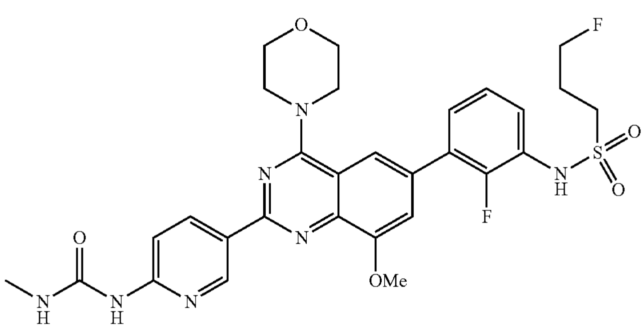 [SMILES: CNC(=O)Nc1ccc(-c2nc(N3CCOCC3)c3cc(-c4cccc(NS(=O)(=O)CCCF)c4F)cc(OC)c3n2)cn1] | 3-fluoro-N-(2-fluoro-3-(8-methoxy-2-(6-(3-methylureido)pyridin-3-yl)-4-morpholinoquinazolin-6-yl)phenyl)propane-1-sulfonamide | 628.30 [M + H]+ | 9 |

TABLE 2-continued

| Ex | Structure Name | Mass (ESI-MS) | Scheme |
|---|---|---|---|
| 40 | 3-fluoro-N-(2-fluoro-3-(8-methoxy-4-morpholino-2-(1H-pyrrolo[2,3-b]pyridin-5-yl)quinazolin-6-yl)phenyl)propane-1-sulfonamide | 595.30 [M + H]⁺ | 9 |
| 41 | (S)-N-(3-(2-(6-aminopyridin-3-yl)-8-methoxy-4-(3-methylmorpholino)quinazolin-6-yl)-2-fluorophenyl)-3-fluoropropane-1-sulfonamide | 586.20 [M + H]⁺ | 9 |
| 42 | (R)-N-(3-(2-(6-aminopyridin-3-yl)-8-methoxy-4-(3-methylmorpholino)quinazolin-6-yl)-2-fluorophenyl)-3-fluoropropane-1-sulfonamide | 585.10 [M + H]⁺ | 9 |
| 43 | (R)-N-(3-(2-(2-aminopyrimidin-5-yl)-8-methoxy-4-(3-methylmorpholino)quinazolin-6-yl)-2-fluorophenyl)-3-fluoropropane-1-sulfonamide | 586.40 [M + H] | 9 |
| 44 | (R)-3-fluoro-N-(2-fluoro-3-(8-methoxy-4-(3-methylmorpholino)-2-(1H-pyrrolo[2,3-b]pyridin-5-yl)quinazolin-6-yl)phenyl)propane-1-sulfonamide | 607.40 [M − H]⁻ | 9 |

| Ex | Structure Name | Mass (ESI-MS) | Scheme |
|---|---|---|---|
| 45 | (S)-N-(3-(2-(2-aminopyrimidin-5-yl)-8-methoxy-4-(3-methylmorpholino)quinazolin-6-yl)-2-fluorophenyl)-3-fluoropropane-1-sulfonamide | 586.20 [M + H]+ | 9 |
| 46 | N-(3-(2-(6-aminopyridin-3-yl)-4-morpholinoquinazolin-6-yl)-2-fluorophenyl)-3-fluoropropane-1-sulfonamide | 541.20 [M + H]+ | 9 |
| 47 | N-(3-(2-(2-aminopyrimidin-5-yl)-8-methoxy-4-morpholinoquinazolin-6-yl)-2-fluorophenyl)-2-fluorobenzenesulfonamide | 604.30 [M − H]− | 9 |
| 48 | N-(3-(2-(6-amino-5-chloropyridin-3-yl)-8-methoxy-4-morpholinoquinazolin-6-yl)-2-fluorophenyl)propane-1-sulfonamide | 587.40 [M + H]+ | 9 |
| 49 | 3-fluoro-N-(2-fluoro-3-(8-methoxy-4-morpholino-2-(6-(propylamino)pyridin-3-yl)quinazolin-6-yl)phenyl)propane-1-sulfonamide | 613.20 [M + H]+ | 9 |

TABLE 2-continued

| Ex | Structure | Structure Name | Mass (ESI-MS) | Scheme |
|----|-----------|----------------|---------------|--------|
| 50 | 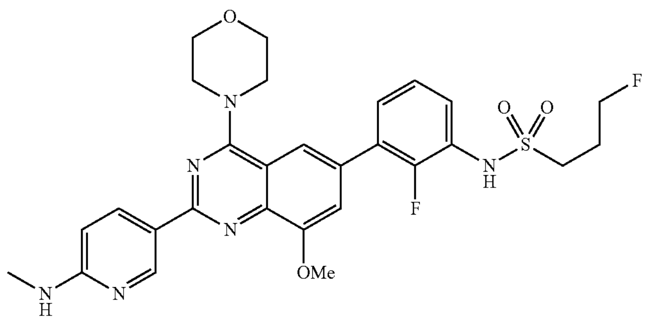 [SMILES: CNc1ccc(-c2nc(N3CCOCC3)c3cc(-c4cccc(NS(=O)(=O)CCCF)c4F)cc(OC)c3n2)cn1] | 3-fluoro-N-(2-fluoro-3-(8-methoxy-2-(6-(methylamino)pyridin-3-yl)-4-morpholinoquinazolin-6-yl)phenyl)propane-1-sulfonamide | 585.30 [M + H]+ | 9 |
| 51 | 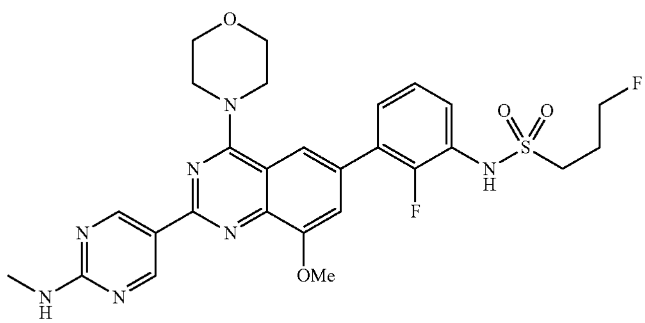 [SMILES: CNc1ncc(-c2nc(N3CCOCC3)c3cc(-c4cccc(NS(=O)(=O)CCCF)c4F)cc(OC)c3n2)cn1] | 3-fluoro-N-(2-fluoro-3-(8-methoxy-2-(2-(methylamino)pyrimidin-5-yl)-4-morpholinoquinazolin-6-yl)phenyl)propane-1-sulfonamide | 586.10 [M + H]+ | 9 |
| 52 | 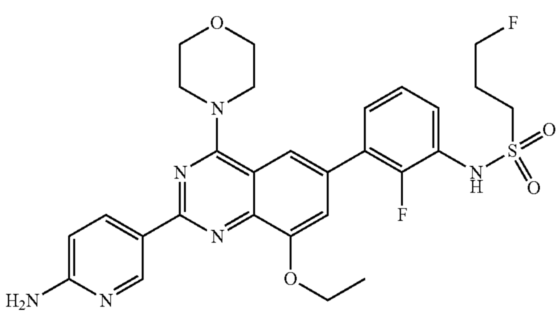 [SMILES: CCOc1cc(-c2cccc(NS(=O)(=O)CCCF)c2F)cc2c(N3CCOCC3)nc(-c3ccc(N)nc3)nc12] | N-(3-(2-(6-aminopyridin-3-yl)-8-ethoxy-4-morpholinoquinazolin-6-yl)-2-fluorophenyl)-3-fluoropropane-1-sulfonamide | 585.30 [M + H]+ | 10 |
| 53 | 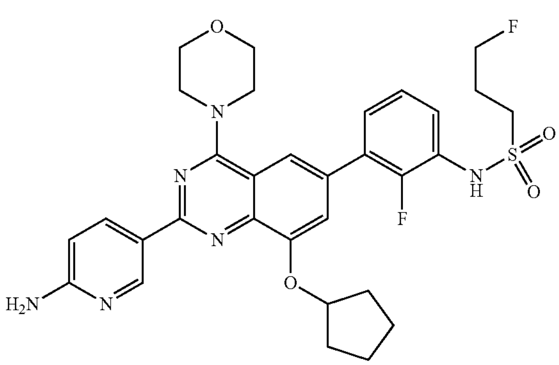 [SMILES: Nc1ccc(-c2nc(N3CCOCC3)c3cc(-c4cccc(NS(=O)(=O)CCCF)c4F)cc(OC4CCCC4)c3n2)cn1] | N-(3-(2-(6-aminopyridin-3-yl)-8-(cyclopentyloxy)-4-morpholinoquinazolin-6-yl)-2-fluorophenyl)-3-fluoropropane-1-sulfonamide | 625.40 [M + H]+ | 10 |

TABLE 2-continued

| Ex | Structure | Structure Name | Mass (ESI-MS) | Scheme |
|---|---|---|---|---|
| 54 | 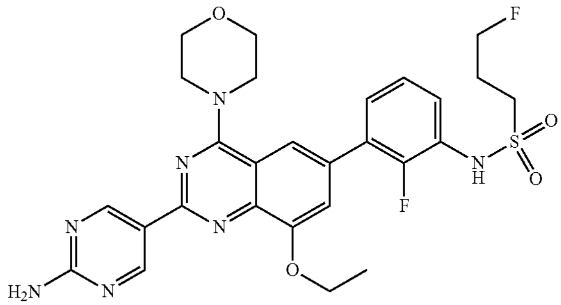 [SMILES: CCOc1cc(-c2cccc(NS(=O)(=O)CCCF)c2F)cc2c(N3CCOCC3)nc(-c3cnc(N)nc3)nc12] | N-(3-(2-(2-aminopyrimidin-5-yl)-8-ethoxy-4-morpholinoquinazolin-6-yl)-2-fluorophenyl)-3-fluoropropane-1-sulfonamide | 584.30 [M − H]⁻ | 10 |
| 55 | 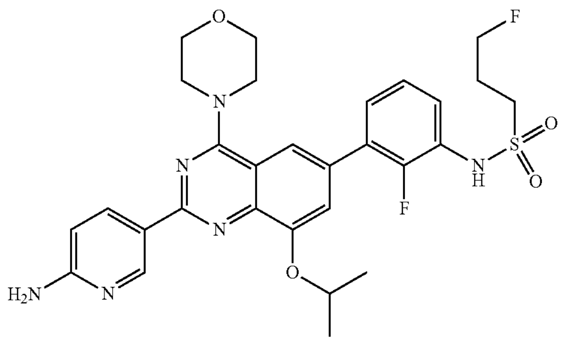 [SMILES: CC(C)Oc1cc(-c2cccc(NS(=O)(=O)CCCF)c2F)cc2c(N3CCOCC3)nc(-c3ccc(N)nc3)nc12] | N-(3-(2-(6-aminopyridin-3-yl)-8-isopropoxy-4-morpholinoquinazolin-6-yl)-2-fluorophenyl)-3-fluoropropane-1-sulfonamide | 599.30 [M + H]⁺ | 10 |
| 56 | 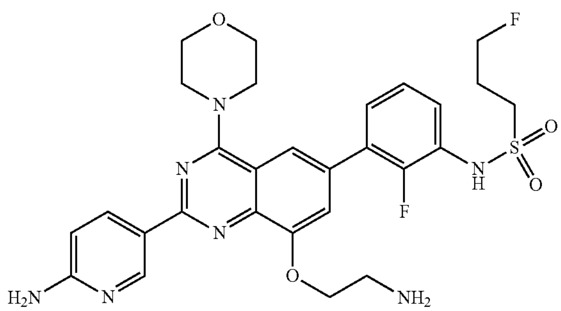 [SMILES: NCCOc1cc(-c2cccc(NS(=O)(=O)CCCF)c2F)cc2c(N3CCOCC3)nc(-c3ccc(N)nc3)nc12] | N-(3-(8-(2-aminoethoxy)-2-(6-aminopyridtn-3-yl)-4-morpholinoquinazolin-6-yl)-2-fluorophenyl)-3-fluoropropane-1-sulfonamide | 600.30 [M + H]⁺ | 10 |
| 57 | 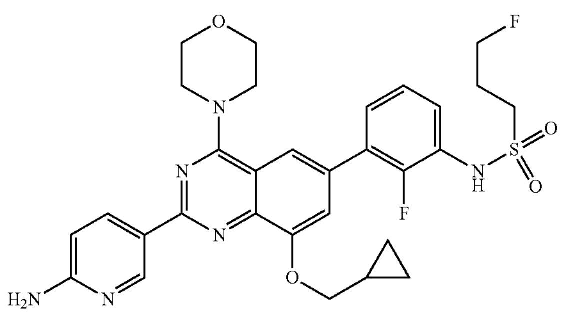 [SMILES: Nc1ccc(-c2nc(N3CCOCC3)c3cc(-c4cccc(NS(=O)(=O)CCCF)c4F)cc(OCC4CC4)c3n2)cn1] | N-(3-(2-(6-aminopyridin-3-yl)-8-(cyclopropylmethoxy)-4-morpholinoquinazolin-6-yl)-2-fluorophenyl)-3-fluoropropane-1-sulfonamide | 611.40 [M + H]⁺ | 10 |
| 58 | 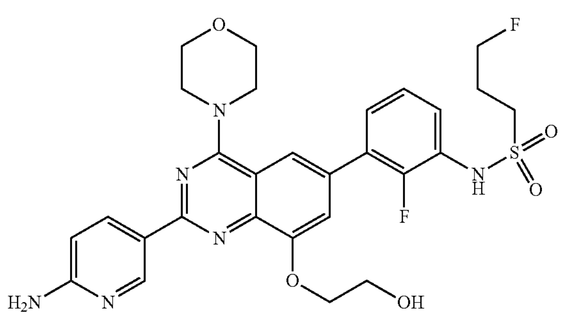 [SMILES: Nc1ccc(-c2nc(N3CCOCC3)c3cc(-c4cccc(NS(=O)(=O)CCCF)c4F)cc(OCCO)c3n2)cn1] | N-(3-(2-(6-aminopyridin-3-yl)-8-(2-hydroxyethoxy)-4-morpholinoquinazolin-6-yl)-2-fluorophenyl)-3-fluoropropane-1-sulfonamide | 601.40 [M + H]⁺ | 10 |

TABLE 2-continued

| Ex | Structure | Structure Name | Mass (ESI-MS) | Scheme |
|---|---|---|---|---|
| 59 | 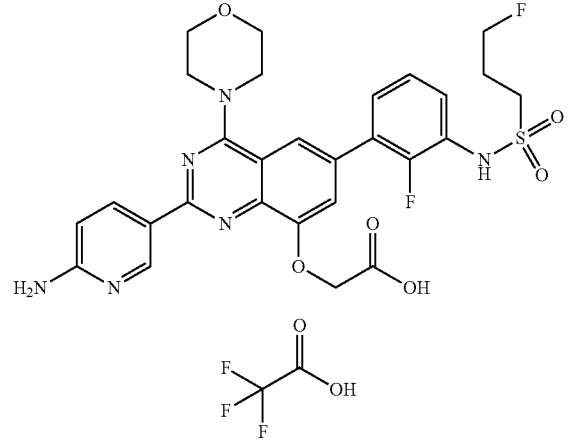 | 2-((2-(6-aminopyridin-3-yl)-6-(2-fluoro-3-(3-fluoropropylsulfonamido)phenyl)-4-morpholino-quinazolin-8-yl)oxy)acetic acid 2,2,2-trifluoroacetate | 615.30 [M + H]+ | 10 |
| 60 | 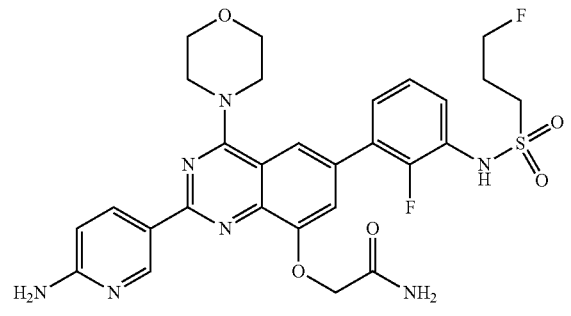 [SMILES: NC(=O)COc1cc(-c2cccc(NS(=O)(=O)CCCF)c2F)cc2c(N3CCOCC3)nc(-c3ccc(N)nc3)nc12] | 2-((2-(6-aminopyridin-3-yl)-6-(2-fluoro-3-(3-fluoropropylsulfonamido)phenyl)-4-morpholino-quinazolin-8-yl)oxy)acetamide | 614.30 [M + H]+ | 10 |
| 61 | 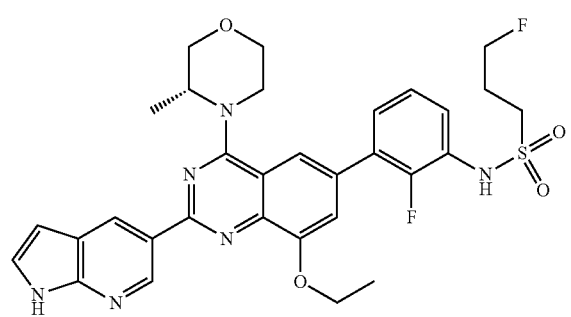 [SMILES: CCOc1cc(-c2cccc(NS(=O)(=O)CCCF)c2F)cc2c(N3CCOC[C@H]3C)nc(-c3cnc4[nH]ccc4c3)nc12] | (R)-N-(3-(8-ethoxy-4-(3-methylmorpholino)-2-(1H-pyrrolo[2,3-b]pyridin-5-yl)quinazolin-6-yl)-2-fluorophenyl)-3-fluoropropane-1-sulfonamide | 623.50 [M + H]+ | 10 |
| 62 | 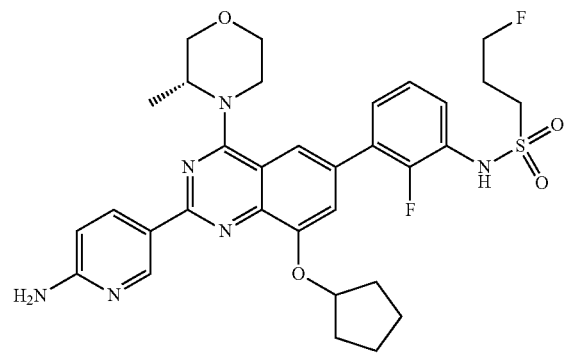 [SMILES: C[C@@H]1COCCN1c1nc(-c2ccc(N)nc2)nc2c(OC3CCCC3)cc(-c3cccc(NS(=O)(=O)CCCF)c3F)cc12] | (R)-N-(3-(2-(6-aminopyridin-3-yl)-8-(cyclopentyloxy)-4-(3-methylmorpholino)quinazolin-6-yl)-2-fluorophenyl)-3-fluoropropane-1-sulfonamide | 639.40 [M + H]+ | 10 |

TABLE 2-continued

| Ex | Structure | Structure Name | Mass (ESI-MS) | Scheme |
|---|---|---|---|---|
| 63 | 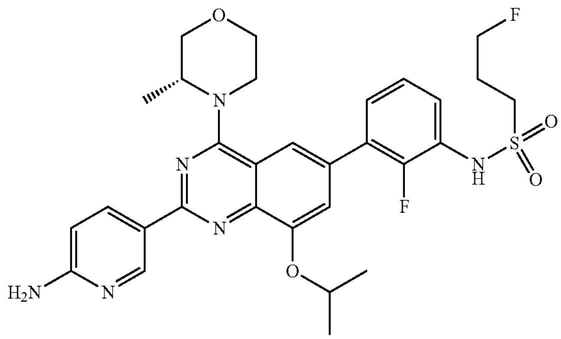 [SMILES: CC(C)Oc1cc(-c2cccc(NS(=O)(=O)CCCF)c2F)cc2c(N3CCOC[C@H]3C)nc(-c3ccc(N)nc3)nc12] | (R)-N-(3-(2-(6-aminopyridin-3-yl)-8-isopropoxy-4-(3-methylmorpholino)quinazolin-6-yl)-2-fluorophenyl)-3-fluoropropane-1-sulfonamide | 613.10 [M + H]+ | 10 |
| 64 | 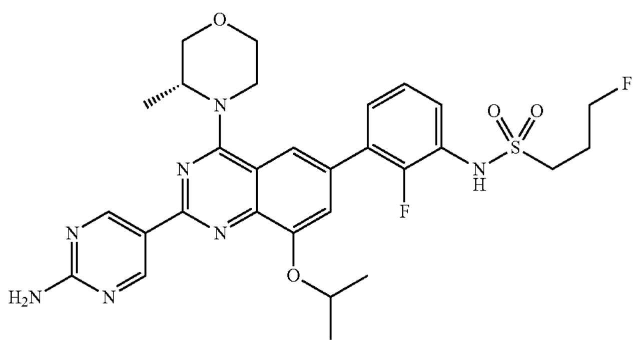 [SMILES: CC(C)Oc1cc(-c2cccc(NS(=O)(=O)CCCF)c2F)cc2c(N3CCOC[C@H]3C)nc(-c3cnc(N)nc3)nc12] | (R)-N-(3-(2-(2-aminopyrimidin-5-yl)-8-isopropoxy-4-(3-methylmorpholino)quinazolin-6-yl)-2-fluorophenyl)-3-fluoropropane-1-sulfonamide | 614.40 [M + H]+ | 10 |
| 65 | 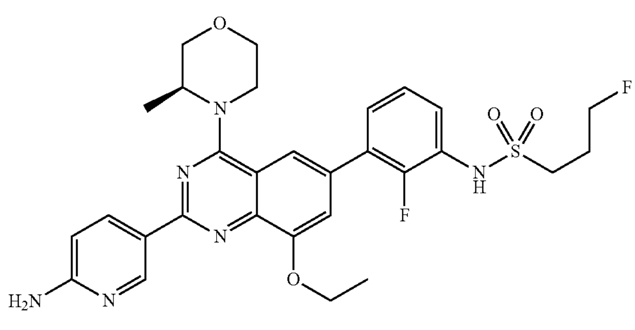 [SMILES: CCOc1cc(-c2cccc(NS(=O)(=O)CCCF)c2F)cc2c(N3CCOC[C@@H]3C)nc(-c3ccc(N)nc3)nc12] | (S)-N-(3-(2-(6-aminopyridin-3-yl)-8-ethoxy-4-(3-methylmorpholino)quinazolin-6-yl)-2-fluorophenyl)-3-fluoropropane-1-sulfonamide | 599.50 [M + H]+ | 10 |
| 66 | 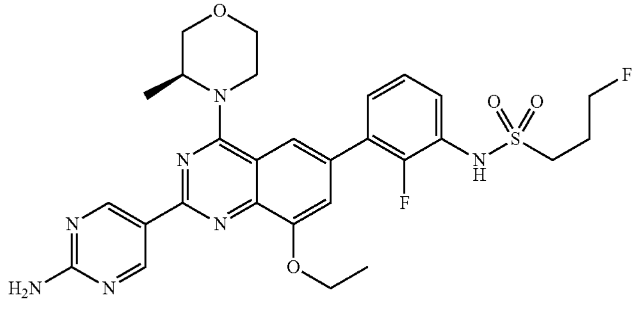 [SMILES: CCOc1cc(-c2cccc(NS(=O)(=O)CCCF)c2F)cc2c(N3CCOC[C@@H]3C)nc(-c3cnc(N)nc3)nc12] | (S)-N-(3-(2-(2-aminopyrimidin-5-yl)-8-ethoxy-4-(3-methylmorpholino)quinazolin-6-yl)-2-fluorophenyl)-3-fluoropropane-1-sulfonamide | 600.30 [M + H]+ | 10 |

TABLE 2-continued

| Ex | Structure Name | Mass (ESI-MS) | Scheme |
|---|---|---|---|
| 67 | N-(3-(2-(6-aminopyridin-3-yl)-8-(2-methoxyethoxy)-4-morpholinoquinazolin-6-yl)-2-fluorophenyl)-3-fluoropropane-1-sulfonamide | 615.30 [M + H]+ | 10 |
| 68 | N-(3-(2-(2-aminopyrimidin-5-yl)-8-(2-methoxyethoxy)-4-morpholinoquinazolin-6-yl)-2-fluorophenyl)-3-fluoropropane-1-sulfonamide | 616.40 [M + H]+ | 10 |
| 69 | N-(3-(2-(2-aminopyrimidin-5-yl)-4,8-dimorpholinoquinazolin-6-yl)-2-fluorophenyl)-3-fluoropropane-1-sulfonamide | 627.30 [M + H]+ | 11 |
| 70 | N-(3-(2-(6-aminopyridin-3-yl)-4-morpholino-8-(pyrrolidin-1-yl)quinazolin-6-yl)-2-fluorophenyl)-3-fluoropropane-1-sulfonamide | 610.40 [M + H]+ | 11 |

TABLE 2-continued

| Ex | Structure | Structure Name | Mass (ESI-MS) | Scheme |
|---|---|---|---|---|
| 71 | 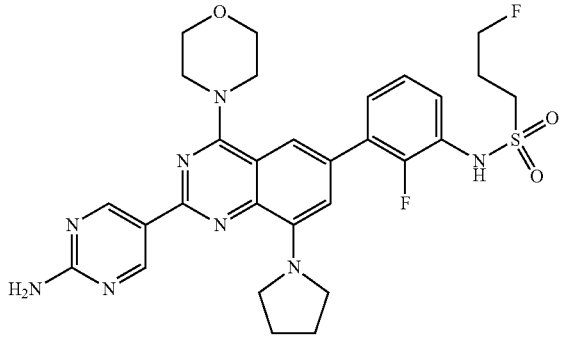 [SMILES: Nc1ncc(-c2nc(N3CCOCC3)c3cc(-c4cccc(NS(=O)(=O)CCCF)c4F)cc(N4CCCC4)c3n2)cn1] | N-(3-(2-(2-aminopyrimidin-5-yl)-4-morphollno-8-(pyrrolidin-1-yl)quinazolin-6-yl)-2-fluorophenyl)-3-fluoropropane-1-sulfonamide | 611.50 [M + H]+ | 11 |
| 72 | 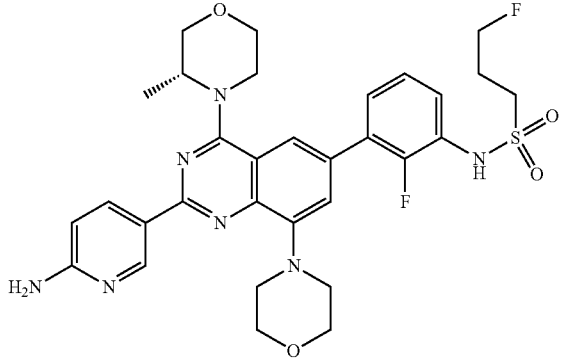 [SMILES: C[C@@H]1COCCN1c1nc(-c2ccc(N)nc2)nc2c(N3CCOCC3)cc(-c3cccc(NS(=O)(=O)CCCF)c3F)cc12] | (R)-N-(3-(2-(6-aminopyridin-3-yl)-4-(3-methylmorpholino)-8-morpholinoquinazolin-6-yl)-2-fluorophenyl)-3-fluoropropane-1-sulfonamide | 640.30 [M + H]+ | 11 |
| 73 | 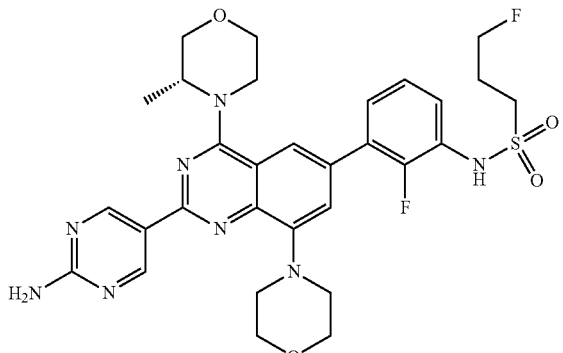 | (R)-N-(3-(2-(2-aminopyrimidin-5-yl)-4-(3-methylmorpholino)-8-morpholinoqulnazolin-6-yl)-2-fluorophenyl)-3-fluoropropane-1-sulfonamide | 641.20 [M + H]+ | 11 |
| 74 | 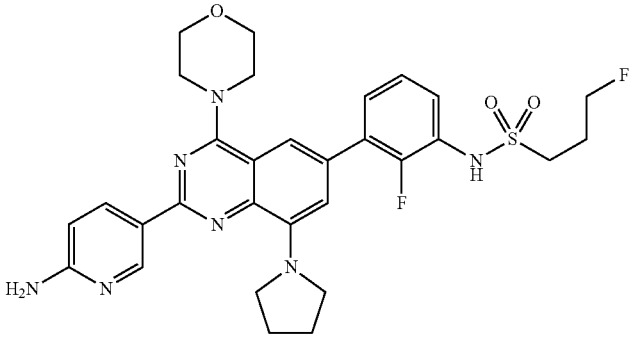 [SMILES: Nc1ccc(-c2nc(N3CCOCC3)c3cc(-c4cccc(NS(=O)(=O)CCCF)c4F)cc(N4CCCC4)c3n2)cn1] | (R)-N-(3-(2-(6-aminopyridin-3-yl)-4-(3-methylmorpholino)-8-(pyrrolidin-1-yl)quinazolin-6-yl)-2-fluorophenyl)-3-fluoropropane-1-sulfonamide | 624.50 [M + H]+ | 11 |

TABLE 2-continued

| Ex | Structure | Structure Name | Mass (ESI-MS) | Scheme |
|---|---|---|---|---|
| 75 | 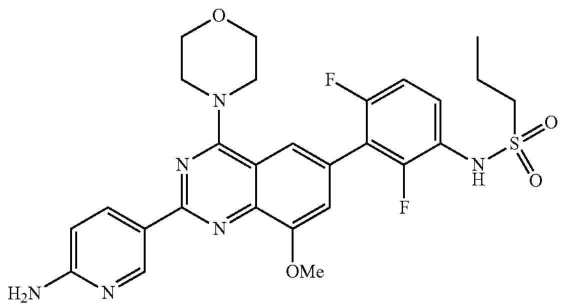 [SMILES: CCCS(=O)(=O)Nc1ccc(F)c(-c2cc(OC)c3nc(-c4ccc(N)nc4)nc(N4CCOCC4)c3c2)c1F] | N-(3-(2-(6-aminopyridin-3-yl)-8-methoxy-4-morpholinoquinazolin-6-yl)-2,4-difluorophenyl)propane-1-sulfonamide | 571.40 [M + H]+ | 12 |
| 76 | 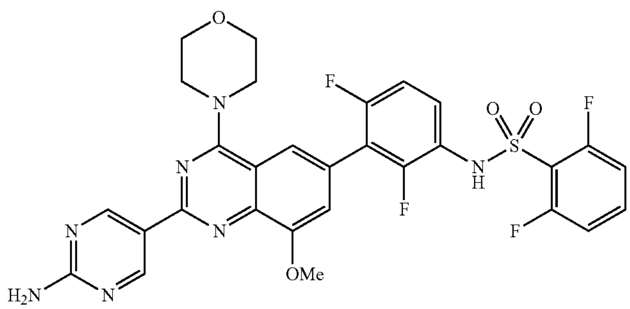 [SMILES: COc1cc(-c2c(F)ccc(NS(=O)(=O)c3c(F)cccc3F)c2F)cc2c(N3CCOCC3)nc(-c3cnc(N)nc3)nc12] | N-(3-(2-(2-aminopyrimidin-5-yl)-8-methoxy-4-morpholinoquinazolin-6-yl)-2,4-difluorophenyl)-2,6-difluorobenzenesulfonamide | 640.20 [M − H]− | 12 |
| 77 | 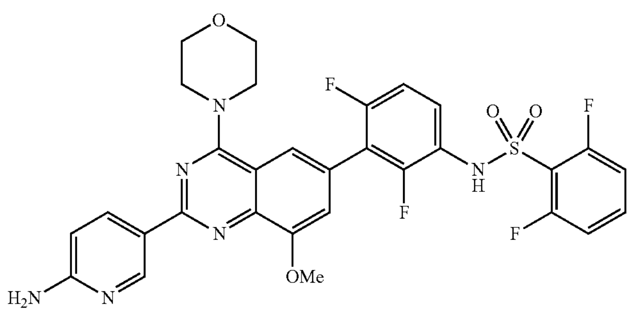 [SMILES: COc1cc(-c2c(F)ccc(NS(=O)(=O)c3c(F)cccc3F)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2,4-difluorophenyl)-2,6-difluorobenzenesulfonamide | 641.10 [M + H]+ | 12 |
| 78 | 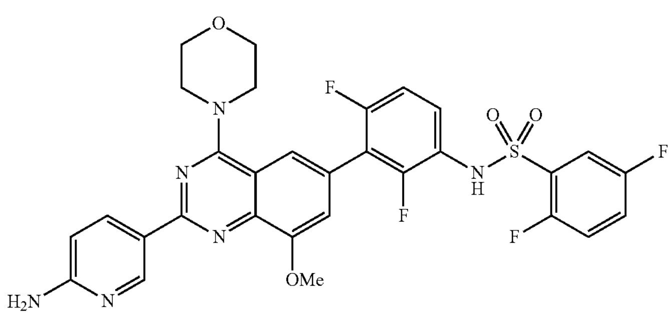 [SMILES: COc1cc(-c2c(F)ccc(NS(=O)(=O)c3cc(F)ccc3F)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-2,4-difluorophenyl)-2,5-difluorobenzenesulfonamide | 639.40 [M − H]− | 12 |
| 79 | 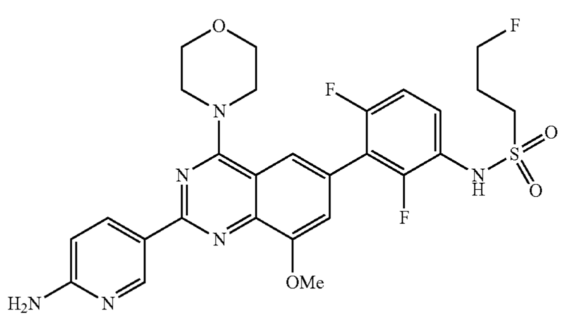 | N-(3-(2-(6-aminopyridin-3-yl)-8-methoxy-4-morpholinoquinazolin-6-yl)-2,4-difluorophenyl)-3-fluoropropane-1-sulfonamide | 589.40 [M + H]+ | 12 |

TABLE 2-continued

| Ex | Structure | Structure Name | Mass (ESI-MS) | Scheme |
|---|---|---|---|---|
| 80 | 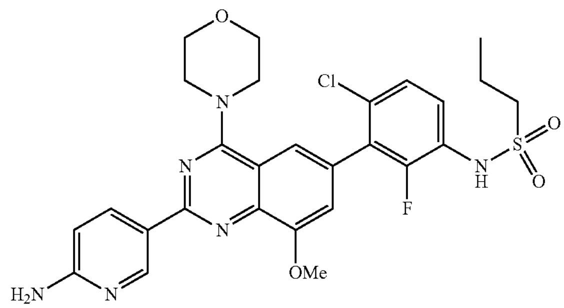 [SMILES: CCCS(=O)(=O)Nc1ccc(Cl)c(-c2cc(OC)c3nc(-c4ccc(N)nc4)nc(N4CCOCC4)c3c2)c1F] | N-(3-(2-(6-aminopyridin-3-yl)-8-methoxy-4-morpholinoquinazolin-6-yl)-4-chloro-2-fluorophenyl)propane-1-sulfonamide | 585.20 [M − H]⁻ | 12 |
| 81 | 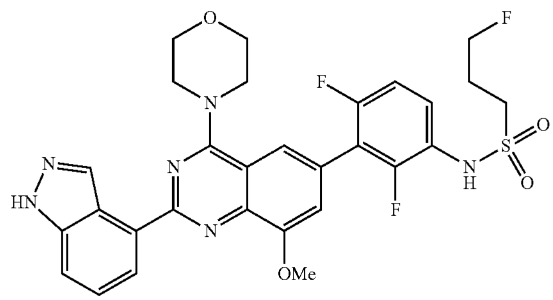 [SMILES: COc1cc(-c2c(F)ccc(NS(=O)(=O)CCCF)c2F)cc2c(N3CCOCC3)nc(-c3cccc4[nH]ncc34)nc12] | N-(3-(2-(1H-indazol-4-yl)-8-methoxy-4-morpholinoquinazolin-6-yl)-2,4-difluorophenyl)-3-fluoropropane-1-sulfonamide | 613.10 [M + H]⁺ | 12 |
| 82 | 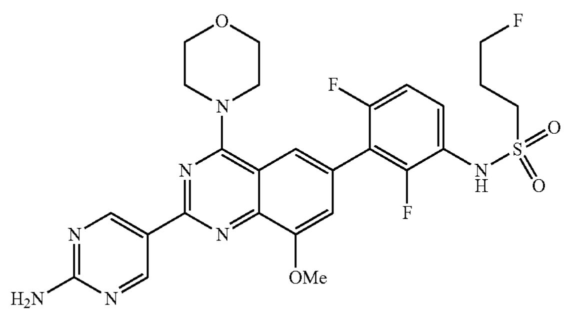 | N-(3-(2-(2-aminopyrimidin-5-yl)-8-methoxy-4-morpholinoquinazolin-6-yl)-2,4-difluorophenyl)-3-fluoropropane-1-sulfonamide | 588.30 [M − H]⁻ | 12 |
| 83 | 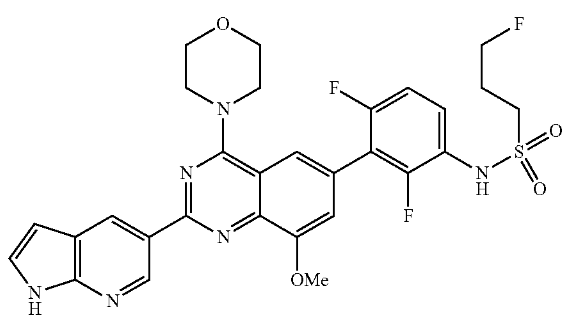 [SMILES: COc1cc(-c2c(F)ccc(NS(=O)(=O)CCCF)c2F)cc2c(N3CCOCC3)nc(-c3cnc4[nH]ccc4c3)nc12] | N-(2,4-difluoro-3-(8-methoxy-4-morpholino-2-(1H-pyrrolo[2,3-b]pyridin-5-yl)quinazolin-6-yl)phenyl)-3-(fluoropropane-1-sulfonamide | 613.10 [M + H]⁺ | 12 |
| 84 | 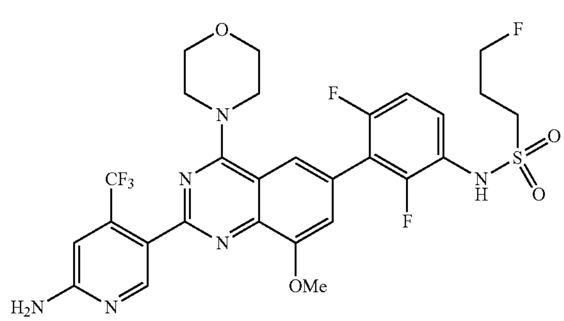 | N-(3-(2-(6-amino-4-(trifluoromethyl)pyridin-3-yl)-8-methoxy-4-morpholinoquinazolin-6-yl)-2,4-difluorophenyl)-3-fluoropropane-1-sulfonamide | 657.30 [M + H]⁺ | 12 |

TABLE 2-continued

| Ex | Structure | Structure Name | Mass (ESI-MS) | Scheme |
|---|---|---|---|---|
| 85 | 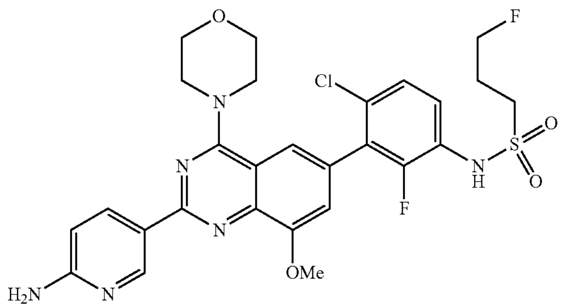 [SMILES: COc1cc(-c2c(Cl)ccc(NS(=O)(=O)CCCF)c2F)cc2c(N3CCOCC3)nc(-c3ccc(N)nc3)nc12] | N-(3-(2-(6-aminopyridin-3-yl)-8-methoxy-4-morpholinoquinazolin-6-yl)-4-chloro-2-fluorophenyl)-3-fluoropropane-1-sulfonamide | 603.30 [M − H]⁻ | 12 |
| 86 | 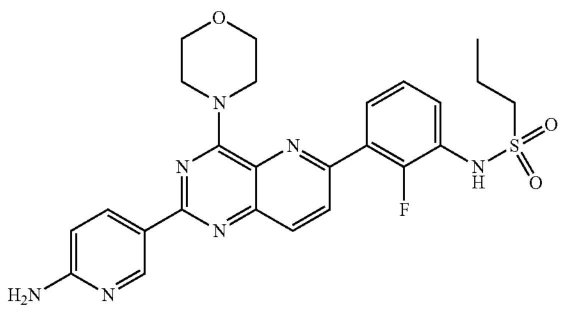 [SMILES: CCCS(=O)(=O)Nc1cccc(-c2ccc3nc(-c4ccc(N)nc4)nc(N4CCOCC4)c3n2)c1F] | N-(3-(2-(6-aminopyridin-3-yl)-4-morpholinopyrido[3,2-d]pyrimidin-6-yl)-2-fluorophenyl)propane-1-sulfonamide | 524.20 [M + H]⁺ | 13 |
| 87 | 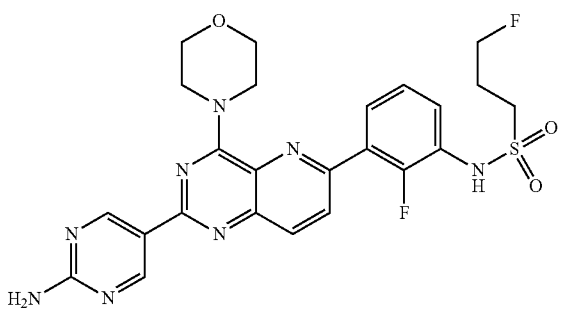 [SMILES: Nc1ncc(-c2nc(N3CCOCC3)c3nc(-c4cccc(NS(=O)(=O)CCCF)c4F)ccc3n2)cn1] | N-(3-(2-(2-aminopyrimidin-5-yl)-4-morpholinopyrido[3,2-d]pyrimidin-6-yl)-2-fluorophenyl)-3-fluoropropane-1-sulfonamide | 541.40 [M − H]⁻ | 13 |
| 88 | 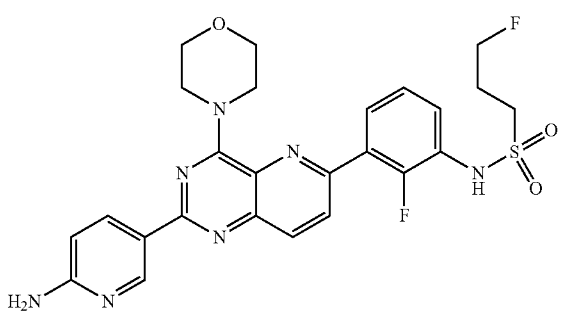 [SMILES: Nc1ccc(-c2nc(N3CCOCC3)c3nc(-c4cccc(NS(=O)(=O)CCCF)c4F)ccc3n2)cn1] | N-(3-(2-(6-aminopyridin-3-yl)-4-morpholinopyrido[3,2-d]pyrimidin-6-yl)-2-fluorophenyl)-3-fluoropropane-1-sulfonamide | 540.30 [M − H]⁻ | 13 |
| 89 | 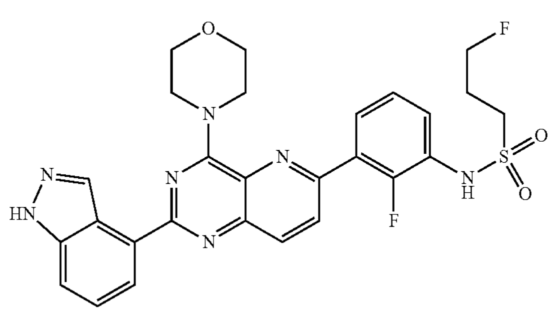 [SMILES: O=S(=O)(CCCF)Nc1cccc(-c2ccc3nc(-c4cccc5[nH]ncc45)nc(N4CCOCC4)c3n2)c1F] | N-(3-(2-(1H-indazol-4-yl)-4-morpholinopyrido[3,2-d]pyrimidin-6-yl)-2-fluorophenyl)-3-fluoropropane-1-sulfonamide | 564.30 [M − H]⁻ | 13 |

TABLE 2-continued

| Ex | Structure | Structure Name | Mass (ESI-MS) | Scheme |
|---|---|---|---|---|
| 90 | 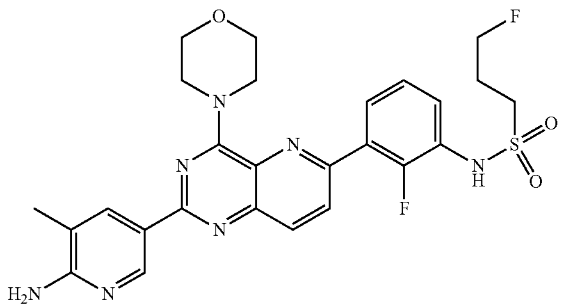 [SMILES: Cc1cc(-c2nc(N3CCOCC3)c3nc(-c4cccc(NS(=O)(=O)CCCF)c4F)ccc3n2)cnc1N] | N-(3-(2-(6-amino-5-methylpyridin-3-yl)-4-morpholinopyrido[3,2-d]pyrimidin-6-yl)-2-fluorophenyl)-3-fluoropropane-1-sulfonamide | 556.40 [M + H]+ | 13 |
| 91 | 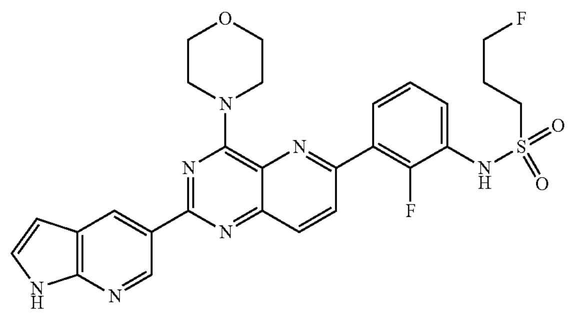 [SMILES: O=S(=O)(CCCF)Nc1cccc(-c2ccc3nc(-c4cnc5[nH]ccc5c4)nc(N4CCOCC4)c3n2)c1F] | 3-fluoro-N-(2-fluoro-3-(4-morpholino-2-(1H-pyrrolo[2,3-b]pyridin-5-yl)pyrido[3,2-d]pyrimidin-6-yl)phenyl)propane-1-sulfonamide | 564.40 [M − H]− | 13 |
| 92 | 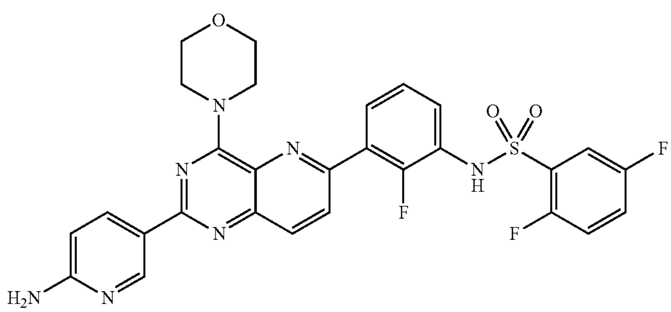 [SMILES: Nc1ccc(-c2nc(N3CCOCC3)c3nc(-c4cccc(NS(=O)(=O)c5cc(F)ccc5F)c4F)ccc3n2)cn1] | N-(3-(2-(6-aminopyridin-3-yl)-4-morpholinopyrido[3,2-d]pyrimidin-6-yl)-2-fluorophenyl)-2,5-difluorobenzenesulfonamide | 594.30 [M + H]+ | 13 |
| 93 | 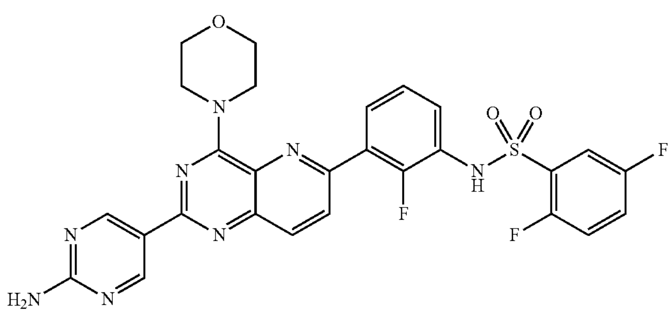 [SMILES: Nc1ncc(-c2nc(N3CCOCC3)c3nc(-c4cccc(NS(=O)(=O)c5cc(F)ccc5F)c4F)ccc3n2)cn1] | N-(3-(2-(2-aminopyrimidin-5-yl)-4-morpholinopyrido[3,2-d]pyrimidin-6-yl)-2-fluorophenyl)-2,5-difluorobenzenesulfonamide | 595.30 [M + H]+ | 13 |
| 94 | 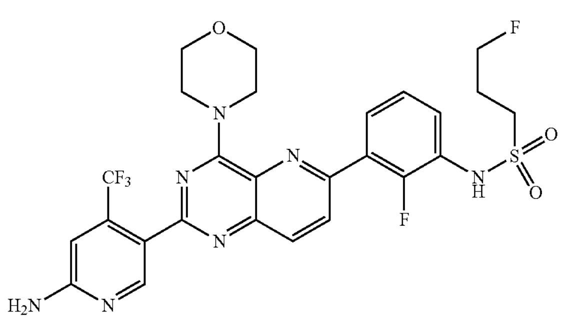 [SMILES: Nc1cc(C(F)(F)F)c(-c2nc(N3CCOCC3)c3nc(-c4cccc(NS(=O)(=O)CCCF)c4F)ccc3n2)cn1] | N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide | 610.30 [M + H]+ | 13 |

TABLE 2-continued

| Ex | Structure Name | Mass (ESI-MS) | Scheme |
|---|---|---|---|
| 95 | N-(3-(2-(6-aminopyridin-3-yl)-4-morpholinopyrido[3,2-d]pyrimidin-6-yl)-2-fluorophenyl)-2,6-difluorobenzenesulfonamide | 594.30 [M + H]+ | 13 |
| 96 | (R)-N-(3-(2-(6-aminopyridin-3-yl)-4-(3-methylmorpholino)pyrido[3,2-d]pyrimidin-6-yl)-2-fluorophenyl)-3-fluoropropane-1-sulfonamide | 556.40 [M + H]+ | 13 |
| 97 | (R)-N-(3-(2-(2-aminopyrimidin-5-yl)-4-(3-methylmorpholino)pyrido[3,2-d]pyrimidin-6-yl)-2-fluorophenyl)-3-fluoropropane-1-sulfonamide | 557.30 [M + H]+ | 13 |
| 98 | N-(3-(2-(2-aminopyrimidin-5-yl)-4-morpholinopyrido[3,2-d]pyrimidin-6-yl)-2-fluorophenyl)-2,6-difluorobenzenesulfonamide | 595.30 [M + H]+ | 13 |
| 99 | 3-fluoro-N-(2-fluoro-3-(2-(6-((2-hydroxyethyl)amino)pyridin-3-yl)-4-morpholinopyrido[3,2-d]pyrimidin-6-yl)phenyl)propane-1-sulfonamide | 586.20 [M + H]+ | 13 |

US 9,499,495 B2

143 144

TABLE 2-continued

| Ex | Structure | Structure Name | Mass (ESI-MS) | Scheme |
|---|---|---|---|---|
| 100 | 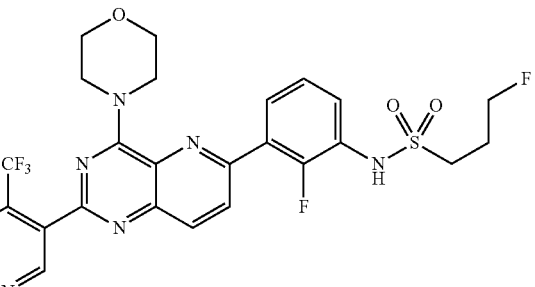 | N-(3-(2-(2-amino-4-(trifluoromethyl)pyrimidin-5-yl)-4-morpholinopyrido[3,2-d]pyrimidin-6-yl)-2-fluorophenyl)-3-fluoropropane-1-sulfonamide | 611.20 [M + H]⁺ | 13 |
| 101 | 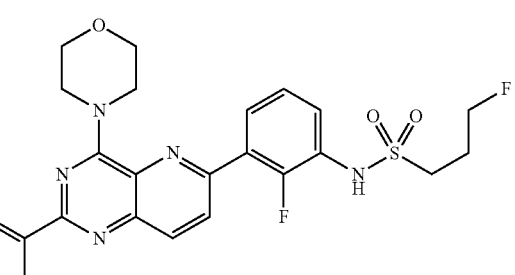 | N-(3-(2-(6-amino-4-methylpyrtdin-3-yl)-4-morpholinopyrldo[3,2-d]pyrimidin-6-yl)-2-fluorophenyl)-3-fluoropropane-1-sulfonamide | 554.50 [M − H]⁻ | 13 |
| 102 | 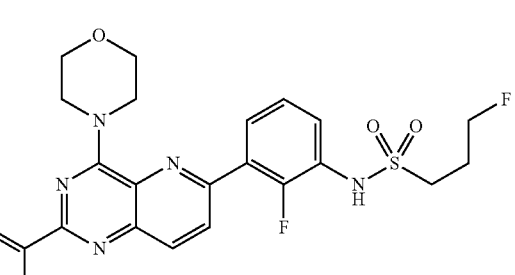 | N-(3-(2-(6-amino-4-fluoropyridin-3-yl)-4-morpholinopyrido[3,2-d]pyrimidin-6-yl)-2-fluorophenyl)-3-fluoropropane-1-sulfonamide | 560.20 [M + H]⁺ | 13 |
| 103 | 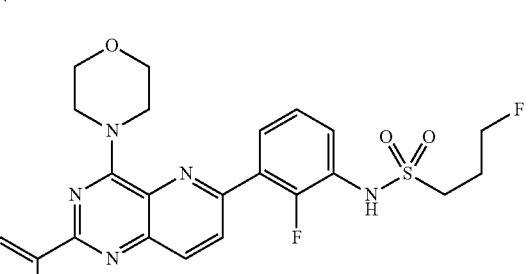 | N-(3-(2-(6-amino-5-chloropyridin-3-yl)-4-morpholinopyrido[3,2-d]pyrimidin-6-yl)-2-fluorophenyl)-3-fluoropropane-1-sulfonamide | 576.20 [M + H]⁺ | 13 |
| 104 | 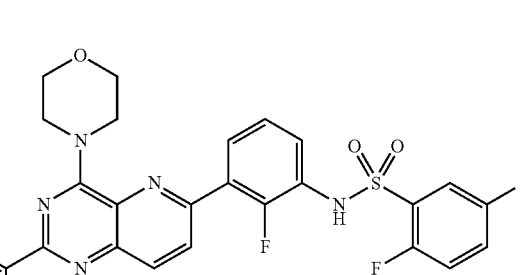 | N-(3-(2-(6-amino-4-(trifluoromethyl)pyridin-3-yl)-4-morpholinopyrido[3,2-d]pyrimidin-6-yl)-2-fluorophenyl)-2,5-difluorobenzenesulfonamide | 660.30 [M − H]⁻ | 13 |

TABLE 2-continued

| Ex | Structure Name | Mass (ESI-MS) | Scheme |
|---|---|---|---|
| 105 | N-(3-(2-(6-amino-5-fluoropyridin-3-yl)-4-morpholinopyrido[3,2-d]pyrimidin-6-yl)-2-fluorophenyl)-3-fluoropropane-1-sulfonamide | 560.20 [M + H]+ | 13 |
| 106 | N-(3-(2-(6-amino-4-(trifluoromethyl)pyridin-3-yl)-4-morpholinopyrido[3,2-d]pyrimidin-6-yl)-2-fluorophenyl)-2,6-difluorobenzenesulfonamide | 662.30 [M + H]+ | 13 |
| 107 | (R)-N-(3-(2-(6-amino-4-(trifluoromethyl)pyridin-3-yl)-4-(3-methylmorpholino)pyrido[3,2-d]pyrimidin-6-yl)-2-fluorophenyl)-3-fluoropropane-1-sulfonamide | 624.30 [M + H]+ | 13 |
| 108 | (S)-N-(3-(2-(6-amino-4-(trifluoromethyl)pyridin-3-yl)-4-(3-methylmorpholino)pyrido[3,2-d]pyrimidin-6-yl)-2-fluorophenyl)-3-fluoropropane-1-sulfonamide | 624.50 [M + H]+ | 13 |
| 109 | N-(3-(2-(2-amino-4-methylpyrimidin-5-yl)-4-morpholinopyrido[3,2-d]pyrimidin-6-yl)-2-fluorophenyl)-3-fluoropropane-1-sulfonamide | 557.30 [M + H]+ | 13 |

TABLE 2-continued

| Ex | Structure | Structure Name | Mass (ESI-MS) | Scheme |
|---|---|---|---|---|
| 110 | 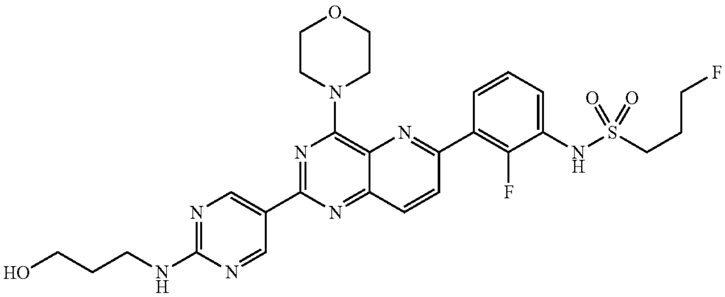 [SMILES: O=S(=O)(CCCF)Nc1cccc(-c2ccc3nc(-c4cnc(NCCCO)nc4)nc(N4CCOCC4)c3n2)c1F] | 3-fluoro-N-(2-fluoro-3-(2-(2-((3-hydroxypropyl)amino)pyrimidin-5-yl)-4-morpholinopyrido[3,2-d]pyrimidin-6-yl)phenyl)propane-1-sulfonamide | 601.30 [M + H]⁺ | 13 |
| 111 | 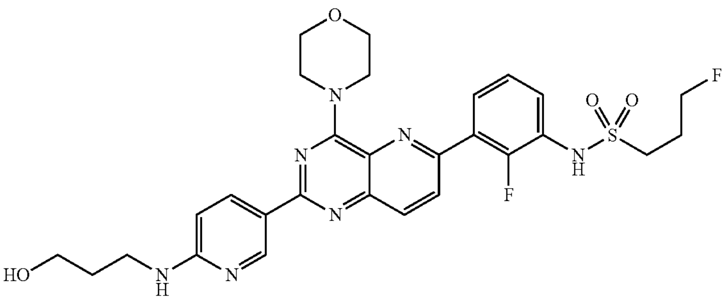 [SMILES: O=S(=O)(CCCF)Nc1cccc(-c2ccc3nc(-c4ccc(NCCCO)nc4)nc(N4CCOCC4)c3n2)c1F] | 3-fluoro-N-(2-fluoro-3-(2-(6-((3-hydroxypropyl)amino)pyridin-3-yl)-4-morpholinopyrido[3,2-d]pyrimidin-6-yl)phenyl)propane-1-sulfonamide | 598.40 [M − H]⁻ | 13 |
| 112 | 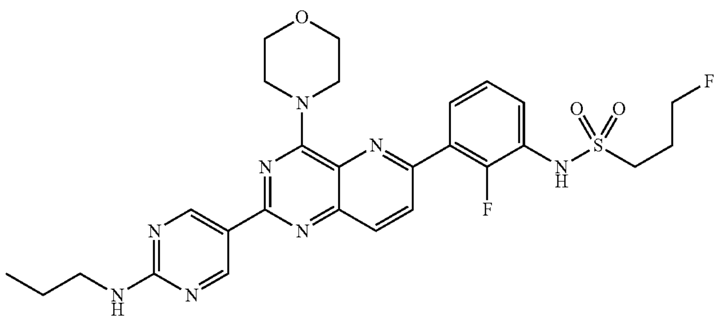 [SMILES: CCCNc1ncc(-c2nc(N3CCOCC3)c3nc(-c4cccc(NS(=O)(=O)CCCF)c4F)ccc3n2)cn1] | 3-fluoro-N-(2-fluoro-3-(4-morpholino-2-(2-(propylamino)pyrimidin-5-yl)pyrido[3,2-d]pyrimidin-6-yl)phenyl)propane-1-sulfonamide | 585.10 [M + H]⁺ | 13 |
| 113 | 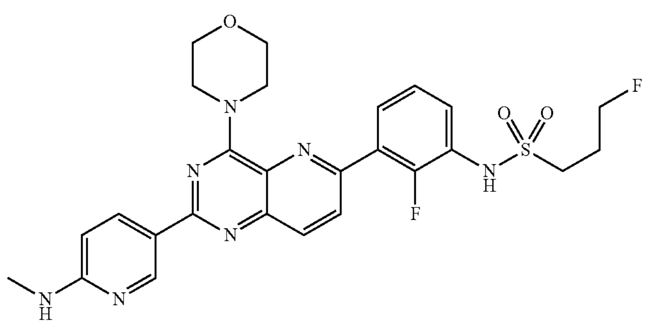 [SMILES: CNc1ccc(-c2nc(N3CCOCC3)c3nc(-c4cccc(NS(=O)(=O)CCCF)c4F)ccc3n2)cn1] | 3-fluoro-N-(2-fluoro-3-(2-(6-(methylamino)pyridin-3-yl)-4-morpholinopyrido[3,2-d]pyrimidin-6-yl)phenyl)propane-1-sulfonamide | 556.0 [M + H]⁺ | 13 |
| 114 | 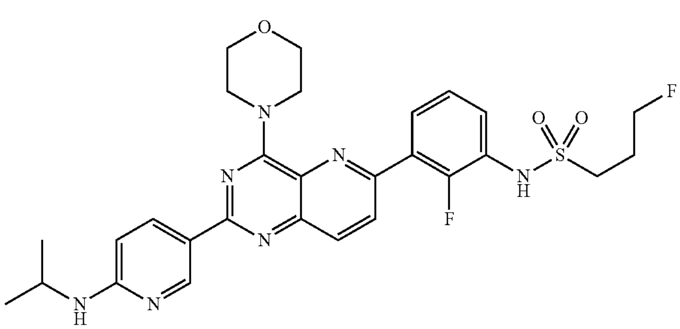 [SMILES: CC(C)Nc1ccc(-c2nc(N3CCOCC3)c3nc(-c4cccc(NS(=O)(=O)CCCF)c4F)ccc3n2)cn1] | 3-fluoro-N-(2-fluoro-3-(2-(6-(isopropylamino)pyridin-3-yl)-4-morpholinopyrido[3,2-d]pyrimidin-6-yl)phenyl)propane-1-sulfonamide | 584.20 [M + H]⁺ | 13 |

TABLE 2-continued

| Ex | Structure Name | Mass (ESI-MS) | Scheme |
|---|---|---|---|
| 115 | 3-fluoro-N-(2-fluoro-3-(4-morpholino-2-(6-(propylamino)pyridin-3-yl)pyrido[3,2-d]pyrimidin-6-yl)phenyl)propane-1-sulfonamide | 584.40 [M + H]+ | 13 |
| 116 | N-(3-(2-(2-aminopyrimidin-5-yl)-8-methyl-4-morpholinoquinazolin-6-yl)-2-fluorophenyl)-3-fluoropropane-1-sulfonamide | 556.40 [M + H]+ | 14 |
| 117 | N-(3-(2-(6-aminopyridin-3-yl)-8-methyl-4-morpholinoquinazolin-6-yl)-2-fluorophenyl)-3-fluoropropane-1-sulfonamide | 555.30 [M + H]+ | 14 |
| 118 | N-(3-(2-(1H-indazol-4-yl)-8-methyl-4-morpholinoquinazolin-6-yl)-2-fluorophenyl)-3-fluoropropane-1-sulfonamide | 579.40 [M + H]+ | 14 |
| 119 | (R)-N-(3-(2-(2-aminopyrimidin-5-yl)-8-ethyl-4-(3-methylmorpholino)quinazolin-6-yl)-2-fluorophenyl)-3-fluoropropane-1-sulfonamide | 584.30 [M + H]+ | 14 |

TABLE 2-continued

| Ex | Structure Name | Mass (ESI-MS) | Scheme |
|---|---|---|---|
| 120 | N-(3-(2-(6-aminopyridin-3-yl)-7-methoxy-4-morpholinoquinazolin-6-yl)-2-fluorophenyl)-3-fluoropropane-1-sulfonamide | 569.30 [M − H]− | 16 |
| 121 | 3-fluoro-N-(2-fluoro-3-(2-(2-(methylamino)pyrimidin-5-yl)-4-morpholinopyrido[3,2-d]pyrimidin-6-yl)phenyl)propane-1-sulfonamide | 557.3 [M + H]+ | 13 |
| 122 | N-(3-(2-(2-(ethylamino)pyrimidin-5-yl)-4-morpholinopyrido[3,2-d]pyrimidin-6-yl)-2-fluorophenyl)-3-fluoropropane-1-sulfonamide | 569.4 [M − H]− | 13 |
| 123 | N-(3-(2-(6-(ethylamino)pyridin-3-yl)-4-morpholinopyrido[3,2-d]pyrimidin-6-yl)-2-fluorophenyl)-3-fluoropropane-1-sulfonamide | 570.4 [M + H]+ | 13 |
| 124 | N-(5-(6-(2-fluoro-3-(3-fluoropropylsulfonamido)phenyl)-8-methoxy-4-morpholinoquinazolin-2-yl)pyridin-2-yl)acetamide | 613.3 [M + H]+ | 9 |

TABLE 2-continued

| Ex | Structure | Structure Name | Mass (ESI-MS) | Scheme |
|---|---|---|---|---|
| 125 | 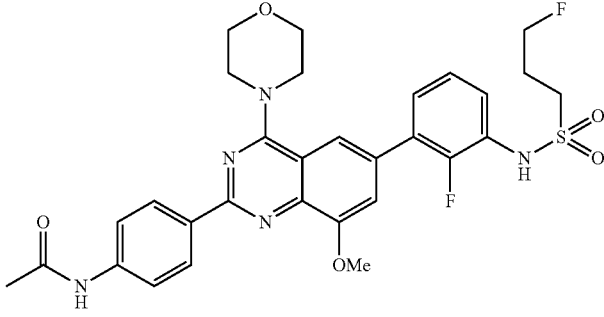 [SMILES: COc1cc(-c2cccc(NS(=O)(=O)CCCF)c2F)cc2c(N3CCOCC3)nc(-c3ccc(NC(C)=O)cc3)nc12] | N-(4-(6-(2-fluoro-3-(3-fluoropropylsulfonamido)phenyl)-8-methoxy-4-morpholinoquinazolin-2-yl)phenyl)acetamide | 612.3 [M + H]+ | 9 |
| 126 | 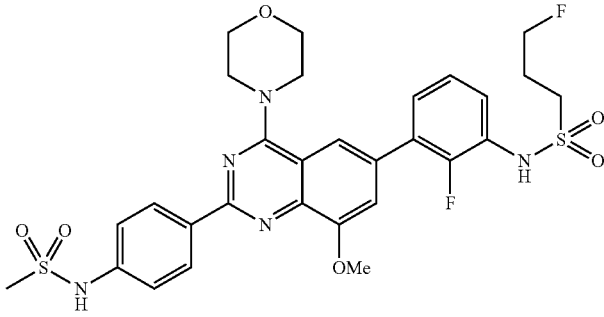 [SMILES: COc1cc(-c2cccc(NS(=O)(=O)CCCF)c2F)cc2c(N3CCOCC3)nc(-c3ccc(NS(C)(=O)=O)cc3)nc12] | 3-fluoro-N-(2-fluoro-3-(8-methoxy-2-(4-(methylsulfonamido)phenyl)-4-morpholinoquinazolin-6-yl)phenyl)propane-1-sulfonamide | 646.4 [M − H]− | 9 |
| 127 | 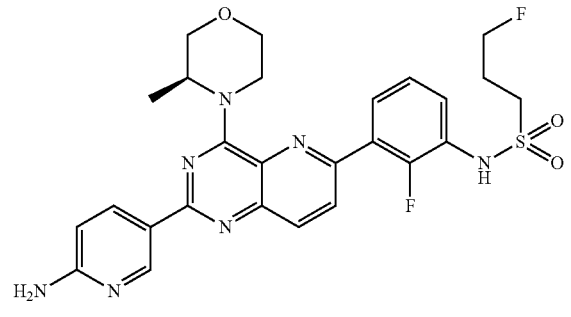 [SMILES: C[C@H]1COCCN1c1nc(-c2ccc(N)nc2)nc2ccc(-c3cccc(NS(=O)(=O)CCCF)c3F)nc12] | (S)-N-(3-(2-(6-aminopyridin-3-yl)-4-(3-methylmorpholino)pyrido[3,2-d]pyrimidin-6-yl)-2-fluorophenyl)-3-fluoropropane-1-sulfonamide | 556.6 [M + H]+ | 13 |
| 128 | 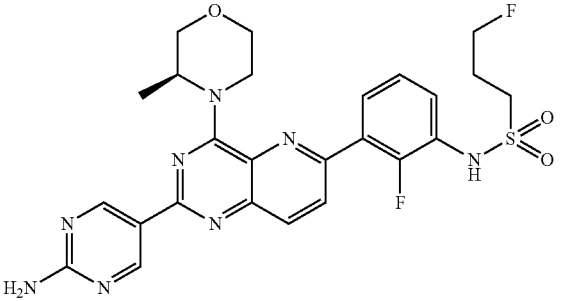 [SMILES: C[C@H]1COCCN1c1nc(-c2cnc(N)nc2)nc2ccc(-c3cccc(NS(=O)(=O)CCCF)c3F)nc12] | (S)-N-(3-(2-(2-aminopyrimidin-5-yl)-4-(3-methylrnorpholino)pyrido[3,2-d]pyrimidin-6-yl)-2-fluorophenyl)-3-fluoropropane-1-sulfonamide | 557.3 [M + H]+ | 13 |

| Ex | Structure Name | Mass (ESI-MS) | Scheme |
|---|---|---|---|
| 129 | (S)-N-(3-(2-(6-amino-4-fluoropyridin-3-yl)-4-(3-methylmorpholino)pyrido[3,2-d]pyrimidin-6-yl)-2-fluorophenyl)-3-fluoropropane-1-sulfonamide | 574.3 [M + H]+ | 13 |
| 130 | (S)-N-(3-(2-(6-amino-4-methylpyridin-3-yl)-4-(3-methylmorpholino)pyrido[3,2-d]pyrimidin-6-yl)-2-fluorophenyl)-3-fluoropropane-1-sulfonamide | 570.2 [M + H]+ | 13 |
| 131 | (S)-N-(3-(2-(2-amino-4-methylpyrimidin-5-yl)-4-(3-methylmorpholino)pyrido[3,2-d]pyrimidin-6-yl)-2-fluorophenyl)-3-fluoropropane-1-sulfonamide | 571.3 [M + H]+ | 13 |
| 132 | (S)-N-(3-(2-(2-amino-4-methylpyrimidin-5-yl)-4-(3-methylmorpholino)pyrido[3,2-d]pyrimidin-6-yl)-2-fluorophenyl)-2,5-difluorobenzenesulfonamide | 623.1 [M + H]+ | 13 |
| 133 | 3-fluoro-N-(2-fluoro-3-(2-(6-((2-methoxyethyl)amino)pyridin-3-yl)-4-morpholinopyrido[3,2-d]pyrimidin-6-yl)phenyl)propane-1-sulfonamide | 600.2 [M + H]+ | 13 |

| Ex | Structure Name | Mass (ESI-MS) | Scheme |
|---|---|---|---|
| 134 | (R)-N-(3-(2-(6-amino-5-fluoropyridin-3-yl)-8-methoxy-4-(3-methylmorpholino)quinazolin-6-yl)-2-fluorophenyl)-3-fluoropropane-1-sulfonamide | 603.1 [M + H]+ | 9 |
| 135 | (R)-N-(3-(2-(6-amino-4-fluoropyridin-3-yl)-8-methoxy-4-(3-methylmorpholino)quinazolin-6-yl)-2-fluorophenyl)-3-fluoropropane-1-sulfonamide | 603.3 [M + H]+ | 9 |
| 136 | (R)-3-fluoro-N-(2-fluoro-3-(8-methoxy-2-(2-(methylamino)pyrimidin-5-yl)-4-(3-methylmorpholino)quinazolin-6-yl)phenyl)propane-1-sulfonamide | 600.1 [M + H]+ | 9 |
| 137 | (R)-N-(3-(2-(2-aminopyrimidin-5-yl)-8-ethoxy-4-(3-methylmorpholino)quinazolin-6-yl)-2-fluorophenyl)-3-fluoropropane-1-sulfonamide | 600.3 [M + H]+ | 10 |
| 138 | (R)-N-(3-(8-ethoxy-2-(2-(methylamino)pyrimidin-5-yl)-4-(3-methylmorpholino)quinazolin-6-yl)-2-fluorophenyl)-3-fluoropropane-1-sulfonamide | 614.3 [M + H]+ | 10 |

| Ex | Structure Name | Mass (ESI-MS) | Scheme |
|---|---|---|---|
| 139 | 3-fluoro-N-(2-fluoro-3-(2-(4-(3-methylureido)phenyl)-4-morpholinopyrido[3,2-d]pyrimidin-6-yl)phenyl)propane-1-sulfonamide | 598.3 [M + H]+ | 13 |
| 140 | (R)-N-(3-(2-(6-amino-4-fluoropyridin-3-yl)-4-(3-methylmorpholino)pyrido[3,2-d]pyrimidin-6-yl)-2-fluorophenyl)-3-fluoropropane-1-sulfonamide | 574.3 [M + H]+ | 13 |
| 141 | (R)-N-(3-(2-(2-aminopyrimidin-5-yl)-8-(2-fluoroethoxy)-4-(3-methylmorpholino)quinazolin-6-yl)-2-fluorophenyl)-3-fluoropropane-1-sulfonamide | 618.2 [M + H]+ | 10 |
| 142 | (R)-N-(3-(2-(6-amino-5-fluoropyridin-3-yl)-8-(2-fluoroethoxy)-4-(3-methylmorpholino)quinazolin-6-yl)-2-fluorophenyl)-3-fluoropropane-1-sulfonamide | 635.3 [M + H]+ | 10 |
| 143 | (R)-N-(3-(2-(5-aminopyrazin-2-yl)-8-methoxy-4-(3-methylmorpholino)quinazolin-6-yl)-2-fluorophenyl)-3-fluoropropane-1-sulfonamide | 586.4 [M + H]+ | 9 |

TABLE 2-continued

| Ex | Structure | Structure Name | Mass (ESI-MS) | Scheme |
|---|---|---|---|---|
| 144 | 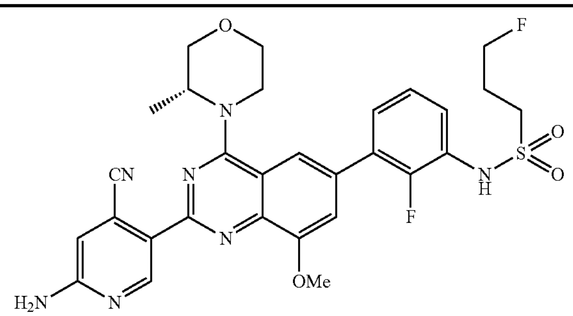 | (R)-N-(3-(2-(6-amino-4-cyanopyridin-3-yl)-8-methoxy-4-(3-methylmorpholino)quinazolin-6-yl)-2-fluorophenyl)-3-fluoropropane-1-sulfonamide | 610.1 [M + H]+ | 9 |

Example 145

A. B-RAF$_{V600E}$ Radiometric Assay

Compound inhibition for B-RAF$_{V600E}$ was determined through radiometric assay using a BRAF enzyme (Catalog No. 14-557, Millipore, USA) and MEK-K97M protein as a substrate (Catalog No. 0785-0000-1, ProqQinase GmbH, Germany). The B-RAF kinase catalyzes the phosphorylation of MEK protein in the presence of gamma ATP (PLC-101, Jonaki, CCMB, Hyderabad), cold ATP and Mg$^{2+}$.

The phosphorylated protein product is detected by the scintillation counter Topcount® machine (Perkin Elmer). This assay has been adapted from the method previously reported by Yeh et al. (2007, Clinical Cancer Research; 13, 1576-1583). The assay measures the B-RAF mediated transfer of 32P from the gamma position of radiolabeled ATP onto MEK1-KD. The labeled phosphorylated protein was measured in MicroBeta® Trilux Counter (Perkin Elmer). The assay was validated with reference compounds RAF1 Kinase Inhibitor I and ZM 336372 inhibitor which are reported to be inhibitors of B-RAF enzyme (Lackey, 2000, Medicinal Chemistry Letters; 10(3):223-226; Kupcho, "Fluorescent High throughput kinase cascade assays for inhibitor characterization, RAF-MEK-ERK pathway, www-.invitrogen.com, and Hall-Jackson, 1999, Chemical Biology; 6(8):559-568). B-RAF enzyme mixture (13 µL) was added to compound wells containing 2 µL of the NCE in 1% DMSO and incubated for 45 min at rt on a shaking incubator at 300 rpm. MEK-K97M (0.5 µg) and cold ATP to a final concentration of 5 µM, and hot ATP 0.1 µCi in a volume of 10 µL was added to each well and incubated for 2 h at rt on a shaking incubator at 300 rpm. The reaction was stopped by addition of 8N HCl (13 µL) containing ATP (1 mM: 495 µL 1N HCl and 5 µL 100 mM ATP). Aliquot (30 µL) was then transferred to the center of a 2 cm×2 cm P81 paper. P81 paper was washed 8×5 min each with ortho-phosphoric acid (0.5%). P81 papers are washed twice with acetone for 5 mM Assay squares were allowed to dry for 15 mM at 37° C. P81 paper are transferred to Optiplate™ (Perkin Elmer) and counted in a Topcount® counter (Perkin Elmer). Data was plotted against the compound concentration to generate dose-response curves and IC$_{50}$ values were determined using a sigmoidal dose response curve fit GraphPad Prism® v5 software.

B. mTOR kinase TR-FRET Assay

Compound inhibition for mTOR kinase was determined by homogeneous TR-FRET assay using ULight-p70 S6K (Thr 389) peptide as substrate. mTOR enzyme (Millipore, US; 5 jag) was used in the assay. The reaction buffer was HEPES (50 mM, pH 7.5), EGTA (1 mM), and MnCl$_2$ (3 mM). Test compound was pre-incubated with mTOR for 30 min followed by 50 nM ULight-p70 S6K (Thr 389) peptide along with ATP (20 µM).

After incubating the reaction mixture for 30 min, Eu-labeled anti-phospho-substrate antibody (1 nM, Perkin Elmer, USA) was added. Fluorescence emission at 615 and 665 nM was measured upon excitation at 340 nM. The compound dilution was carried out in 100% DMSO followed by a buffer dilution. The kinase reaction was incubated for 1 h at rt followed by the addition of substrate-ATP mix and incubated at rt for 1 h. The reaction was terminated by the addition of EDTA followed by the addition of detection mix. IC$_{50}$ values were determined using a sigmoidal dose response curve fit, GraphPad Prism® v5 software.

C. PI3 Kinase alpha TR-FRET Assay

Compound inhibition for PI3Kα was determined in a homogeneous TR-FRET assay using a PI3Kα assay kit (Millipore, US, Catalog #33-016). The PI3 kinase catalyzes phosphorylation of phosphatidylinositol, 5-bisphosphate (PIP2) to phosphatidylinositol 3,4,5-trisphosphate (PIP3) in the presence of ATP and Mg$^{2+}$. The PIP3 product is detected by displacement of biotin-PIP3 from an energy transfer complex consisting of Europium labeled anti-GST monoclonal antibody, a GST-tagged pleckstrin homology (PH) domain, biotinylated PIP3 and Streptavidin-Allophycocyanin (APC). Excitation of Europium in the complex results in an energy transfer to the APC and a fluorescence emission at 665 nm.

Compounds tested were dissolved in DMSO and directly distributed into 384-well plates at a volume of 0.5 µL. P110/P85a/PIP2 mixture (14.5 µL) was added to compound wells and incubated for 30 min at rt for 60 min. P110/P85a was expressed in SF9 cells and purified in-house. 5 ng P110/P85a was used in the assay. The kinase reaction was started by the addition of ATP. The assay concentrations of both PIP2 and ATP were 40 µM. The reaction mixture was incubated for 30 min and was terminated by the addition of stop mix and detection mix. Fluorescence was measured at 615 and 665 nm upon excitation at 340 nm in a Victor V5 fluorometer (Perkin Elmer, US). The fluorescence emission ratio at 665 to 615 nm, proportional to the kinase activity, was plotted against the compound concentration to generate dose-response curves and IC$_{50}$ values were determined.

D. XTT Assay for Cell Viability

Cell lines (A375 ATCC No. CRL-1619, A2058 ATCC No. CRL-11147 and RKO ATCC No. CRL-2577, American Type Culture Collection (ATCC), Manassas Va.) once attaining ~80% confluency were trypsinized, centrifuged and resuspended in fresh media. Cells (1000-2000/per well) were seeded in 96-well plate and incubated over-night at 37° C. in a 5% $CO_2$ incubator. Compound dilutions were prepared in 100% DMSO followed by dilutions in the respective media. The cells were treated with NCEs for 72 h at 37° C. in 5% $CO_2$ incubator. After 72 h, freshly prepared XTT (1 mg/ml)/PMS (25 µM) solution was added, incubated for 2 to 3 h at 37° C. and the absorbance was measured at 450 nm using an ELISA plate reader. Keeping DMSO control as 100%, the effect of the compound to inhibit the cell proliferation was calculated and the $GI_{50}$ values were determined using sigmoidal dose response curve fit in GraphPad Prism® v5 software.

E. Measurement of pERK, pS6RP, pAKT-S473, and pAKT-T308 by In Cell Western (ICW) Assays Cell lines A375, A2058 and RKO obtained from the ATCC as provided above, were grown, and after attaining ~80% confluency were trypsinized, centrifuged and resuspended in fresh media. The cells were seeded at the specified density (20,000 to 50,000) in a 96-well format black-well clear bottom plate (Corning) and incubated overnight at 37° C. in a 5% $CO_2$ incubator. The next day, compound dilutions of test compounds were prepared in 100% DMSO followed by dilutions in respective media. Treatment of test compounds was performed for 3 h at 37° C. in 5% $CO_2$ incubator. Following 3 h drug treatment, the conditional media was discarded and the cells were washed once with cPBS (PBS containing 0.1% magnesium chloride hexahydrate and 0.1% anhydrous calcium chloride) and fixed with 4% paraformaldehyde in cPBS for 1 h at rt. After fixing, the cells were given three washes using cPBST (cPBS containing 0.1% Triton™ X-100 reagent) and then blocked using blocking solution (5% skimmed milk powder or 5% BSA prepared in cPBST) for 2 h at rt with shaking at 300 rpm. The cells were again washed thrice with cPBST and incubated with primary antibody phospho-p44/42 MAPK(Erk1/2)(Thr202/204) antibody (Cell Signaling, Catalog # 9101L), phospho S6 ribosomal protein (Cell Signaling, Catalog #4858L), phospho AKT (Thr 308) (Cell Signaling, Catalog #9275) or phospho AKT (Ser 473) (Cell Signaling, Catalog #4060L) in specified dilutions (1:500-1:2500), prepared in respective blocking solutions, in a racker overnight at 4° C. The next day, the cells were washed with 1× Delfia® wash buffer (4×1 wash) and incubated with secondary antibody (Delfia®-Eu-N1 labeled anti-rabbit antibody; PerkinElmer, Catalog #AD0105; dilutions: 1:2000 to 1:6000 in Delfia® assay buffer (PerkinElmer, Catalog #1244-111)) for 2 h at rt in the dark at 300 rpm. The cells were then given four washes with 1× Delfia® wash buffer and incubated with Wallac Delfia® Enhancement solution (100 µL; PerkinElmer, Catalog #1244-105) for 20 min at rt in the dark at 300 rpm. The fluorescence emission was then read at 615 nM with an excitation wavelength of 340 nM using a Victor V5 Fluorometer (Perkin Elmer, US). The cells were then washed once with 1×cPBS and incubated with 100 µL of 0.5 mg/mL of Hoechst 33258 dye prepared in cPBS and read at 460 nm with 355 nm excitation, thereby evaluating the correction factor.

PLX-4032 (B-RAF inhibitor), BEZ-235 (PI3K/mTOR inhibitor) and GDC-0941 (PI3K inhibitor) were taken as the standards for pERK, pS6RP/pAKT (S473) and pAKT (T308) inhibitions, respectively, as are shown in the following Table. The % inhibition for the test compounds of formula (I) (new chemical entities (NCEs)) was calculated keeping DMSO control as 0% and the $IC_{50}$ values were determined using sigmoidal dose response curve fit in GraphPad Prism® v5 software.

| Analytes | Group | Conc | Avg Reading range - Relative Fluorescent Units (RFU) | % Inhibition |
|---|---|---|---|---|
| A375-pERK inhibition | Background | No cells | 500-1000 | — |
| | Positive control | 0.1% DMSO | 50000-90000 | 0.0 |
| | Standard | PLX-4032 (10 mM) | 3000-10000 | 85%-90% |
| | NCE's | 10 mM | 2000-10000 | 85%-90% |
| RKO-pERK inhibition | Background | No cells | 500-1000 | — |
| | Positive control | 0.1% DMSO | 50000-90000 | 0.0 |
| | Standard | PLX-4032 (10 mM) | 8000-10000 | 75%-85% |
| | NCE's | 10 mM | 8000-10000 | 80%-90% |
| RKO-pS6RP inhibition | Background | No cells | 1000-2000 | — |
| | Positive control | 0.1% DMSO | 40000-80000 | 0.0 |
| | Standard | BEZ-235 (10 mM) | 4000-16000 | 80%-90% |
| | NCE's | 10 mM | 2000-12000 | 70%-95% |
| RKO-pAKT(Ser473) inhibition | Background | No cells | 700-1000 | — |
| | Positive control | 0.1% DMSO | 50000-60000 | 0.0 |
| | Standard | BEZ-235 (10 mM) | 5000-9000 | 80%-90% |
| | NCE's | 10 mM | 4000-20000 | 85%-90% |
| RKO-pAKT(Thr308) inhibition | Background | No cells | 500-5000 | — |
| | Positive control | 0.1% DMSO | 30000-80000 | 0.0 |
| | Standard | GDC-0941 (10 mM) | 2000-30000 | 55%-65% |
| | NCE's | 10 mM | 10000-30000 | 50%-70% |

Data from the B-RAF radiometric assay, the PI3K and mTOR TR-FRET assays, the XTT cell viability assays and the in-cell Western assays for Examples 1-120 are shown in Table 3.

TABLE 3

| | Kinase assay | | | A375 cells | | RKO cells | | | |
|---|---|---|---|---|---|---|---|---|---|
| | | | | | | | | pAKT | |
| Ex | B-Raf | PI3Kα | mTOR | pERK | XTT | pERK | pS6RP | (T308) | XTT |
| 1 | A | | A | B | B | B | | | C |
| 2 | A | B | | B | B | | | | |

TABLE 3-continued

|    | Kinase assay | | | A375 cells | | RKO cells | | | |
|----|------|-------|------|------|-----|------|-------|------|-----|
|    |      |       |      |      |     |      |       | pAKT |     |
| Ex | B-Raf | PI3Kα | mTOR | pERK | XTT | pERK | pS6RP | (T308) | XTT |
| 3  | A | B |   | A | C |   |   |   |   |
| 4  | B |   | B |   |   |   |   |   |   |
| 5  | A |   | A | A | A | A | A |   | B |
| 6  | A |   | A | B | B |   |   |   |   |
| 7  | B | A | B | B | B |   |   |   | B |
| 8  | B | B |   | B | B |   |   |   | B |
| 9  | A |   | B | B | B |   |   |   |   |
| 10 | B |   | B |   |   |   |   |   |   |
| 11 | A | B | A | A | B |   | B |   | B |
| 12 | B |   | A | C |   |   |   |   |   |
| 13 | A |   | B | B | B |   |   |   |   |
| 14 | B |   | A | B | B |   |   |   |   |
| 15 | B |   | B | B | B |   |   |   |   |
| 16 | B |   | B | B |   |   |   |   |   |
| 17 | A |   | A | B | B |   |   |   |   |
| 18 | B |   | B | B | B |   |   |   |   |
| 19 | A |   | B | B | B |   |   |   |   |
| 20 | A |   | B | B | B |   |   |   |   |
| 21 | B |   | B | B | C |   |   |   |   |
| 22 | A |   | B | A | B |   |   |   |   |
| 23 | B |   | B |   |   |   |   |   |   |
| 24 | B |   | B |   |   |   |   |   |   |
| 25 | B | B |   | B |   |   |   |   |   |
| 26 | B | B |   | B | B |   |   |   |   |
| 27 | A |   | B | A | B |   |   |   |   |
| 28 | A |   | B | A | B |   |   |   |   |
| 29 | A |   | B | A | B |   |   |   |   |
| 30 | A |   | B | A | B | A | B |   | B |
| 31 | B |   | B |   |   |   |   |   |   |
| 32 | B |   | A | B |   |   |   |   |   |
| 33 | B |   | B | B | B |   |   |   |   |
| 34 | B |   | A |   |   |   |   |   |   |
| 35 | A |   | B |   |   |   |   |   |   |
| 36 | A | B |   | A | B |   |   |   | C |
| 37 | A | B |   | A | B |   |   |   | C |
| 38 | A |   | B | A | B |   |   |   |   |
| 39 | A | B | A | A | A |   |   |   |   |
| 40 | A |   | A | A | B |   | B |   |   |
| 41 | A |   | A | A | B |   |   |   |   |
| 42 | A |   | A | A | A | A | B |   | B |
| 43 | A | B | A | A | A | A | B |   | B |
| 44 | B |   | B |   |   |   |   |   |   |
| 45 | B |   | B | B | B |   |   |   |   |
| 46 | A |   | B | A | B |   |   |   |   |
| 47 | A |   | B | B | B |   |   |   |   |
| 48 | A | B |   |   |   |   |   |   |   |
| 49 | A |   | B |   |   |   |   |   |   |
| 50 | A |   | A | A | A |   |   |   | B |
| 51 | A |   | A | A | A |   |   |   | B |
| 52 | A |   | B | A | A | A | B |   | B |
| 53 | A |   | A | A | A |   |   |   | B |
| 54 | A |   | B | A | B |   |   |   |   |
| 55 | A |   | B | A | A | A | B |   | B |
| 56 | A | B | A | A |   |   |   |   |   |
| 57 | A |   | B | A |   |   |   |   |   |
| 58 | A |   | A | B |   |   |   |   |   |
| 59 | B |   | A |   |   |   |   |   |   |
| 60 | A |   | A | C | C |   |   |   |   |
| 61 | A |   | B |   |   |   |   |   |   |
| 62 | A |   | A | A | A |   |   |   | B |
| 63 | A |   | A | A | A | A | B |   | B |
| 64 | A |   | B | A | A |   | B |   |   |
| 65 | A |   | A | A | B |   | B |   | B |
| 66 | A |   | B |   |   |   |   |   |   |
| 67 | A |   | A | B |   |   | B |   | A |
| 68 | A |   | A | A |   |   | B |   | B |
| 69 | A | B | A | A | A |   |   |   |   |
| 70 | A |   | B | B | A |   |   |   |   |
| 71 | B |   | A | A | B |   |   |   |   |
| 72 | A |   | A |   |   |   |   |   |   |
| 73 | A |   | A | A | A | A | B |   | B |
| 74 | A |   | B |   |   |   |   |   |   |
| 75 | A |   | A | A | B |   |   |   |   |
| 76 | A |   | B | B | B |   |   |   |   |

TABLE 3-continued

| | Kinase assay | | | A375 cells | | RKO cells | | | |
| | | | | | | | | pAKT | |
| Ex | B-Raf | PI3Kα | mTOR | pERK | XTT | pERK | pS6RP | (T308) | XTT |
|---|---|---|---|---|---|---|---|---|---|
| 77 | A | | B | B | B | | | | |
| 78 | A | | B | A | B | | | | |
| 79 | A | B | A | A | A | | B | B | B |
| 80 | A | | B | B | B | | | | |
| 81 | A | B | | A | B | | | | |
| 82 | A | | B | A | A | | | | |
| 83 | A | | B | | | | | | |
| 84 | A | B | | | | | | | |
| 85 | A | | B | | | | | | |
| 86 | B | A | A | B | B | | | | B |
| 87 | A | A | A | B | B | | B | B | B |
| 88 | A | A | A | B | B | B | B | B | B |
| 89 | A | B | B | | | | | | |
| 90 | A | B | B | B | B | | | | |
| 91 | A | A | A | | | | | | |
| 92 | A | A | B | A | A | B | | C | C |
| 93 | A | A | B | B | B | | | C | B |
| 94 | A | A | A | A | B | A | B | B | B |
| 95 | A | B | A | B | B | | | | C |
| 96 | A | B | B | A | A | A | B | | B |
| 97 | A | A | B | A | B | | B | | B |
| 98 | A | A | B | | | | | | |
| 99 | A | B | A | A | B | A | B | | B |
| 100 | A | A | | B | B | A | | B | B |
| 101 | A | A | B | A | B | B | A | B | B |
| 102 | A | A | A | B | B | B | B | | B |
| 103 | A | B | | B | | | | C | C |
| 104 | A | A | | A | A | B | | | |
| 105 | A | A | | B | B | B | | C | C |
| 106 | A | A | A | C | B | | | | |
| 107 | A | B | | | | | | | |
| 108 | A | A | B | A | B | B | | C | B |
| 109 | A | A | | A | B | B | | C | |
| 110 | A | B | | A | C | | | | |
| 111 | A | B | A | B | B | | | | |
| 112 | A | B | | | | | | | |
| 113 | A | A | A | A | B | | | C | B |
| 114 | A | | B | A | B | | | | B |
| 115 | A | B | B | | | | | | |
| 116 | A | B | B | A | A | | | | |
| 117 | A | | A | A | B | | | | C |
| 118 | A | | B | | B | | | | C |
| 119 | A | | B | | | | | | |
| 120 | A | B | A | A | B | | | | |
| 121 | A | A | B | B | | | | | |
| 122 | A | B | | | | | | | |
| 123 | A | | A | A | | | | | |
| 124 | A | | B | | | | | | |
| 125 | B | | A | A | | | | | |
| 126 | B | | B | | | | | | |
| 127 | B | A | A | B | | | | | |
| 128 | A | A | B | B | | | | | |
| 129 | A | A | A | B | B | | | | |
| 130 | B | A | B | B | | | | | |
| 131 | B | A | B | B | | | | | |
| 132 | A | A | B | B | | | | | |
| 133 | A | | B | | | | | | |
| 134 | A | C | A | A | A | A | A | | B |
| 135 | A | C | A | A | A | A | B | | B |
| 136 | A | | B | | | A | | | B |
| 137 | A | | B | A | B | A | | | A |
| 138 | A | | B | | | | | | |
| 139 | A | A | A | B | B | B | | B | B |
| 140 | A | | B | B | B | A | | | B |
| 141 | A | | B | | | | | | |
| 142 | A | | B | | | | | | |
| 143 | A | | B | | | | | | |
| 144 | A | | B | | | | | | |

A: IC$_{50}$ = 1-100 nM
B: IC$_{50}$ = >100-1000 nM
C: IC$_{50}$ = >1000-10000 nM

Example 146

Protein Biomarkers for Monitoring Inhibition of RAS/RAF/MEK/ERK and PI3K/AKT/PTEN/mTOR Pathways The compounds described herein were tested for their ability to inhibit a combination of various biomarkers (pERK, pS6RP, pS6K, pAKT-S473 and pAKT-T308) in vitro in cultured cells and also in lysates made from tumor samples. Representative results are shown in the FIGURE, where the decrease in the phosphorylation of the various biomarkers in tumor cell lysates from mice was assessed on a Western blot. Biochemical analysis was done according to the protocols provided by the antibody providers as described in detail in Example 89E. For the experiment shown in The FIGURE, mice bearing the tumors derived from a colon cancer cell line RKO were treated with a compound of the invention for 4 hours (for pERK ½ and pS6RP analytes) or for 8 hours (for pAKT-S473 and pAKT-T308 analytes). The tumors were then excised, lysed and analyzed for the total and phospho-protein levels on a Western blot. Each lane represents the lysate from the tumor derived from a single animal, and there were four animals per treatment group. The percent inhibition of phospho-protein signal is indicated above each lane. Panel A). Total and phospho-protein levels of ERK protein. Panel B). Total and phospho-protein levels of S6 protein. Panel C). Total and phospho-protein (S473) levels of AKT. Panel D). Total and phospho-protein (T308) levels of AKT. The decrease in the signal of the band corresponding to a given phospho-protein indicates an inhibitory effect of the compound on the target protein.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of formula (I):

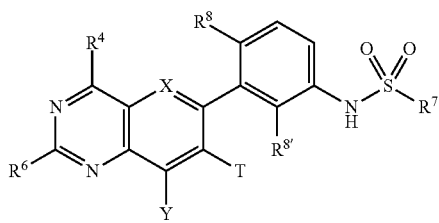

wherein:
X is CH or N;
Y is H, optionally substituted $C_1$-$C_6$ alkyl, $OR^1$ or $NR^2R^3$;
T is H or $C_1$-$C_6$ alkoxy;
$R^1$ is optionally substituted $C_1$-$C_6$ alkyl, optionally substituted ($C_1$-$C_6$ alkyl)OH, optionally substituted ($C_1$-$C_6$ alkyl)O$C_1$-$C_6$ alkyl, optionally substituted $C_3$-$C_8$ cycloalkyl, optionally substituted ($C_1$-$C_6$ alkyl)NH$_2$, optionally substituted ($C_1$-$C_6$ alkyl)CO$_2$H, or optionally substituted ($C_1$-$C_6$ alkyl)CONH$_2$;
$R^2$ and $R^3$ are joined to form an optionally substituted heterocycle;
$R^4$ is optionally substituted morpholine;
$R^6$ is optionally substituted aryl or optionally substituted heteroaryl;
$R^7$ is optionally substituted aryl, optionally substituted $C_1$-$C_6$ alkyl, or optionally substituted heteroaryl;
$R^8$ is H or halogen; and
$R^{8'}$ is halogen.

2. The compound according to claim 1, wherein $R^4$ is morpholine.

3. The compound according to claim 1, wherein $R^4$ is morpholine substituted by $C_1$-$C_6$ alkyl.

4. The compound according to claim 3, wherein $R^4$ is:

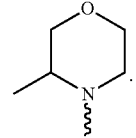

5. The compound according to claim 1, wherein $R^7$ is an optionally substituted aryl.

6. The compound according to claim 5, wherein $R^7$ is phenyl substituted by one or more halogen.

7. The compound according to claim 6, wherein $R^7$ is:

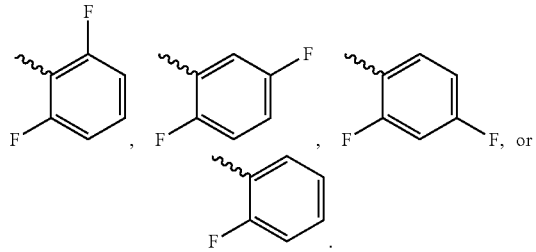

8. The compound according to claim 1, wherein $R^7$ is optionally substituted $C_1$-$C_6$ alkyl.

9. The compound according to claim 8, wherein $R^7$ is $C_1$-$C_6$ alkyl optionally substituted by one or more F.

10. The compound according to claim 8, wherein $R^7$ is i-propyl, i-butyl, n-propyl, ethyl, n-butyl, $CH_2CH_2CH_2F$, or $CH_2CH_2CF_3$.

11. The compound according to claim 1, wherein $R^7$ is optionally substituted heteroaryl.

12. The compound according to claim 11, wherein $R^7$ is thiophene.

13. The compound according to claim 1, wherein $R^6$ is:

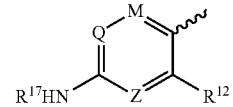

wherein:
M is N or $CR^{10}$;
Q is N or $CR^{13}$;
Z is N or $CR^{14}$;
$R^{10}$ is H, $C_1$-$C_6$ alkyl, halogen, CN or $CF_3$;
$R^{12}$ to $R^{14}$ are, independently, H, halogen, $C_1$-$C_6$ alkyl, or $CF_3$;
$R^{17}$ is NHC(O)NHN$R^9$, H, $C_1$-$C_6$ alkyl, ($C_1$-$C_6$ alkyl)-NH$_2$ or ($C_1$-$C_6$ alkyl)-OH, ($C_1$-$C_6$ alkyl)-O—($C_1$-$C_6$ alkyl), CO($C_1$-$C_6$ alkyl) or SO$_2$($C_1$-$C_6$ alkyl); or R¹³ and R¹⁷ or R¹⁴ and R¹⁷ are joined to form an optionally unsaturated ring; and
R⁹ is $C_1$-$C_6$ alkyl, $C_1$-$C_6$ hydroxyalkyl, or heteroaryl.

14. The compound according to claim 13, wherein R⁶ is:

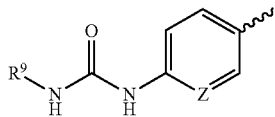

wherein:
Z is CH or N;
R⁹ is $C_1$-$C_6$ alkyl, $C_1$-$C_6$ hydroxyalkyl, or heteroaryl.

15. The compound according to claim 13, wherein R⁹ is $CH_3$, $CH_2CH_2OH$, or pyridine-4-yl.

16. The compound according to claim 13, wherein R⁶ is an optionally substituted pyrimidine, optionally substituted pyridine, optionally substituted pyrrole[2,3-b]pyridine, optionally substituted indazole or optionally substituted benzimidazole.

17. The compound according to claim 13, wherein R⁶ is:

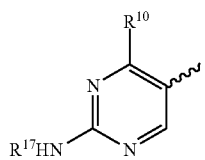

wherein:
R¹⁰ is H, $C_1$-$C_6$ alkyl or $CF_3$; and
R¹⁷ is H, $C_1$-$C_6$ alkyl, ($C_1$-$C_6$ alkyl)-$NH_2$ or ($C_1$-$C_6$ alkyl)-OH.

18. The compound according to claim 13, wherein R⁶ is:

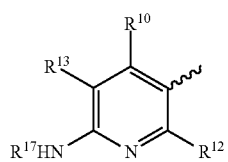

wherein:
R¹⁰, R¹² and R¹³ are, independently, H, halogen, $C_1$-$C_6$ alkyl, CN or $CF_3$; and
R¹⁷ is H, $C_1$-$C_6$ alkyl, ($C_1$-$C_6$ alkyl)-$NH_2$ or ($C_1$-$C_6$ alkyl)-OH; or
R¹³ and R¹⁷ are joined to form an optionally unsaturated 5-membered ring.

19. The compound according to claim 18, wherein R⁶ is:

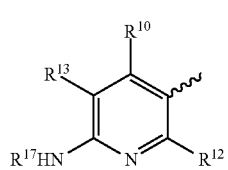

wherein:
R¹⁰ is H, $C_1$-$C_6$ alkyl, halogen, CN or $CF_3$;
R¹² is H or halogen;
R¹³ is H, halogen or $C_1$-$C_6$ alkyl; and R¹⁷ is H, $C_1$-$C_6$ alkyl, ($C_1$-$C_6$ alkyl)-$NH_2$ or ($C_1$-$C_6$ alkyl)-OH; or
R¹³ and R¹⁷ are joined to form an optionally unsaturated 5-membered ring.

20. The compound according to claim 19, wherein R⁶ is:

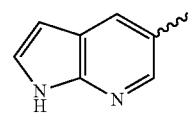

21. The compound according to claim 1, wherein R⁶ is:

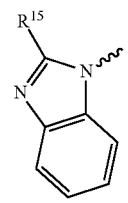

wherein, R¹⁵ is $C_1$-$C_6$ fluoroalkyl or $C_1$-$C_6$ hydroxyalkyl.

22. The compound according to claim 21, wherein R⁶ is:

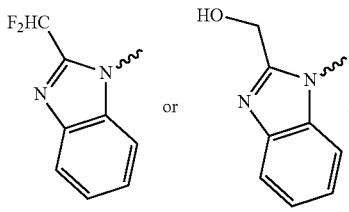

23. The compound according to claim 1, wherein R⁶ is the following and is bound through any carbon atom:

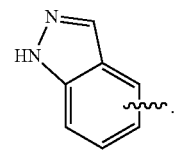

24. The compound according to claim 23, wherein R⁶ is:

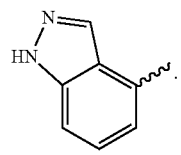

25. The compound according to claim 1, which is selected from the group consisting of:
2,6-difluoro-N-(2-fluoro-3-(8-methoxy-2-(4-(3-methylureido)phenyl)-4-morpholinoquinazolin-6-yl)phenyl)benzenesulfonamide;
N-(3-(2-(1H-indazol-4-yl)-8-methoxy-4-morpholinoquinazolin-6-yl)-2-fluorophenyl)propane-1-sulfonamide;

N-(3-(2-(6-((2-aminoethyl)amino)pyridin-3-yl)-8-methoxy-4-morpholinoquinazolin-6-yl)-2-fluorophenyl)propane-1-sulfonamide;

N-(3-(2-(6-aminopyridin-3-yl)-8-(2-hydroxyethoxy)-4-morpholinoquinazolin-6-yl)-2-fluorophenyl)propane-1-sulfonamide;

N-(3-(2-(6-aminopyridin-3-yl)-4,8-dimorpholinoquinazolin-6-yl)-2-fluorophenyl)-3-fluoropropane-1-sulfonamide;

N-(3-(2-(2-aminopyrimidin-5-yl)-8-methoxy-4-morpholinoquinazolin-6-yl)-2,4-difluorophenyl)propane-1-sulfonamide;

N-(3-(2-(2-aminopyrimidin-5-yl)-4-morpholinopyrido[3,2-d]pyrimidin-6-yl)-2-fluorophenyl)propane-1-sulfonamide;

N-(3-(2-(6-aminopyridin-3-yl)-8-methyl-4-morpholinoquinazolin-6-yl)-2-fluorophenyl)propane-1-sulfonamide;

N-(3-(2-(2-(difluoromethyl)-1H-benzo[d]imidazol-1-yl)-8-methoxy-4-morpholinoquinazolin-6-yl)-2-fluorophenyl)propane-1-sulfonamide;

N-(2-fluoro-3-(2-(2-(hydroxymethyl)-1H-benzo[d]imidazol-1-yl)-8-methoxy-4-morpholinoquinazolin-6-yl)phenyl)propane-1-sulfonamide;

N-(3-(2-(2-aminopyrimidin-5-yl)-7-methoxy-4-morpholinoquinazolin-6-yl)-2-fluorophenyl)-3-fluoropropane-1-sulfonamide;

2,6-difluoro-N-(2-fluoro-3-(2-(4-(3-(2-hydroxyethyl)ureido)phenyl)-8-methoxy-4-morpholinoquinazolin-6-yl)phenyl)benzenesulfonamide;

N-(3-(2-(2-aminopyrimidin-5-yl)-8-methoxy-4-morpholinoquinazolin-6-yl)-2-fluorophenyl)-2,6-difluorobenzenesulfonamide;

N-(2-fluoro-3-(8-methoxy-2-(4-(3-methylureido)phenyl)-4-morpholinoquinazolin-6-yl)phenyl)propane-1-sulfonamide;

N-(3-(2-(2-aminopyrimidin-5-yl)-8-methoxy-4-morpholinoquinazolin-6-yl)-2-fluorophenyl)propane-1-sulfonamide;

2,6-difluoro-N-(2-fluoro-3-(8-methoxy-4-morpholino-2-(1H-pyrrolo[2,3-b]pyridin-5-yl)quinazolin-6-yl)phenyl)benzenesulfonamide;

N-(3-(2-(6-aminopyridin-3-yl)-8-methoxy-4-morpholinoquinazolin-6-yl)-2-fluorophenyl)propane-1-sulfonamide;

N-(3-(2-(6-amino-2-fluoropyridin-3-yl)-8-methoxy-4-morpholinoquinazolin-6-yl)-2-fluorophenyl)propane-1-sulfonamide;

N-(3-(2-(6-aminopyridin-3-yl)-8-methoxy-4-morpholinoquinazolin-6-yl)-2-fluorophenyl)-2,6-difluorobenzenesulfonamide;

N-(3-(2-(2-aminopyrimidin-5-yl)-8-methoxy-4-morpholinoquinazolin-6-yl)-2-fluorophenyl)-2-methylpropane-1-sulfonamide;

N-(3-(2-(2-aminopyrimidin-5-yl)-8-methoxy-4-morpholinoquinazolin-6-yl)-2-fluorophenyl)ethanesulfonamide;

N-(3-(2-(2-aminopyrimidin-5-yl)-8-methoxy-4-morpholinoquinazolin-6-yl)-2-fluorophenyl)-2,5-difluorobenzenesulfonamide;

N-(3-(2-(2-aminopyrimidin-5-yl)-8-methoxy-4-morpholinoquinazolin-6-yl)-2-fluorophenyl)butane-1-sulfonamide;

N-(3-(2-(2-aminopyrimidin-5-yl)-8-methoxy-4-morpholinoquinazolin-6-yl)-2-fluorophenyl)-2,4-difluorobenzenesulfonamide;

N-(3-(2-(6-amino-4-(trifluoromethyl)pyridin-3-yl)-8-methoxy-4-morpholinoquinazolin-6-yl)-2-fluorophenyl)propane-1-sulfonamide;

N-(3-(2-(6-amino-5-methylpyridin-3-yl)-8-methoxy-4-morpholinoquinazolin-6-yl)-2-fluorophenyl)propane-1-sulfonamide;

N-(3-(2-(2-aminopyrimidin-5-yl)-8-methoxy-4-morpholinoquinazolin-6-yl)-2-fluorophenyl)-3-fluoropropane-1-sulfonamide;

N-(3-(2-(6-aminopyridin-3-yl)-8-methoxy-4-morpholinoquinazolin-6-yl)-2-fluorophenyl)-2,5-difluorobenzenesulfonamide;

N-(3-(2-(6-aminopyridin-3-yl)-8-methoxy-4-morpholinoquinazolin-6-yl)-2-fluorophenyl)-2-fluorobenzenesulfonamide;

N-(3-(2-(6-aminopyridin-3-yl)-8-methoxy-4-morpholinoquinazolin-6-yl)-2-fluorophenyl)-3-fluoropropane-1-sulfonamide;

N-(3-(2-(6-aminopyridin-3-yl)-8-methoxy-4-morpholinoquinazolin-6-yl)-2-fluorophenyl)-3,3,3-trifluoropropane-1-sulfonamide;

3-fluoro-N-(2-fluoro-3-(8-methoxy-2-(4-(3-methylureido)phenyl)-4-morpholinoquinazolin-6-yl)phenyl)propane-1-sulfonamide;

N-(3-(2-(6-aminopyridin-3-yl)-8-methoxy-4-morpholinoquinazolin-6-yl)-2-fluorophenyl)propane-2-sulfonamide;

N-(2-fluoro-3-(8-methoxy-4-morpholino-2-(4-(3-(pyridin-4-yl)ureido)phenyl)quinazolin-6-yl)phenyl)propane-1-sulfonamide;

N-(3-(2-(2-amino-4-methylpyrimidin-5-yl)-8-methoxy-4-morpholinoquinazolin-6-yl)-2-fluorophenyl)-3-fluoropropane-1-sulfonamide;

N-(3-(2-(6-amino-4-(trifluoromethyl)pyridin-3-yl)-8-methoxy-4-morpholinoquinazolin-6-yl)-2-fluorophenyl)-3-fluoropropane-1-sulfonamide;

N-(3-(2-(1H-indazol-4-yl)-8-methoxy-4-morpholinoquinazolin-6-yl)-2-fluorophenyl)-3-fluoropropane-1-sulfonamide;

N-(3-(2-(6-aminopyridin-3-yl)-8-methoxy-4-morpholinoquinazolin-6-yl)-2-fluorophenyl)thiophene-2-sulfonamide;

3-fluoro-N-(2-fluoro-3-(8-methoxy-2-(6-(3-methylureido)pyridin-3-yl)-4-morpholinoquinazolin-6-yl)phenyl)propane-1-sulfonamide;

3-fluoro-N-(2-fluoro-3-(8-methoxy-4-morpholino-2-(1H-pyrrolo[2,3-b]pyridin-5-yl)quinazolin-6-yl)phenyl)propane-1-sulfonamide;

(S)—N-(3-(2-(6-aminopyridin-3-yl)-8-methoxy-4-(3-methylmorpholino)quinazolin-6-yl)-2-fluorophenyl)-3-fluoropropane-1-sulfonamide;

(R)—N-(3-(2-(6-aminopyridin-3-yl)-8-methoxy-4-(3-methylmorpholino)quinazolin-6-yl)-2-fluorophenyl)-3-fluoropropane-1-sulfonamide;

(R)—N-(3-(2-(2-aminopyrimidin-5-yl)-8-methoxy-4-(3-methylmorpholino)quinazolin-6-yl)-2-fluorophenyl)-3-fluoropropane-1-sulfonamide;

(R)-3-fluoro-N-(2-fluoro-3-(8-methoxy-4-(3-methylmorpholino)-2-(1H-pyrrolo[2,3-b]pyridin-5-yl)quinazolin-6-yl)phenyl)propane-1-sulfonamide;

(S)—N-(3-(2-(2-aminopyrimidin-5-yl)-8-methoxy-4-(3-methylmorpholino)quinazolin-6-yl)-2-fluorophenyl)-3-fluoropropane-1-sulfonamide;

N-(3-(2-(6-aminopyridin-3-yl)-4-morpholinoquinazolin-6-yl)-2-fluorophenyl)-3-fluoropropane-1-sulfonamide;

N-(3-(2-(2-aminopyrimidin-5-yl)-8-methoxy-4-morpholinoquinazolin-6-yl)-2-fluorophenyl)-2-fluorobenzenesulfonamide;

N-(3-(2-(6-amino-5-chloropyridin-3-yl)-8-methoxy-4-morpholinoquinazolin-6-yl)-2-fluorophenyl)propane-1-sulfonamide;

3-fluoro-N-(2-fluoro-3-(8-methoxy-4-morpholino-2-(6-(propylamino)pyridin-3-yl)quinazolin-6-yl)phenyl)propane-1-sulfonamide;

3-fluoro-N-(2-fluoro-3-(8-methoxy-2-(6-(methylamino)pyridin-3-yl)-4-morpholinoquinazolin-6-yl)phenyl)propane-1-sulfonamide;

3-fluoro-N-(2-fluoro-3-(8-methoxy-2-(2-(methylamino)pyrimidin-5-yl)-4-morpholinoquinazolin-6-yl)phenyl)propane-1-sulfonamide;

N-(3-(2-(6-aminopyridin-3-yl)-8-ethoxy-4-morpholinoquinazolin-6-yl)-2-fluorophenyl)-3-fluoropropane-1-sulfonamide;

N-(3-(2-(6-aminopyridin-3-yl)-8-(cyclopentyloxy)-4-morpholinoquinazolin-6-yl)-2-fluorophenyl)-3-fluoropropane-1-sulfonamide;

N-(3-(2-(2-aminopyrimidin-5-yl)-8-ethoxy-4-morpholinoquinazolin-6-yl)-2-fluorophenyl)-3-fluoropropane-1-sulfonamide;

N-(3-(2-(6-aminopyridin-3-yl)-8-isopropoxy-4-morpholinoquinazolin-6-yl)-2-fluorophenyl)-3-fluoropropane-1-sulfonamide;

N-(3-(8-(2-aminoethoxy)-2-(6-aminopyridin-3-yl)-4-morpholinoquinazolin-6-yl)-2-fluorophenyl)-3-fluoropropane-1-sulfonamide;

N-(3-(2-(6-aminopyridin-3-yl)-8-(cyclopropylmethoxy)-4-morpholinoquinazolin-6-yl)-2-fluorophenyl)-3-fluoropropane-1-sulfonamide;

N-(3-(2-(6-aminopyridin-3-yl)-8-(2-hydroxyethoxy)-4-morpholinoquinazolin-6-yl)-2-fluorophenyl)-3-fluoropropane-1-sulfonamide;

2-((2-(6-aminopyridin-3-yl)-6-(2-fluoro-3-(3-fluoropropylsulfonamido)phenyl)-4-morpholinoquinazolin-8-yl)oxy)acetic acid 2,2,2-trifluoroacetate;

2-((2-(6-aminopyridin-3-yl)-6-(2-fluoro-3-(3-fluoropropylsulfonamido)phenyl)-4-morpholinoquinazolin-8-yl)oxy)acetamide;

(R)—N-(3-(8-ethoxy-4-(3-methylmorpholino)-2-(1H-pyrrolo[2,3-b]pyridin-5-yl)quinazolin-6-yl)-2-fluorophenyl)-3-fluoropropane-1-sulfonamide;

(R)—N-(3-(2-(6-aminopyridin-3-yl)-8-(cyclopentyloxy)-4-(3-methylmorpholino)quinazolin-6-yl)-2-fluorophenyl)-3-fluoropropane-1-sulfonamide;

(R)—N-(3-(2-(6-aminopyridin-3-yl)-8-isopropoxy-4-(3-methylmorpholino)quinazolin-6-yl)-2-fluorophenyl)-3-fluoropropane-1-sulfonamide;

(R)—N-(3-(2-(2-aminopyrimidin-5-yl)-8-isopropoxy-4-(3-methylmorpholino)quinazolin-6-yl)-2-fluorophenyl)-3-fluoropropane-1-sulfonamide;

(S)—N-(3-(2-(6-aminopyridin-3-yl)-8-ethoxy-4-(3-methylmorpholino)quinazolin-6-yl)-2-fluorophenyl)-3-fluoropropane-1-sulfonamide;

(S)—N-(3-(2-(2-aminopyrimidin-5-yl)-8-ethoxy-4-(3-methylmorpholino)quinazolin-6-yl)-2-fluorophenyl)-3-fluoropropane-1-sulfonamide;

N-(3-(2-(6-aminopyridin-3-yl)-8-(2-methoxyethoxy)-4-morpholinoquinazolin-6-yl)-2-fluorophenyl)-3-fluoropropane-1-sulfonamide;

N-(3-(2-(2-aminopyrimidin-5-yl)-8-(2-methoxyethoxy)-4-morpholinoquinazolin-6-yl)-2-fluorophenyl)-3-fluoropropane-1-sulfonamide;

N-(3-(2-(2-aminopyrimidin-5-yl)-4,8-dimorpholinoquinazolin-6-yl)-2-fluorophenyl)-3-fluoropropane-1-sulfonamide;

N-(3-(2-(6-aminopyridin-3-yl)-4-morpholino-8-(pyrrolidin-1-yl)quinazolin-6-yl)-2-fluorophenyl)-3-fluoropropane-1-sulfonamide;

N-(3-(2-(2-aminopyrimidin-5-yl)-4-morpholino-8-(pyrrolidin-1-yl)quinazolin-6-yl)-2-fluorophenyl)-3-fluoropropane-1-sulfonamide;

(R)—N-(3-(2-(6-aminopyridin-3-yl)-4-(3-methylmorpholino)-8-morpholinoquinazolin-6-yl)-2-fluorophenyl)-3-fluoropropane-1-sulfonamide;

(R)—N-(3-(2-(2-aminopyrimidin-5-yl)-4-(3-methylmorpholino)-8-morpholinoquinazolin-6-yl)-2-fluorophenyl)-3-fluoropropane-1-sulfonamide;

(R)—N-(3-(2-(6-aminopyridin-3-yl)-4-(3-methylmorpholino)-8-(pyrrolidin-1-yl)quinazolin-6-yl)-2-fluorophenyl)-3-fluoropropane-1-sulfonamide;

N-(3-(2-(6-aminopyridin-3-yl)-8-methoxy-4-morpholinoquinazolin-6-yl)-2,4-difluorophenyl)propane-1-sulfonamide;

N-(3-(2-(2-aminopyrimidin-5-yl)-8-methoxy-4-morpholinoquinazolin-6-yl)-2,4-difluorophenyl)-2,6-difluorobenzenesulfonamide;

N-(3-(2-(6-aminopyridin-3-yl)-8-methoxy-4-morpholinoquinazolin-6-yl)-2,4-difluorophenyl)-2,6-difluorobenzenesulfonamide;

N-(3-(2-(6-aminopyridin-3-yl)-8-methoxy-4-morpholinoquinazolin-6-yl)-2,4-difluorophenyl)-2,5-difluorobenzenesulfonamide;

N-(3-(2-(6-aminopyridin-3-yl)-8-methoxy-4-morpholinoquinazolin-6-yl)-2,4-difluorophenyl)-3-fluoropropane-1-sulfonamide;

N-(3-(2-(6-aminopyridin-3-yl)-8-methoxy-4-morpholinoquinazolin-6-yl)-4-chloro-2-fluorophenyl)propane-1-sulfonamide;

N-(3-(2-(1H-indazol-4-yl)-8-methoxy-4-morpholinoquinazolin-6-yl)-2,4-difluorophenyl)-3-fluoropropane-1-sulfonamide;

N-(3-(2-(2-aminopyrimidin-5-yl)-8-methoxy-4-morpholinoquinazolin-6-yl)-2,4-difluorophenyl)-3-fluoropropane-1-sulfonamide;

N-(2,4-difluoro-3-(8-methoxy-4-morpholino-2-(1H-pyrrolo[2,3-b]pyridin-5-yl)quinazolin-6-yl)phenyl)-3-fluoropropane-1-sulfonamide;

N-(3-(2-(6-amino-4-(trifluoromethyl)pyridin-3-yl)-8-methoxy-4-morpholinoquinazolin-6-yl)-2,4-difluorophenyl)-3-fluoropropane-1-sulfonamide;

N-(3-(2-(6-aminopyridin-3-yl)-8-methoxy-4-morpholinoquinazolin-6-yl)-4-chloro-2-fluorophenyl)-3-fluoropropane-1-sulfonamide;

N-(3-(2-(6-aminopyridin-3-yl)-4-morpholinopyrido[3,2-d]pyrimidin-6-yl)-2-fluorophenyl)propane-1-sulfonamide;

N-(3-(2-(2-aminopyrimidin-5-yl)-4-morpholinopyrido[3,2-d]pyrimidin-6-yl)-2-fluorophenyl)-3-fluoropropane-1-sulfonamide;

N-(3-(2-(6-aminopyridin-3-yl)-4-morpholinopyrido[3,2-d]pyrimidin-6-yl)-2-fluorophenyl)-3-fluoropropane-1-sulfonamide;

N-(3-(2-(1H-indazol-4-yl)-4-morpholinopyrido[3,2-d]pyrimidin-6-yl)-2-fluorophenyl)-3-fluoropropane-1-sulfonamide;

N-(3-(2-(6-amino-5-methylpyridin-3-yl)-4-morpholinopyrido[3,2-d]pyrimidin-6-yl)-2-fluorophenyl)-3-fluoropropane-1-sulfonamide;

3-fluoro-N-(2-fluoro-3-(4-morpholino-2-(1H-pyrrolo[2,3-b]pyridin-5-yl)pyrido[3,2-d]pyrimidin-6-yl)phenyl)propane-1-sulfonamide;
N-(3-(2-(6-aminopyridin-3-yl)-4-morpholinopyrido[3,2-d]pyrimidin-6-yl)-2-fluorophenyl)-2,5-difluorobenzenesulfonamide;
N-(3-(2-(2-aminopyrimidin-5-yl)-4-morpholinopyrido[3,2-d]pyrimidin-6-yl)-2-fluorophenyl)-2,5-difluorobenzenesulfonamide;
N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide;
N-(3-(2-(6-aminopyridin-3-yl)-4-morpholinopyrido[3,2-d]pyrimidin-6-yl)-2-fluorophenyl)-2,6-difluorobenzenesulfonamide;
(R)—N-(3-(2-(6-aminopyridin-3-yl)-4-(3-methylmorpholino)pyrido[3,2-d]pyrimidin-6-yl)-2-fluorophenyl)-3-fluoropropane-1-sulfonamide;
(R)—N-(3-(2-(2-aminopyrimidin-5-yl)-4-(3-methylmorpholino)pyrido[3,2-d]pyrimidin-6-yl)-2-fluorophenyl)-3-fluoropropane-1-sulfonamide;
N-(3-(2-(2-aminopyrimidin-5-yl)-4-morpholinopyrido[3,2-d]pyrimidin-6-yl)-2-fluorophenyl)-2,6-difluorobenzenesulfonamide;
3-fluoro-N-(2-fluoro-3-(2-(6-((2-hydroxyethyl)amino)pyridin-3-yl)-4-morpholinopyrido[3,2-d]pyrimidin-6-yl)phenyl)propane-1-sulfonamide;
N-(3-(2-(2-amino-4-(trifluoromethyl)pyrimidin-5-yl)-4-morpholinopyrido[3,2-d]pyrimidin-6-yl)-2-fluorophenyl)-3-fluoropropane-1-sulfonamide;
N-(3-(2-(6-amino-4-methylpyridin-3-yl)-4-morpholinopyrido[3,2-d]pyrimidin-6-yl)-2-fluorophenyl)-3-fluoropropane-1-sulfonamide;
N-(3-(2-(6-amino-4-fluoropyridin-3-yl)-4-morpholinopyrido[3,2-d]pyrimidin-6-yl)-2-fluorophenyl)-3-fluoropropane-1-sulfonamide;
N-(3-(2-(6-amino-5-chloropyridin-3-yl)-4-morpholinopyrido[3,2-d]pyrimidin-6-yl)-2-fluorophenyl)-3-fluoropropane-1-sulfonamide;
N-(3-(2-(6-amino-4-(trifluoromethyl)pyridin-3-yl)-4-morpholinopyrido[3,2-d]pyrimidin-6-yl)-2-fluorophenyl)-2,5-difluorobenzenesulfonamide;
N-(3-(2-(6-amino-5-fluoropyridin-3-yl)-4-morpholinopyrido[3,2-d]pyrimidin-6-yl)-2-fluorophenyl)-3-fluoropropane-1-sulfonamide;
N-(3-(2-(6-amino-4-(trifluoromethyl)pyridin-3-yl)-4-morpholinopyrido[3,2-d]pyrimidin-6-yl)-2-fluorophenyl)-2,6-difluorobenzenesulfonamide;
(R)—N-(3-(2-(6-amino-4-(trifluoromethyl)pyridin-3-yl)-4-(3-methylmorpholino)pyrido[3,2-d]pyrimidin-6-yl)-2-fluorophenyl)-3-fluoropropane-1-sulfonamide;
(S)—N-(3-(2-(6-amino-4-(trifluoromethyl)pyridin-3-yl)-4-(3-methylmorpholino)pyrido[3,2-d]pyrimidin-6-yl)-2-fluorophenyl)-3-fluoropropane-1-sulfonamide;
N-(3-(2-(2-amino-4-methylpyrimidin-5-yl)-4-morpholinopyrido[3,2-d]pyrimidin-6-yl)-2-fluorophenyl)-3-fluoropropane-1-sulfonamide;
3-fluoro-N-(2-fluoro-3-(2-(2-((3-hydroxypropyl)amino)pyrimidin-5-yl)-4-morpholinopyrido[3,2-d]pyrimidin-6-yl)phenyl)propane-1-sulfonamide;
3-fluoro-N-(2-fluoro-3-(2-(6-((3-hydroxypropyl)amino)pyridin-3-yl)-4-morpholinopyrido[3,2-d]pyrimidin-6-yl)phenyl)propane-1-sulfonamide;
3-fluoro-N-(2-fluoro-3-(4-morpholino-2-(2-(propylamino)pyrimidin-5-yl)pyrido[3,2-d]pyrimidin-6-yl)phenyl)propane-1-sulfonamide;
3-fluoro-N-(2-fluoro-3-(2-(6-(methylamino)pyridin-3-yl)-4-morpholinopyrido[3,2-d]pyrimidin-6-yl)phenyl)propane-1-sulfonamide;
3-fluoro-N-(2-fluoro-3-(2-(6-(isopropylamino)pyridin-3-yl)-4-morpholinopyrido[3,2-d]pyrimidin-6-yl)phenyl)propane-1-sulfonamide;
3-fluoro-N-(2-fluoro-3-(4-morpholino-2-(6-(propylamino)pyridin-3-yl)pyrido[3,2-d]pyrimidin-6-yl)phenyl)propane-1-sulfonamide;
N-(3-(2-(2-aminopyrimidin-5-yl)-8-methyl-4-morpholinoquinazolin-6-yl)-2-fluorophenyl)-3-fluoropropane-1-sulfonamide;
N-(3-(2-(6-aminopyridin-3-yl)-8-methyl-4-morpholinoquinazolin-6-yl)-2-fluorophenyl)-3-fluoropropane-1-sulfonamide;
N-(3-(2-(1H-indazol-4-yl)-8-methyl-4-morpholinoquinazolin-6-yl)-2-fluorophenyl)-3-fluoropropane-1-sulfonamide;
(R)—N-(3-(2-(2-aminopyrimidin-5-yl)-8-ethyl-4-(3-methylmorpholino)quinazolin-6-yl)-2-fluorophenyl)-3-fluoropropane-1-sulfonamide;
N-(3-(2-(6-aminopyridin-3-yl)-7-methoxy-4-morpholinoquinazolin-6-yl)-2-fluorophenyl)-3-fluoropropane-1-sulfonamide;
3-fluoro-N-(2-fluoro-3-(2-(2-(methylamino)pyrimidin-5-yl)-4-morpholinopyrido[3,2-d]pyrimidin-6-yl)phenyl)propane-1-sulfonamide;
N-(3-(2-(2-(ethylamino)pyrimidin-5-yl)-4-morpholinopyrido[3,2-d]pyrimidin-6-yl)-2-fluorophenyl)-3-fluoropropane-1-sulfonamide;
N-(3-(2-(6-(ethylamino)pyridin-3-yl)-4-morpholinopyrido[3,2-d]pyrimidin-6-yl)-2-fluorophenyl)-3-fluoropropane-1-sulfonamide;
N-(5-(6-(2-fluoro-3-(3-fluoropropylsulfonamido)phenyl)-8-methoxy-4-morpholinoquinazolin-2-yl)pyridin-2-yl)acetamide;
N-(4-(6-(2-fluoro-3-(3-fluoropropylsulfonamido)phenyl)-8-methoxy-4-morpholinoquinazolin-2-yl)phenyl)acetamide;
3-fluoro-N-(2-fluoro-3-(8-methoxy-2-(4-(methylsulfonamido)phenyl)-4-morpholinoquinazolin-6-yl)phenyl)propane-1-sulfonamide;
(S)—N-(3-(2-(6-aminopyridin-3-yl)-4-(3-methylmorpholino)pyrido[3,2-d]pyrimidin-6-yl)-2-fluorophenyl)-3-fluoropropane-1-sulfonamide;
(S)—N-(3-(2-(2-aminopyrimidin-5-yl)-4-(3-methylmorpholino)pyrido[3,2-d]pyrimidin-6-yl)-2-fluorophenyl)-3-fluoropropane-1-sulfonamide;
(S)—N-(3-(2-(6-amino-4-fluoropyridin-3-yl)-4-(3-methylmorpholino)pyrido[3,2-d]pyrimidin-6-yl)-2-fluorophenyl)-3-fluoropropane-1-sulfonamide;
(S)—N-(3-(2-(6-amino-4-methylpyridin-3-yl)-4-(3-methylmorpholino)pyrido[3,2-d]pyrimidin-6-yl)-2-fluorophenyl)-3-fluoropropane-1-sulfonamide;
(S)—N-(3-(2-(2-amino-4-methylpyrimidin-5-yl)-4-(3-methylmorpholino)pyrido[3,2-d]pyrimidin-6-yl)-2-fluorophenyl)-3-fluoropropane-1-sulfonamide;
(S)—N-(3-(2-(2-amino-4-methylpyrimidin-5-yl)-4-(3-methylmorpholino)pyrido[3,2-d]pyrimidin-6-yl)-2-fluorophenyl)-2,5-difluorobenzenesulfonamide;
3-fluoro-N-(2-fluoro-3-(2-(6-((2-methoxyethyl)amino)pyridin-3-yl)-4-morpholinopyrido[3,2-d]pyrimidin-6-yl)phenyl)propane-1-sulfonamide;
(R)—N-(3-(2-(6-amino-5-fluoropyridin-3-yl)-8-methoxy-4-(3-methylmorpholino)quinazolin-6-yl)-2-fluorophenyl)-3-fluoropropane-1-sulfonamide;

(R)—N-(3-(2-(6-amino-4-fluoropyridin-3-yl)-8-methoxy-4-(3-methylmorpholino)quinazolin-6-yl)-2-fluorophenyl)-3-fluoropropane-1-sulfonamide;

(R)-3-fluoro-N-(2-fluoro-3-(8-methoxy-2-(2-(methylamino)pyrimidin-5-yl)-4-(3-methylmorpholino)quinazolin-6-yl)phenyl)propane-1-sulfonamide;

(R)—N-(3-(2-(2-aminopyrimidin-5-yl)-8-ethoxy-4-(3-methylmorpholino)quinazolin-6-yl)-2-fluorophenyl)-3-fluoropropane-1-sulfonamide;

(R)—N-(3-(8-ethoxy-2-(2-(methylamino)pyrimidin-5-yl)-4-(3-methylmorpholino)quinazolin-6-yl)-2-fluorophenyl)-3-fluoropropane-1-sulfonamide;

3-fluoro-N-(2-fluoro-3-(2-(4-(3-methylureido)phenyl)-4-morpholinopyrido[3,2-d]pyrimidin-6-yl)phenyl)propane-1-sulfonamide;

(R)—N-(3-(2-(6-amino-4-fluoropyridin-3-yl)-4-(3-methylmorpholino)pyrido[3,2-d]pyrimidin-6-yl)-2-fluorophenyl)-3-fluoropropane-1-sulfonamide;

(R)—N-(3-(2-(2-aminopyrimidin-5-yl)-8-(2-fluoroethoxy)-4-(3-methylmorpholino)quinazolin-6-yl)-2-fluorophenyl)-3-fluoropropane-1-sulfonamide;

(R)—N-(3-(2-(6-amino-5-fluoropyridin-3-yl)-8-(2-fluoroethoxy)-4-(3-methylmorpholino)quinazolin-6-yl)-2-fluorophenyl)-3-fluoropropane-1-sulfonamide;

(R)—N-(3-(2-(5-aminopyrazin-2-yl)-8-methoxy-4-(3-methylmorpholino)quinazolin-6-yl)-2-fluorophenyl)-3-fluoropropane-1-sulfonamide; and (R)—N-(3-(2-(6-amino-4-cyanopyridin-3-yl)-8-methoxy-4-(3-methylmorpholino)quinazolin-6-yl)-2-fluorophenyl)-3-fluoropropane-1-sulfonamide.

26. The compound according to claim 1, which is a salt of an acid or base.

27. The compound according to claim 26, wherein said acid salt is selected from the group consisting of acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic acid, trifluoroacetic, and camphorsulfonic.

28. The compound according to claim 26, wherein the base salt is selected from the group consisting of sodium, lithium, potassium, monomethylammonium, dimethylammonium, trimethylammonium, monoethylammonium, diethylammonium, triethylammonium, monopropylammonium, dipropylammonium, tripropylammonium, ethyl-dimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, and phenylmonoethanolammonium.

29. A composition comprising a compound of claim 1 and a pharmaceutically acceptable carrier.

30. A kit comprising a compound of claim 1.

31. The kit according to claim 30, further comprising a chemotherapeutic.

32. A method for treating a condition treatable by inhibiting the RAS/RAF/MEK/ERK and/or PI3K/AKT/PTEN/mTOR pathways, said method comprising administering a therapeutically effective amount of a compound of claim 1 to a patient in need thereof.

33. A method for treating a disease characterized by an abnormal cellular proliferation resulting from a dysregulated RAS/RAF/MEK/ERK and/or PI3K/AKT/PTEN/mTOR pathways, said method comprising administering of a therapeutically effective amount of a compound of claim 1 to a patient in need thereof.

34. The method according to claim 33, wherein said disease is cancer.

35. The method according to claim 34, wherein said cancer is of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma.

36. The method according to claim 35, wherein said patient has at least one solid tumor.

37. A method for treating a condition treatable by inhibiting the RAS/RAF/MEK/ERK and/or PI3K/AKT/PTEN/mTOR pathways to a patient in need thereof, comprising:
  assaying a sample from a patient to detect the presence of a B-RAF, PI3K or PTEN mutation or a combination thereof; and
  administering to a patient having a B-RAF, PI3K, or PTEN mutation as determined by the assaying step a therapeutically effective amount of a compound of claim 1.

38. The method according to claim 37, wherein said disease is cancer.

39. The method according to claim 38, wherein said cancer is of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma.

40. The method according to claim 39, wherein said patient has at least one solid tumor.

41. The method according to claim 37, wherein the patient has a B-RAF and an mTOR mutation.

42. The method according to claim 37, wherein the patient has a B-RAF and a PI3K mutation.

43. The method according to claim 37, wherein the patient has a B-RAF mutation, an mTOR and a PI3K mutation.

* * * * *